(12) United States Patent
Kreutzer et al.

(10) Patent No.: US 8,546,143 B2
(45) Date of Patent: *Oct. 1, 2013

(54) COMPOSITIONS AND METHODS FOR INHIBITING EXPRESSION OF A TARGET GENE

(75) Inventors: Roland Kreutzer, Weidenberg (DE);
Stefan Limmer, Kulmbach (DE); Sylvia Limmer, Kulmbach (DE); Philipp Hadwiger, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/894,018

(22) Filed: Sep. 29, 2010

(65) Prior Publication Data

US 2011/0111493 A1    May 12, 2011

Related U.S. Application Data

(63) Continuation of application No. 10/384,339, filed on Mar. 7, 2003, now Pat. No. 7,829,693, which is a continuation-in-part of application No. PCT/EP02/00152, filed on Jan. 9, 2002.

(30) Foreign Application Priority Data

| Jan. 9, 2001 | (DE) | 101 00 586 |
| Oct. 26, 2001 | (DE) | 101 55 280 |
| Nov. 29, 2001 | (DE) | 10 158 411 |
| Dec. 7, 2001 | (DE) | 101 60 151 |

(51) Int. Cl.
*C12Q 1/68* (2006.01)
*C12N 15/88* (2006.01)
*C07H 21/02* (2006.01)
*C07H 21/04* (2006.01)

(52) U.S. Cl.
USPC .......... 435/455; 435/6; 435/91.1; 435/91.31; 435/458; 536/23.1; 536/24.31; 536/24.5

(58) Field of Classification Search
USPC ........ 435/6, 91.1, 91.31, 455, 458; 536/23.1, 536/24.5, 24.31
See application file for complete search history.

(56) References Cited

U.S. PATENT DOCUMENTS 7,105,656 B2 * 9/2006 Colgan ..................... 536/24.33
7,829,693 B2 * 11/2010 Kreutzer et al. ............. 536/24.5

FOREIGN PATENT DOCUMENTS

DE    10160151.4    6/2003

OTHER PUBLICATIONS

Holen et al., Nucleic Acids Research, vol. 30, No. 8, pp. 1757-1766 (2002).*
James, H.A, et al., "The therapeutic potential of ribozymes," Blood (1998) 91:371-82.
Jansen, B., et al., "Chemosensitisation of malignant melanoma by BCL2 antisense therapy," *The Lancet* (2000) 356:1728-1733.
Skorski, T. et al., Suppression of Philadelphia$_1$ leukemia cell growth in mice by BCR-ABL antisense oligodeoxynucleotides, *Proc. Natl. Acad. Sci. USA* (1994) 91:4504-4508.

* cited by examiner

*Primary Examiner* — Jane Zara
(74) *Attorney, Agent, or Firm* — Fenwick & West LLP

(57) ABSTRACT

The present invention relates to a double-stranded ribonucleic acid (dsRNA) having a nucleotide sequence which is substantially identical to at least a part of a target gene and which is no more than 49, preferably less than 25, nucleotides in length, and which comprises a complementary (antisense) RNA strand having a 1 to 4 nucleotide overhang at the 3'-end and a blunt 5'-end. The invention further relates to a pharmaceutical composition comprising the dsRNA and a pharmaceutically acceptable carrier. The pharmaceutical compositions are useful for inhibiting the expression of a target gene, as well as for treating diseases caused by expression of the target gene, at low dosages (i.e., less than 5 milligrams, preferably less than 25 micrograms, per kg body weight per day). The invention also relates to methods for inhibiting the expression of a target gene, as well as methods for treating diseases caused by the expression of the gene.

18 Claims, 20 Drawing Sheets

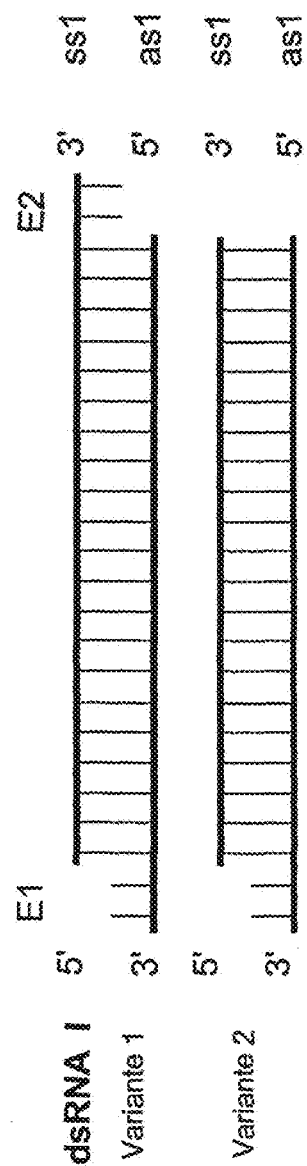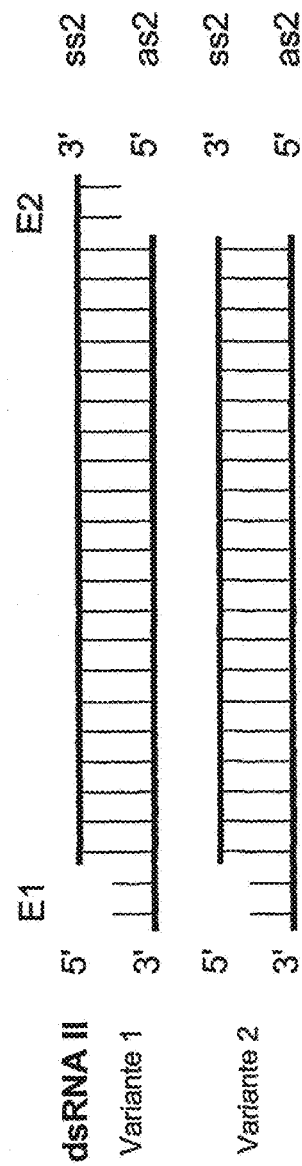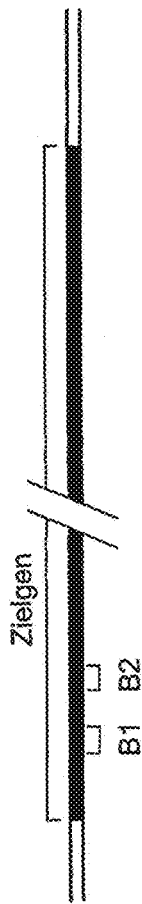

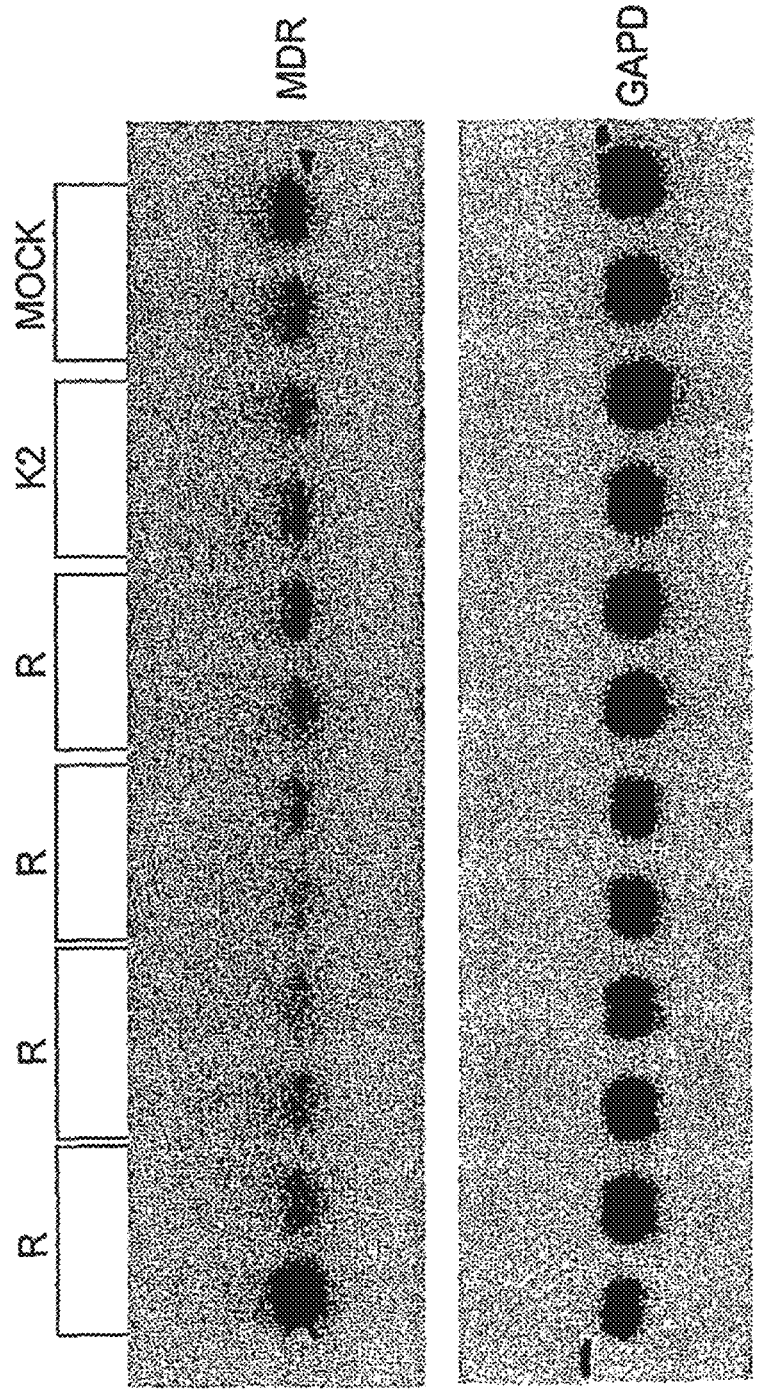

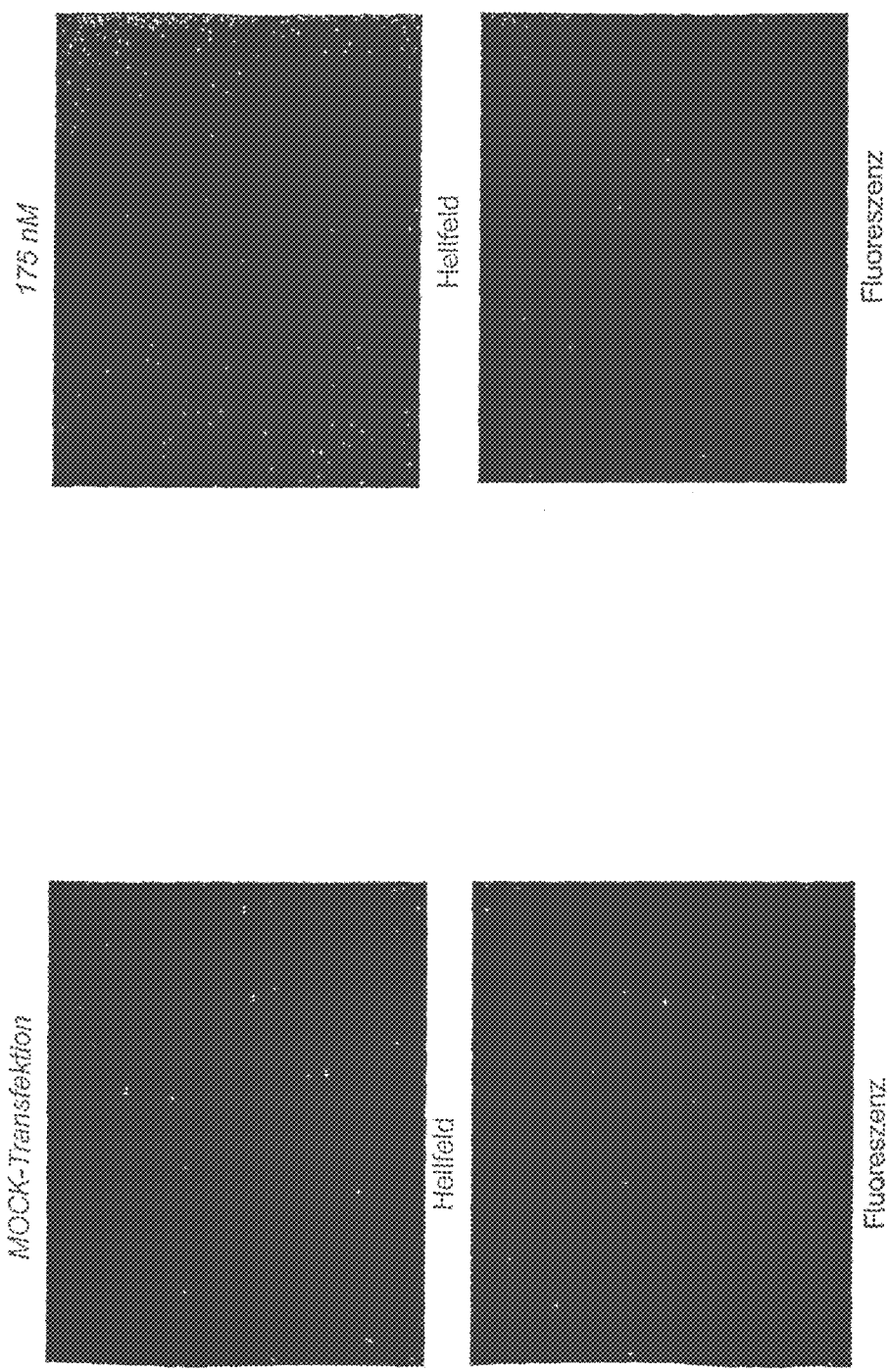

US 8,546,143 B2

COMPOSITIONS AND METHODS FOR INHIBITING EXPRESSION OF A TARGET GENE

RELATED APPLICATIONS

This application is a continuation of U.S. application Ser. No. 10/384,339, filed on Mar. 7, 2003, which is a continuation-in-part of International Application No. PCT/EP02/00152 (WO02/55693), which designated the United States and was filed on Jan. 9, 2002, which claims the benefit of German Patent No. 101 00 586.5, filed on Jan. 9, 2001, German patent No. 101 55 280.7, filed on Oct. 26, 2001, German Patent No. 101 58 411.3, filed Nov. 29, 2001, and German Patent No. 101 60 151.4, filed Dec. 7, 2001. The entire teachings of the above application(s) are incorporated herein by reference for all purposes.

FIELD OF THE INVENTION

This invention relates to double-stranded ribonucleic acid (dsRNA), and its use in mediating RNA interference in vitro and in vivo.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. The therapeutic benefits of being able to selectively silence these abnormal or foreign genes are obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and 1. Gibson, *Blood* (1998) 91:371). However, both of these agents have inherent limitations. Antisense approaches, using either single-stranded RNA or DNA, act in a 1:1 stoichiometric relationship and thus have low efficacy (Skorski et al., supra). For example, Jansen et al. report that, in a small percentage of patients, relatively high doses (2 mg/kg body weight per day) of antisense RNA resulted in biologically significant levels (i.e., long-term plasma concentrations above 1 mg/L) of encoded protein (Jansen, B., et al., *The Lancet* (2000) 356: 1728-1733). However, no detectable level of plasma protein was observed at lower dosages (e.g., 0.6 mg). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). Briefly, the RNAse III Dicer enzyme processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.) and *Drosophila* (see, e.g., Yang, D., et al., *Curr. Biol.* (2000) 10:1191-1200). Despite successes in these organisms, until recently the general perception in the art has been that RNAi cannot be made to work in mammals. It was believed that protocols used for invertebrate and plant systems would not be effective in mammals due to the interferon response, which leads to an overall block to translation and the onset of apoptosis (see, e.g., Wianny, F., et al., *Nature Cell Biol.* (2000) 2:70-75); Fire, A., *Trends Genet.* (1999) 15:358-363; and Tuschl, T., et al., *Genes Dev.* (1999) 13(24):3191-97). At least one group of scientists believed that RNAi could only be made to work in mammals if the PKR response could be neutralized or some way avoided, although no suggestions were given as to how this might be achieved (Fire, *Trends Genet.* (1999), supra; and Montgomery and Fire, *Trends Genet.* (1998) 14:255-258). However, WO 00/44895 (Limmer) demonstrated for the first time that dsRNA can induce RNAi in mammalian cells, provided that the dsRNA meets certain structural requirements, including a defined length limitation.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target gene at a low dose, would be highly desirable. Compositions comprising such agents would be useful for treating diseases caused by abnormal expression or activity of a gene.

SUMMARY OF THE INVENTION

The present invention discloses double-stranded ribonucleic acid (dsRNA), as well as compositions and methods for inhibiting the expression of a target gene in a cell using the dsRNA. The present invention also discloses compositions and methods for treating diseases caused by the expression or activity of the target gene. The dsRNA of the invention, which is no more than 49 nucleotides in length, comprises an RNA strand (complementary RNA strand) having a region which is complementary to an RNA transcript of at least a part of a target gene. The 3-'end of the complementary RNA strand comprises a nucleotide overhang of 1 to 4 nucleotides; the 5'-end of the complementary RNA strand is blunt.

In one aspect, the invention relates to a double-stranded ribonucleic acid (dsRNA), which is no more than 49 nucleotides in length, comprises a sense RNA strand and a complementary RNA strand. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be an oncogene, a cytokine gene, an idiotype protein gene, a prion gene, a gene that encodes a protein that induces angiogenesis, a gene that encodes an adhesion protein, a gene that encodes a cell surface receptor, a gene that encodes a protein involved in a metastasizing and/or invasive process, a gene that encodes a proteinase, a gene that encodes a protein that regulates apoptosis, a gene that encodes a EGF receptor, a MDR1 gene, a gene of a human papilloma virus, a hepatitis C virus, or a human immunodeficiency virus. In one embodiment, the target gene comprises a sequence of SEQ ID NO:1-140.

In another aspect, the invention relates to a method of inhibiting the expression of a target gene in a cell. The method comprises introducing a double-stranded ribonucleic acid (dsRNA) into the cell, and maintaining the cell for a time sufficient to obtain degradation of the mRNA transcript of the target gene, thereby inhibiting expression of the target gene. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be any gene whose expression is to be inhibited, such as the target genes described above.

In yet another aspect, the invention relates to a pharmaceutical composition for inhibiting the expression of a target gene in a mammal. The pharmaceutical composition comprises a dsRNA, as described above, and a pharmaceutically acceptable carrier. The dosage unit of dsRNA may be in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression is to be inhibited, such as the target genes described above. The pharmaceutically acceptable carrier may be an aqueous solution, such as phosphate buffered saline, and may comprise a micellar structure, such as a liposome, capsid, capsoid, polymeric nanocapsule, or polymeric microcapsule. The pharmaceutical composition may be formulated to be administered by inhalation, infusion, injection, or orally, preferably by intravenous or intraperitoneal injection.

In another aspect, the invention relates to a method for treating a disease caused by the expression of a target gene in a mammal. The method comprises administering a pharmaceutical composition, as described above, comprising a double-stranded ribonucleic acid (dsRNA) and a pharmaceutically acceptable carrier. The dosage unit of dsRNA maybe in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilo-gram body weight of the mammal. The target gene may be any gene whose expression causes a disease in an organism, such as the target genes described elsewhere herein.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1 is a diagram of a first dsRNA (A) and a second dsRNA (B).

FIG. 2 is a diagram of a target gene.

FIG. 27 shows a comparison of a transmitted light- and fluorescence microscopic imaging of a transfection with 175 nM dsRNA (Sequence R1 in Table 4).

DETAILED DESCRIPTION OF THE INVENTION

Figure 3:
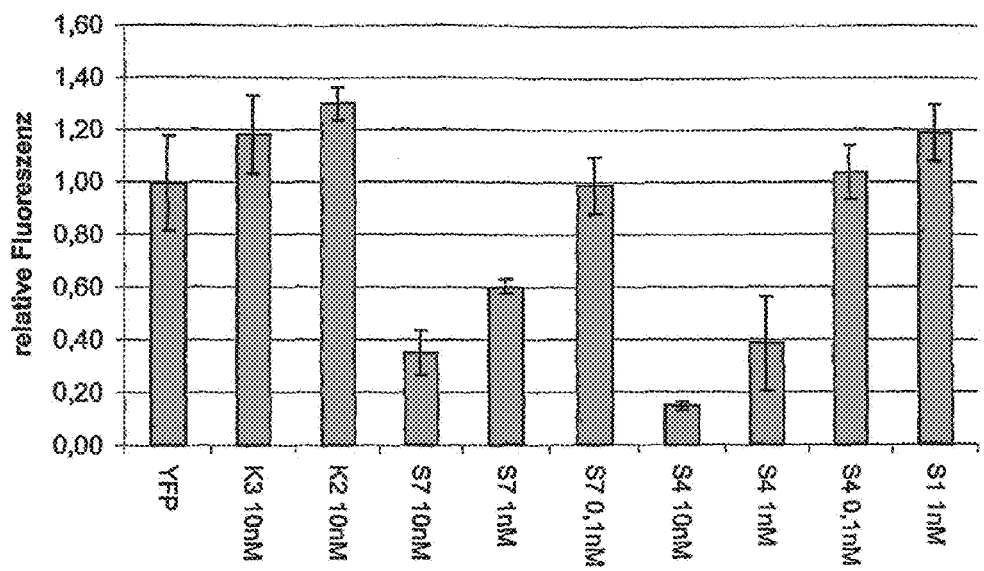
FIG. 3 relative YFP fluorescence after application of various dsRNAs in NIH/3T3 cells (first experiment).
Figure 4:
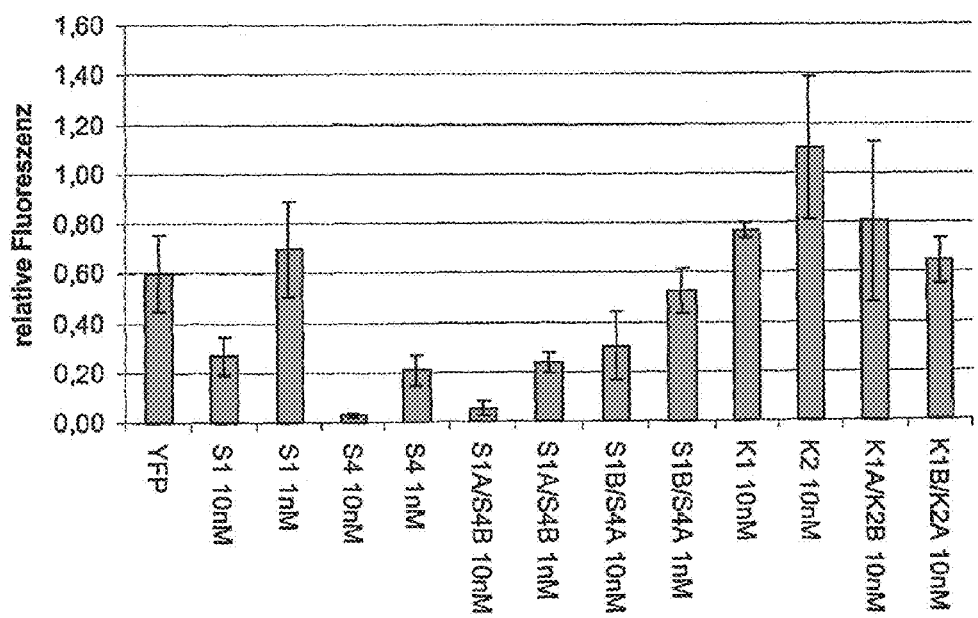
FIG. 4 relative YFP fluorescence after application of various dsRNAs in NIH/3T3 cells (second experiment).
Figure 5:
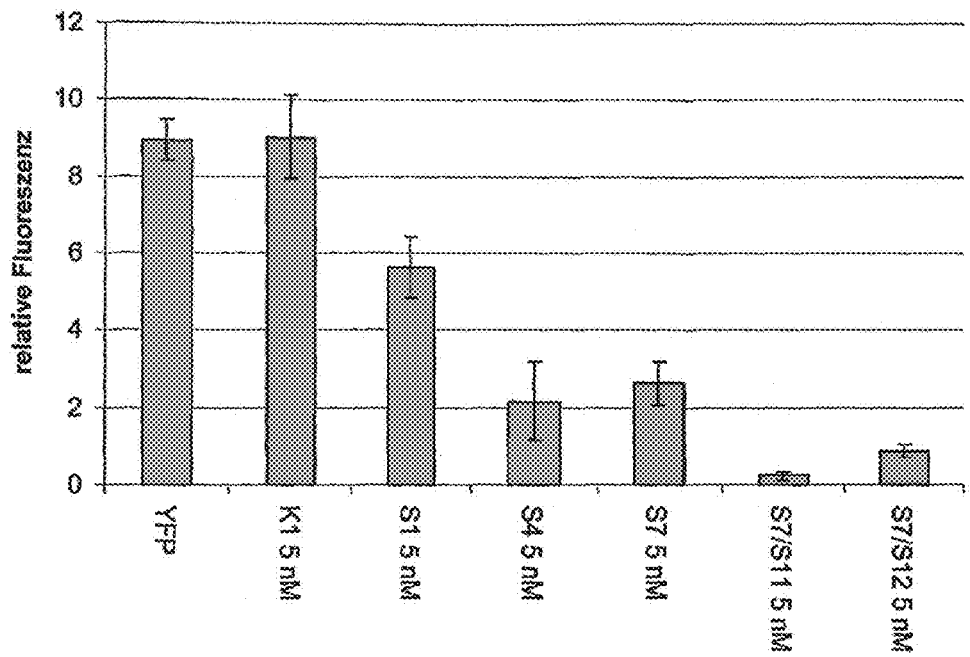
FIG. 5 relative YFP fluorescence after application of various dsRNAs in NIH/3T3 cells (third experiment).
Figure 6:
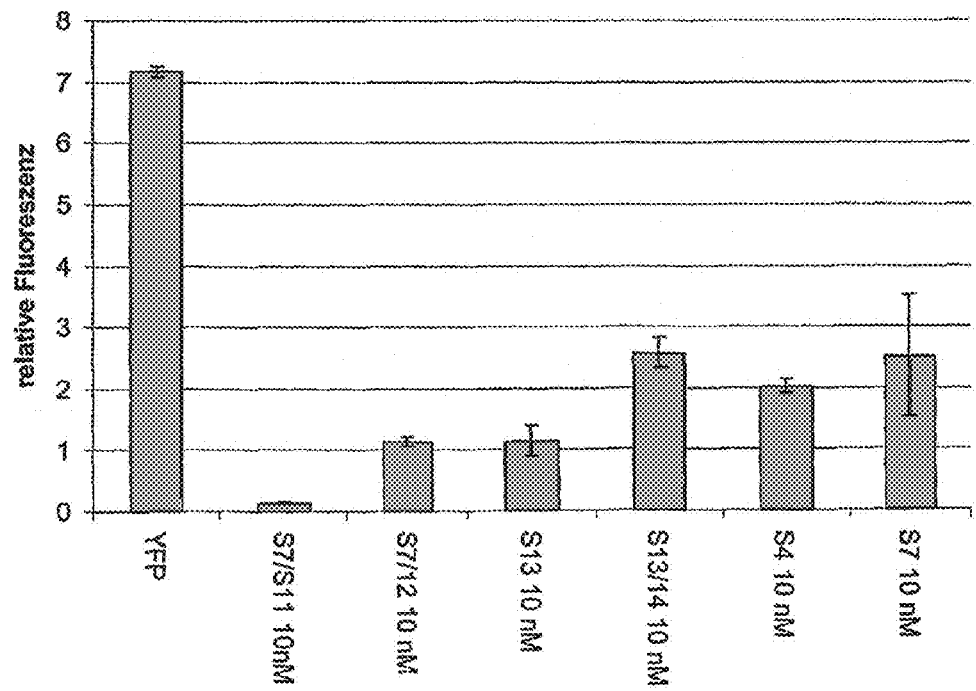
FIG. 6 relative YFP fluorescence after application of various dsRNAs in NIH/3T3 cells (fourth experiment).
Figure 7:
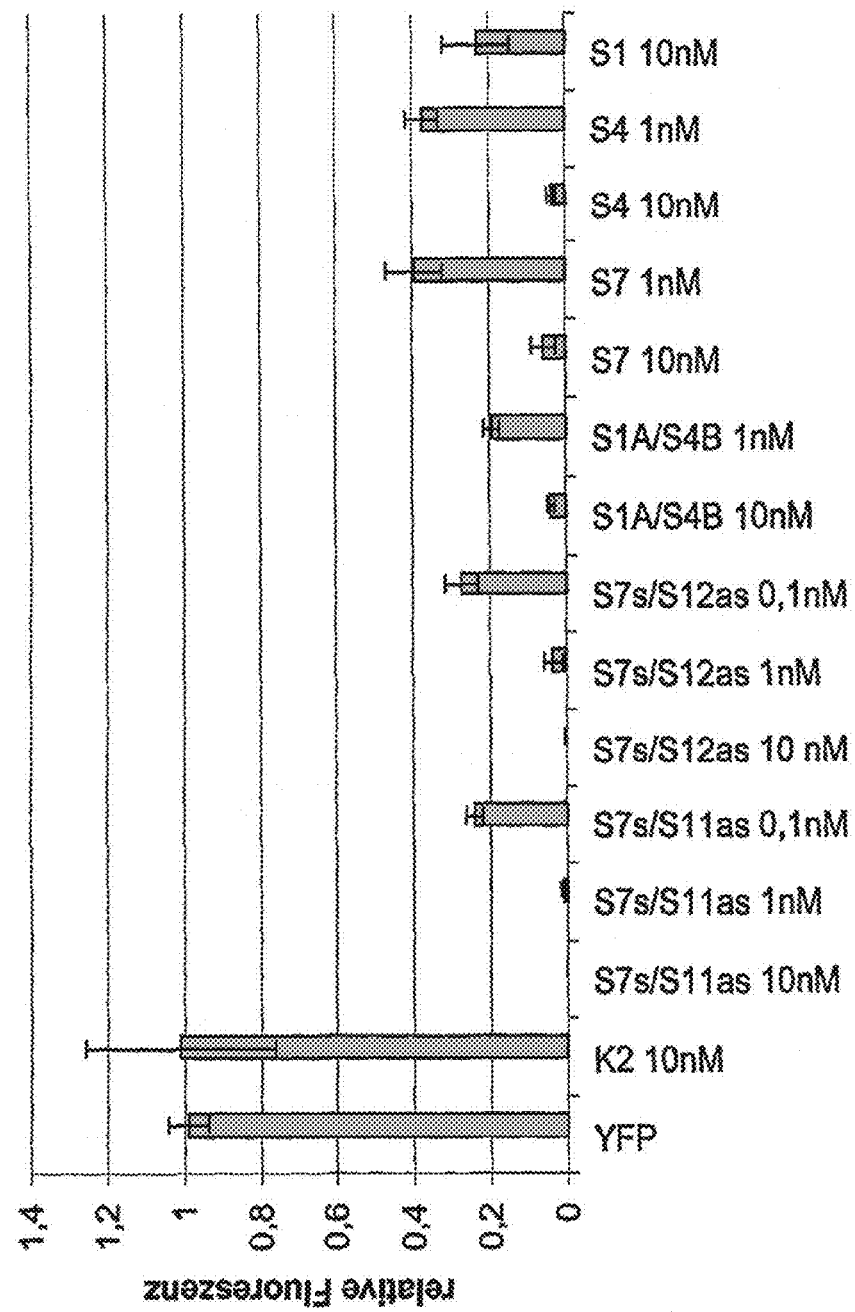
FIG. 7 relative YFP fluorescence after application of various dsRNAs in NIH/3T3 cells (fifth experiment).
Figure 8:
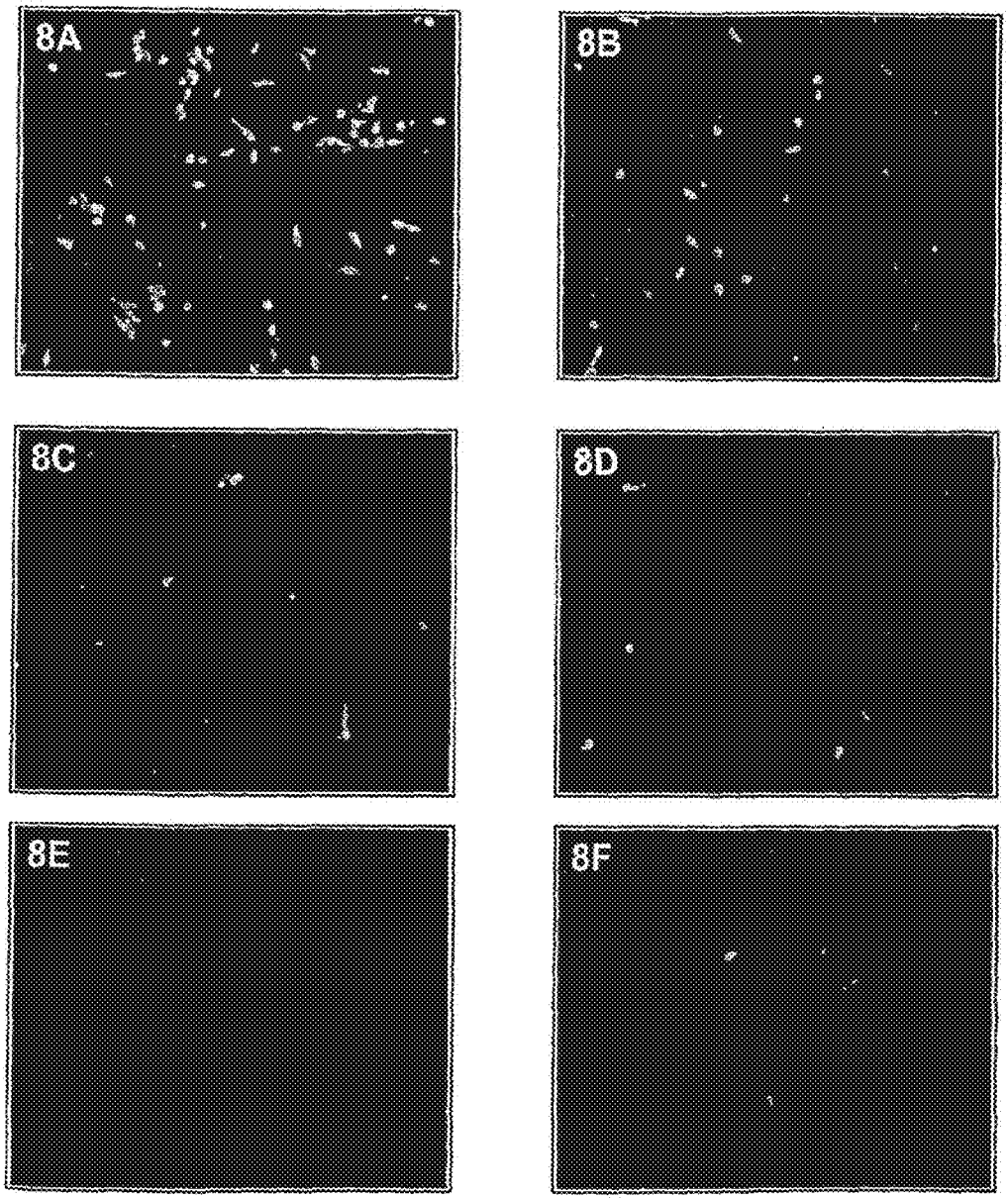
FIG. 8 fluorescence microscopic imaging of NIH/3T3 cells after transfection with pcDNA-YFP or after cotransfection with pcDNA-YFP and various dsRNAs.
Figure 9:
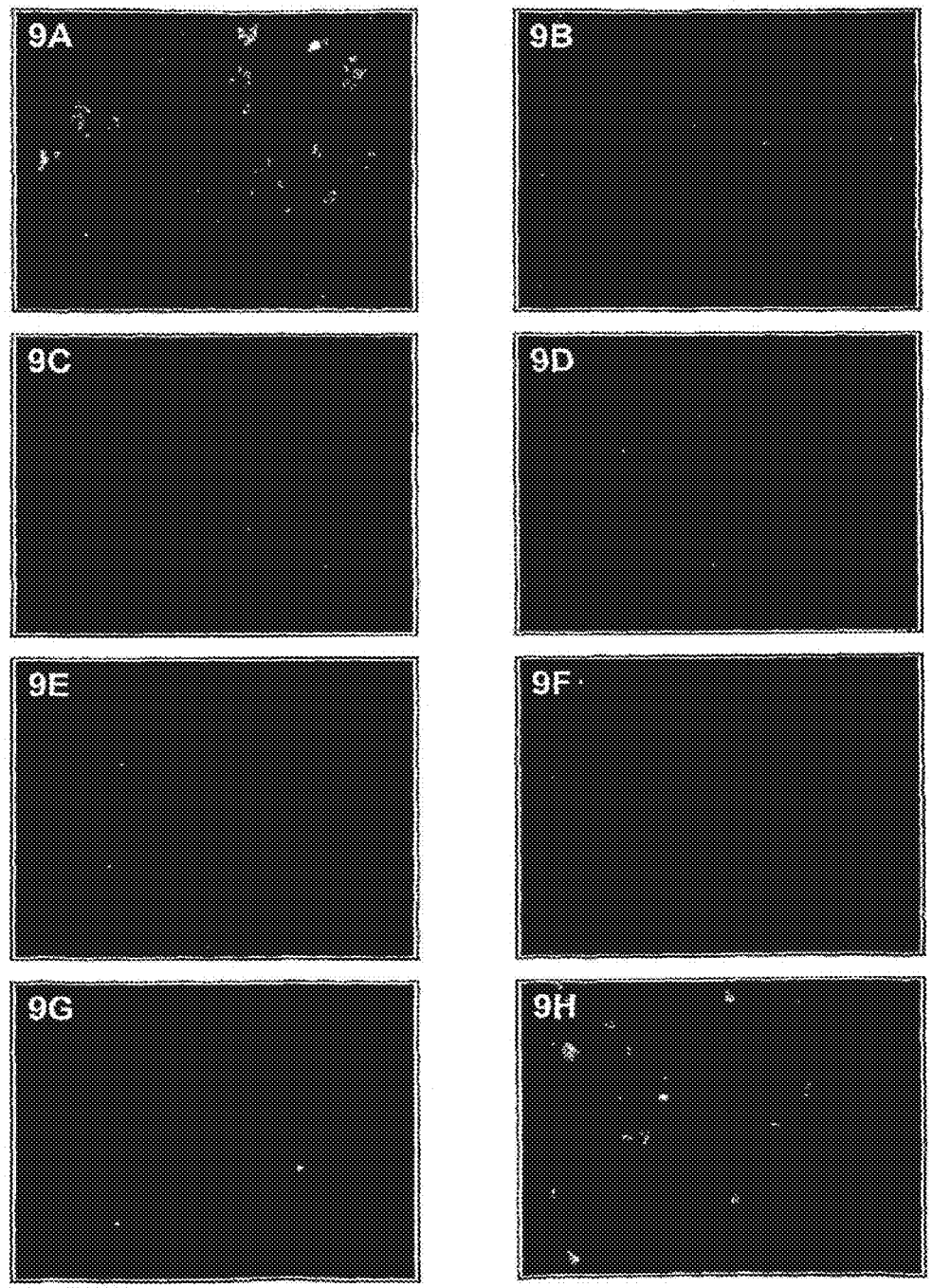
FIG. 9 fluorescence microscopic imaging of HeLa-S3 cells after transfection with pcDNA-YFP or after cotransfection with pcDNA-YFP and various dsRNAs.
Figure 10:
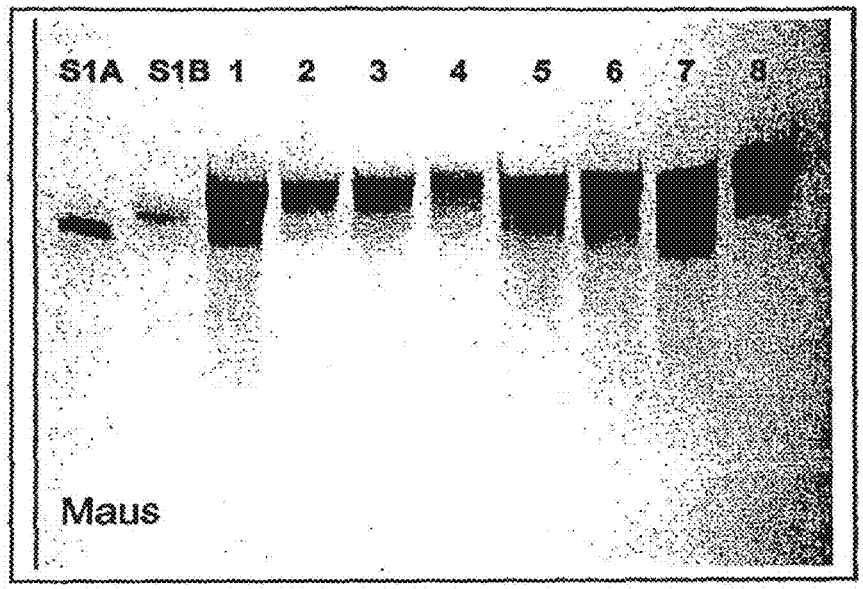
FIG. 10 is a gel electrophoretic separation of S 1 after incubation in mouse serum.
Figure 11:
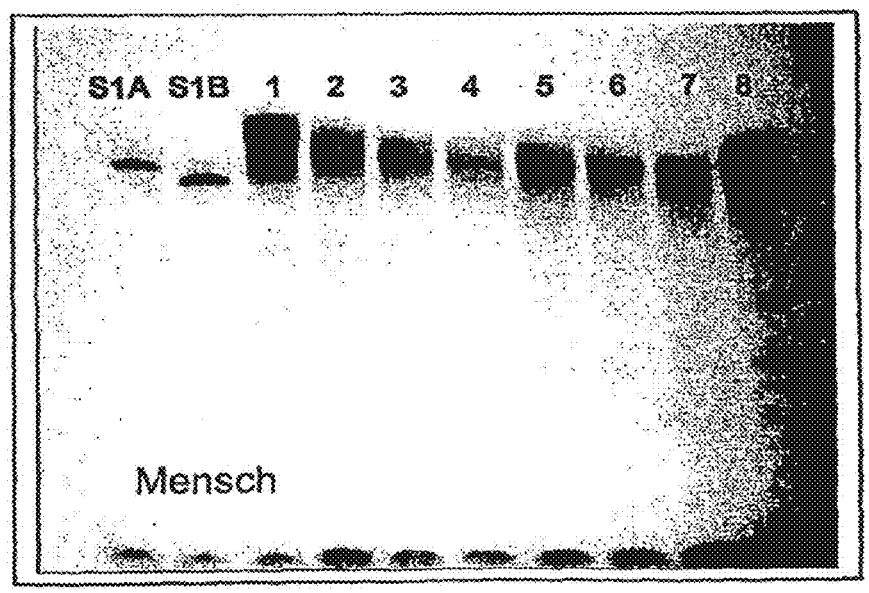
FIG. 11 is a gel electrophoretic separation of S 1 after incubation in human serum.
Figure 12:
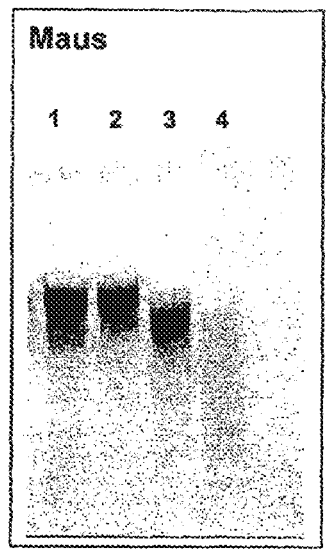
FIG. 12 is a gel electrophoretic separation of S7 after incubation in mouse serum.
Figure 13:
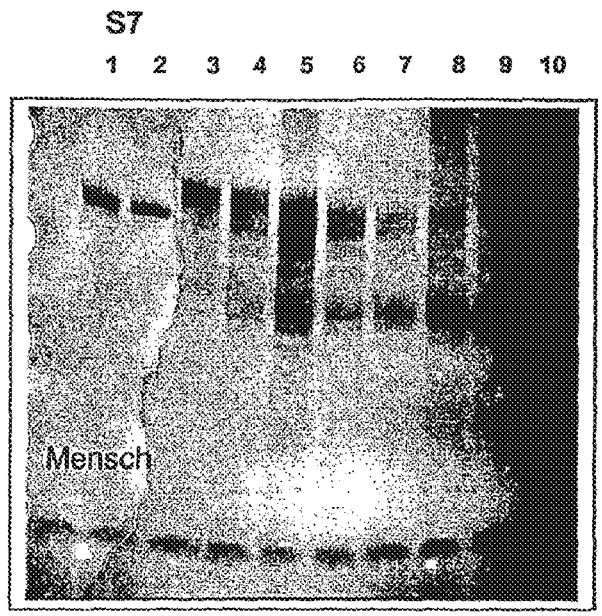
FIG. 13 is a gel electrophoretic separation of S7 after incubation in human serum.
Figure 14:
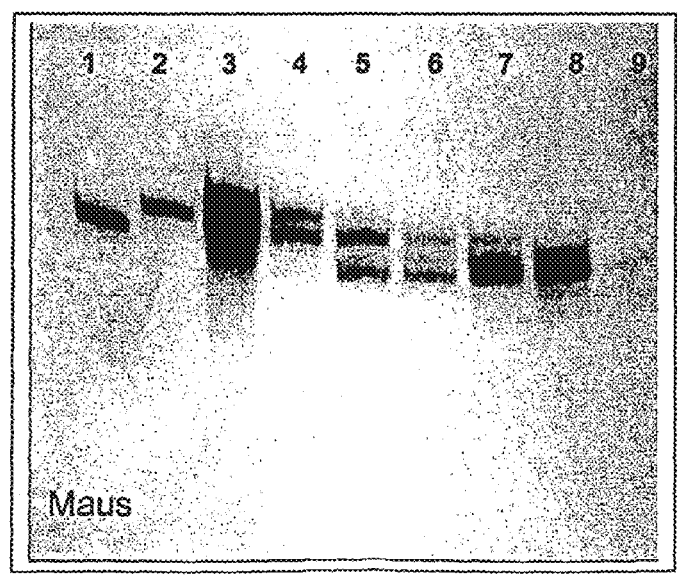
FIG. 14 is a gel electrophoretic separation of K3 after incubation in mouse serum.
Figure 15:
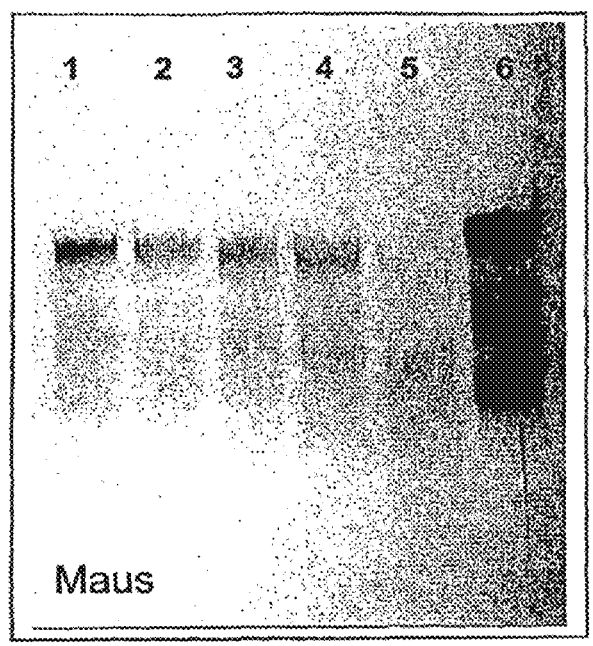
FIG. 15 is a gel electrophoretic separation of PKCl12 after incubation in mouse serum.
Figure 16:
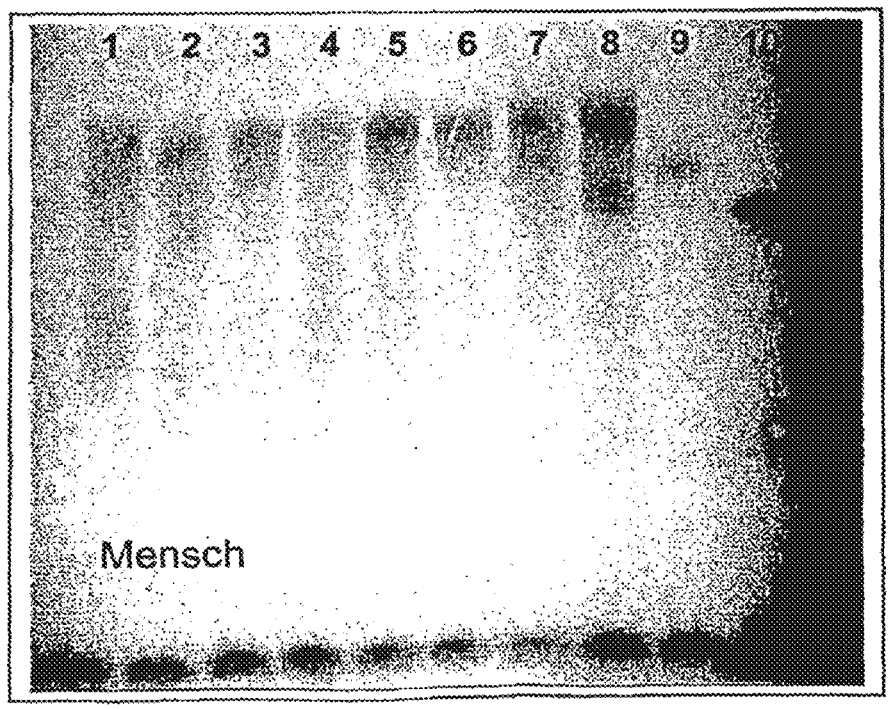
FIG. 16 is a gel electrophoretic separation of S1A/S4B after incubation in human serum.
Figure 17:
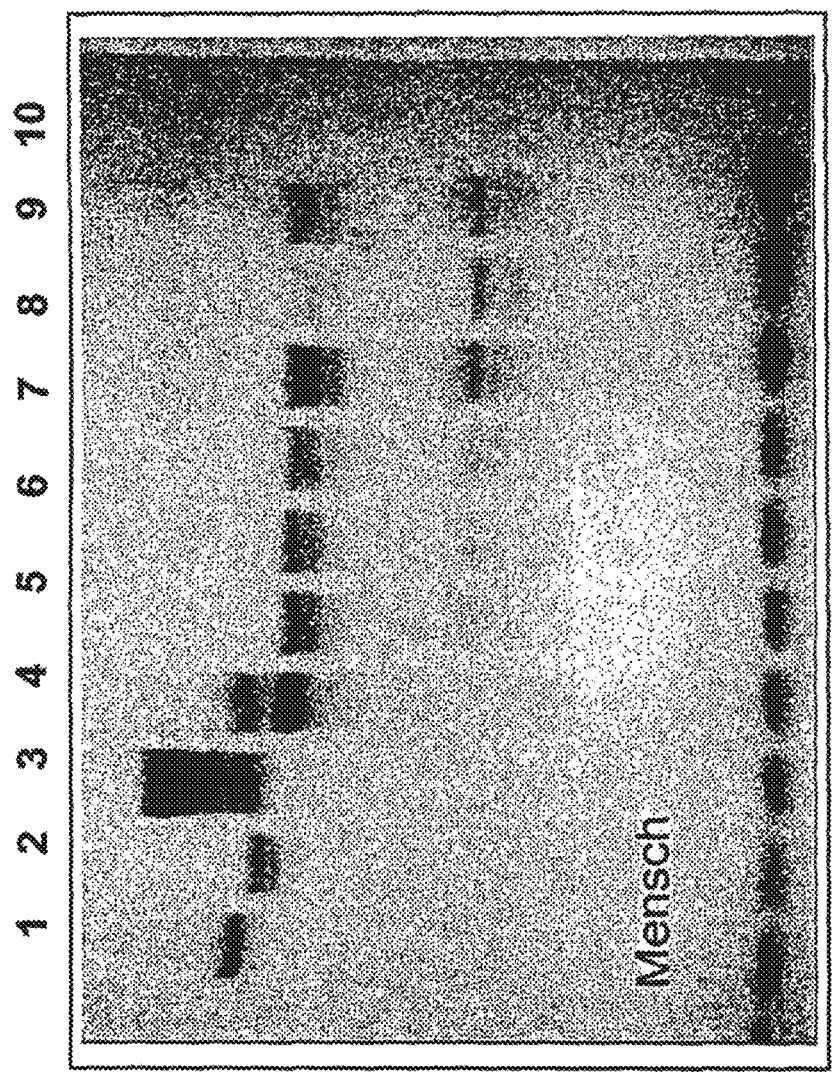
FIG. 17 is a gel electrophoretic separation of K2 after incubation in human serum.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by expression of a target gene using dsRNA. dsRNA directs the sequence-specific degradation of mRNA through a process known as RNA interference (RNAi). The process occurs in a wide variety of organisms, including mammals and other vertebrates. The dsRNA of the invention is no more than 49 nucleotides in length, and comprises an RNA strand (complementary RNA strand) having a region that is complementary to an RNA transcript of at least a portion of a target gene. The complementary RNA strand has a nucleotide overhang of 1 to 4 nucleotides at the 3'-end; the 5'-end is blunt. Using transgenic mice, the present inventors have demonstrated that very low dosages of these dsRNA can specifically and efficiently mediate RNAi, resulting in significant inhibition of expression of the target gene. The present invention encompasses these dsRNAs and compositions comprising dsRNA and their use for specifically inactivating gene function. The use of these dsRNAs enables the targeted degradation of mRNAs of genes that are implicated in a wide variety of disease processes, including cellular proliferative disorders, hematopoietic disorders, immune disorders, and certain infectious diseases. Thus, the methods and compositions of the present invention comprising these dsRNAs are useful for treating diseases and disorders caused by the expression or activity of a particular gene.

The following detailed description discloses how to make and use the dsRNA and compositions containing dsRNA to inhibit the expression of a target gene, as well as compositions and methods for treating diseases and disorders caused by the expression of the gene. The pharmaceutical compositions of the present invention comprise a dsRNA having a nucleotide sequence of no more than 49 nucleotides in length, preferably less than 25 nucleotides in length, and which is substantially identical to at least a part of the target gene, together with a pharmaceutically acceptable carrier. The dsRNA has a single-stranded nucleotide overhang of 1 to 4 nucleotides at the 3'-end of the complementary RNA strand; the 5'-end is blunt.

Accordingly, certain aspects of the present invention relate to pharmaceutical compositions comprising the dsRNA of the present invention together with a pharmaceutically acceptable carrier, methods of using the compositions to inhibit expression of a target gene, and methods of using the pharmaceutical compositions to treat diseases caused by the expression or activity of a particular gene.

I. DEFINITIONS

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a matrix for transcription, as well as a section of an RNA strand of a (+) strand RNA virus. A target gene, usually the sense strand, is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or *plasmodium*).

Examples of genes which can be targeted for treatment include, without limitation, an oncogene (Hanahan, D. and R. A. Weinberg, Cell (2000) 100:57; and Yokota, J., Carcinogenesis (2000) 21(3):497-503); a cytokine gene (Rubinstein, M., et al., Cytokine Growth Factor Rev. (1998) 9(2):175-81); a idiotype (1d) protein gene (Benezra, R., et al., Oncogene (2001) 20(58):8334-41; Norton, J. D., J Cell Sci. (2000) 113(22):3897-905); a prion gene (Prusiner, S. B., et al., Cell (1998) 93(3):337-48; Safar, J., and S. B. Prusiner, Prog. Brain Res. (1998) 117:421-34); a gene that expresses molecules that induce angiogenesis (Gould, V. E. and B. M. Wagner, Hum. Pathol. (2002) 33(11):1061-3); adhesion molecules (Chothia, C. and E. Y. Jones, Annu. Rev. Biochem. (1997) 66:823-62; Parise, L. V., et al., Semin. Cancer Biol. (2000) 10(6):407-14); cell surface receptors (Deller, M. C., and YE. Jones, Curr. Opin. Struct. Biol. (2000) 10(2):213-9); genes of proteins that are involved in metastasizing and/or invasive processes (Boyd, D., Cancer Metastasis Rev. (1996) 15(1):77-89; Yokota, J., Carcinogenesis (2000) 21(3):497-503); genes of proteases as well as of molecules that regulate apoptosis and the cell cycle (Matrisian, L. M., Curr. Biol. (1999) 9(20): R776-8; Krepela, E., Neoplasma (2001) 48(5):332-49; Basbaum and Werb, Curr. Opin. Cell Biol. (1996) 8:731-738; Birkedal-Hansen, et al., Crit. Rev. Oral Biol. Med. (1993) 4:197-250; Mignatti and Rifkin, Physiol. Rev. (1993) 73:161-195; Stetler-Stevenson, et al., Annu. Rev. Cell Biol. (1993) 9:541-573; Brinkerhoff, E., and L. M. Matrisan, Nature Reviews (2002) 3:207-214; Strasser, A., et al., Annu. Rev. Biochem. (2000) 69:217-45; Chao, D. T. and S. J. Korsmeyer, Annu. Rev. Immunol. (1998) 16:395-419; Mullauer, L., et al., Mutat. Res. (2001) 488(3):211-31; Fotedar, R., et al., Prog. Cell Cycle Res. (1996) 2:147-63; Reed, J. C., Am. J Pathol. (2000) 157(5):1415-30; D'Ari, R., Bioassays (2001) 23(7): 563-5); genes that express the EGF receptor; Mendelsohn, J. and J. Baselga, Oncogene (2000) 19(56):6550-65; Normanno, N., et al., Front. Biosci. (2001) 6:D685-707); and the multi-drug resistance 1 gene, MDR1 gene (Childs, S., and V. Ling, Imp. Adv. Oncol. (1994) 21-36).

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to an mRNA transcript of a portion of the target gene. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. The dsRNA is no more than 49, preferably less than 25, and most preferably between 19 and 23, nucleotides in length. dsRNAs of this length are particularly efficient in inhibiting the expression of the target gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J Applied Math*. (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, the terms "pathogen" and "pathogenic organism" refer to an organism capable of producing disease, including, without limitation, a virus, viroid, or plasmodium. As used herein, the term "pathogen" includes organisms capable of causing disease in animals and/or plants.

As used herein, a "transformed cell" is a cell into which a dsRNA molecule has been introduced by means of recombinant DNA techniques.

II. DOUBLE-STRANDED RIBONUCLEIC ACID (dsRNA)

In one embodiment, the invention relates to a double-stranded ribonucleic acid (dsRNA) having a nucleotide sequence which is substantially identical to at least a portion of a target gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA transcript of the target (DNA) gene or a gene of a (+) strand RNA virus. The dsRNA has no more than 49 nucleotides, preferably less than 25 nucleotides, and most preferably 23 nucleotides in length. The dsRNA can be synthesized by standard methods known in the art, e.g., by use of an automated DNA synthesizer, such as are commercially available from Biosearch, Applied Biosystems, Inc. In specific embodiments, the dsRNA can comprise the sequence set forth in SEQ ID NO:141-173, or a complement or equivalent thereof.

At least one end of the dsRNA has a single-stranded nucleotide overhang of 1 to 4, preferably 1 or 2 nucleotides. The single-stranded overhang is located at the 3'-terminal end of the complementary (antisense) RNA strand, and the 5'-end of the complementary RNA strand is blunt (i.e., no overhang). Such dsRNAs have improved stability and inhibitory activity, thus allowing administration at low dosages, i.e., less than 5 mg/kg body weight of the recipient per day. In another embodiment, one or more of the nucleotides in the overhang is replaced with a nucleoside thiophosphate. dsRNAs having a nucleotide overhang at the 3'-end of the antisense have unexpectedly superior inhibitory properties than their blunt-ended counterparts. Moreover, the present inventors have discovered that the presence of a nucleotide overhang at the 3'-overhang of the antisense strand strengthens the interference activity of the dsRNA, without affecting its overall stability. Such dsRNAs have proven particularly stable and effective in vivo, as well as in a variety of cells, cell culture mediums, blood, and serum.

In another embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexaethylene glycol linker. In this case, the dsRNAs are produced by solid phase synthesis and the hexa-ethylene glycol linker is incorporated according to standard methods (e.g., Williams, D. J., and K. B. Hall, *Biochem*. (1996) 35:14665-14670). In a preferred embodiment, the 5'-end of the complementary (antisense) RNA strand and the 3'-end of the second (sense) RNA strand are chemically linked via a hexa-ethylene glycol linker.

In yet another embodiment, the target gene is an oncogene; a cytokinin gene; an idiotype protein gene (Id protein gene); a prion gene; a gene that expresses a protein that induces angiogenesis, an adhesion molecule; a cell surface receptor; a gene of a protein involved in a metastasizing and/or invasive process; a gene of a proteinase; a gene of a protein that regulates apoptosis and the cell cycle; a gene that expresses the EGF receptor; or a MDR1 gene, all of which are described elsewhere herein.

In one embodiment, the target gene is the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J Natl. Cancer Inst*. (1989) 81:1683-1685) also may render MDR.

In yet another embodiment, the invention relates to a method for treating viral diseases, including but not limited to hepatitis C, hepatitis B, herpes simplex virus (HSY), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

III. PHARMACEUTICAL COMPOSITIONS COMPRISING dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of a target gene.

In another embodiment, the invention relates to a pharmaceutical composition comprising at least two dsRNAs, both designed to target the same gene, and a pharmaceutically acceptable carrier. Because of the duplicative targeting of mRNA by a plurality of dsRNAs, pharmaceutical compositions comprising multiple dsRNAs provide improved efficiency of inhibition as compared to compositions comprising a single dsRNA. In this embodiment, the individual dsRNAs are prepared as described in the preceding section, which is incorporated by reference herein. One dsRNA (referred to herein as "dsRNA I") has a nucleotide sequence ("complementary region I") which is substantially identical to at least a portion of the target gene (referred to herein as "region A" of the target gene). Additional dsRNAs are prepared, each of which has a nucleotide sequence that is substantially identical to a different region of the target gene. For example, a second dsRNA ("dsRNA II") may have a nucleotide sequence ("complementary region II") that is substantially identical to a "region B" of the target gene. Region A and region B, which reflect distinct regions of the same target gene, may overlap each other, be adjacent to one another, or be physically separated within the target gene. dsRNA I and dsRNA II may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to two dsRNAs (dsRNA I and dsRNA II) which target two regions (region A and region B) of the target gene, the present invention encompasses any number of dsRNAs, each of which targets a distinct region of the target gene.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y, *Int. J Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A W., et al, *J. Exp. Med.* (1988) 167(2):353-71; Zeng X X et al., *Blood.* (1988) 92(10):3529-36; Eriksson, B., et al., *Exp. Hematol.* (1999) 27(4):682-8; and Kovalchuk, A., et al., *J. Exp. Med.* (2000) 192(8):1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. METHODS FOR TREATING DISEASES CAUSED BY EXPRESSION OF A TARGET GENE

In one embodiment, the invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

Examples of genes which can be targeted for treatment include, without limitation, an oncogene; a cytokine gene; a idiotype (Id) protein; a prion gene; a gene that expresses molecules that induce angiogenesis; an adhesion molecule; a cell surface receptor; a gene of a protein involved in a metastasizing and/or invasive process; a gene of a proteases as or a protein that regulates apoptosis and the cell cycle; a gene that expresses the EGF receptor; and the multi-drug resistance 1 gene, MDR1 gene, all of which are described elsewhere herein.

In one embodiment, a pharmaceutical compositions comprising dsRNA is used to inhibit the expression of the multi-drug resistance 1 gene ("MDRI"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oneal.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J Natl. Cancer Inst.* (1989) 81:1683-1685) also may render MDR.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. METHODS FOR INHIBITING EXPRESSION OF A TARGET GENE

In yet another aspect, the invention relates to a method for inhibiting the expression of a target gene in an organism. The method comprises administering a composition of the invention to the organism such that expression of the target gene is silenced. The organism may be an animal or a plant. Because of their high specificity, the dsRNAs of the present invention specifically target RNAs (primary or processed) of target genes, and at surprisingly low dosages. Compositions and methods for inhibiting the expression of a target gene using dsRNAs can be performed as described elsewhere herein.

In one embodiment, the invention comprises administering a composition comprising a dsRNA, wherein the dsRNA comprises a nucleotide sequence which is complementary to at least a part of an RNA transcript of the target gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any gene one wishes to silence, thereby specifically inhibiting its expression. Examples of human genes which can be targeted for silencing include, without limitation, an oncogene; cytokinin gene; idiotype protein gene (Id protein gene); prion gene; gene that expresses molecules that induce angiogenesis, adhesion molecules, and cell surface receptors; genes of proteins that are involved in metastasizing and/or invasive processes; genes of proteases as well as of molecules that regulate apoptosis and the cell cycle; genes that express the EGF receptor; the multi-drug resistance 1 gene (MDRI gene); a gene or component of a virus, particularly a human pathogenic virus, that is expressed in pathogenic organisms, preferably in plasmodia.

The methods for inhibition the expression of a target gene can also be applied to any plant gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

RNA Interference in a Mouse Mode

In this Example, double stranded siRNAs are used to inhibit GFP gene expression in transgenic mice.
Synthesis and Preparation of dsRNAs Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 nM NaClO$_4$, pH 6.8, 10% acetonitrile; the high-salt buffer was: 20 mM Tris, 400 mM NaClO4, pH 6.S, 10% acetonitrile. flow rate: 3 ml/min). Formation of double stranded siRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours, In addition, dsRNA molecules with linkers may be produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

| Name | SEQ ID NO. | DsRNA sequence | Nucleotide number (overhang at the 3'-end of the S1 double-stranded region-overhang at the 3'-end of S2) |
|---|---|---|---|
| S1 | SEQ ID NO: 148 | (S2) 5'-CCACAUGAAGCAGCACGACUUC-3' | 0-22-0 |
|  | SEQ ID NO: 149 | (S1) 3'-GGUGUACUUCGUCGUGCUGAAG-5' |  |

-continued

| Name | SEQ ID NO. | DsRNA sequence | Nucleotide number (overhang at the 3'-end of the S1 double-stranded region-overhang at the 3'-end of S2) |
|---|---|---|---|
| S7 | SEQ ID NO: 150<br>SEQ ID NO: 151 | (S2) 5'-CCACAUGAAGCAGCACGACUU-3'<br>(S1) 3'-CUGGUGUACUUCGUCGUGCUG-5' | 2-19-2 |
| K1 | SEQ ID NO: 153<br>SEQ ID NO: 154 | (S2) 5'-ACAGGAUGAGGAUCGUUUCGCA-3'<br>(S1) 3'-UGUCCUACUCCUAGCAAAGCGU-5' | 0-22-0 |
| K3 | SEQ ID NO: 155<br>SEQ ID NO: 156 | (S2) 5'-GAUGAGGAUCGUUUCGCAUGA-3'<br>(S1) 3'-UCCUACUCCUAGCAAAGCGUA-5' | 2-19-2 |
| K4 | SEQ ID NO: 155<br>SEQ ID NO: 156 | (S2) 5'-GAUGAGGAUCGUUUCGCAUGA-3'<br>(S1) 3'-UCCUACUCCUAGCAAAGCGUACU-5' | 2-21-0 |
| S7/S11 | SEQ ID NO: 150<br>SEQ ID NO: 159 | (S2) 5'-CCACAUGAAGCAGCACGACUU-3'<br>(S1) 3'-CUGGUGUACUUCGUCGUGCUGAA-5' | 2-21-0 |

RNAi Administration

DsRNA are administered systemically either orally, by means of inhalation, infusion, or injection, preferably by intravenous or intraperitoneal infusion or injection in combination with pharmaceutically acceptable carriers. Examples of suitable carriers are found in standard pharmaceutical texts, e.g. "Remington's Pharmaceutical Sciences", 16th edition, Mack Publishing Company, Easton, Pa., 1980. A preparation that is suitable for inhalation, infusion, or injection preferably consists of dsRNA and a physiologically tolerated solvent, preferably a physiological saline solution or a physiologically tolerated buffer, preferably a phosphate buffered saline solution. The invention anticipates the use of a double-stranded ribonucleic acid in a dosage of a maximum of 5 mg/kg body weight per day.

GFP Laboratory Mice:

The transgenic laboratory mouse strain TgN (GFPU) 5Nagy (Jackson Laboratory, Bar Harbor, Me.), which expresses GFP in all cells studied to date (with the help of a beta actin promoter and a CMV intermediate early enhancer) (Hadjantonakis A K et al., 1998, Nature Genetics 19: 220-222), was used. The GFP transgenic mice may be clearly differentiated on the basis of fluorescence (using a UV lamp) from the corresponding wild types (WT). The following experiments were carried out using GFP-heterozygote animals that were bred by mating a WT animal each with a heterozygote GFP-type animal. The animals were kept under controlled conditions in groups of 3-5 animals in Type III Makrolon cages (Ehret Co., Emmendingen, Germany) at a constant temperature of 22° C. and a light-to-dark rhythm of 12 hours. Granulated softwood (8/15, Altromin Co., Lage, Germany) was strewn on the bottom of the cages. The animals received tap water and Altromin 1324 pelleted standard feed (Altromin Co.) ad libitum.

In Vivo Experiment:

Heterozygote GFP animals were placed in cages as described above in groups of 3. DsRNA solution was injected intravenously (i.v.) into the caudal vein in 12-hour rotation (between 5:30 and 7:00 and between 17:30 and 19:00) over 5 days. Injection volume was 60 μl per 10 g body weight, and dosage was 2.5 mg dsRNA or 50 μg per kg body weight. The groups were organized as follows:

Group A: PBS (phosphate buffered saline) 60 μl per 10 g body weight each,

Group B: 2.5 mg per kg body weight of a non-specific control dsRNA (K1 control with smooth ends and a double-stranded region of 22 nucleotide pairs), Group C, 2.5 mg per kg body weight of another non-specific control dsRNA (K3 control with 2 nucleotide [nt] overhangs and both 3'-ends and a double-stranded region of 19 nucleotide pairs), Group D: 2.5 mg per kg body weight of dsRNA (directed specifically against GFP, henceforth designated as S1, with smooth ends and a double-stranded region of 22 nucleotide pairs), Group E: 2.5 mg dsRNA per kg body weight (directed specifically against GFP, henceforth designated as S7, with 2 nt overhangs and the 3'-ends of both strands, and a double-stranded region of 19 nucleotide pairs), Group F: 50 μg S1 dsRNA per kg body weight (in other words 1/50 the dosage of Group D).

After the last injection of a series of 10 injections, the animals were sacrificed after 14-20 hours, and the organs and blood were removed as described below.

Organ Removal:

Immediately after the animals were killed by C02 inhalation, the blood and various organs were removed (thymus, lungs, heart, spleen, stomach, intestines, pancreas, brain, kidneys, and liver). The organs were quickly rinsed in cold sterile PBS and dissected with a sterile scalpel. A portion was fixed for 24 hours for immunohistochemical staining in methyl Carnoy (MC, 60% methanol, 30% chloroform, 10% glacial acetic acid); another portion was immediately flash-frozen in liquid nitrogen for freeze sections and protein isolation, and stored at −80° C.; and another smaller portion was frozen for RNA isolation at −80° C. in RNAeasy Protect (QIAGEN GmbH, Max Volmer Str. 4, 40724 Hilden). Immediately after removal, the blood was kept on ice for 30 minutes, mixed, centrifuged for 5 minutes at 2000 rpm (Mini Spin, Eppendorf A G, Barkhausenweg 1, 22331, Hamburg, Germany), and the supernatant fluid was drawn off and stored at −80° C. (designated here as plasma).

Processing the Biopsies:

After fixing the tissue for 24 hours in MC, the tissue pieces were dehydrated in an ascending alcohol series at room temperature: 40 minutes each 70% methanol, 80% methanol, 2×96% methanol and 3×100% isopropanol. After that the tissue was warmed up in 100% isopropanol at 60° C. in an incubator, after which it was incubated for 1 hour in an isopropanol/paraffin mixture at 60° C. and 3× for 2 hours in paraffin, and then embedded in paraffin. Tissue sections 3 µm in thickness were prepared for immunoperoxidase staining, using a rotation microtome (Leica Microsystems Nussloch GmbH, Heidelberger Str. 17-19, 69226 Nussloch, Germany), placed on microscopic slides (Superfrost, Vogel GmbH & Co. KG, Medical Technology and Electronics, Marburger Str. 81, 35396 Giessen, Germany), and incubated for 30 minutes at 60° C.

Immunoperoxidase Staining for GFP:

The sections were deparaffinized for 3×5 minutes in xylol, rehydrated in a descending alcohol series (3×3 min. 100% ethanol, 2×2 min. 95% ethanol), and then incubated for 20 minutes in 3% H202/methanol to block endogenous peroxidases. Next, all incubation steps were carried out in a moist chamber. After 3×3 min. washing with PBS, the sections were incubated with a first antibody (goat anti-GFP antibody, sc-5384, Santa Cruz Biotechnology, Inc., Berheimer Str. 89-2, 69115 Heidelberg, Germany) 1:500 in 1% BSA/PBS overnight at 4° C. The sections were then incubated with the biotinylated secondary antibody (donkey anti-goat IgG; Santa Cruz Biotechnology; 1:2000 dilution) for 30 minutes at room temperature, after which they were incubated for 30 minutes with Avidin D peroxidase (1:2000 dilution, Vector Laboratories, 30 Ingold Road, Burlingame, Calif. 94010). After each antibody incubation, the sections were washed in PBS for 3×3 min., and buffer residue was removed from the sections along with cell material. All antibodies were diluted with 1% bovine serum albumin (BSA)/PBS. The sections were stained with 3,3'-diamino benzidine (DAB) using the DAB Substrate Kit (Vector Laboratories) in accordance with the manufacturer's instructions. Gill's Hematoxylin III (Merck KgaA, Frankfurter Str. 250, 64293 Darmstadt) was used as the nuclear counterstain. After dehydration in an ascending alcohol series and 3×5 minutes xylol, the sections were covered with Entellan (Merck). Microscopic evaluation of the stains was accomplished using a IX50 microscope from OLYMPUS Optical Co. (Europe) GmbH, Wendenstr. 14-18 20097 Hamburg, Germany, fitted with a CCD camera (Hamamatsu Photonics K. K., Systems Division, 8012 Jokocho Hamamatsu City, 431-3196 Japan).

Protein Isolation from Tissue Pieces:

Frozen tissue samples were added to 800 µl isolation buffer (50 m HEPES, pH 7.5; 150 mM NaCl; 1 mM EDTA; 2.5 mM EGTA; 10% glycerol; 0.1% Tween; 1 mM DTT; 10 mM β-glycerol phosphate; 1 mM NaF; 0.1 mM Na3VO4 with a "complete" protease inhibitor tablet from Roche Diagnostics GmbH, Roche Applied Science, Sandhofer Str. 116, 68305 Mannheim), and homogenized for 2×30 seconds with an ultraturrax (DIAX 900, Dispersion Tool 6G, HEIDOLPH Instruments GmbH & Co. KG, Walpersdorfer Str. 12, 91126 Schwabach), and cooled on ice in between steps. After incubation for 30 minutes on ice, the homogenate was mixed and centrifuged for 20 minutes at 10,000 g, 4° C. (3K30, SIGMA Laboratory Centrifuge GmbH, An der Unteren Söse 50,37507 Osterode am Harz). The supernatant fluid was again incubated for 10 minutes on ice, mixed, and centrifuged for 20 minutes at 15,000 g, 4° C. Protein determination of the supernatant fluid was determined according to Bradford, 1976, modified according to Zor & Selinger, 1996, using the Roti-Nanoquant system (Carl Roth GmbH & Co., Schoemperlenstr. 1-5, 76185 Karlsruhe, Germany) in accordance with manufacturer's instructions. BSA was used for protein calibration in a concentration range of 10 to 100 µg/ml.

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS; 3.3 ml distilled water; 250 µl ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µM tris/HCl, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DTT (dithiotreithol), 0.02% bromophenol blue, 20% glycerin) was then added to the proteins, which were then denatured on a heat block at 100° C., centrifuged on ice after cooling off, and then applied to the gel. The same plasma and protein quantities were used in each lane (3 µl plasma or 25 µg total protein each). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Proteins separated by SDS-PAGE were transferred to a PVDF (polyvinyl difluoride) membrane (Hybond-P, Amersham Biosciences Europe GmbH, Munzinger Str. 9, 79111 Freiburg, Germany) using the semidry transfer method according to Kyhse-Anderson (J. Biochem. Biophys. Methods 10: 203-210, 1984) at room temperature and constant amperage of 0.8 mA/cm2 for 1.5 hours in Tris/Glycerin transfer buffer (39 mM glycerin, 46 mM tris, 0.1% SDS, and 20% methanol). After immunodetection both the gels and the blots, as well as the blot membranes, were stained with Coomassie (0.1% Coomassie G250, 45% methanol, 10% glacial acetic acid) in order to check for electrophoretic transfer. The blot membranes were incubated after transfer in 1% skim milk powder/PBS for 1 hour at room temperature to saturate nonspecific bonds. Next, each membrane was washed three times for 3 minutes with 0.1% Tween-20/PBS. All subsequent antibody incubations and wash steps were done in 0.1% Tween-20/PBS. The primary antibody (goat anti-GFP antibody, sc-5384, Santa Cruz Biotechnology) was incubated for one hour at room temperature at a dilution of 1:1000. After washing 3×5 minutes, the membranes were incubated with a horseradish peroxidase coupled secondary antibody (donkey anti-goat IgG, Santa Cruz Biotechnology), at a dilution of 1:10,000. Detection of horseradish peroxidase was then achieved using the ECL system (Amersham) in accordance with the manufacturer's instructions.

Figure 18:
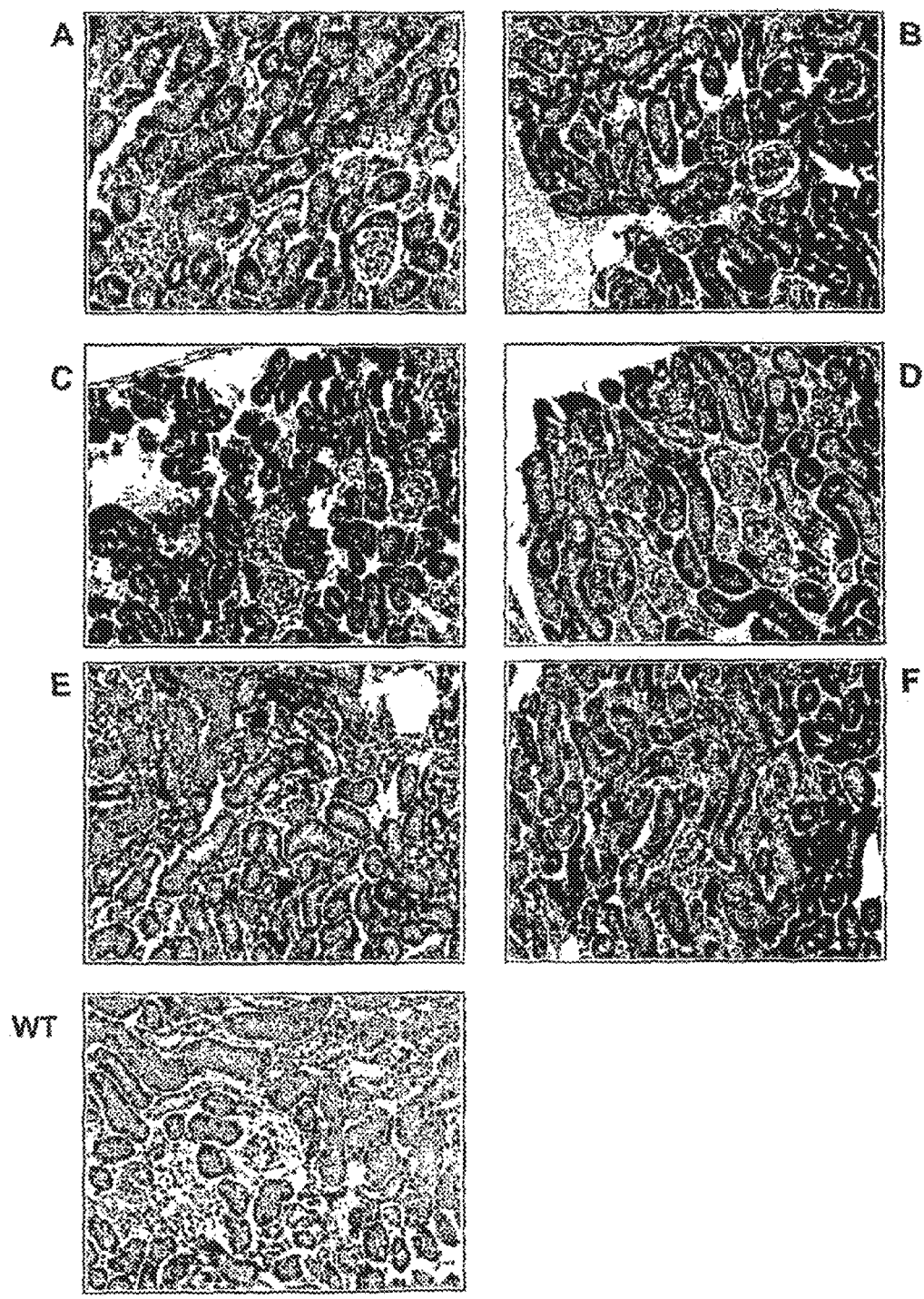
FIG. 18 is a GFP-specific immunoperoxidase staining of kidney paraffin sections from transgenic GFP mice.
Figure 19:
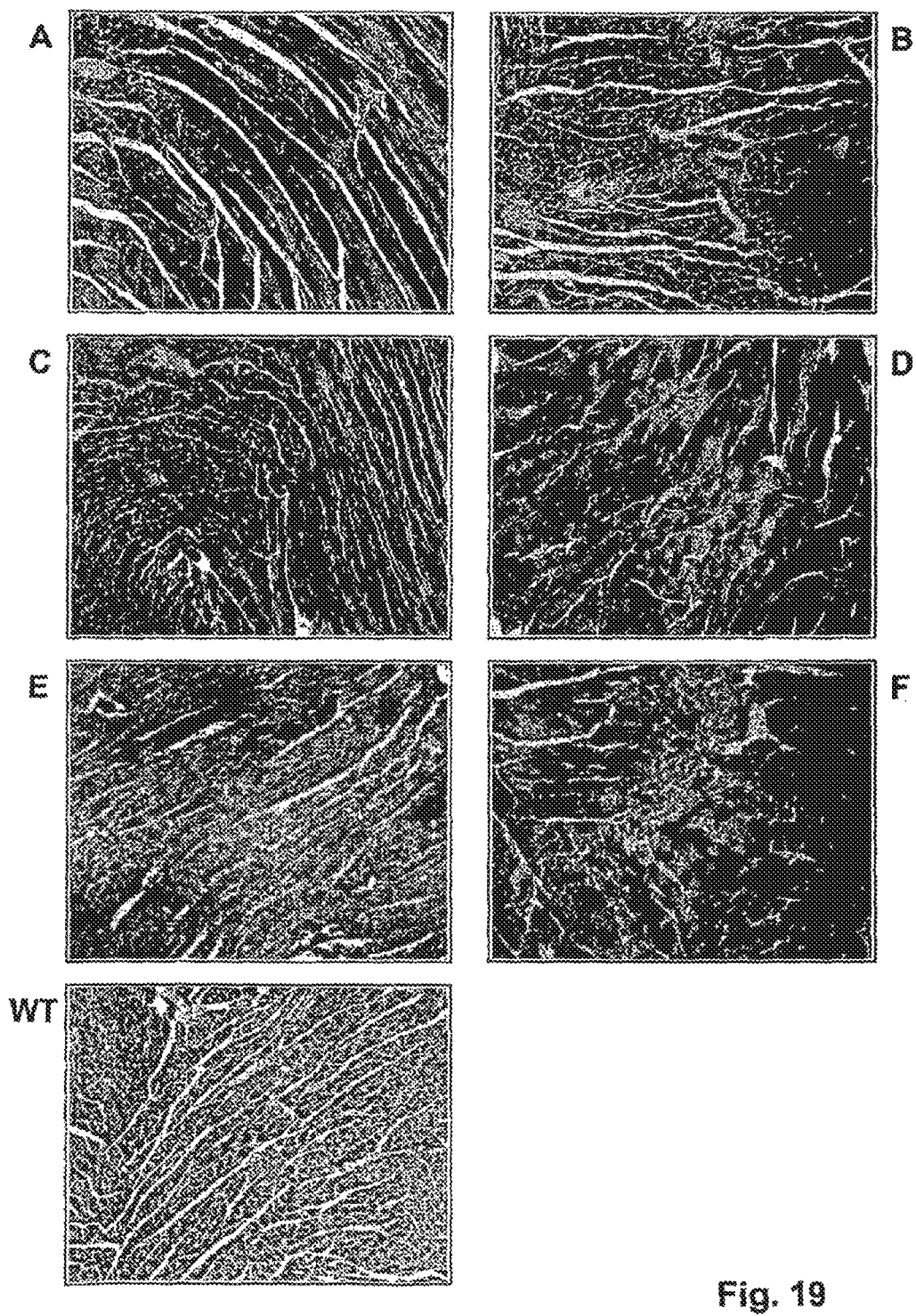
FIG. 19 is a GFP-specific immunoperoxidase staining of heart paraffin sections from transgenic GFP mice.
Figure 20:
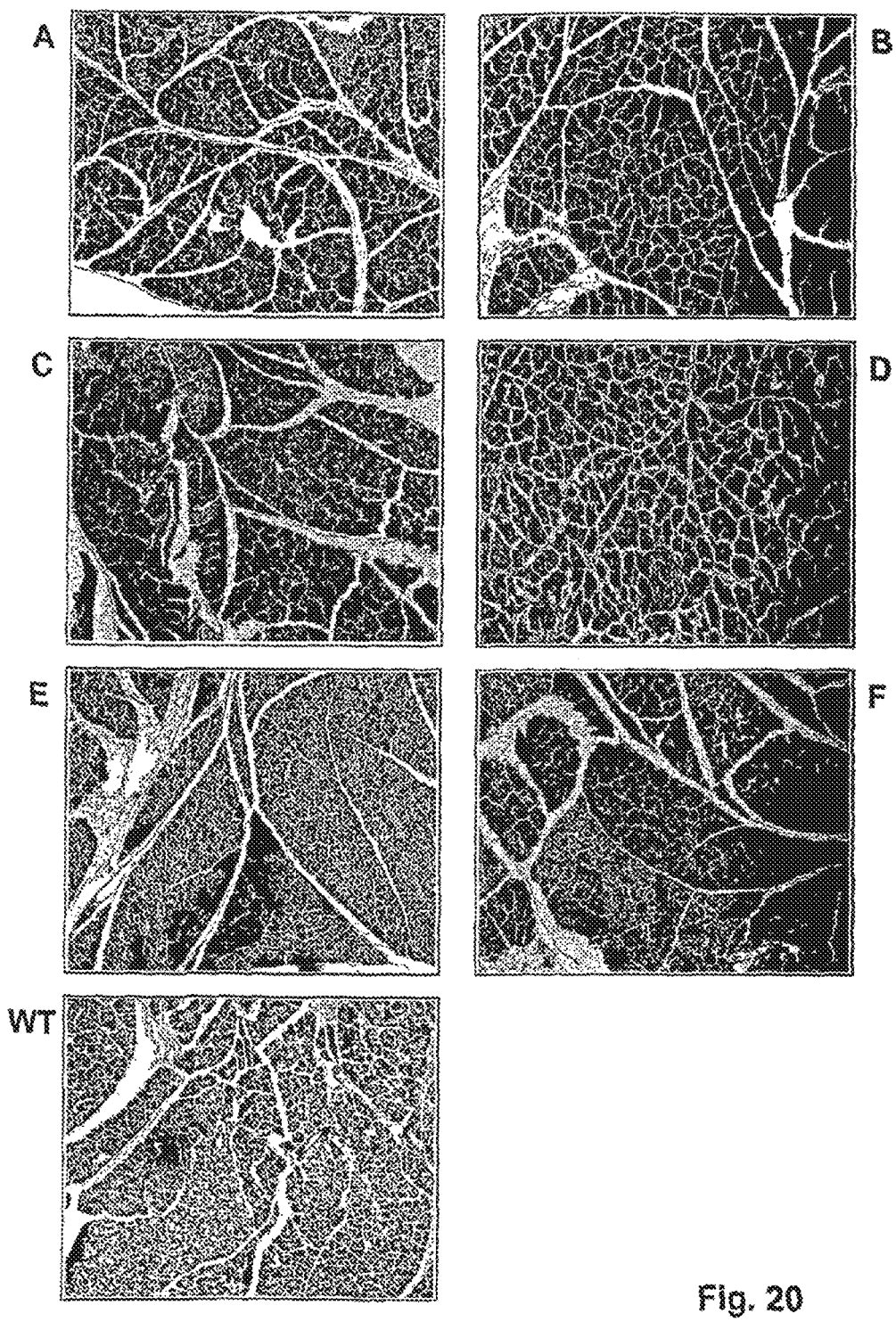
FIG. 20 is a GFP-specific immunoperoxidase staining of pancreas paraffin sections from transgenic GFP mice.
Figure 21:
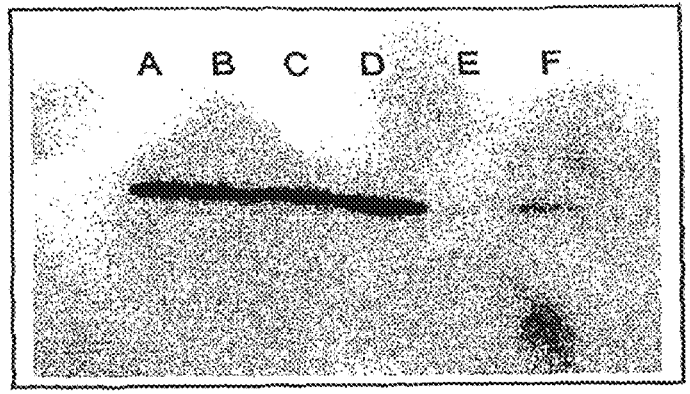
FIG. 21 is a Western blot analysis of GFP expression in plasma.
Figure 22:
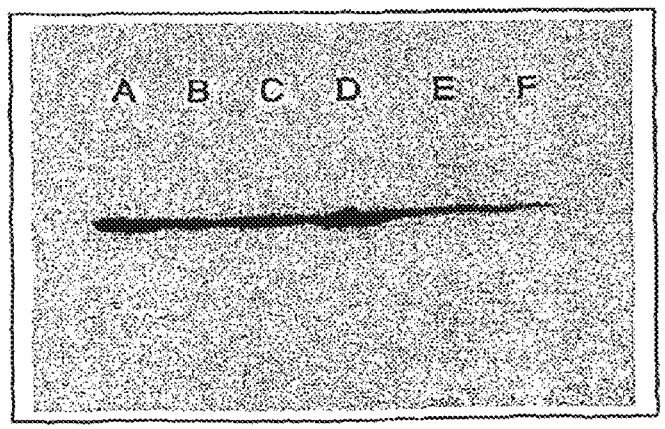
FIG. 22 is a Western blot analysis of GFP expression in kidney.
Figure 23:
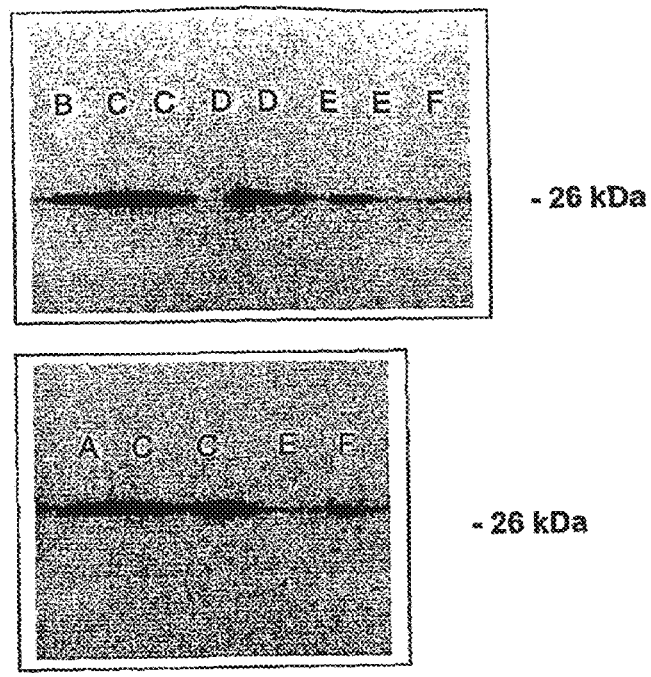
FIG. 23 is a Western blot analysis of GFP expression in heart.

FIGS. 18 to 20 show inhibition of GFP expression after intravenous injection of specific anti-GFP dsRNA, by means of immunoperoxidase GFP staining of 3 µm paraffin sections. Over the course of the experiment, the anti-GFP dsRNA, with a double-stranded region of 22 nucleotide (nt) pairs without overhangs at the 3'-ends (D) and the corresponding non-specific control dsRNA (B), as well as the specific anti-GFP dsRNA, with a double-stranded region consisting of 19 nucleotide pairs with 2 nt overhangs at the 3'-ends (E), and the corresponding non-specific control dsRNA (C) were applied in 12-hour rotation over 5 days. (F) received 1/50 the dosage of Group (D). Animals not administered dsRNA (A) and WT animals were used as further controls. FIG. 18 shows the inhibition of GFP expression in kidney sections; FIG. 19 in heart sections; and FIG. 20 in pancreas tissue. FIGS. 21 to 23 show Western blot analyses of GFP expression in plasma and tissues. FIG. 21 shows the inhibition of GFP expression in plasma; FIG. 22 in kidney; and FIG. 23 in heart. FIG. 23 shows the total protein isolate from various animals. The same quantities of total protein were used for each track. In the animals that were given non-specific control dsRNA (animals in Groups B and C), GFP is not reduced in comparison with animals that received no dsRNA. Animals that received the specific anti-GFP dsRNA with 2 nt overhangs at the 3'-ends of both strands and a double-stranded region consisting of 19 nucleotide pairs showed significantly inhibited GFP expression in the tissues studied (heart, kidneys, pancreas, and blood), compared with untreated animals (FIGS. 18-23). Of the animals in Groups D and F, who were given specific anti-GFP dsRNA, with blunt ends and a double-stranded region consisting of 22 nucleotide pairs, only those animals that received the dsRNA at a dosage of 50 µg/kg body weight per day demonstrated specific inhibition of GFP expression. However, the degree of inhibition was less marked than that seen with the animals in Group E.

A summary evaluation of GFP expression in tissue sections and Western blot shows that the inhibition of GFP expression is greatest in blood and in kidneys (FIGS. 18, 21 and 22).

Example 2

Inhibition of EGFR Gene Expression with Effort-Specific siRNA

The epidermal growth factor (=EGF) receptor (=EGFR) belongs to the tyrosine kinase receptors, transmembrane proteins with an intrinsic tyrosin kinase activity that are involved in the control of a series of cellular processes such as cell growth, cell differentiation, migratory processes, and cell vitality (reviewed in: Van der Geer et al., 1994). The EGFR family consists of 4 members, EGFR (ErbB1), HER2 (ErbB2), HER3 (ErbB3), and HER4 (ErbB4) with a transmembrane domain, a cysteine-rich extracellular domain, and a catalytic intracellular domain. The EGFR sequence, a 170-kDa protein, was first described by Ullrich et al., 1984.

EGFR is activated by peptide growth factors such as EGF, TGFα (transforming growth factor), amphiregulin, betacellulin, HB-EGF (heparin binding EGF-like growth factor), and neuregulins. Ligand binding induces the formation of homodimers or heterodimers with subsequent autophosphorylation of cytoplasmic tyrosine (Ullrich & Schlessinger, 1990; Alroy & Yarden, 1997). The phosphorylated amino acids form the binding sites of numerous proteins that are involved in the initial steps of a complex signal transduction pathway. EGFR is involved in many cancers, and is therefore an appropriate target for therapeutic approaches (Huang & Harari, 1999). The mechanisms that lead to aberrant EGFR activity may be related to overexpression, amplification, constitutive activation of mutant receptor forms, or autocrine loops (Voldberg et al., 1997). Overexpression of EGFR has been described for a series of tumors such as breast cancer (Walker & Dearing, 1999), non-minor lung cancer (Fontaninii et al., 1998), pancreatic cancer, colon cancer (Salomon et al., 1995), and glioblastoma (Rieske et al., 1998). For malignant glioblastoma, in particular, there have to date been no effective and specific therapeutic agents.

Example 3

Efficacy of Inhibition of EGFR Gene Expression

To test the effectiveness of dsRNA for the specific inhibition of EGFR gene expression, U-87 MG cells (human glioblastoma cells), ECCAC (European Collection of Animal Cell Culture) No. 89081402 were transfected with the specific anti-EGF-receptor-directed dsRNA (SEQ ID NO:51). After approximately 72 hours of incubation, the cells were harvested, the protein was isolated, and EGFR expression was analyzed by Western blot.

Test Protocol:
Synthesis and Preparation of dsRNAs

Oligoribonucleotides were synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM tris, 10 mM $NaClO_4$, pH 6.8, 10% acetonitrile; flow rate: 3 ml/min). Formation of double stranded siRNAs was then achieved by heating a stoichiometric mixture of the individual complementary strands (10 M) to 95° C. for 5 minutes in 25 mM Tris-HCl, pH 7.5, and 100 mM NaCl, followed by subsequent cooling for 6 hours to room temperature dsRNA molecules with linkers were produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) was coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite was comparable to the incorporation of nucleoside phosphoramidites.

Seeding the Cells:

All cells were cultured under sterile conditions at an appropriate workstation (HS18/Hera Safe, Kendro, Heraeus). U-87 MG cells were incubated in a $CO_2$-incubator (T20, Hera Cell, Kendro, Heraeus) at 37° C., 5% $CO_2$ and saturated atmospheric humidity in DMEM (Dulbecco's modified eagle medium, Biochrom) with 10% FCS (fetal calf serum, Biochrom), 2 mM L-glutamine (Biochromone) mM sodium pyruvate (Biochrom), 1×NEAA (nonessential amino acids, Biochrom), and penicillin/streptomycin (100 IU/100 µg/ml, Biochrom). In order to maintain the cells in an exponential growth state, the cells were passaged every 3 days. 24 hours before dsRNA application by means of transfection, the cells were trypsinized (10× trypsin/EDTA, Biochrom, Germany) and placed in a 6-well plate (6-well plates, Schubert & Weiss Laboratories, GmbH) in 1.5 µl growth medium.

DsRNA Application in Cultured U-87 MG Cells:

Cells were transfected with dsRNA using the OLIGOFECTAMINE™ reagent (Life Technologies) in accordance with the manufacturer's instructions. Total transfection volume was 1 ml. First, the dsRNA was diluted in serum-free medium: 0.5 µl of a 20 µM stock solution of specific anti-EGFR directed dsRNA and 9.5 µl of a 20 µM stock solution of nonspecific dsRNA (K1A/K2B) diluted with 175 µl serum-free medium (200 nM dsRNA in the transfection incubate or 10 nM specific EGFR-dsRNA) per well. The OLIGOFECTAMINE™ reagent was also diluted in serum-free medium: 3 µl with 12 µl medium per well and then incubated for 10 minutes at room temperature. Then the diluted OLIGOFECTAMINE™ reagent was added to the medium of diluted dsRNA, mixed, and incubated for a further 20 minutes at room temperature. The medium was changed during incubation. The cells were washed 1× with 1 ml serum-free medium and further incubated with 800 µl serum-free medium until the dsRNA/OLIGOFECTAMINE™ reagent was added. After the addition of 200 μl dsRNA/OLIGO-FECTAMINE™ reagent per well, the cells incubated up until protein isolation.

Protein Isolation:

Approximately 72 hours after transfection, the cells were harvested and total protein was isolated. The medium was removed, and the cell monolayer was washed once with PBS. After the addition of 200 μl protein isolation buffer (1× "Complete" protease inhibitor, Roche, 50 mM HEPES, pH 7.5, 150 mM NaCl, 1 mM EDTA, 2.5 mM EGTA, 10% glycerin, 0.1% Tween-20, 1 mM DTT, 10 mM β-glycerine phosphate, 1 mM NaF, 0.1 mM $Na_3 VO_4$) the cells were removed with the help of a cell scraper, incubated for 10 minutes on ice, transferred to an Eppendorf reagent vessel, and stored at −80° C. for at least 30 minutes. After thawing, the lysate was homogenized at the third setting for 10 seconds with a disperser (DIAX 900, 6G disperser, Heidolph Instruments GmbH, Schwabach), incubated on ice for 10 minutes, and then centrifuged for 15 minutes at 14,000×g at 4° C. (3K30, Sigma). Quantitation of total protein in the supernatant was determined according to Bradford using the Roti-Nanoquant system from Roth (Roth GmbH, Karlsruhe) in accordance with the manufacturer's instructions. 200 μl protein solution at a suitable dilution is mixed with 800 μl 1× working solution, and extinction was measured in semi-microcuvettes at 450 nm and 590 nm against distilled water in a Beckman spectrophotometer (DU 250). BSA dilutions were used for calibration (beaded BSA, Sigma).

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 μl 10% SDS; 3.3 ml distilled water; 250 μl ammonium persulfate (10%); 9 μl TEMED (N,N,N',N'-tetramethylendiamine), and covered over with 0.1% SDS until polymerization occurred. A collection gel was then poured on: 0.83 μl acrylamide/bisacrylamide (30%, 0.9%), 630 μl 1 M tris/Hel, pH 6.8; 3.4 ml distilled water; 50 μl 10% SDS; 50 μl 10% ammonium persulfate; 5 μl TEMED.

A corresponding quantity of 4× sample buffer (200 mM Tris, pH 6.8, 4% SDS, 100 mM DIT (dithiotreithol), 0.02% bromophenol blue, 20% glycerin) was then added to the proteins, which were then denatured on a heat block at 100° C., centrifuged on ice after cooling off, and then applied to the gel (35 μg total protein/lane). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Transfer of the proteins from SDS-PAGE to a PVDF (polyvinyl difluoride) membrane (Hybond-P, Amersham) was done using a semidry method according to Kyhse-Anderson (J. Biochem. Biophys. Methods 10:203-210, 1984) at room temperature and a constant 0.8 $mA/cm^2$ for 1.5 hours. A cathode buffer (30 mM Tris, 40 mM glycine, 10% methanol, and 0.1% SDS, pH 9.4), anode buffer I (300 mM Tris, pH 10.4, 10% methanol), and anode buffer II (30 mM Tris, pH 10.4, 10% methanol) were used as the transfer buffers. Before assembling the blot stack with 3MM Whatman paper (Schleicher & Schüll) the gel was incubated in cathode buffer, and the PVDF membrane (previously for 30 seconds in 100% methanol) in anode buffer II (5 minutes): 2 layers of 3MM paper (anode buffer I), 1 layer 3MM paper (anode buffer II), PVDF membrane, gel, 3 layers 3MM paper (cathode buffer). To analyze electrophoretic transfer, both the post-blot gels and the blot membranes were stained after immunodetection using Coomassie (0.1% Coomassie G250, 45% methanol, 10% glacial acetic acid).

After transfer, the blot membrane was incubated in 1% skim milk powder/PBS/0.1% Tween-20 for one hour at room temperature. After that, the membrane was washed three times for 3 minutes with 0.1% Tween-20/PBS. All subsequent antibody incubations and washings were done using 0.1% Tween-20/PBS. The primary antibody (human EGFR extracellular domain, specific goat IgG, Catalogue No. AF231, R&D Systems) was incubated with shaking for two hours at room temperature at a concentration of 1.5 μg/ml. After washing 3×5 minutes, the membrane was incubated for one hour at room temperature with the secondary antibody (labeled donkey anti-goat IgG horseradish peroxidase, Santa Cruz Biotechnology) at a dilution of 1:10,000. After washing (3×3 minutes in PBS/0.1% Tween-20) horseradish peroxidase was detected by ECL reaction (enhanced chemoluminescence). To 18 ml of distilled water, 200 μl Solution A (250 mM luminol, Roth, dissolved in DMSO), 89 μl Solution B (90 mM pcoumaric acid, Sigma, dissolved in DMSO), and 2 ml 30% $H_2O_2$ solution were added. Depending on membrane size, 4-6 ml were pipetted directly onto the membrane, incubated for 1 minute at room temperature, and then placed immediately on X-Ray film (Biomax MS, Kodak).

The sequences used here are depicted in Table 3 below, as well as in SEQ ID NOS:153, 157, 158, 168-173.

TABLE 3

| | | | | |
|---|---|---|---|---|
| ES-7 | SEQ ID NO: 168 | (A) | 5'-AACACCGCAGCAUGUCAAGAU-3' | 2-19-2 |
| | SEQ ID NO: 169 | (B) | 3'-UUUUGUGGCGUCGUACAGUUC-5' | |
| ES-8 | SEQ ID NO: 170 | (A) | 5'-AAGUUAAAAUUCCCGUCGCUAU-3' | $2^5$-19-$2^5$ |
| | SEQ ID NO: 171 | (B) | 3'-CAAUUUUAAGGGCAGCGAUAGU-5' | |
| ES2A/ | SEQ ID NO: 172 | (A) | 5'-AGUGUGAUCCAAGCUGUCCCAA-3' | 0-22-0 |
| ES5B | SEQ ID NO: 173 | (B) | 3'-UUUCACACUAGGUUCGACAGGGUU-5' | |
| K2 | SEQ ID NO: 157 | (A) | 5'-ACAGGAUGAGGAUCGUUUCGCAUG-3' | 2-22-2 |
| | SEQ ID NO: 158 | (B) | 3'-UCUGUCCUACUCCUAGCAAAGCGU-5' | |
| K1A/ | SEQ ID NO: 153 | (A) | 5'-ACAGGAUGAGGAUCGUUUCGCA-3' | 0-22-2 |
| KWB | SEQ ID NO: 158 | (B) | 3'-UCUGUCCUACUCCUAGCAAAGCGU-5' | |

Example 4

Figure 24:
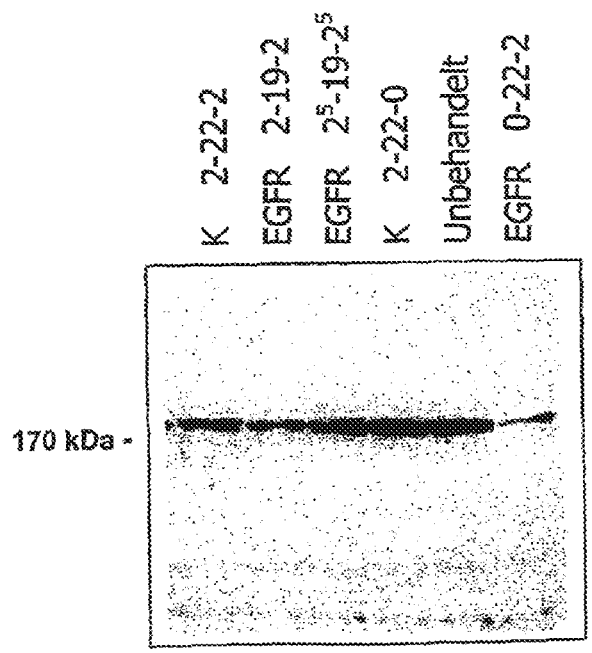
FIG. 24 is a Western blot analysis of EGFR expression in U-87 MG glioblastoma cells.

Inhibition of EGFR Expression in U-87 MG Glioblastoma Cells 24 hours after seeding the cells, U-87 MG glioblastoma cells were transfected with 10 nM dsRNA and oligofectamine. After 72 hours, the cells were harvested and total protein isolated and loaded on to a 7.5% SDS-PAGE gel. 35 µg total protein was applied to each lane. The corresponding Western blot analysis (see FIG. 24) shows that with the specific anti-EGFR-directed dsRNA with a 2 nt overhang at the 3'-end of the antisense strand, EGFR expression in U-87 MG cells is significantly inhibited in comparison to the corresponding controls. This inhibition of expression of an endogenous gene by means of specific dsRNA confirms the results noted in Example II. The inhibition of EGFR expression mediated by ES-7 and ES-8 is notably smaller. The dsRNAs used in FIG. 24 are shown in Table 3.

Example 5

Treatment of a Breast Cancer Patient with EGFR siRNA

In this Example, EGFR-specific double stranded siRNA is injected into a breast cancer patient and shown to specifically inhibit EGFR gene expression.

SiRNA Synthesis

EGFR-specific siRNAs directed against the fusion sequence of EGFR are chemically synthesized with or without a hexaethylene glycol linker as described above siRNA Administration and Dosage The present example provides for pharmaceutical compositions for the treatment of human breast cancer patients comprising a therapeutically effective amount of a EGFR-specific siRNA as disclosed herein, in combination with a pharmaceutically acceptable carrier or excipient. SiRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare siRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa., 1980.

The dosage of the siRNAs will vary depending on the form of administration. In the case of an injection, the therapeutically effective dose of siRNA per injection is in a dosage range of approximately 1-500 g/kg body weight, preferably 100 g/kg body weight. In addition to the active ingredient, the compositions usually also contain suitable buffers, for example phosphate buffer, to maintain an appropriate pH and sodium chloride, glucose or mannitol to make the solution isotonic. The administering physician will determine the daily dosage which will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The siRNAs of the present invention may be administered alone or with additional siRNA species or in combination with other pharmaceuticals.

RNA Purification and Analysis

Efficacy of the siRNA treatment is determined at defined intervals after the initiation of treatment using real time PCR or RNAse protection assays on total RNA extracted tissue biopsies. Cytoplasmic RNA from whole blood, taken prior to and during treatment, is purified with the help of the RNeasy Kit (Qiagen, Hilden) and Bcr-abl mRNA levels are quantitated by real time RT-PCR. Real-time Taqman-RT-PCR is performed as described previously (Eder M et al. Leukemia 1999; 13: 1383-1389; Scherr M et al. BioTechniques. 2001; 31: 520-526). Analysis by real time PCR at regular intervals, for example every 1-2 weeks, provides the attending physician with a rapid and accurate assessment of treatment efficacy as well as the opportunity to modify the treatment regimen in response to the patient's symptoms and disease progression.

Example 6

EGFR-Specific siRNA Expression Vectors

In another aspect of the invention, siRNA molecules that interact with target RNA molecules and modulate gene expression activity are expressed from transcription units inserted into DNA or RNA vectors (see for example Couture et A, 1996, TIG., 12, 5 1 0, Skillern et A, International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292).

The individual strands of a siRNA can be transcribed by promoters on two separate expression vectors and cotransfected into a target cell. Alternatively each individual strand of the siRNA can be transcribed by promoters both of which are located on the same expression plasmid. In a preferred embodiment, the siRNA is expressed as an inverted repeat joined by a linker polynucleotide sequence such that the siRNA has a stem and loop structure.

The recombinant siRNA expression vectors are preferably DNA plasmids or viral vectors. siRNA expressing viral vectors can be constructed based on, but not limited to, adeno-associated virus (for a review, see Muzyczka et al. (1992, Curr. Topics in Micro. and Immunol. 158:97-129)), adenovirus (see, for example, Berkner et al. (1988, BioTechniques 6:616), Rosenfeld et al. (1991, Science 252:431-434), and Rosenfeld et al. (1992, Cell 68:143-155)), or alphavirus as well as others known in the art. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving siRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268276); the endothelin regulatory sequence for endothelial cells (Lee, 1990, J. Biol. Chem. 265:10446-50); the keratin regulatory sequence for epidennis; the myosin light chain-2 regulatory sequence for heart (Lee et al., 1992, J. Biol. Chem. 267: 15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since NMC expression is induced by cytokines, expression of a test gene operably linked to this promoter can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et at, 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the siRNA transgene.

Preferably, recombinant vectors capable of expressing siRNA molecules are delivered as described below, and persist in target cells. Alternatively, viral vectors can be used that provide for transient expression of siRNA molecules. Such vectors can be repeatedly administered as necessary. Once expressed, the siRNAs bind to target RNA and modulate its function or expression. Delivery of siRNA expressing vectors can be systemic, such as by intravenous or intramuscular administration, by administration to target cells ex-planted from the patient followed by reintroduction into the patient, or by any other means that allows for introduction into a desired target cell.

SiRNA expression DNA plasmids are typically transfected into target cells as a complex with cationic lipid carriers (e.g. Oligofectamine) or non-cationic lipid-based carriers (e.g. Transit-TKO™). Multiple lipid transfections for siRNA-mediated knockdowns targeting different regions of a single target gene or multiple target genes over a period of a week or more are also contemplated by the present invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

For a review of techniques that can be used to generate and assess transgenic animals, skilled artisans can consult Gordon (IwL Rev. CytoL 1 1 5:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., Bio/Technology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Science, 244:1281, 1986; Wagner et al., U.S. Pat. No. 5,175,385; and Krimpenfort et al., U.S. Pat. No. 5,175,384.

The EGFR-specific siRNAs described above can also be generally inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 7

Method of Determining an Effective Dose of a siRNA

A therapeutically effective amount of a composition containing a sequence that encodes an EGFR-specific siRNA, (i.e., an effective dosage), is an amount that inhibits expression of the polypeptide encoded by the EGFR target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the siRNA may be desired. When an inducible promoter is included in the construct encoding an siRNA, expression is assayed upon delivery to the subject of an appropriate dose of the substance used to induce expression.

Appropriate doses of a composition depend upon the potency of the molecule (the sequence encoding the siRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently commercially available transfection kits (Lipofectamine, Oligofectamine, both from Invitrogen; TransMessenger, Qiagen), of which the TransMessenger kit proved to be the most suitable for this cell line.

Four short double-stranded ribonucleic acids (R1-R4) were tested (see Table 4). The ribonucleic acids are homologous with segments of the coding sequence of MDR1 (SEQ ID NO:30). Sequences R1-R3 consist of a 22-mer sense strand and a 24-mer antisense strand, whereby the resulting double strand exhibits a 2-nucleotide overhang at its 3'-end (0-22-2).

Sequence R4 corresponds to R1; however it consists of a 19-mer double-stranded, each with 2-nucleotide overhangs at each 3'-end (2-19-2).

TABLE 4

| Name | SEQ ID NO. | Sequence | Position in Data bank-# AF016535 |
|---|---|---|---|
| Seq R1 | SEQ ID NO: 141 | 5'-CCA UCU CGA AAA GAA GUU AAG A-3' | 1320-1342 |
|  | SEQ ID NO: 142 | 3'-UG GGU AGA CGU UUU CUU CAA UUC U-5' | 1335-1318 |
| Seq R2 | SEQ ID NO: 143 | 5'-UAU AGG UUC CAG GCU UGC UGU A-3' | 2599-2621 |
|  | SEQ ID NO: 152 | 3'-CG AUA UCC AAG GUC CGA ACG ACA U-5' | 2621-2597 |
| Seq R3 | SEQ ID NO: 144 | 5'-CCA GAG AAG GCC GCA CCU GCA U-3' | 3778-3799 |
|  | SEQ ID NO: 145 | 3'-UC GGU CUC UUC CGG CGU GGA CGU A-5' | 3799-3776 |
| Seq R4 | SEQ ID NO: 146 | 5'-CCA UUC CGA AAA GAA GUU AAG-3' | 1320-1341 |
|  | SEQ ID NO: 147 | 3'-UG GGU AGA GCU UUU CUU CAA U-5' | 1339-1318 Position in Data bank-# AF402779 |
| K1A/ K2B | SEQ ID NO: 153 SEQ ID NO: 158 | 5'-ACA GGA UGA GGA UCG UUU CGC A-3' 3'-UC UGU CCU ACU CCU AGC AAA GCG U-5' | 2829-2808 2808-2831 | increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). In addition, the attending physician will monitor the symptoms associated with the disease or disorder afflicting the patient and compare with those symptoms recorded prior to the initiation of siRNA treatment.

Example 8

Inhibiting Expression of Multi-Drug Resistance Gene 1 (MDR1) Using a MDR-1 Specific siRNA Inhibition of MDR1 expression by MDR-1 specific siRNA was tested using the colon cancer cell line LS174T (ATCC—American Type Culture Collection; Tom et al., 1976). Expression of MDR1 in this cell line is inducible by adding rifampicin to the culture medium (Geick et al., 2001). Cells were transfected with MDR-1 specific siRNA using a variety of The sequences shown in Table 4 are designated as sequences SEQ ID NOS:141-147, 152, 153, and 158 in the sequence listing. Cells were first seeded in 12-well plates at $3.8 \times 10^5$ cells/well. A day later, dsRNA was transfected into the cells in duplicate at a concentration of 175 nM. For each transfection assay, 93.3 µl EC-R buffer (TransMessenger kits, Qiagen, Hilden) was mixed with 3.2 µl Enhancer R prior to the addition of 3.5 µl of the particular 20 µM dsRNA, mixed well, and incubated for 5 minutes at room temperature. After the addition of 60 TransMessenger transfection reagent, the transfection assay was mixed vigorously for 10 seconds, and then incubated for a further 10 minutes at room temperature. The cells were then washed once with PBS (phosphate-buffered saline), and 200 µl fresh medium without FCS was added to the cells in each well. After 10-minute incubation, 100 µl FCS-free medium was pipetted into each transfection assay, mixed, and the mixture was then pipetted drop by drop onto the cells (the dsRNA concentration of 175 µM relates to 400 µl medium total volume). The dsRNA/TransMessenger complexes were incubated with the cells for 4 hours at 37° C. in FCS-free medium. The medium was then changed and replaced with fresh medium containing 10 µM rifampin and 10% FCS. A non-specific dsRNA sequence that exhibits no homologies with the MDR1 gene sequence was used (K) as a control, and a MOCK transfection was conducted that contained all reagents except for dsRNA.

The cells were harvested after 24, 48, and 72 hours, and total RNA was extracted with the RNeasy mini kit from Qiagen. 10 µg total protein from each sample was then separated by electrophoresis on a 1% agarose-formaldehyde gel, blotted on a nylon membrane, and then hybridized as an internal control with specific probes that had been randommarked with 5'-$\alpha^{32}$p-dCTP, first against MDR1, and after the blot had been stripped, against GAPDH, and then exposed on x-ray film. The x-ray film was digitized (Image Master, VDS, Pharmacia) and quantified using Image-Quant software and standardized against the GAPDH signal.

Figure 25A:
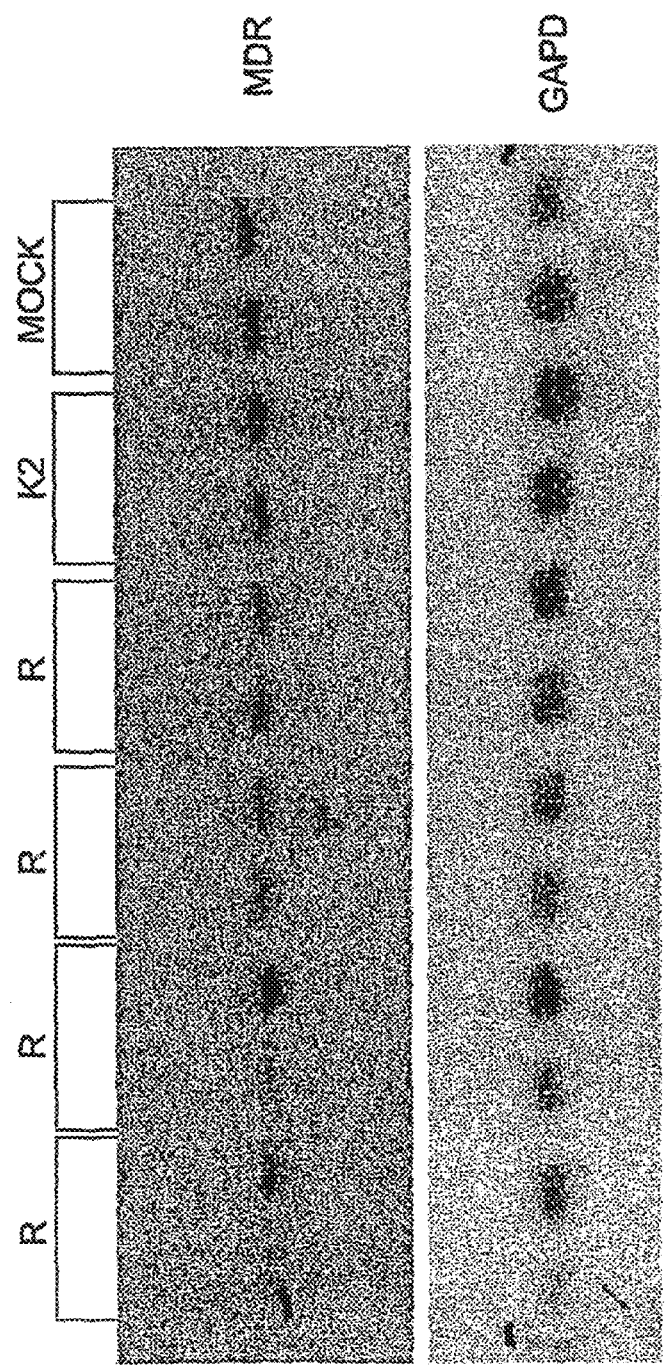
FIG. 25 show a Northern blot analysis of the MDRI mRNA level in colon carcinoma cell line LSI74T, whereby the cells were harvested after 74 hours (FIG. 25a); and quantification of the bands in FIG. 25a, whereby the averages are represented by two values (FIG. 25b).
Figure 25B:
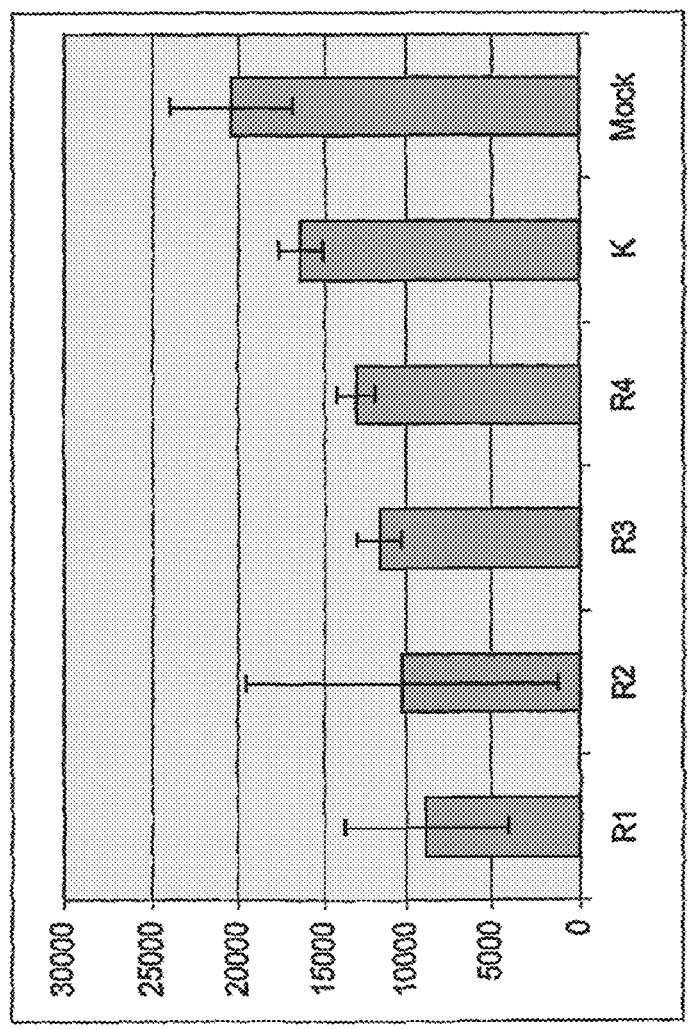
Figure 26B:
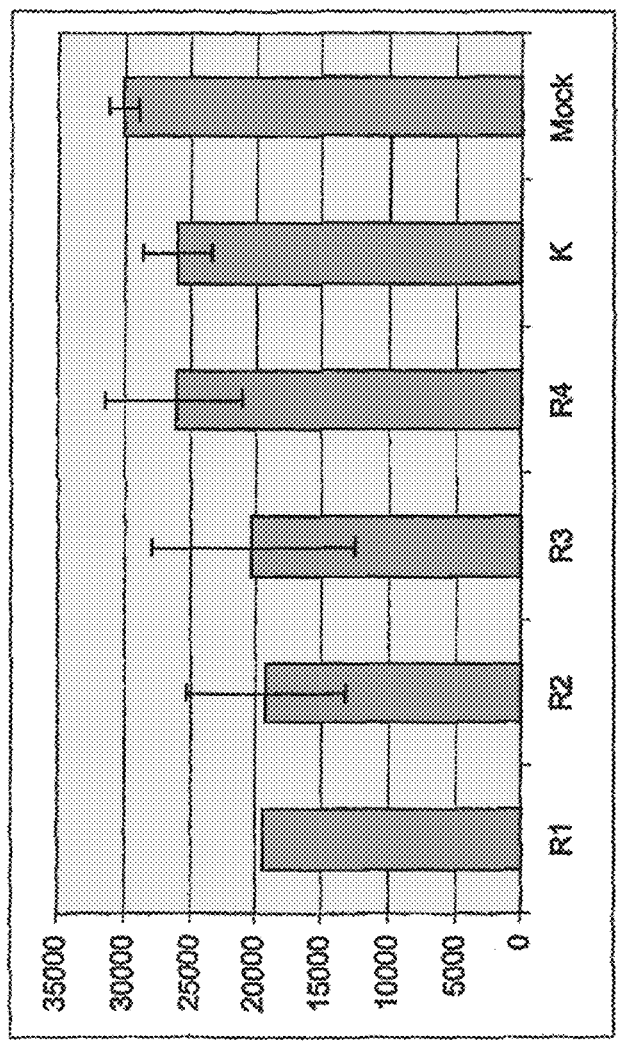
FIG. 26 shows a Northern blot analysis of the MDRI mRNA level in colon carcinoma cell line LS174T, whereby the cells were harvested after 48 hours (FIG. 26a); and quantification of the bands in FIG. 26a, whereby the averages of two values are represented (FIG. 26b).

FIGS. 25 and 26 show Northern blots (FIGS. 26a, 26a) with quantitative analysis of the MDR1-specific signal after adjustment with the corresponding GAPDH values (FIGS. 25b, 26p). A reduction in the MDR1-mRNA by as much as 55% was observed in comparison to the MOCK transfection, and by as much as 45% in comparison to the nonspecific control transfection. After 48 hours there was a significant reduction in the MDR1-mRNA level in the dsRNA constructs designated as R1, R2, and R3 (Table 4). With the R4 dsRNA constructs, no significant reduction compared to controls was observed after 48 hours (FIGS. 26a and 26b). After 74 hours, there was an even stronger reduction in MDR1-mRNA levels in the presence of R1, R2, and R3 as compared to the values observed at 48 hours (FIGS. 25a and 26b). A significant decrease in the MDR1-mRNA level was seen at this time with R4 as well. Thus, the constructs with a 2 nt overhang at the 3'-end of the antisense strand and a double-stranded region consisting of 22 nucleotide pairs reduces the MDR1-mRNA level more efficiently than do constructs with 2 nt overhangs at the 3'-end of both strands (antisense strand and sense strand) and a double-stranded region consisting of 19 nucleotide pairs, apparently independent of the sequence region homologous to the MDR1 gene in each case (after 48 hours; FIG. 26b). The results strengthen the findings in Example IV, which describe the inhibition of EGFR gene expression by means of specific dsRNAs after transfection in U-87 MG cells.

Transfection efficiency was determined in a separate experiment with the help of a DNA oligonucleotide marked with Texas red (TexRed-A[GATC]$_5$T; also transfected with 175 nM) (FIGS. 27a, 27b; 400x enlargement, 48 hours after transfection). Transfection efficiency was approximately 50% on the basis of red fluorescent cells in comparison to total cell number. If one takes the transfection rate of cells of approximately 50% into consideration, then the observed decrease in the MDR1-mRNA level by approximately 45-55% (compared with the controls) indicates that MDR1-mRNA was almost completely and specifically broken down in all cells that were successfully transfected with specific dsRNA.

---

SEQUENCE LISTING

<160> NUMBER OF SEQ ID NOS: 173

<210> SEQ ID NO 1
<211> LENGTH: 2955
<212> TYPE: DNA
<213> ORGANISM: Homo sapiens
<300> PUBLICATION INFORMATION:
<302> TITLE: Eph A1
<310> PATENT DOCUMENT NUMBER: NM00532

<400> SEQUENCE: 1

```
atggagcggc gctggcccct ggggctaggg ctggtgctgc tgctctgcgc cccgctgccc      60 ccggggcgc gcgccaagga agttactctg atggacacaa gcaaggcaca gggagagctg     120
ggctggctgc tggatccccc aaaagatggg tggagtgaac agcaacagat actgaatggg     180
acacccctct acatgtacca ggactgccca atgcaaggac gcagagacac tgaccactgg     240
cttcgctcca attggatcta ccgcggggag gaggcttccc gcgtccacgt ggagctgcag     300
ttcaccgtgc gggactgcaa gagtttccct gggggagccg ggcctctggg ctgcaaggag     360
accttcaacc ttctgtacat ggagagtgac caggatgtgg gcattcagct ccgacggccc     420
ttgttccaga aggtaaccac ggtggctgca gaccagagct tcaccattcg agaccttgcg     480
tctggctccg tgaagctgaa tgtggagcgc tgctctctgg gccgcctgac ccgccgtggc     540
ctctacctcg ctttccacaa cccgggtgcc tgtgtggccc tggtgtctgt ccgggtcttc     600
taccagcgct gtcctgagac cctgaatggc ttggcccaat tccagacac tctgcctggc     660 cccgctgggt tggtggaagt ggcgggcacc tgcttgcccc acgcgcgggc cagccccagg     720
ccctcaggtg cacccgcat gcactgcagc cctgatggcg agtggctggt gcctgtagga     780
cggtgccact gtgagcctgg ctatgaggaa ggtggcagtg gcgaagcatg tgttgcctgc     840
cctagcggct cctaccggat ggacatggac acacccatt gtctcacgtg cccccagcag     900
agcactgctg agtctgaggg ggccaccatc tgtacctgtg agagcggcca ttacagagct     960 ccggggagg gccccaggt ggcatgcaca ggtccccct cggcccccg aaacctgagc    1020
```

-continued

```
ttctctgcct cagggactca gctctccctg cgttgggaac ccccagcaga tacgggggga    1080
cgccaggatg tcagatacag tgtgaggtgt tcccagtgtc agggcacagc acaggacggg    1140
gggccctgcc agccctgtgg ggtgggcgtg cacttctcgc cgggggcccg ggcgctcacc    1200
acacctgcag tgcatgtcaa tggccttgaa ccttatgcca actacacctt taatgtggaa    1260
gcccaaaatg gagtgtcagg gctgggcagc tctggccatg ccagcacctc agtcagcatc    1320
agcatgggga tgcagagtc actgtcaggc ctgtctctga actggtgaa gaaagaaccg     1380 aggcaactag agctgacctg ggcggggtcc cggccccgaa gccctggggc gaacctgacc    1440
tatgagctgc acgtgctgaa ccaggatgaa gaacggtacc agatggttct agaacccagg    1500
gtcttgctga cagagctgca gcctgacacc acatacatcg tcagagtccg aatgctgacc    1560
ccactgggtc ctggcccttt ctcccctgat catgagtttc ggaccagccc accagtgtcc    1620
aggggcctga ctggaggaga gattgtagcc gtcatctttg ggctgctgct tggtgcagcc    1680
ttgctgcttg ggattctcgt tttccggtcc aggagagccc agcggcagag gcagcagagg    1740
cacgtgaccg cgccaccgat gtggatcgag aggacaagct gtgctgaagc cttatgtggt    1800
acctccaggc atacgaggac cctgcacagg gagccttgga ctttacccgg aggctggtct    1860
aattttcctt cccgggagct tgatccagcg tggctgatgg tggacactgt cataggagaa    1920
ggagagtttg gggaagtgta tcgagggacc ctcaggctcc ccagccagga ctgcaagact    1980
gtggccatta agaccttaaa agacacatcc ccaggtggcc agtggtggaa cttccttcga    2040
gaggcaacta tcatgggcca gtttagccac ccgcatattc tgcatctgga aggcgtcgtc    2100
acaaagcgaa agccgatcat gatcatcaca gaatttatgg agaatgcagc cctggatgcc    2160
ttcctgaggg agcgggagga ccagctggtc cctgggcagc tagtggccat gctgcagggc    2220
atagcatctg gcatgaacta cctcagtaat acaattatg tccaccggga cctggctgcc     2280
agaaacatct tggtgaatca aaacctgtgc tgcaaggtgt ctgactttgg cctgactcgc    2340
ctcctggatg actttgatgg cacatacgaa acccagggag gaaagatccc tatccgttgg    2400
acagcccctg aagccattgc ccatcggatc ttcaccacag ccagcgatgt gtggagcttt    2460
gggattgtga tgtgggaggt gctgagcttt ggggacaagc cttatgggga gatgagcaat    2520
caggaggtta tgaagagcat tgaggatggg taccggttgc cccctcctgt ggactgccct    2580
gcccctctgt atgagctcat gaagaactgc tgggcatatg accgtgcccg ccggccacac    2640
ttccagaagc ttcaggcaca tctggagcaa ctgcttgcca accccactc cctgcggacc     2700 attgccaact ttgaccccag ggtgactctt cgcctgccca gctgagtgg ctcagatggg     2760 atcccgtatc gaaccgtctc tgagtggctc gagtccatac gcatgaaacg ctacatcctg    2820
cacttccact cggctgggct ggacaccatg gagtgtgtgc tggagctgac cgctgaggac    2880
ctgacgcaga tgggaatcac actgcccggg caccagaagc gcattctttg cagtattcag    2940
ggattcaagg actga                                                    2955
```

<210> SEQ ID NO 2
<211> LENGTH: 3042
<212> TYPE: DNA
<213> ORGANISM: Homo sapiens
<300> PUBLICATION INFORMATION:
<302> TITLE: ephrin A2
<310> PATENT DOCUMENT NUMBER: XM002088

<400> SEQUENCE: 2

```
gaagttgcgc gcaggccggc gggcgggagc ggacaccgag gccggcgtgc aggcgtgcgg     60
gtgtgcggga gccgggctcg gggggatcgg accgagagcg agaagcgcgg catggagctc    120
```

```
caggcagccc gcgcctgctt cgccctgctg tggggctgtg cgctggccgc ggccgcggcg      180
gcgcagggca aggaagtggt actgctggac tttgctgcag ctggagggga gctcggctgg      240
ctcacacacc cgtatggcaa agggtgggac ctgatgcaga acatcatgaa tgacatgccg      300
atctacatgt actccgtgtg caacgtgatg tctggcgacc aggacaactg gctccgcacc      360
aactgggtgt accgaggaga ggctgagcgt atcttcattg agctcaagtt tactgtacgt      420
gactgcaaca gcttccctgg tggcgccagc tcctgcaagg agactttcaa cctctactat      480
gccgagtcgg acctggacta cggcaccaac ttccagaagc gcctgttcac caagattgac      540
accattgcgc ccgatgagat caccgtcagc agcgacttcg aggcacgcca cgtgaagctg      600
aacgtggagg agcgctccgt ggggccgctc acccgcaaag gcttctacct ggccttccag      660
gatatcggtg cctgtgtggc gctgctctcc gtccgtgtct actacaagaa gtgccccgag      720
ctgctgcagg gcctggccca cttccctgag accatcgccg ctctgatgc accttccctg       780 gccactgtgg ccggcacctg tgtggaccat gccgtggtgc caccgggggg tgaagagccc      840
cgtatgcact gtgcagtgga tggcgagtgg ctggtgccca ttgggcagtg cctgtgccag      900
gcaggctacg agaaggtgga ggatgcctgc caggcctgct cgcctggatt ttttaagttt      960
gaggcatctg agagcccctg cttggagtgc cctgagcaca cgctgccatc ccctgagggt     1020
gccacctcct gcgagtgtga ggaaggcttc ttccgggcac ctcaggaccc agcgtcgatg     1080
ccttgcacac gacccccctc cgcccacac tacctcacag ccgtgggcat gggtgccaag      1140
gtggagctgc gctggacgcc ccctcaggac agcggggcc gcgaggacat tgtctacagc      1200
gtcacctgcg aacagtgctg gcccgagtct ggggaatgcg gccgtgtgac ggccagtgtg     1260
cgctactcgg agcctcctca cggactgacc cgcaccagtg tgacagtgag cgacctggag     1320
ccccacatga actacacctt caccgtggag gcccgcaatg gcgtctcagg cctggtaacc     1380
agccgcagct ccgtactgc cagtgtcagc atcaaccaga cagagccccc caaggtgagg      1440
ctggagggcc gcagcaccac ctcgcttagc gtctcctgga gcatccccc gccgcagcag      1500 agccgagtgt ggaagtacga ggtcacttac cgcaagaagg gagactccaa cagctacaat     1560
gtgcgccgca ccgagggttt ctccgtgacc ctggacgacc tggcccccaga caccacctac     1620 ctggtccagg tgcaggcact gacgcaggag ggccagggg ccggcagcaa ggtgcacgaa      1680
ttccagacgc tgtccccgga gggatctggc aacttggcgg tgattggcgg cgtggctgtc     1740
ggtgtggtcc tgcttctggt gctggcagga gttggcttct ttatccaccg caggaggaag     1800
aaccagcgtg cccgccagtc cccggaggac gtttacttct ccaagtcaga acaactgaag     1860
cccctgaaga catacgtgga ccccacaca tatgaggacc caaccaggc tgtgttgaag       1920 ttcactaccg agatccatcc atcctgtgtc actcggcaga aggtgatcgg agcaggagag     1980 tttgggagg tgtacaaggg catgctgaag acatcctcgg ggaagaagga ggtgccggtg      2040
gccatcaaga cgctgaaagc cggctacaca gagaagcagc gagtggactt cctcggcgag     2100
gccggcatca tgggccagtt cagccaccac aacatcatcc gcctagaggg cgtcatctcc     2160
aaatacaagc ccatgatgat catcactgag tacatggaga tggggccct ggacaagttc      2220 cttcgggaga aggatggcga gttcagcgtg ctgcagctgg tgggcatgct gcggggcatc     2280
gcagctggca tgaagtacct ggccaacatg aactatgtgc accgtgacct ggctgcccgc     2340
aacatcctcg tcaacagcaa cctggtctgc aaggtgtctg actttggcct gtcccgcgtg     2400
ctggaggacg accccgaggc cacctacacc accagtggcg gcaagatccc catccgctgg     2460
accgccccgg aggccatttc ctaccggaag ttcacctctg ccagcgacgt gtggagcttt     2520
```

| | |
|---|---|
| ggcattgtca tgtgggaggt gatgacctat ggcgagcggc cctactggga gttgtccaac | 2580 |
| cacgaggtga tgaaagccat caatgatggc ttccggctcc ccacacccat ggactgcccc | 2640 |
| tccgccatct accagctcat gatgcagtgc tggcagcagg agcgtgcccg ccgcccaag | 2700 |
| ttcgctgaca tcgtcagcat cctggacaag ctcattcgtg ccctgactc cctcaagacc | 2760 |
| ctggctgact tgacccccg cgtgtctatc cggctcccca gcacgagcgg ctcggagggg | 2820 |
| gtgcccttcc gcacggtgtc cgagtggctg gagtccatca gatgcagca gtatacggag | 2880 |
| cacttcatgg cggccggcta cactgccatc gagaaggtgg tgcagatgac caacgacgac | 2940 |
| atcaagagga ttggggtgcg gctgcccggc caccagaagc gcatcgccta cagcctgctg | 3000 |
| ggactcaagg accaggtgaa cactgtgggg atccccatct ga | 3042 |

<210> SEQ ID NO 3
<211> LENGTH: 2953
<212> TYPE: DNA
<213> ORGANISM: Homo sapiens
<300> PUBLICATION INFORMATION:
<302> TITLE: ephrin A3
<310> PATENT DOCUMENT NUMBER: NM005233

<400> SEQUENCE: 3

| | |
|---|---|
| atggattgtc agctctccat cctcctcctt ctcagctgct ctgttctcga cagcttcggg | 60 |
| gaactgattc cgcagccttc caatgaagtc aatctactgg attcaaaaac aattcaaggg | 120 |
| gagctgggct ggatctctta tccatcacat gggtgggaag agatcagtgg tgtggatgaa | 180 |
| cattacacac ccatcaggac ttaccaggtg tgcaatgtca tggaccacag tcaaaacaat | 240 |
| tggctgagaa caaactgggt ccccaggaac tcagctcaga gatttatgt ggagctcaag | 300 |
| ttcactctac gagactgcaa tagcattcca ttggttttag aacttgcaa ggagacattc | 360 |
| aacctgtact acatggagtc tgatgatgat catggggtga atttcgaga gcatcagttt | 420 |
| acaaagattg acaccattgc agctgatgaa agtttcactc aaatggatct ggggaccgt | 480 |
| attctgaagc tcaacactga gattagaaa gtaggtcctg tcaacaagaa gggattttat | 540 |
| ttggcattc aagatgttgg tgcttgtgtt gccttggtgt ctgtgagagt atacttcaaa | 600 |
| aagtgcccat ttacagtgaa gaatctggct atgtttccag acacggtacc catggactcc | 660 |
| cagtccctgg tggaggttag agggtcttgt gtcaacaatt ctaaggagga agatcctcca | 720 |
| aggatgtact gcagtacaga aggcgaatgg cttgtaccca ttggcaagtg ttcctgcaat | 780 |
| gctggctatg aagaaagagg ttttatgtgc caagcttgtc gaccaggttt ctacaaggca | 840 |
| ttggatggta tatgaagtg tgctaagtgc ccgcctcaca gttctactca ggaagatggt | 900 |
| tcaatgaact gcaggtgtga gaataattac ttccgggcag acaaagaccc tcatccatg | 960 |
| gcttgtaccc gacctccatc ttcaccaaga atgttatct ctaatataaa cgagacctca | 1020 |
| gttatcctgg actggagttg gccccctggac acaggaggcc ggaaagatgt taccttcaac | 1080 |
| atcatatgta aaaatgtgg gtggaatata aaacagtgtg agccatgcag cccaaatgtc | 1140 |
| cgcttcctcc ctcgacagtt tggactcacc aacaccacgg tgcagtgac agaccttctg | 1200 |
| gcacatacta actacacct tgagattgat gccgttaatg gggtgtcaga gctgagctcc | 1260 |
| ccaccaagac agtttgctgc ggtcagcatc acaactaatc aggctgctcc atcacctgtc | 1320 |
| ctgacgatta agaaagatcg gacctccaga aatagcatct ctttgtcctg caagaaccct | 1380 |
| gaacatccta tgggatcat attggactac gaggtcaaat actatgaaaa gcaggaacaa | 1440 |
| gaaacaagtt ataccattct gagggcaaga ggcacaaatg ttaccatcag tagcctcaag | 1500 |

-continued

| | |
|---|---|
| cctgacacta tatacgtatt ccaaatccga gcccgaacag ccgctggata tgggacgaac | 1560 |
| agccgcaagt ttgagtttga aactagtcca gactctttct ccatctctgg tgaaagtagc | 1620 |
| caagtggtca tgatcgccat ttcagcggca gtagcaatta ttctcctcac tgttgtcatc | 1680 |
| tatgttttga ttgggaggtt ctgtggctat aagtcaaaac atggggcaga tgaaaaaga | 1740 |
| cttcattttg gcaatgggca tttaaaactt ccaggtctca ggacttatgt tgacccacat | 1800 |
| acatatgaag accctaccca agctgttcat gagtttgcca aggaattgga tgccaccaac | 1860 |
| atatccattg ataaagttgt tggagcaggt gaatttggag aggtgtgcag tggtcgctta | 1920 |
| aaacttcctt caaaaaaaga gatttcagtg gccattaaaa ccctgaaagt tggctacaca | 1980 |
| gaaaagcaga ggagagactt cctgggagaa gcaagcatta tgggacagtt tgaccacccc | 2040 |
| aatatcattc gactggaagg agttgttacc aaaagtaagc cagttatgat tgtcacagaa | 2100 |
| tacatggaga atggttcctt ggatagtttc ctacgtaaac acgatgccca gtttactgtc | 2160 |
| attcagctag tggggatgct tcagggata gcatctggca tgaagtacct gtcagacatg | 2220 |
| ggctatgttc accgagacct cgctgctcgg aacatcttga tcaacagtaa cttggtgtgt | 2280 |
| aaggtttctg atttcggact ttcgcgtgtc ctggaggatg acccagaagc tgcttataca | 2340 |
| acaagaggag ggaagatccc aatcaggtgg acatcaccag aagctatagc ctaccgcaag | 2400 |
| ttcacgtcag ccagcgatgt atggagttat gggattgttc tctgggaggt gatgtcttat | 2460 |
| ggagagagac catactggga gatgtccaat caggatgtaa ttaaagctgt agatgagggc | 2520 |
| tatcgactgc cacccccat ggactgccca gctgccttgt atcagctgat gctggactgc | 2580 |
| tggcagaaag acaggaacaa cagacccaag tttgagcaga ttgttagtat tctggacaag | 2640 |
| cttatccgga atcccggcag cctgaagatc atcaccagtg cagccgcaag gccatcaaac | 2700 |
| cttcttctgg accaaagcaa tgtggatatc tctaccttcc gcacaacagg tgactggctt | 2760 |
| aatggtgtcc ggacagcaca ctgcaaggaa atcttcacgg gcgtggagta cagttccttgt | 2820 |
| gacacaatag ccaagatttc cacagatgac atgaaaaagg ttggtgtcac cgtggttggg | 2880 |
| ccacagaaga agatcatcag tagcattaaa gctctagaaa cgcaatcaaa gaatggccca | 2940 |
| gttcccgtgt aaa | 2953 |

<210> SEQ ID NO 4
<211> LENGTH: 2784
<212> TYPE: DNA
<213> ORGANISM: Homo sapiens
<300> PUBLICATION INFORMATION:
<302> TITLE: ephrin A4
<310> PATENT DOCUMENT NUMBER: XM002578

<400> SEQUENCE: 4

| | |
|---|---|
| atggatgaaa aaatacacc aatccgaacc taccaagtgt gcaatgtgat ggaacccagc | 60 |
| cagaataact ggctacgaac tgattggatc acccgagaag gggctcagag ggtgtatatt | 120 |
| gagattaaat tcaccttgag ggactgcaat agtcttccgg gcgtcatggg gacttgcaag | 180 |
| gagacgttta acctgtacta ctatgaatca gacaacgaca aagagcgttt catcagagag | 240 |
| aaccagtttg tcaaaattga caccattgct gctgatgaga gcttcaccca gtggacatt | 300 |
| ggtgacagaa tcatgaagct gaacaccgag atccgggatg tagggccatt aagcaaaaag | 360 |
| gggttttacc tggcttttca ggatgtgggg gcctgcatcg ccctggtatc agtccgtgtg | 420 |
| ttctataaaa agtgtccact cacagtccgc aatctggccc agtttcctga caccatcaca | 480 |
| ggggctgata cgtcttccct ggtggaagtt cgaggctcct gtgtcaacaa ctcagaagag | 540 |
| aaagatgtgc caaaaatgta ctgtgggggca gatggtgaat ggctggtacc cattggcaac | 600 |

```
tgcctatgca acgctgggca tgaggagcgg agcggagaat gccaagcttg caaaattgga    660
tattacaagg ctctctccac ggatgccacc tgtgccaagt gcccacccca cagctactct    720
gtctgggaag gagccacctc gtgcacctgt gaccgaggct ttttcagagc tgacaacgat    780
gctgcctcta tgccctgcac ccgtccacca tctgctcccc tgaacttgat ttcaaatgtc    840
aacgagacat ctgtgaactt ggaatggagt agccctcaga atacaggtgg ccgccaggac    900
atttcctata atgtggtatg caagaaatgt ggagctggtg accccagcaa gtgccgaccc    960
tgtggaagtg gggtccacta caccccacag cagaatggct tgaagaccac caaagtctcc   1020
atcactgacc tcctagctca taccaattac acctttgaaa tctgggctgt gaatggagtg   1080
tccaaatata accctaaccc agaccaatca gtttctgtca ctgtgaccac caaccaagca   1140
gcaccatcat ccattgcttt ggtccaggct aaagaagtca agatacag tgtggcactg     1200 gcttggctgg aaccagatcg gcccaatggg gtaatcctgg aatatgaagt caagtattat   1260
gagaaggatc agaatgagcg aagctatcgt atagttcgga cagctgccag gaacacagat   1320
atcaaaggcc tgaaccctct cacttcctat gttttccacg tgcgagccag gacagcagct   1380
ggctatggag acttcagtga gcccttggag gttacaacca acacagtgcc ttcccggatc   1440
attggagatg gggctaactc cacagtcctt ctggtctctg tctcgggcag tgtggtgctg   1500
gtggtaattc tcattgcagc ttttgtcatc agccggagac ggagtaaata cagtaaagcc   1560
aaacaagaag cggatgaaga gaaacatttg aatcaaggtg taagaacata tgtggacccc   1620
tttacgtacg aagatcccaa ccaagcagtg cgagagtttg ccaaagaaat tgacgcatcc   1680
tgcattaaga ttgaaaaagt tataggagtt ggtgaatttg gtgaggtatg cagtgggcgt   1740
ctcaaagtgc ctggcaagag agagatctgt gtggctatca agactctgaa agctggttat   1800
acagacaaac agaggagaga cttcctgagt gaggccagca tcatgggaca gtttgaccat   1860
ccgaacatca ttcacttgga aggcgtggtc actaaatgta aaccagtaat gatcataaca   1920
gagtacatgg agaatggctc cttggatgca ttcctcagga aaaatgatgg cagatttaca   1980
gtcattcagc tggtgggcat gcttcgtggc attgggtctg ggatgaagta tttatctgat   2040
atgagctatg tgcatcgtga tctggccgca cggaacatcc tggtgaacag caacttggtc   2100
tgcaaagtgt ctgattttgg catgtcccga gtgcttgagg atgatccgga agcagcttac   2160
accaccaggg gtggcaagat tcctatccgg tggactgcgc cagaagcaat tgcctatcgt   2220
aaattcacat cagcaagtga tgtatgggc tatggaatcg ttatgtggga agtgatgtcg   2280
tacggggaga ggcctattg ggatatgtcc aatcaagatg tgattaaagc cattgaggaa   2340 ggctatcgt tacccctcc aatggactgc cccattgcgc tccaccagct gatgctagac     2400
tgctggcaga aggagaggag cgacaggcct aaatttgggc agattgtcaa catgttggac   2460
aaactcatcc gcaaccccaa cagcttgaag aggacaggga cggagagctc agacctaac    2520 actgccttgt tggatccaag ctcccctgaa ttctctgctg tggtatcagt gggcgattgg   2580
ctccaggcca ttaaaatgga ccggtataag ataacttca cagctgctgg ttataccaca    2640
ctagaggctg tggtgcacgt gaaccaggag gacctggcaa gaattggtat cacagccatc   2700
acgcaccaga ataagatttt gagcagtgtc caggcaatgc gaacccaaat gcagcagatg   2760
cacggcagaa tggttcccgt ctga                                          2784
```

<210> SEQ ID NO 5
<211> LENGTH: 2997
<212> TYPE: DNA
<213> ORGANISM: Homo sapiens

```
<300> PUBLICATION INFORMATION:
<302> TITLE: ephrin A7
<310> PATENT DOCUMENT NUMBER: XM004485

<400> SEQUENCE: 5
```

| | | | | |
|---|---|---|---|---|
| atggtttttc aaactcggta cccttcatgg attattttat gctacatctg gctgctccgc | 60 |
| tttgcacaca caggggaggc gcaggctgcg aaggaagtac tactgctgga ttctaaagca | 120 |
| caacaaacag agttggagtg gatttcctct ccacccaatg ggtgggaaga aattagtggt | 180 |
| ttggatgaga actataccc gatacgaaca taccaggtgt gccaagtcat ggagcccaac | 240 |
| caaaacaact ggctgcggac taactggatt tccaaaggca atgcacaaag gattttgta | 300 |
| gaattgaaat tcaccctgag ggattgtaac agtcttcctg gagtactggg aacttgcaag | 360 |
| gaaacattta atttgtacta ttatgaaaca gactatgaca ctggcaggaa ataagagaa | 420 |
| aacctctatg taaaaataga caccattgct gcagatgaaa gttttaccca aggtgacctt | 480 |
| ggtgaaagaa agatgaagct taacactgag gtgagagaga ttggaccttt gtccaaaaag | 540 |
| ggattctatc ttgcctttca ggatgtaggg gcttgcatag ctttggtttc tgtcaaagtg | 600 |
| tactacaaga agtgctggtc cattattgag aacttagcta tctttccaga tacagtgact | 660 |
| ggttcagaat tttcctcttt agtcgaggtt cgagggacat gtgtcagcag tgcagaggaa | 720 |
| gaagcggaaa acgccccag gatgcactgc agtgcagaag gagaatggtt agtgcccatt | 780 |
| ggaaaatgta tctgcaaagc aggctaccag caaaaggag acacttgtga accctgtggc | 840 |
| cgtgggttct acaagtcttc ctctcaagat cttcagtgct ctcgttgtcc aactcacagt | 900 |
| ttttctgata agaaggctc ctccagatgt gaatgtgaag atgggtatta cagggctcca | 960 |
| tctgacccac catacgttgc atgcacaagg cctccatctg caccacagaa cctcattttc | 1020 |
| aacatcaacc aaaccacagt aagtttggaa tggagtcctc ctgcagacaa tgggggaaga | 1080 |
| aacgatgtga cctacagaat attgtgtaag cggtgcagtt gggagcaggg cgaatgtgtt | 1140 |
| ccctgtggga gtaacattgg atacatgccc cagcagactg gattagagga taactatgtc | 1200 |
| actgtcatgg acctgctagc ccacgctaat tatacttttg aagttgaagc tgtaaatgga | 1260 |
| gtttctgact taagccgatc ccagaggctc tttgctgctg tcagtatcac cactggtcaa | 1320 |
| gcagctccct cgcaagtgag tggagtaatg aaggagagag tactgcagcg gagtgtcgag | 1380 |
| cttttcctggc aggaaccaga gcatcccaat ggagtcatca cagaatatga atcaagtat | 1440 |
| tacgagaaag atcaaaggga acggacctac tcaacagtaa aaaccaagtc tacttcagcc | 1500 |
| tccattaata atctgaaacc aggaacagtg tatgttttcc agattcgggc ttttactgct | 1560 |
| gctggttatg gaaattacag tcccagactt gatgttgcta cactagagga agctacaggt | 1620 |
| aaaatgtttg aagctacagc tgtctccagt gaacagaatc ctgttattat cattgctgtg | 1680 |
| gttgctgtag ctgggaccat cattttggtg ttcatggtct ttgcttcat cattgggaga | 1740 |
| aggcactgtg ttatagcaa agctgaccaa gaaggcgatg aagagcttta ctttcatttt | 1800 |
| aaatttccag gcaccaaaac ctacattgac cctgaaacct atgaggaccc aaatagagct | 1860 |
| gtccatcaat tcgccaagga gctagatgcc tcctgtatta aaattgagcg tgtgattggt | 1920 |
| gcaggagaat tcggtgaagt ctgcagtggc cgtttgaaac ttccagggaa aagagatgtt | 1980 |
| gcagtagcca taaaacccct gaaagttggt tacacagaaa aacaaaggag agactttttg | 2040 |
| tgtgaagcaa gcatcatggg gcagtttgac cacccaaatg ttgtccattt ggaagggtt | 2100 |
| gttacaagag ggaaaccagt catgatagta atagagttca tggaaaatgg agccctagat | 2160 |
| gcatttctca ggaaacatga tgggcaattt acagtcattc agttagtagg aatgctgaga | 2220 |

-continued

```
ggaattgctg ctggaatgag atatttggct gatatgggat atgttcacag ggaccttgca    2280
gctcgcaata ttcttgtcaa cagcaatctc gtttgtaaag tgtcagattt tggcctgtcc    2340
cgagttatag aggatgatcc agaagctgtc tatacaacta ctggtggaaa aattccagta    2400
aggtggacac cacccgaagc catccagtac cggaaattca catcagccag tgatgtatgg    2460
agctatggaa tagtcatgtg ggaagttatg tcttatggag aaagacctta ttgggacatg    2520
tcaaatcaag atgttataaa agcaatagaa gaaggttatc gtttaccagc acccatggac    2580
tgcccagctg ccttcacca gctaatgttg gattgttggc aaaaggagcg tgctgaaagg     2640
ccaaaatttg aacagatagt tggaattcta gacaaaatga ttcgaaaccc aaatagtctg    2700
aaaactcccc tgggaacttg tagtaggcca ataagccctc ttctggatca aacactcct    2760 gatttcacta ccttttgttc agttggagaa tggctacaag ctattaagat ggaaagatat    2820
aaagataatt tcacggcagc tggctacaat tcccttgaat cagtagccag gatgactatt    2880
gaggatgtga tgagtttagg gatcacactg gttggtcatc aaaagaaaat catgagcagc    2940
attcagacta tgagagcaca aatgctacat ttacatggaa ctggcattca agtgtga      2997
```

<210> SEQ ID NO 6
<211> LENGTH: 3018
<212> TYPE: DNA
<213> ORGANISM: Homo sapiens
<220> FEATURE:
<221> NAME/KEY: CDS
<222> LOCATION: (1)..(3018)

<400> SEQUENCE: 6

```
atg gcc ccc gcc cgg ggc cgc ctg ccc cct gcg ctc tgg gtc gtc acg        48
Met Ala Pro Ala Arg Gly Arg Leu Pro Pro Ala Leu Trp Val Val Thr
1               5                   10                  15 gcc gcg gcg gcg gcg gcc acc tgc gtg tcc gcg gcg cgc ggc gaa gtg        96
Ala Ala Ala Ala Ala Ala Thr Cys Val Ser Ala Ala Arg Gly Glu Val
                20                  25                  30 aat ttg ctg gac acg tcg acc atc cac ggg gac tgg ggc tgg ctc acg       144
Asn Leu Leu Asp Thr Ser Thr Ile His Gly Asp Trp Gly Trp Leu Thr
            35                  40                  45 tat ccg gct cat ggg tgg gac tcc atc aac gag gtg gac gag tcc ttc       192
Tyr Pro Ala His Gly Trp Asp Ser Ile Asn Glu Val Asp Glu Ser Phe
        50                  55                  60 cag ccc atc cac acg tac cag gtt tgc aac gtc atg agc ccc aac cag       240
Gln Pro Ile His Thr Tyr Gln Val Cys Asn Val Met Ser Pro Asn Gln
65                  70                  75                  80 aac aac tgg ctg cgc acg agc tgg gtc ccc cga gac ggc gcc cgg cgc       288
Asn Asn Trp Leu Arg Thr Ser Trp Val Pro Arg Asp Gly Ala Arg Arg
                85                  90                  95 gtc tat gct gag atc aag ttt acc ctg cgc gac tgc aac agc atg cct       336
Val Tyr Ala Glu Ile Lys Phe Thr Leu Arg Asp Cys Asn Ser Met Pro
            100                 105                 110 ggt gtg ctg ggc acc tgc aag gag acc ttc aac ctc tac tac ctg gag       384
Gly Val Leu Gly Thr Cys Lys Glu Thr Phe Asn Leu Tyr Tyr Leu Glu
        115                 120                 125 tcg gac cgc gac ctg ggg gcc agc aca caa gaa agc cag ttc ctc aaa       432
Ser Asp Arg Asp Leu Gly Ala Ser Thr Gln Glu Ser Gln Phe Leu Lys
    130                 135                 140 atc gac acc att gcg gcc gac gag agc ttc aca ggt gcc gac ctt ggt       480
Ile Asp Thr Ile Ala Ala Asp Glu Ser Phe Thr Gly Ala Asp Leu Gly
145                 150                 155                 160 gtg cgg cgt ctc aag ctc aac acg gag gtg cgc agt gtg ggt ccc ctc       528
Val Arg Arg Leu Lys Leu Asn Thr Glu Val Arg Ser Val Gly Pro Leu
                165                 170                 175
```

| | | |
|---|---|---|
| agc aag cgc ggc ttc tac ctg gcc ttc cag gac ata ggt gcc tgc ctg<br>Ser Lys Arg Gly Phe Tyr Leu Ala Phe Gln Asp Ile Gly Ala Cys Leu<br>                    180                          185                    190 | 576 |
| gcc atc ctc tct ctc cgc atc tac tat aag aag tgc cct gcc atg gtg<br>Ala Ile Leu Ser Leu Arg Ile Tyr Tyr Lys Lys Cys Pro Ala Met Val<br>                195                          200                    205 | 624 |
| cgc aat ctg gct gcc ttc tcg gag gca gtg acg ggg gcc gac tcg tcc<br>Arg Asn Leu Ala Ala Phe Ser Glu Ala Val Thr Gly Ala Asp Ser Ser<br>210                          215                        220 | 672 |
| tca ctg gtg gag gtg agg ggc cag tgc gtg cgg cac tca gag gag cgg<br>Ser Leu Val Glu Val Arg Gly Gln Cys Val Arg His Ser Glu Glu Arg<br>225                      230                    235                    240 | 720 |
| gac aca ccc aag atg tac tgc agc gcg gag ggc gag tgg ctc gtg ccc<br>Asp Thr Pro Lys Met Tyr Cys Ser Ala Glu Gly Glu Trp Leu Val Pro<br>                    245                          250                    255 | 768 |
| atc ggc aaa tgc gtg tgc agt gcc ggc tac gag gag cgg cgg gat gcc<br>Ile Gly Lys Cys Val Cys Ser Ala Gly Tyr Glu Glu Arg Arg Asp Ala<br>                      260                          265                    270 | 816 |
| tgt gtg gcc tgt gag ctg ggc ttc tac aag tca gcc cct ggg gac cag<br>Cys Val Ala Cys Glu Leu Gly Phe Tyr Lys Ser Ala Pro Gly Asp Gln<br>                275                          280                    285 | 864 |
| ctg tgt gcc cgc tgc cct ccc cac agc cac tcc gca gct cca gcc gcc<br>Leu Cys Ala Arg Cys Pro Pro His Ser His Ser Ala Ala Pro Ala Ala<br>                    290                          295                    300 | 912 |
| caa gcc tgc cac tgt gac ctc agc tac tac cgt gca gcc ctg gac ccg<br>Gln Ala Cys His Cys Asp Leu Ser Tyr Tyr Arg Ala Ala Leu Asp Pro<br>305                      310                    315                    320 | 960 |
| ccg tcc tca gcc tgc acc cgg cca ccc tcg gca cca gtg aac ctg atc<br>Pro Ser Ser Ala Cys Thr Arg Pro Pro Ser Ala Pro Val Asn Leu Ile<br>                          325                          330                    335 | 1008 |
| tcc agt gtg aat ggg aca tca gtg act ctg gag tgg gcc cct ccc ctg<br>Ser Ser Val Asn Gly Thr Ser Val Thr Leu Glu Trp Ala Pro Pro Leu<br>                    340                          345                    350 | 1056 |
| gac cca ggt ggc cgc agt gac atc acc tac aat gcc gtg tgc cgc cgc<br>Asp Pro Gly Gly Arg Ser Asp Ile Thr Tyr Asn Ala Val Cys Arg Arg<br>                    355                          360                    365 | 1104 |
| tgc ccc tgg gca ctg agc cgc tgc gag gca tgt ggg agc ggc acc cgc<br>Cys Pro Trp Ala Leu Ser Arg Cys Glu Ala Cys Gly Ser Gly Thr Arg<br>                370                          375                    380 | 1152 |
| ttt gtg ccc cag cag aca agc ctg gtg cag gcc agc ctg ctg gtg gcc<br>Phe Val Pro Gln Gln Thr Ser Leu Val Gln Ala Ser Leu Leu Val Ala<br>385                      390                    395                    400 | 1200 |
| aac ctg ctg gcc cac atg aac tac tcc ttc tgg atc gag gcc gtc aat<br>Asn Leu Leu Ala His Met Asn Tyr Ser Phe Trp Ile Glu Ala Val Asn<br>                        405                          410                    415 | 1248 |
| ggc gtg tcc gac ctg agc ccc gag ccc cgc cgg gcc gct gtg gtc aac<br>Gly Val Ser Asp Leu Ser Pro Glu Pro Arg Arg Ala Ala Val Val Asn<br>                    420                          425                    430 | 1296 |
| atc acc acg aac cag gca gcc ccg tcc cag gtg gtg atc cgt caa<br>Ile Thr Thr Asn Gln Ala Ala Pro Ser Gln Val Val Ile Arg Gln<br>                        435                          440                    445 | 1344 |
| gag cgg gcg ggg cag acc agc gtc tcg ctg ctg tgg cag gag ccc gag<br>Glu Arg Ala Gly Gln Thr Ser Val Ser Leu Leu Trp Gln Glu Pro Glu<br>                    450                          455                    460 | 1392 |
| cag ccg aac ggc atc atc ctg gag tat gag atc aag tac tac gag aag<br>Gln Pro Asn Gly Ile Ile Leu Glu Tyr Glu Ile Lys Tyr Tyr Glu Lys<br>465                      470                    475                    480 | 1440 |
| gac aag gag atg cag agc tac tcc acc ctc aag gcc gtc acc acc aga<br>Asp Lys Glu Met Gln Ser Tyr Ser Thr Leu Lys Ala Val Thr Thr Arg<br>                        485                          490                    495 | 1488 |

| | |
|---|---|
| gcc acc gtc tcc ggc ctc aag ccg ggc acc cgc tac gtg ttc cag gtc<br>Ala Thr Val Ser Gly Leu Lys Pro Gly Thr Arg Tyr Val Phe Gln Val<br>500 505 510 | 1536 |
| cga gcc cgc acc tca gca ggc tgt ggc cgc ttc agc cag gcc atg gag<br>Arg Ala Arg Thr Ser Ala Gly Cys Gly Arg Phe Ser Gln Ala Met Glu<br>515 520 525 | 1584 |
| gtg gag acc ggg aaa ccc cgg ccc cgc tat gac acc agg acc att gtc<br>Val Glu Thr Gly Lys Pro Arg Pro Arg Tyr Asp Thr Arg Thr Ile Val<br>530 535 540 | 1632 |
| tgg atc tgc ctg acg ctc atc acg ggc ctg gtg gtg ctt ctg ctc ctg<br>Trp Ile Cys Leu Thr Leu Ile Thr Gly Leu Val Val Leu Leu Leu Leu<br>545 550 555 560 | 1680 |
| ctc atc tgc aag aag agg cac tgt ggc tac agc aag gcc ttc cag gac<br>Leu Ile Cys Lys Lys Arg His Cys Gly Tyr Ser Lys Ala Phe Gln Asp<br>565 570 575 | 1728 |
| tcg gac gag gag aag atg cac tat cag aat gga cag gca ccc cca cct<br>Ser Asp Glu Glu Lys Met His Tyr Gln Asn Gly Gln Ala Pro Pro Pro<br>580 585 590 | 1776 |
| gtc ttc ctg cct ctg cat cac ccc ccg gga aag ctc cca gag ccc cag<br>Val Phe Leu Pro Leu His His Pro Pro Gly Lys Leu Pro Glu Pro Gln<br>595 600 605 | 1824 |
| ttc tat gcg gaa ccc cac acc tac gag gag cca ggc cgg gcg ggc cgc<br>Phe Tyr Ala Glu Pro His Thr Tyr Glu Glu Pro Gly Arg Ala Gly Arg<br>610 615 620 | 1872 |
| agt ttc act cgg gag atc gag gcc tct agg atc cac atc gag aaa atc<br>Ser Phe Thr Arg Glu Ile Glu Ala Ser Arg Ile His Ile Glu Lys Ile<br>625 630 635 640 | 1920 |
| atc ggc tct gga gac tcc ggg gaa gtc tgc tac ggg agg ctg cgg gtg<br>Ile Gly Ser Gly Asp Ser Gly Glu Val Cys Tyr Gly Arg Leu Arg Val<br>645 650 655 | 1968 |
| cca ggg cag cgg gat gtg ccc gtg gcc atc aag gcc ctc aaa gcc ggc<br>Pro Gly Gln Arg Asp Val Pro Val Ala Ile Lys Ala Leu Lys Ala Gly<br>660 665 670 | 2016 |
| tac acg gag aga cag agg cgg gac ttc ctg agc gag gcg tcc atc atg<br>Tyr Thr Glu Arg Gln Arg Arg Asp Phe Leu Ser Glu Ala Ser Ile Met<br>675 680 685 | 2064 |
| ggg caa ttc gac cat ccc aac atc atc cgc ctc gag ggt gtc gtc acc<br>Gly Gln Phe Asp His Pro Asn Ile Ile Arg Leu Glu Gly Val Val Thr<br>690 695 700 | 2112 |
| cgt ggc cgc ctg gca atg att gtg act gag tac atg gag aac ggc tct<br>Arg Gly Arg Leu Ala Met Ile Val Thr Glu Tyr Met Glu Asn Gly Ser<br>705 710 715 720 | 2160 |
| ctg gac acc ttc ctg agg acc cac gac ggg cag ttc acc atc atg cag<br>Leu Asp Thr Phe Leu Arg Thr His Asp Gly Gln Phe Thr Ile Met Gln<br>725 730 735 | 2208 |
| ctg gtg ggc atg ctg aga gga gtg ggt gcc ggc atg cgc tac ctc tca<br>Leu Val Gly Met Leu Arg Gly Val Gly Ala Gly Met Arg Tyr Leu Ser<br>740 745 750 | 2256 |
| gac ctg ggc tat gtc cac cga gac ctg gcc gcc cgc aac gtc ctg gtt<br>Asp Leu Gly Tyr Val His Arg Asp Leu Ala Ala Arg Asn Val Leu Val<br>755 760 765 | 2304 |
| gac agc aac ctg gtc tgc aag gtg tct gac ttc ggg ctc tca cgg gtg<br>Asp Ser Asn Leu Val Cys Lys Val Ser Asp Phe Gly Leu Ser Arg Val<br>770 775 780 | 2352 |
| ctg gag gac gac ccg gat gct gcc tac acc acc acg ggc ggg aag atc<br>Leu Glu Asp Asp Pro Asp Ala Ala Tyr Thr Thr Thr Gly Gly Lys Ile<br>785 790 795 800 | 2400 |
| ccc atc cgc tgg acg gcc cca gag gcc atc gcc ttc cgc acc ttc tcc<br>Pro Ile Arg Trp Thr Ala Pro Glu Ala Ile Ala Phe Arg Thr Phe Ser<br>805 810 815 | 2448 |

-continued

| | | | | | | | | | | | | |
|---|---|---|---|---|---|---|---|---|---|---|---|---|
| tcg | gcc | agc | gac | gtg | tgg | agc | ttc | ggc | gtg | gtc | atg | tgg | gag | gtg | ctg | 2496 |
| Ser | Ala | Ser | Asp | Val | Trp | Ser | Phe | Gly | Val | Val | Met | Trp | Glu | Val | Leu | |
| | | 820 | | | | | 825 | | | | | 830 | | | | |

```
tcg gcc agc gac gtg tgg agc ttc ggc gtg gtc atg tgg gag gtg ctg      2496
Ser Ala Ser Asp Val Trp Ser Phe Gly Val Val Met Trp Glu Val Leu
        820                 825                 830 gcc tat ggg gag cgg ccc tac tgg aac atg acc aac cgg gat gtc atc      2544
Ala Tyr Gly Glu Arg Pro Tyr Trp Asn Met Thr Asn Arg Asp Val Ile
            835                 840                 845 agc tct gtg gag gag ggg tac cgc ctg ccc gca ccc atg ggc tgc ccc      2592
Ser Ser Val Glu Glu Gly Tyr Arg Leu Pro Ala Pro Met Gly Cys Pro
850                 855                 860 cac gcc ctg cac cag ctc atg ctc gac tgt tgg cac aag gac cgg gcg      2640
His Ala Leu His Gln Leu Met Leu Asp Cys Trp His Lys Asp Arg Ala
865                 870                 875                 880 cag cgg cct cgc ttc tcc cag att gtc agt gtc ctc gat gcg ctc atc      2688
Gln Arg Pro Arg Phe Ser Gln Ile Val Ser Val Leu Asp Ala Leu Ile
                885                 890                 895 cgc agc cct gag agt ctc agg gcc acc gcc aca gtc agc agg tgc cca      2736
Arg Ser Pro Glu Ser Leu Arg Ala Thr Ala Thr Val Ser Arg Cys Pro
            900                 905                 910 ccc cct gcc ttc gtc cgg agc tgc ttt gac ctc cga ggg ggc agc ggt      2784
Pro Pro Ala Phe Val Arg Ser Cys Phe Asp Leu Arg Gly Gly Ser Gly
        915                 920                 925 ggc ggt ggg ggc ctc acc gtg ggg gac tgg ctg gac tcc atc cgc atg      2832
Gly Gly Gly Gly Leu Thr Val Gly Asp Trp Leu Asp Ser Ile Arg Met
    930                 935                 940 ggc cgg tac cga gac cac ttc gct gcg ggc gga tac tcc tct ctg ggc      2880
Gly Arg Tyr Arg Asp His Phe Ala Ala Gly Gly Tyr Ser Ser Leu Gly
945                 950                 955                 960 atg gtg cta cgc atg aac gcc cag gac gtg cgc gcc ctg ggc atc acc      2928
Met Val Leu Arg Met Asn Ala Gln Asp Val Arg Ala Leu Gly Ile Thr
                965                 970                 975 ctc atg ggc cac cag aag aag atc ctg ggc agc att cag acc atg cgg      2976
Leu Met Gly His Gln Lys Lys Ile Leu Gly Ser Ile Gln Thr Met Arg
            980                 985                 990 gcc cag ctg acc agc acc cag ggg  ccc cgc cgg cac ctc tga             3018
Ala Gln Leu Thr Ser Thr Gln Gly  Pro Arg Arg His Leu
        995                 1000                1005

<210> SEQ ID NO 7
<211> LENGTH: 1497
<212> TYPE: DNA
<213> ORGANISM: Homo sapiens
<300> PUBLICATION INFORMATION:
<308> DATABASE ACCESSION NUMBER: U83508
<309> DATABASE ENTRY DATE: 1996-12-31
<300> PUBLICATION INFORMATION:
<302> TITLE: angiopoietin 2
<310> PATENT DOCUMENT NUMBER: U83508

<400> SEQUENCE: 7
atgacagttt tcctttcctt tgctttcctc gctgccattc tgactcacat agggtgcagc        60
aatcagcgcc gaagtccaga aaacagtggg agaagatata accggattca acatgggcaa       120
tgtgcctaca ctttcattct tccagaacac gatggcaact gtcgtgagag tacgacagac       180
cagtacaaca caaacgctct gcagagagat gctccacact ggaaccgga tttctcttcc        240 cagaaacttc aacatctgga acatgtgatg gaaaattata ctcagtggct gcaaaaactt       300
gagaattaca ttgtggaaaa catgaagtcg gagatggccc agatacagca gaatgcagtt       360
cagaaccaca ggctaccat gctggagata ggaaccagcc tcctctctca gactgcagag       420
cagaccagaa agctgacaga tgttgagacc caggtactaa atcaaactte tcgacttgag       480 atacagctgc tggagaattc attatccacc tacaagctag agaagcaact tcttcaacag       540
```

| | | |
|---|---|---|
| acaaatgaaa tcttgaagat ccatgaaaaa aacagtttat tagaacataa aatcttagaa | 600 | |
| atggaaggaa acacaagga agagttggac accttaaagg aagagaaaga gaaccttcaa | 660 | |
| ggcttggtta ctcgtcaaac atatataatc caggagctgg aaaagcaatt aaacagagct | 720 | |
| accaccaaca acagtgtcct tcagaagcag caactggagc tgatggacac agtccacaac | 780 | |
| cttgtcaatc tttgcactaa agaaggtgtt ttactaaagg gaggaaaaag agaggaagag | 840 | |
| aaaccattta gagactgtgc agatgtatat caagctggtt ttaataaaag tggaatctac | 900 | |
| actatttata ttaataatat gccagaaccc aaaaagtgt tttgcaatat ggatgtcaat | 960 | |
| gggggaggtt ggactgtaat acaacatcgt gaagatggaa gtctagattt ccaaagaggc | 1020 | |
| tggaaggaat ataaaatggg ttttggaaat ccctccggtg aatattggct ggggaatgag | 1080 | |
| tttatttttg ccattaccag tcagaggcag tacatgctaa gaattgagtt aatggactgg | 1140 | |
| gaagggaacc gagcctattc acagtatgac agattccaca taggaaatga aaagcaaaac | 1200 | |
| tataggttgt atttaaaagg tcacactggg acagcaggaa aacagagcag cctgatctta | 1260 | |
| cacggtgctg atttcagcac taaagatgct gataatgaca actgtatgtg caaatgtgcc | 1320 | |
| ctcatgttaa caggaggatg gtggtttgat gcttgtggcc cctccaatct aaatggaatg | 1380 | |
| ttctatactg cgggacaaaa ccatggaaaa ctgaatggga taaagtggca ctacttcaaa | 1440 | |
| gggcccagtt actccttacg ttccacaact atgatgattc gacctttaga tttttga | 1497 | |

<210> SEQ ID NO 8
<211> LENGTH: 3417
<212> TYPE: DNA
<213> ORGANISM: Homo sapiens
<300> PUBLICATION INFORMATION:
<310> PATENT DOCUMENT NUMBER: XM001924
<300> PUBLICATION INFORMATION:
<302> TITLE: Tie1

<400> SEQUENCE: 8

| | | |
|---|---|---|
| atggtctggc gggtgccccc tttcttgctc cccatcctct tcttggcttc tcatgtgggc | 60 | |
| gcggcgtgg acctgacgct gctggccaac ctgcggctca cggaccccca gcgcttcttc | 120 | |
| ctgacttgcg tgtctgggga ggccggggcg gggaggggct cggacgcctg ggcccgccc | 180 | |
| ctgctgctgg agaaggacga ccgtatcgtg cgcaccccgc ccgggccacc cctgcgcctg | 240 | |
| gcgcgcaacg gttcgcacca ggtcacgctt cgcggcttct ccaagccctc ggacctcgtg | 300 | |
| ggcgtcttct cctgcgtggg cggtgctggg gcgcggcgca cgcgcgtcat ctacgtgcac | 360 | |
| aacagccctg gagcccacct gcttccagac aaggtcacac acactgtgaa caaaggtgac | 420 | |
| accgctgtac tttctgcacg tgtgcacaag gagaagcaga cagacgtgat ctggaagagc | 480 | |
| aacggatcct acttctacac cctggactgg catgaagccc aggatgggcg gttcctgctg | 540 | |
| cagctcccaa atgtgcagcc accatcgagc ggcatctaca gtgccactta cctggaagcc | 600 | |
| agcccctgg gcagcgcctt ctttcggctc atcgtgcggg gttgtggggc tgggcgctgg | 660 | |
| gggccaggct gtaccaagga gtgcccaggt tgcctacatg gaggtgtctg ccacgaccat | 720 | |
| gacggcgaat gtgtatgccc ccctggcttc actggcaccc gctgtgaaca ggcctgcaga | 780 | |
| gagggccgtt ttgggcagag ctgccaggag cagtgcccag gcatatcagg ctgccggggc | 840 | |
| ctcaccttct gcctcccaga cccctatggc tgctcttgtg atctggctg agaggaagc | 900 | |
| cagtgccaag aagcttgtgc ccctggtcat tttggggctg attgccgact ccagtgccag | 960 | |
| tgtcagaatg gtggcacttg tgaccggttc agtggttgtg tctgccccctc tggggcat | 1020 | |
| ggagtgcact gtgagaagtc agaccggatc ccccagatcc tcaacatggc ctcagaactg | 1080 | |

```
gagttcaact tagagacgat gccccggatc aactgtgcag ctgcaggaa ccccttcccc      1140
gtgcggggca gcatagagct acgcaagcca gacggcactg tgctcctgtc caccaaggcc      1200
attgtggagc cagagaagac cacagctgag ttcgaggtgc cccgcttggt tcttgcggac      1260
agtgggttct gggagtgccg tgtgtccaca tctggcggcc aagacagccg gcgcttcaag      1320
gtcaatgtga aagtgccccc cgtgcccctg gctgcacctc ggctcctgac caagcagagc      1380
cgccagcttg tggtctcccc gctggtctcg ttctctgggg atggacccat ctccactgtc      1440
cgcctgcact accggcccca ggacagtacc atggactggt cgaccattgt ggtggacccc      1500
agtgagaacg tgacgttaat gaacctgagg ccaaagacag atacagtgt tcgtgtgcag      1560
ctgagccggc caggggaagg aggagagggg gcctgggggc ctcccacccct catgaccaca      1620
gactgtcctg agcctttgtt gcagccgtgg ttggagggct ggcatgtgga aggcactgac      1680
cggctgcgag tgagctggtc cttgcccttg gtgcccgggc cactggtggg cgacggtttc      1740
ctgctgcgcc tgtgggacgg gacacggggg caggagcggg gggagaacgt ctcatccccc      1800
caggcccgca ctgccctcct gacgggactc acgcctggca cccactacca gctggatgtg      1860
cagctctacc actgcaccct cctgggcccg gcctcgcccc ctgcacacgt gcttctgccc      1920
cccagtgggc ctccagcccc ccgacacctc cacgcccagg ccctctcaga ctccgagatc      1980
cagctgacat ggaagcaccc ggaggctctg cctgggccaa tatccaagta cgttgtggag      2040
gtgcaggtgg ctgggggtgc aggagaccca ctgtggatag acgtggacag gcctgaggag      2100
acaagcacca tcatccgtgg cctcaacgcc agcacgcgct accctcttccg catgcgggcc      2160
agcattcagg ggctcgggga ctggagcaac acagtagaag agtccaccct gggcaacggg      2220
ctgcaggctg agggcccagt ccaagagagc cgggcagctg aagagggcct ggatcagcag      2280
ctgatcctgg cggtggtggg ctccgtgtct gccacctgcc tcaccatcct ggctgccctt      2340
ttaaccctgg tgtgcatccg cagaagctgc ctgcatcgga gacgcacctt cacctaccag      2400
tcaggctcgg gcgaggagac catcctgcag ttcagctcag ggaccttgac acttacccgg      2460
cggccaaaac tgcagcccga gccctgagc tacccagtgc tagagtggga ggacatcacc      2520
tttgaggacc tcatcgggga ggggaacttc ggccaggtca tccgggccat gatcaagaag      2580
gacgggctga agatgaacgc agccatcaaa atgctgaaag agtatgcctc tgaaaatgac      2640
catcgtgact ttgcgggaga actggaagtt ctgtgcaaat tgggggcatca ccccaacatc      2700
atcaacctcc tgggggcctg taagaaccga ggttacttgt atatcgctat tgaatatgcc      2760
ccctacggga acctgctaga ttttctgcgg aaaagccggg tcctagagac tgacccagct      2820
tttgctcgag agcatgggac agcctctacc cttagctccc ggcagctgct gcgtttcgcc      2880
agtgatgcgg ccaatggcat gcagtacctg agtgagaagc agttcatcca cagggacctg      2940
gctgcccgga tgtgctggt cggagagaac ctggcctcca agattgcaga cttcggcctt      3000
tctcggggag aggaggttta tgtgaagaag acgatggggc gtctccctgt gcgctggatg      3060
gccattgagt ccctgaacta cagtgtctat accaccaaga gtgatgtctg gtcctttgga      3120
gtccttcttt gggagatagt gagccttgga ggtacaccct actgtggcat gacctgtgcc      3180
gagctctatg aaaagctgcc ccagggctac cgcatggagc agcctcgaaa ctgtgacgat      3240
gaagtgtacg agctgatgcg tcagtgctgg cgggaccgtc cctatgagcg accccccttt      3300
gcccagattg cgctacagct aggccgcatg ctggaagcca ggaaggccta tgtgaacatg      3360
tcgctgtttg agaacttcac ttacgcgggc attgatgcca cagctgagga ggcctga        3417
```

```
<210> SEQ ID NO 9
<211> LENGTH: 3375
<212> TYPE: DNA
<213> ORGANISM: Homo sapiens
<300> PUBLICATION INFORMATION:
<302> TITLE: TEK
<310> PATENT DOCUMENT NUMBER: L06139

<400> SEQUENCE: 9
```

| | | | | | |
|---|---|---|---|---|---|
| atggactctt | tagccagctt | agttctctgt | ggagtcagct | tgctcctttc | tggaactgtg | 60 |
| gaaggtgcca | tggacttgat | cttgatcaat | tccctacctc | ttgtatctga | tgctgaaaca | 120 |
| tctctcacct | gcattgcctc | tgggtggcgc | cccatgagc | ccatcaccat | aggaagggac | 180 |
| tttgaagcct | taatgaacca | gcaccaggat | ccgctggaag | ttactcaaga | tgtgaccaga | 240 |
| gaatgggcta | aaaagttgt | ttggaagaga | aaaaggcta | gtaagatcaa | tggtgcttat | 300 |
| ttctgtgaag | ggcgagttcg | aggagaggca | atcaggatac | gaaccatgaa | gatgcgtcaa | 360 |
| caagcttcct | tcctaccagc | tactttaact | atgactgtgg | acaagggaga | taacgtgaac | 420 |
| atatctttca | aaaaggtatt | gattaaagaa | gaagatgcag | tgatttacaa | aaatggttcc | 480 |
| ttcatccatt | cagtgccccg | gcatgaagta | cctgatattc | tagaagtaca | cctgcctcat | 540 |
| gctcagcccc | aggatgctgg | agtgtactcg | gccaggtata | taggaggaaa | cctcttcacc | 600 |
| tcggccttca | ccaggctgat | agtccggaga | tgtgaagccc | agaagtgggg | acctgaatgc | 660 |
| aaccatctct | gtactgcttg | tatgaacaat | ggtgtctgcc | atgaagatac | tggagaatgc | 720 |
| atttgccctc | tgggtttat | gggaaggacg | tgtgagaagg | cttgtgaact | gcacacgttt | 780 |
| ggcagaactt | gtaagaaag | gtgcagtgga | caagagggat | gcaagtctta | tgtgttctgt | 840 |
| ctccctgacc | cctatgggtg | ttcctgtgcc | acaggctgga | agggtctgca | gtgcaatgaa | 900 |
| gcatgccacc | ctggttttta | cgggccagat | tgtaagctta | ggtgcagctg | caacaatggg | 960 |
| gagatgtgtg | atcgcttcca | aggatgtctc | tgctctccag | gatggcaggg | gctccagtgt | 1020 |
| gagagagaag | gcataccgag | gatgacccca | aagatagtgg | atttgccaga | tcatatagaa | 1080 |
| gtaaacagtg | gtaaatttaa | tcccatttgc | aaagcttctg | gctggccgct | acctactaat | 1140 |
| gaagaaatga | ccctggtgaa | gccggatggg | acagtgctcc | atccaaaaga | ctttaaccat | 1200 |
| acggatcatt | tctcagtagc | catattcacc | atccaccgga | tcctccccc | tgactcagga | 1260 |
| gtttgggtct | gcagtgtgaa | cacagtggct | gggatggtgg | aaaagccctt | caacatttct | 1320 |
| gttaaagttc | ttccaaagcc | cctgaatgcc | ccaaacgtga | ttgacactgg | acataacttt | 1380 |
| gctgtcatca | acatcagctc | tgagccttac | tttgggatg | accaatcaa | atccaagaag | 1440 |
| cttctataca | aacccgttaa | tcactatgag | gcttggcaac | atattcaagt | gacaaatgag | 1500 |
| attgttacac | tcaactattt | ggaacctcgg | acagaatatg | aactctgtgt | gcaactggtc | 1560 |
| cgtcgtggag | agggtgggga | agggcatcct | ggacctgtga | gacgcttcac | aacagcttct | 1620 |
| atcggactcc | ctcctccaag | aggtctaaat | ctcctgccta | aagtcagac | cactctaaat | 1680 |
| ttgacctggc | aaccaatatt | tccaagctcg | gaagatgact | tttatgttga | agtggagaga | 1740 |
| aggtctgtgc | aaaaaagtga | tcagcagaat | attaaagttc | caggcaactt | gacttcggtg | 1800 |
| ctacttaaca | acttacatcc | cagggagcag | tacgtggtcc | gagctagagt | caacaccaag | 1860 |
| gcccagggg | aatggagtga | agatctcact | gcttggaccc | ttagtgacat | tcttcctcct | 1920 |
| caaccagaaa | acatcaagat | tccaacatt | acacactcct | cggctgtgat | tcttggaca | 1980 |
| atattggatg | ctattctat | ttcttctatt | actatccgtt | acaaggttca | aggcaagaat | 2040 |
| gaagaccagc | acgttgatgt | gaagataaag | aatgccacca | tcattcagta | tcagctcaag | 2100 |

-continued

| | |
|---|---|
| ggcctagagc ctgaaacagc ataccaggtg gacattttg cagagaacaa catagggtca | 2160 |
| agcaacccag cctttctca tgaactggtg accctcccag aatctcaagc caacgcggac | 2220 |
| ctcggagggg ggaagatgct gcttatagcc atccttggct ctgctggaat gacctgcctg | 2280 |
| actgtgctgt tggcctttct gatcatattg caattgaaga gggcaaatgt gcaaaggaga | 2340 |
| atggcccaag ccttccaaaa cgtgagggaa gaaccagctg tgcagttcaa ctcagggact | 2400 |
| ctggccctaa acaggaaggt caaaaacaac ccagatccta caattatcc agtgcttgac | 2460 |
| tggaatgaca tcaaattca agatgtgatt ggggagggca attttggcca agttcttaag | 2520 |
| gcgcgcatca agaaggatgg gttacggatg gatgctgcca tcaaaagaat gaaagaatat | 2580 |
| gcctccaaag atgatcacag ggactttgca ggagaactgg aagttctttg taaacttgga | 2640 |
| caccatccaa acatcatcaa tctcttagga gcatgtgaac atcgaggcta cttgtacctg | 2700 |
| gccattgagt acgcgcccca tggaaacctt ctggacttcc ttcgcaagag ccgtgtgctg | 2760 |
| gagacggacc cagcatttgc cattgccaat agcaccgcgt ccacactgtc ctcccagcag | 2820 |
| ctccttcact tcgctgccga cgtggcccgg gcatggact acttgagcca aaaacagttt | 2880 |
| atccacaggg atctggctgc cagaaacatt ttagttggtg aaaactatgt ggcaaaaata | 2940 |
| gcagattttg gattgtcccg aggtcaagag gtgtacgtga aaaagacaat gggaaggctc | 3000 |
| ccagtgcgct ggatggccat cgagtcactg aattacagtg tgtacacaac caacagtgat | 3060 |
| gtatggtcct atggtgtgtt actatgggag attgttagct taggaggcac accctactgc | 3120 |
| gggatgactt gtgcagaact ctacgagaag ctgccccagg ctacagact ggagaagccc | 3180 |
| ctgaactgtg atgatgaggt gtatgatcta atgagacaat gctggcggga aagccttat | 3240 |
| gagaggccat catttgccca gatattggtg tccttaaaca gaatgttaga ggagcgaaag | 3300 |
| acctacgtga ataccacgct ttatgagaag tttacttatg caggaattga ctgttctgct | 3360 |
| gaagaagcgg cctag | 3375 |

<210> SEQ ID NO 10
<211> LENGTH: 2400
<212> TYPE: DNA
<213> ORGANISM: Homo sapiens
<220> FEATURE:
<221> NAME/KEY: CDS
<222> LOCATION: (1)..(2397)
<300> PUBLICATION INFORMATION:
<300> PUBLICATION INFORMATION:
<302> TITLE: beta5 integrin
<310> PATENT DOCUMENT NUMBER: X53002

<400> SEQUENCE: 10

| | |
|---|---|
| atg ccg cgg gcc ccg gcg ccg ctg tac gcc tgc ctc ctg ggg ctc tgc<br>Met Pro Arg Ala Pro Ala Pro Leu Tyr Ala Cys Leu Leu Gly Leu Cys<br>1               5                   10                  15 | 48 |
| gcg ctc ctg ccc cgg ctc gca ggt ctc aac ata tgc act agt gga agt<br>Ala Leu Leu Pro Arg Leu Ala Gly Leu Asn Ile Cys Thr Ser Gly Ser<br>        20                  25                  30 | 96 |
| gcc acc tca tgt gaa gaa tgt ctg cta atc cac cca aaa tgt gcc tgg<br>Ala Thr Ser Cys Glu Glu Cys Leu Leu Ile His Pro Lys Cys Ala Trp<br>    35                  40                  45 | 144 |
| tgc tcc aaa gag gac ttc gga agc cca cgg tcc atc acc tct cgg tgt<br>Cys Ser Lys Glu Asp Phe Gly Ser Pro Arg Ser Ile Thr Ser Arg Cys<br>50                  55                  60 | 192 |
| gat ctg agg gca aac ctt gtc aaa aat ggc tgt gga ggt gag ata gag<br>Asp Leu Arg Ala Asn Leu Val Lys Asn Gly Cys Gly Gly Glu Ile Glu<br>65                  70                  75                  80 | 240 |
| agc cca gcc agc agc ttc cat gtc ctg agg agc ctg ccc ctc agc agc<br>Ser Pro Ala Ser Ser Phe His Val Leu Arg Ser Leu Pro Leu Ser Ser | 288 |

-continued

```
Ser Pro Ala Ser Ser Phe His Val Leu Arg Ser Leu Pro Leu Ser Ser
             85                  90                  95 aag ggt tcg ggc tct gca ggc tgg gac gtc att cag atg aca cca cag      336
Lys Gly Ser Gly Ser Ala Gly Trp Asp Val Ile Gln Met Thr Pro Gln
            100                 105                 110 gag att gcc gtg aac ctc cgg ccc ggt gac aag acc acc ttc cag cta      384
Glu Ile Ala Val Asn Leu Arg Pro Gly Asp Lys Thr Thr Phe Gln Leu
            115                 120                 125 cag gtt cgc cag gtg gag gac tat cct gtg gac ctg tac tac ctg atg      432
Gln Val Arg Gln Val Glu Asp Tyr Pro Val Asp Leu Tyr Tyr Leu Met
        130                 135                 140 gac ctc tcc ctg tcc atg aag gat gac ttg gac aat atc cgg agc ctg      480
Asp Leu Ser Leu Ser Met Lys Asp Asp Leu Asp Asn Ile Arg Ser Leu
145                 150                 155                 160 ggc acc aaa ctc gcg gag gag atg agg aag ctc acc agc aac ttc cgg      528
Gly Thr Lys Leu Ala Glu Glu Met Arg Lys Leu Thr Ser Asn Phe Arg
                165                 170                 175 ttg gga ttt ggg tct ttt gtt gat aag gac atc tct cct ttc tcc tac      576
Leu Gly Phe Gly Ser Phe Val Asp Lys Asp Ile Ser Pro Phe Ser Tyr
            180                 185                 190 acg gca ccg agg tac cag acc aat ccg tgc att ggt tac aag ttg ttt      624
Thr Ala Pro Arg Tyr Gln Thr Asn Pro Cys Ile Gly Tyr Lys Leu Phe
        195                 200                 205 cca aat tgc gtc ccc tcc ttt ggg ttc cgc cat ctg ctg cct ctc aca      672
Pro Asn Cys Val Pro Ser Phe Gly Phe Arg His Leu Leu Pro Leu Thr
    210                 215                 220 gac aga gtg gac agc ttc aat gag gaa gtt cgg aaa cag agg gtg tcc      720
Asp Arg Val Asp Ser Phe Asn Glu Glu Val Arg Lys Gln Arg Val Ser
225                 230                 235                 240 cgg aac cga gat gcc cct gag ggg ggc ttt gat gca gta ctc cag gca      768
Arg Asn Arg Asp Ala Pro Glu Gly Gly Phe Asp Ala Val Leu Gln Ala
                245                 250                 255 gcc gtc tgc aag gag aag att ggc tgg cga aag gat gca ctg cat ttg      816
Ala Val Cys Lys Glu Lys Ile Gly Trp Arg Lys Asp Ala Leu His Leu
            260                 265                 270 ctg gtg ttc aca aca gat gat gtg ccc cac atc gca ttg gat gga aaa      864
Leu Val Phe Thr Thr Asp Asp Val Pro His Ile Ala Leu Asp Gly Lys
        275                 280                 285 ttg gga ggc ctg gtg cag cca cac gat ggc cag tgc cac ctg aac gag      912
Leu Gly Gly Leu Val Gln Pro His Asp Gly Gln Cys His Leu Asn Glu
    290                 295                 300 gcc aac gag tac aca gca tcc aac cag atg gac tat cca tcc ctt gcc      960
Ala Asn Glu Tyr Thr Ala Ser Asn Gln Met Asp Tyr Pro Ser Leu Ala
305                 310                 315                 320 ttg ctt gga gag aaa ttg gca gag aac aac atc aac ctc atc ttt gca      1008
Leu Leu Gly Glu Lys Leu Ala Glu Asn Asn Ile Asn Leu Ile Phe Ala
                325                 330                 335 gtg aca aaa aac cat tat atg ctg tac aag aat ttt aca gcc ctg ata      1056
Val Thr Lys Asn His Tyr Met Leu Tyr Lys Asn Phe Thr Ala Leu Ile
            340                 345                 350 cct gga aca acg gtg gag att tta gat gga gac tcc aaa aat att att      1104
Pro Gly Thr Thr Val Glu Ile Leu Asp Gly Asp Ser Lys Asn Ile Ile
        355                 360                 365 caa ctg att att aat gca tac aat agt atc cgg tct aaa gtg gag ttg      1152
Gln Leu Ile Ile Asn Ala Tyr Asn Ser Ile Arg Ser Lys Val Glu Leu
    370                 375                 380 tca gtc tgg gat cag cct gag gat ctt aat ctc ttc ttt act gct acc      1200
Ser Val Trp Asp Gln Pro Glu Asp Leu Asn Leu Phe Phe Thr Ala Thr
385                 390                 395                 400 tgc caa gat ggg gta tcc tat cct ggt cag agg aag tgt gag ggt ctg      1248
```

```
Cys Gln Asp Gly Val Ser Tyr Pro Gly Gln Arg Lys Cys Glu Gly Leu
            405                 410                 415 aag att ggg gac acg gca tct ttt gaa gta tca ttg gag gcc cga agc    1296
Lys Ile Gly Asp Thr Ala Ser Phe Glu Val Ser Leu Glu Ala Arg Ser
            420                 425                 430 tgt ccc agc aga cac acg gag cat gtg ttt gcc ctg cgg ccg gtg gga    1344
Cys Pro Ser Arg His Thr Glu His Val Phe Ala Leu Arg Pro Val Gly
            435                 440                 445 ttc cgg gac agc ctg gag gtg ggg gtc acc tac aac tgc acg tgc ggc    1392
Phe Arg Asp Ser Leu Glu Val Gly Val Thr Tyr Asn Cys Thr Cys Gly
            450                 455                 460 tgc agc gtg ggg ctg gaa ccc aac agc gcc agg tgc aac ggg agc ggg    1440
Cys Ser Val Gly Leu Glu Pro Asn Ser Ala Arg Cys Asn Gly Ser Gly
465                 470                 475                 480 acc tat gtc tgc ggc ctg tgt gag tgc agc ccc ggc tac ctg ggc acc    1488
Thr Tyr Val Cys Gly Leu Cys Glu Cys Ser Pro Gly Tyr Leu Gly Thr
                485                 490                 495 agg tgc gag tgc cag gat ggg gag aac cag agc gtg tac cag aac ctg    1536
Arg Cys Glu Cys Gln Asp Gly Glu Asn Gln Ser Val Tyr Gln Asn Leu
            500                 505                 510 tgc cgg gag gca gag ggc aag cca ctg tgc agc ggg cgt ggg gac tgc    1584
Cys Arg Glu Ala Glu Gly Lys Pro Leu Cys Ser Gly Arg Gly Asp Cys
            515                 520                 525 agc tgc aac cag tgc tcc tgc ttc gag agc gag ttt ggc aag atc tat    1632
Ser Cys Asn Gln Cys Ser Cys Phe Glu Ser Glu Phe Gly Lys Ile Tyr
            530                 535                 540 ggg cct ttc tgt gag tgc gac aac ttc tcc tgt gcc agg aac aag gga    1680
Gly Pro Phe Cys Glu Cys Asp Asn Phe Ser Cys Ala Arg Asn Lys Gly
545                 550                 555                 560 gtc ctc tgc tca ggc cat ggc gag tgt cac tgc ggg gaa tgc aag tgc    1728
Val Leu Cys Ser Gly His Gly Glu Cys His Cys Gly Glu Cys Lys Cys
                565                 570                 575 cat gca ggt tac atc ggg gac aac tgt aac tgc tcg aca gac atc agc    1776
His Ala Gly Tyr Ile Gly Asp Asn Cys Asn Cys Ser Thr Asp Ile Ser
            580                 585                 590 aca tgc cgg ggc aga gat ggc cag atc tgc agc gag cgt ggg cac tgt    1824
Thr Cys Arg Gly Arg Asp Gly Gln Ile Cys Ser Glu Arg Gly His Cys
            595                 600                 605 ctc tgt ggg cag tgc caa tgc acg gag ccg ggg gcc ttt ggg gag atg    1872
Leu Cys Gly Gln Cys Gln Cys Thr Glu Pro Gly Ala Phe Gly Glu Met
            610                 615                 620 tgt gag aag tgc ccc acc tgc ccg gat gca tgc agc acc aag aga gat    1920
Cys Glu Lys Cys Pro Thr Cys Pro Asp Ala Cys Ser Thr Lys Arg Asp
625                 630                 635                 640 tgc gtc gag tgc ctg ctg ctc cac tct ggg aaa cct gac aac cag acc    1968
Cys Val Glu Cys Leu Leu Leu His Ser Gly Lys Pro Asp Asn Gln Thr
                645                 650                 655 tgc cac agc cta tgc agg gat gag gtg atc aca tgg gtg gac acc atc    2016
Cys His Ser Leu Cys Arg Asp Glu Val Ile Thr Trp Val Asp Thr Ile
            660                 665                 670 gtg aaa gat gac cag gag gct gtg cta tgt ttc tac aaa acc gcc aag    2064
Val Lys Asp Asp Gln Glu Ala Val Leu Cys Phe Tyr Lys Thr Ala Lys
            675                 680                 685 gac tgc gtc atg atg ttc acc tat gtg gag ctc ccc agt ggg aag tcc    2112
Asp Cys Val Met Met Phe Thr Tyr Val Glu Leu Pro Ser Gly Lys Ser
            690                 695                 700 aac ctg acc gtc ctc agg gag cca gag tgt gga aac acc ccc aac gcc    2160
Asn Leu Thr Val Leu Arg Glu Pro Glu Cys Gly Asn Thr Pro Asn Ala
705                 710                 715                 720 atg acc atc ctc ctg gct gtg gtc ggt agc atc ctc ctt gtt ggg ctt    2208
```

|  |  |  |  |  |  |  |  |  |  |  |  |  |
|---|---|---|---|---|---|---|---|---|---|---|---|---|
| Met | Thr | Ile | Leu | Leu | Ala | Val | Val | Gly | Ser | Ile | Leu | Leu | Val | Gly | Leu |
|  |  |  | 725 |  |  |  |  | 730 |  |  |  |  | 735 |  |  |

```
gca ctc ctg gct atc tgg aag ctg ctt gtc acc atc cac gac cgg agg      2256
Ala Leu Leu Ala Ile Trp Lys Leu Leu Val Thr Ile His Asp Arg Arg
            740                 745                 750 gag ttt gca aag ttt cag agc gag cga tcc agg gcc cgc tat gaa atg      2304
Glu Phe Ala Lys Phe Gln Ser Glu Arg Ser Arg Ala Arg Tyr Glu Met
            755                 760                 765 gct tca aat cca tta tac aga aag cct atc tcc acg cac act gtg gac      2352
Ala Ser Asn Pro Leu Tyr Arg Lys Pro Ile Ser Thr His Thr Val Asp
            770                 775                 780 ttc acc ttc aac aag ttc aac aaa tcc tac aat ggc act gtg gac tga      2400
Phe Thr Phe Asn Lys Phe Asn Lys Ser Tyr Asn Gly Thr Val Asp
785                 790                 795

<210> SEQ ID NO 11
<211> LENGTH: 2367
<212> TYPE: DNA
<213> ORGANISM: Homo sapiens
<300> PUBLICATION INFORMATION:
<302> TITLE: beta3 integrin
<310> PATENT DOCUMENT NUMBER: NM000212

<400> SEQUENCE: 11
atgcgagcgc ggccgcggcc ccggccgctc tgggcgactg tgctggcgct ggggcgctg      60 gcgggcgttg gcgtaggagg gcccaacatc tgtaccacgc gaggtgtgag ctcctgccag     120
cagtgcctgg ctgtgagccc catgtgtgcc tggtgctctg atgaggccct gcctctgggc     180
tcacctcgct gtgacctgaa ggagaatctg ctgaaggata ctgtgcccc agaatccatc      240 gagttcccag tgagtgaggc ccgagtacta gaggacaggc ccctcagcga caagggctct     300
ggagacagct cccaggtcac tcaagtcagt ccccagagga ttgcactccg gctccggcca     360
gatgattcga gaatttctc catccaagtc cggcaggtgg aggattaccc tgtggacatc      420
tactacttga tggacctgtc ttactccatg aaggatgatc tgtggagcat ccagaacctg     480
ggtaccaagc tggccaccca gatgcgaaag ctcaccagta acctgcggat tggcttcggg     540
gcatttgtgg acaagcctgt gtcaccatac atgtatatct ccccaccaga ggccctcgaa     600
aaccccctgc tatgatatga gaccaccctgc ttgcccatgt ttggctacaa acacgtgctg    660
acgctaactg accaggtgac ccgcttcaat gaggaagtga gaagcagag tgtgtcacgg      720 aaccgagatg ccccagaggg tggctttgat gccatcatgc aggctacagt ctgtgatgaa     780
aagattggct ggaggaatga tgcatccac ttgctggtgt ttaccactga tgccaagact      840
catatagcat tggacggaag gctggcaggc attgtccagc taatgacgg gcagtgtcat      900 gttggtagtg acaatcatta ctctgcctcc actaccatgg attatccct tttgggggctg    960 atgactgaga agctatccca gaaaaacatc aatttgatct ttgcagtgac tgaaaatgta    1020
gtcaatctct atcagaacta tagtgagctc atcccaggga ccacagttgg ggttctgtcc    1080
atggattcca gcaatgtcct ccagctcatt gttgatgctt atgggaaaat ccgttctaaa    1140
gtagagctgg aagtgcgtga cctccctgaa gagttgtctc tatccttcaa tgccacctgc    1200
ctcaacaatg aggtcatccc tggcctcaag tcttgtatgg gactcaagat ggagacacg     1260 gtgagcttca gcattgaggc caaggtgcga ggctgtcccc aggagaagga gaagtccttt    1320
accataaagc ccgtgggctt caaggacagc ctgatcgtcc aggtcacctt tgattgtgac    1380
tgtgcctgcc aggcccaagc tgaacctaat agccatcgct gcaacaatgg caatgggacc    1440
tttgagtgtg gggtatgccg ttgtgggcct ggctggctgg atcccagtg tgagtgctca    1500
```

| | |
|---|---|
| gaggaggact atcgcccttc ccagcaggac gaatgcagcc cccggggaggg tcagcccgtc | 1560 |
| tgcagccagc ggggcgagtg cctctgtggt caatgtgtct gccacagcag tgactttggc | 1620 |
| aagatcacgg gcaagtactg cgagtgtgac gacttctcct gtgtccgcta caaggggag | 1680 |
| atgtgctcag gccatggcca gtgcagctgt ggggactgcc tgtgtgactc cgactggacc | 1740 |
| ggctactact gcaactgtac cacgcgtact gacacctgca tgtccagcaa tgggctgctg | 1800 |
| tgcagcggcc gcggcaagtg tgaatgtggc agctgtgtct gtatccagcc gggctcctat | 1860 |
| ggggacacct gtgagaagtg ccccaccctgc ccagatgcct gcacctttaa gaaagaatgt | 1920 |
| gtggagtgta agaagtttga ccgggagccc tacatgaccg aaaataccctg caaccgttac | 1980 |
| tgccgtgacg agattgagtc agtgaaagag cttaaggaca ctggcaagga tgcagtgaat | 2040 |
| tgtacctata agaatgagga tgactgtgtc gtcagattcc agtactatga agattctagt | 2100 |
| ggaaagtcca tcctgtatgt ggtagaagag ccagagtgtc ccaagggccc tgacatcctg | 2160 |
| gtggtcctgc tctcagtgat gggggccatt ctgctcattg ccttgccgc cctgctcatc | 2220 |
| tggaaactcc tcatcaccat ccacgaccga aaagaattcg ctaaatttga ggaagaacgc | 2280 |
| gccagagcaa atgggacac agccaacaac ccactgtata agaggccac gtctaccttc | 2340 |
| accaatatca cgtaccgggg cacttaa | 2367 |

<210> SEQ ID NO 12
<211> LENGTH: 3147
<212> TYPE: DNA
<213> ORGANISM: Homo sapiens
<300> PUBLICATION INFORMATION:
<302> TITLE: alpha v intergrin
<310> PATENT DOCUMENT NUMBER: NM0022210

<400> SEQUENCE: 12

| | |
|---|---|
| atggcttttc cgccgcggcg acggctgcgc ctcggtcccc gcggcctccc gcttcttctc | 60 |
| tcgggactcc tgctacctct gtgccgcgcc ttcaacctag acgtggacag tcctgccgag | 120 |
| tactctggcc ccgagggaag ttacttcggc ttcgccgtgg atttcttcgt gcccagcgcg | 180 |
| tcttcccgga tgtttcttct cgtgggagct cccaaagcaa acaccaccca gcctgggatt | 240 |
| gtggaaggag ggcaggtcct caaatgtgac tggtcttcta cccgccggtg ccagccaatt | 300 |
| gaatttgatg caacaggcaa tagagattat gccaaggatg atccattgga atttaagtcc | 360 |
| catcagtggt ttggagcatc tgtgaggtcg aaacaggata aaattttggc ctgtgcccca | 420 |
| ttgtaccatt ggagaactga gatgaaacag gagcgagagc tgttggaac atgctttctt | 480 |
| caagatggaa caaagactgt tgagtatgct ccatgtagat cacaagatat tgatgctgat | 540 |
| ggacagggat tttgtcaagg aggattcagc attgatttta ctaaagctga cagagtactt | 600 |
| cttggtggtc ctggtagctt ttattggcaa ggtcagctta tttcggatca agtggcagaa | 660 |
| atcgtatcta aatacgaccc caatgtttac agcatcaagt ataataacca attagcaact | 720 |
| cggactgcac aagctatttt tgatgacagc tatttgggtt attctgtggc tgtcggagat | 780 |
| ttcaatggtg atggcataga tgactttgtt tcaggagttc caagagcagc aaggactttg | 840 |
| ggaatggttt atatttatga tggaagaaac atgtcctcct tatacaattt tactggcgag | 900 |
| cagatggctg catattttcgg attttctgta gctgccactg acattaatgg agatgattat | 960 |
| gcagatgtgt ttattggagc acctctcttc atggatcgtg gctctgatgg caaactccaa | 1020 |
| gaggtggggc aggtctcagt gtctctacag agagcttcag gagacttcca gacgacaaag | 1080 |
| ctgaatggat tgaggtctt tgcacggttt ggcagtgcca gctcctttt gggagatctg | 1140 |
| gaccaggatg gtttcaatga tattgcaatt gctgctccat atgggggtga agataaaaaa | 1200 |

```
ggaattgttt atatcttcaa tggaagatca acaggcttga acgcagtccc atctcaaatc    1260
cttgaagggc agtgggctgc tcgaagcatg ccaccaagct ttggctattc aatgaaagga    1320
gccacagata tagacaaaaa tggatatcca gacttaattg taggagcttt tggtgtagat    1380
cgagctatct tatacagggc cagaccagtt atcactgtaa atgctggtct tgaagtgtac    1440
cctagcattt taaatcaaga caataaaacc tgctcactgc ctggaacagc tctcaaagtt    1500
tcctgtttta atgttaggtt ctgcttaaag gcagatggca aaggagtact tcccaggaaa    1560
cttaatttcc aggtggaact tcttttggat aaactcaagc aaaagggagc aattcgacga    1620
gcactgtttc tctacagcag gtccccaagt cactccaaga acatgactat ttcaaggggg    1680
ggactgatgc agtgtgagga attgatagcg tatctgcggg atgaatctga atttagagac    1740
aaactcactc caattactat tttatatgaa tatcggttgg attatagaac agctgctgat    1800
acaacaggct tgcaacccat tcttaaccag ttcacgcctg ctaacattag tcgacaggct    1860
cacattctac ttgactgtgg tgaagacaat gtctgtaaac ccaagctgga agtttctgta    1920
gatagtgatc aaaagaagat ctatattggg gatgacaacc ctctgacatt gattgttaag    1980
gctcagaatc aaggagaagg tgcctacgaa gctgagctca tcgtttccat tccactgcag    2040
gctgatttca tcggggttgt ccgaaacaat gaagccttag caagactttc ctgtgcattt    2100
aagacagaaa accaaactcg ccaggtggta tgtgaccttg aaacccaat gaaggctgga    2160 actcaactct tagctggtct tcgtttcagt gtgcaccagc agtcagagat ggatacttct    2220
gtgaaatttg acttacaaat ccaaagctca aatctatttg acaaagtaag cccagttgta    2280
tctcacaaag ttgatcttgc tgttttagct gcagttgaga taagaggagt ctcgagtcct    2340
gatcatatct ttcttccgat tccaaactgg gagcacaagg agaaccctga gactgaagaa    2400
gatgttgggc cagttgttca gcacatctat gagctgagaa acaatggtcc aagttcattc    2460
agcaaggcaa tgctccatct tcagtggcct tacaaatata ataataacac tctgttgtat    2520
atccttcatt atgatattga tggaccaatg aactgcactt cagatatgga gatcaaccct    2580
ttgagaatta agatctcatc tttgcaaaca actgaaaaga atgacacggt tgccgggcaa    2640
ggtgagcggg accatctcat cactaagcgg gatcttgccc tcagtgaagg agatattcac    2700
actttgggtt gtggagttgc tcagtgcttg aagattgtct gccaagttgg gagattagac    2760
agaggaaaga gtgcaatctt gtacgtaaag tcattactgt ggactgagac ttttatgaat    2820
aaagaaaatc agaatcattc ctattctctg aagtcgtctg cttcatttaa tgtcatagag    2880
tttccttata agaatcttcc aattgaggat atcaccaact ccacattggt taccactaat    2940
gtcacctggg gcattcagcc agcgcccatg cctgtgcctg tgtgggtgat cattttagca    3000
gttctagcag gattgttgct actggctgtt ttggtatttg taatgtacag gatgggcttt    3060
tttaaacggg tccggccacc tcaagaagaa caagaaaggg agcagcttca acctcatgaa    3120
aatggtgaag gaaactcaga aacttaa                                       3147
```

<210> SEQ ID NO 13
<211> LENGTH: 402
<212> TYPE: DNA
<213> ORGANISM: Homo sapiens
<300> PUBLICATION INFORMATION:
<302> TITLE: CaSm (cancer associated SM-like oncogene)
<310> PATENT DOCUMENT NUMBER: AF000177

<400> SEQUENCE: 13

```
atgaactata tgcctggcac cgccagcctc atcgaggaca ttgacaaaaa gcacttggtt    60
```

```
ctgcttcgag atggaaggac acttataggc ttttttaagaa gcattgatca atttgcaaac    120
ttagtgctac atcagactgt ggagcgtatt catgtgggca aaaaatacgg tgatattcct    180
cgagggattt ttgtggtcag aggagaaaat gtggtcctac taggagaaat agacttggaa    240
aaggagagtg acacacccct ccagcaagta tccattgaag aaattctaga agaacaaagg    300
gtggaacagc agaccaagct ggaagcagag aagttgaaag tgcaggccct gaaggaccga    360
ggtctttcca ttcctcgagc agatactctt gatgagtact aa                      402
```

<210> SEQ ID NO 14
<211> LENGTH: 1923
<212> TYPE: DNA
<213> ORGANISM: Homo sapiens
<300> PUBLICATION INFORMATION:
<302> TITLE: c-myb
<310> PATENT DOCUMENT NUMBER: NM005375

<400> SEQUENCE: 14

```
atggcccgaa gaccccggca cagcatatat agcagtgacg aggatgatga ggactttgag     60
atgtgtgacc atgactatga tgggctgctt cccaagtctg gaaagcgtca cttggggaaa    120
acaaggtgga cccgggaaga ggatgaaaaa ctgaagaagc tggtggaaca gaatggaaca    180
gatgactgga agttattgc caattatctc ccgaatcgaa cagatgtgca gtgccagcac    240
cgatggcaga aagtactaaa ccctgagctc atcaagggtc cttggaccaa agaagaagat    300
cagagagtga tagagcttgt acagaaatac ggtccgaaac gttggtctgt tattgccaag    360
cacttaaagg ggagaattgg aaaacaatgt agggagaggg gcataaacca cttgaatcca    420
gaagttaaga aaacctcctg gacagaagag gaagacagaa ttatttacca ggcacacaag    480
agactgggga cagatgggc agaaatcgca aagctactgc ctggacgaac tgataatgct    540
atcaagaacc actggaattc tacaatgcgt cggaaggtcg aacaggaagg ttatctgcag    600
gagtcttcaa aagccagcca gccagcagtg gccacaagct tccagaagaa cagtcatttg    660
atgggttttg ctcaggctcc gcctacagct caactccctg ccactggcca gcccactgtt    720
aacaacgact attcctatta ccacatttct gaagcacaaa atgtctccag tcatgttcca    780
taccctgtag cgttacatgt aaatatagtc aatgtccctc agccagctgc cgcagccatt    840
cagagacact ataatgatga agaccctgag aaggaaaagc gaataaagga attagaattg    900
ctcctaatgt caaccgagaa tgagctaaaa ggacagcagg tgctaccaac acagaaccac    960
acatgcagct accccgggtg gcacagcacc accattgccg accacaccag acctcatgga   1020
gacagtgcac ctgtttcctg tttgggagaa caccactcca ctccatctct gccagcggat   1080
cctggctccc tacctgaaga aagcgcctcg ccagcaaggt gcatgatcgt ccaccagggc   1140
accattctgg ataatgttaa gaacctctta gaatttgcag aaacactcca atttatagat   1200
tctttcttaa acacttccag taaccatgaa aactcagact ggaaaatgcc ttctttaact   1260
tccacccccc tcattggtca caaattgact gttacaacac catttcatag agaccagact   1320
gtgaaaactc aaaaggaaaa tactgttttt agaaccccag ctatcaaaag gtcaatctta   1380
gaaagctctc caagaactcc tacaccattc aaacatgcac ttgcagctca agaaattaaa   1440
tacggtcccc tgaagatgct acctcagaca ccctctcatc tagtagaaga tctgcaggat   1500
gtgatcaaac aggaatctga tgaatctgga tttgttgctg agtttcaaga aaatggacca   1560
cccttactga gaaaaatcaa acaagaggtg gaatctccaa ctgataaatc aggaaacttc   1620
ttctgctcac accactggga aggggacagt ctgaataccc aactgttcac gcagacctcg   1680
cctgtgcgag atgcaccgaa tattcttaca agctccgttt taatggcacc agcatcagaa   1740
```

```
gatgaagaca atgttctcaa agcatttaca gtacctaaaa acaggtccct ggcgagcccc    1800
ttgcagcctt gtagcagtac ctgggaacct gcatcctgtg gaaagatgga ggagcagatg    1860
acatcttcca gtcaagctcg taaatacgtg aatgcattct cagcccggac gctggtcatg    1920
tga                                                                  1923

<210> SEQ ID NO 15
<211> LENGTH: 544
<212> TYPE: DNA
<213> ORGANISM: Homo sapiens
<300> PUBLICATION INFORMATION:
<302> TITLE: c-myc
<310> PATENT DOCUMENT NUMBER: J00120

<400> SEQUENCE: 15 gaccccgag ctgtgctgct cgcggccgcc accgccgggc cccggccgtc cctggctccc      60
ctcctgcctc gagaagggca gggcttctca gaggcttggc gggaaaaaga acggaggga    120 ggatcgcgct gagtataaaa gccggttttc ggggctttat ctaactcgct gtagtaattc    180
cagcgagagg cagaggggagc gagcgggcgg ccggctaggg tggaagagcc gggcgagcag    240
agctgcgctg cgggcgtcct gggaagggag atccggagcg aatagggggc ttcgcctctg    300
gcccagccct cccgctgatc ccccagccag cggtccgcaa cccttgccgc atccacgaaa    360
ctttgcccat agcagcgggc gggcactttg cactggaact acaacacccc gagcaaggac    420
gcgactctcc cgacgcgggg aggctattct gcccatttgg ggacacttcc ccgccgctgc    480
caggacccgc ttctctgaaa ggctctcctt gcagctgctt agacgctgga ttttttcgg    540 gtag                                                                 544

<210> SEQ ID NO 16
<211> LENGTH: 618
<212> TYPE: DNA
<213> ORGANISM: Homo sapiens
<300> PUBLICATION INFORMATION:
<302> TITLE: ephrin-A1
<310> PATENT DOCUMENT NUMBER: NM004428

<400> SEQUENCE: 16
atggagttcc tctgggcccc tctcttgggt ctgtgctgca gtctggccgc tgctgatcgc     60
cacaccgtct tctggaacag ttcaaatccc aagttccgga atgaggacta caccatacat    120
gtgcagctga atgactacgt ggacatcatc tgtccgcact atgaagatca ctctgtggca    180
gacgctgcca tggagcagta catactgtac ctggtggagc atgaggagta ccagctgtgc    240
cagccccagt ccaaggacca agtccgctgg cagtgcaacc ggcccagtgc caagcatggc    300
ccggagaagc tgtctgagaa gttccagcgc ttcacacctt tcaccctggg caaggagttc    360
aaagaaggac acagctacta ctacatctcc aaacccatcc accagcatga agaccgctgc    420
ttgaggttga aggtgactgt cagtggcaaa atcactcaca gtcctcaggc ccatgtcaat    480
ccacaggaga agagacttgc agcagatgac ccagaggtgc gggttctaca tagcatcggt    540
cacagtgctg ccccacgcct cttcccactt gcctggactg tgctgctcct tccacttctg    600
ctgctgcaaa ccccgtga                                                  618

<210> SEQ ID NO 17
<211> LENGTH: 642
<212> TYPE: DNA
<213> ORGANISM: Homo sapiens

<400> SEQUENCE: 17
```

```
atggcgcccg cgcagcgccc gctgctcccg ctgctgctcc tgctgttacc gctgccgccg      60
ccgcccttcg cgcgcgccga ggacgccgcc cgcgccaact cggaccgcta cgccgtctac     120
tggaaccgca gcaaccccag gttccacgca ggcgcggggg acgacggcgg gggctacacg     180
gtggaggtga gcatcaatga ctacctggac atctactgcc cgcactatgg ggcgccgctg     240
ccgccggccg agcgcatgga gcactacgtg ctgtacatgg tcaacggcga gggccacgcc     300
tcctgcgacc accgccagcg cggcttcaag cgctgggagt gcaaccggcc cgcggcgccc     360 gggggccgc tcaagttctc ggagaagttc cagctcttca cgcccttctc cctgggcttc     420
gagttccggc ccgccacgga gtattactac atctctgcca cgcctcccaa tgctgtggac     480
cggccctgcc tgcgactgaa ggtgtacgtg cggccgacca cgagaccct gtacgaggct     540 cctgagccca tcttcaccag caataactcg tgtagcagcc cgggcggctg ccgcctcttc     600
ctcagcacca tccccgtgct ctggaccctc ctgggttcct ag                       642

<210> SEQ ID NO 18
<211> LENGTH: 717
<212> TYPE: DNA
<213> ORGANISM: Homo sapiens
<300> PUBLICATION INFORMATION:
<302> TITLE: ephrin-A3
<310> PATENT DOCUMENT NUMBER: XM001787

<400> SEQUENCE: 18
atggcggcgg ctccgctgct gctgctgctg ctgctcgtgc ccgtgccgct gctgccgctg      60
ctggcccaag ggcccggagg ggcgctggga aaccggcatg cggtgtactg aacagctcc     120 aaccagcacc tgcggcgaga gggctacacc gtgcaggtga acgtgaacga ctatctggat     180
atttactgcc cgcactacaa cagctcgggg gtgggcccccg ggcgggacc ggggcccgga     240 ggcggggcag agcagtacgt gctgtacatg gtgagccgca acggctaccg cacctgcaac     300
gccagccagg gcttcaagcg ctgggagtgc aaccggccgc acgccccgca cagccccatc     360
aagttctcgg agaagttcca gcgctacagc gccttctctc tgggctacga gttccacgcc     420
ggccacgagt actactacat ctccacgccc actcacaacc tgcactggaa gtgtctgagg     480
atgaaggtgt tcgtctgctg cgcctccaca tcgcactccg gggagaagcc ggtccccact     540
ctcccccagt tcaccatggg ccccaatatg aagatcaacg tgctggaaga ctttgaggga     600
gagaaccctc aggtgcccaa gcttgagaag agcatcagcg ggaccagccc caaacgggaa     660
cacctgcccc tggccgtggg catcgccttc ttcctcatga cgttcttggc ctcctag       717

<210> SEQ ID NO 19
<211> LENGTH: 606
<212> TYPE: DNA
<213> ORGANISM: Homo sapiens
<300> PUBLICATION INFORMATION:
<302> TITLE: ephrin-A3
<310> PATENT DOCUMENT NUMBER: XM001784

<400> SEQUENCE: 19
atgcggctgc tgccctgct gcggactgtc ctctgggccg cgttcctcgg ctcccctctg      60
cgcgggggct ccagcctccg ccacgtagtc tactggaact ccagtaaccc caggttgctt     120
cgaggagacg ccgtggtgga gctgggcctc aacgattacc tagacattgt ctgcccccac     180
tacgaaggcc cagggccccc tgagggcccc gagacgtttg cttttgtacat ggtggactgg     240 ccaggctatg agtcctgcca ggcagagggc ccccggccct acaagcgctg gtgtgctcc     300 ctgccctttg ccatgttcca attctcagag aagattcagc gcttcacacc cttctcccctc     360
```

```
ggctttgagt tcttacctgg agagacttac tactacatct cggtgcccac tccagagagt    420
tctggccagt gcttgaggct ccaggtgtct gtctgctgca aggagaggaa gtctgagtca    480
gcccatcctg ttgggagccc tgagagagt ggcacatcag ggtggcgagg ggggacact     540 cccagccccc tctgtctctt gctattactg ctgcttctga ttcttcgtct ctgcgaatt    600 ctgtga                                                              606
```

<210> SEQ ID NO 20
<211> LENGTH: 687
<212> TYPE: DNA
<213> ORGANISM: Homo sapiens
<300> PUBLICATION INFORMATION:
<302> TITLE: ephrin-A5
<310> PATENT DOCUMENT NUMBER: NM001962

<400> SEQUENCE: 20

```
atgttgcacg tggagatgtt gacgctggtg tttctggtgc tctggatgtg tgtgttcagc     60
caggacccgg gctccaaggc cgtcgccgac cgctacgctg tctactggaa cagcagcaac    120
cccagattcc agaggggtga ctaccatatt gatgtctgta tcaatgacta cctggatgtt    180
ttctgccctc actatgagga ctccgtccca gaagataaga ctgagcgcta tgtcctctac    240
atggtgaact tgatggcta cagtgcctgc gaccacactt ccaaagggtt caagagatgg    300
gaatgtaacc ggcctcactc tccaaatgga ccgctgaagt tctctgaaaa attccagctc    360
ttcactccct tttctctagg atttgaattc aggccaggcc gagaatattt ctacatctcc    420
tctgcaatcc cagataatgg aagaaggtcc tgtctaaagc tcaaagtctt tgtgagacca    480
acaaatagct gtatgaaaac tataggtgtt catgatcgtg ttttcgatgt aacgacaaa    540 gtagaaaatt cattagaacc agcagatgac accgtacatg agtcagccga gcatcccgc    600 ggcgagaacg cggcacaaac accaaggata cccagccgcc ttttggcaat cctactgttc    660
ctcctggcga tgcttttgac attatag                                       687
```

<210> SEQ ID NO 21
<211> LENGTH: 2955
<212> TYPE: DNA
<213> ORGANISM: Homo sapiens

<400> SEQUENCE: 21

```
atggccctgg attatctact actgctcctc ctggcatccg cagtggctgc gatggaagaa     60
acgttaatgg acaccagaac ggctactgca gagctgggct ggacggccaa tcctgcgtcc    120
gggtgggaag aagtcagtgg ctacgatgaa aacctgaaca ccatccgcac ctaccaggtg    180
tgcaatgtct tcgagcccaa ccagaacaat tggctgctca ccaccttcat caaccggcgg    240
ggggcccatc gcatctacac agagatgcgc ttcactgtga gagactgcag cagcctccct    300
aatgtcccag atcctgcaa ggagaccttc aacttgtatt actatgagac tgactctgtc    360
attgccacca agaagtcagc cttctggtct gaggccccct acctcaaagt agacaccatt    420
gctgcagatg agagcttctc ccaggtggac tttgggggaa ggctgatgaa ggtaaacaca    480
gaagtcagga gctttgggcc tcttactcgg aatggttttt acctcgcttt tcaggattat    540
ggagcctgta tgtctcttct ttctgtccgt gtcttcttca aaagtgtcc cagcattgtg    600 caaaattttg cagtgtttcc agagactatg acaggggcag agagcacatc tctggtgatt    660
gctcggggca catgcatccc caacgcagag gaagtgacg tgcccatcaa actctactgc    720
aacggggatg gggaatggat ggtgcctatt ggcgatgca cctgcaagcc tggctatgag    780
```

-continued

```
cctgagaaca gcgtggcatg caaggcttgc cctgcaggga cattcaaggc cagccaggaa    840
gctgaaggct gctcccactg cccctccaac agccgctccc ctgcagaggc gtctcccatc    900
tgcacctgtc ggaccggtta ttaccgagcg gactttgacc ctccagaagt ggcatgcact    960
agcgtcccat caggtccccg caatgttatc tccatcgtca atgagacgtc catcattctg   1020
gagtggcacc ctccaaggga gacaggtggg cgggatgatg tgacctacaa catcatctgc   1080
aaaaagtgcc gggcagaccg ccggagctgc tcccgctgtg acgacaatgt ggagtttgtg   1140
cccaggcagc tgggcctgac ggagtgccgc gtctccatca gcagcctgtg ggcccacacc   1200
ccctacacct ttgacatcca ggccatcaat ggagtctcca gcaagagtcc cttcccccca   1260
cagcacgtct ctgtcaacat caccacaaac caagccgccc cctccaccgt tcccatcatg   1320
caccaagtca gtgccactat gaggagcatc accttgtcat ggccacagcc ggagcagccc   1380
aatggcatca tcctggacta tgagatccgg tactatgaga aggaacacaa tgagttcaac   1440
tcctccatgg ccaggagtca gaccaacaca gcaaggattg atgggctgcg gcctggcatg   1500
gtatatgtgg tacaggtgcg tgcccgcact gttgctggct acggcaagtt cagtggcaag   1560
atgtgcttcc agactctgac tgacgatgat tacaagtcag agctgaggga gcagctgccc   1620
ctgattgctg gctcggcagc ggccggggtc gtgttcgttg tgtccttggt ggccatctct   1680
atcgtctgta gcaggaaacg ggcttatagc aaagaggctg tgtacagcga taagctccag   1740
cattacagca caggccgagg ctccccaggg atgaagatct acattgaccc cttcacttat   1800
gaggatccca acgaagctgt ccgggagttt gccaaggaga ttgatgtatc ttttgtgaaa   1860
attgaagagg tcatcggagc aggggagttt ggagaagtgt acaaggggcg tttgaaactg   1920
ccaggcaaga gggaaatcta cgtggccatc aagaccctga aggcagggta ctcggagaag   1980
cagcgtcggg actttctgag tgaggcgagc atcatgggcc agttcgacca tcctaacatc   2040
attcgcctgg agggtgtggt caccaagagt cggcctgtca tgatcatcac agagttcatg   2100
gagaatggtg cattggattc tttcctcagg caaaatgacg ggcagttcac cgtgatccag   2160
cttgtgggta tgctcagggg catcgctgct ggcatgaagt acctggctga gatgaattat   2220
gtgcatcggg acctggctgc taggaacatt ctggtcaaca gtaacctggt gtgcaaggtg   2280
tccgactttg gcctctcccg ctacctccag gatgacacct cagatcccac ctacaccagc   2340
tccttgggag ggaagatccc tgtgagatgg acagctccag aggccatcgc ctaccgcaag   2400
ttcacttcag ccagcgacgt ttggagctat gggatcgtca tgtgggaagt catgtcattt   2460
ggagagagac cctattggga tatgtccaac caagatgtca tcaatgccat cgagcaggac   2520
taccggctgc cccccaccat ggactgtcca gctgctctac accagctcat gctggactgt   2580
tggcagaagg accggaacag ccggccccgg tttgcggaga ttgtcaacac cctagataag   2640
atgatccgga acccggcaag tctcaagact gtggcaacca tcaccgccgt gccttcccag   2700
cccctgctcg accgctccat cccagacttc acggccttta ccaccgtgga tgactggctc   2760
agcgccatca aaatggtcca gtacagggac agcttcctca ctgctggctt cacctccctc   2820
cagctggtca cccagatgac atcagaagac ctcctgagaa taggcatcac cttggcaggc   2880
catcagaaga agatcctgaa cagcattcat tctatgaggg tccagataag tcagtcacca   2940
acggcaatgg catga                                                    2955
```

<210> SEQ ID NO 22
<211> LENGTH: 3168
<212> TYPE: DNA
<213> ORGANISM: Homo sapiens

<400> SEQUENCE: 22

```
atggctctgc ggaggctggg ggccgcgctg ctgctgctgc cgctgctcgc cgccgtggaa      60
gaaacgctaa tggactccac tacagcgact gctgagctgg gctggatggt gcatcctcca     120
tcagggtggg aagaggtgag tggctacgat gagaacatga acacgatccg cacgtaccag     180
gtgtgcaacg tgtttgagtc aagccagaac aactggctac ggaccaagtt tatccggcgc     240
cgtggcgccc accgcatcca cgtggagatg aagttttcgg tgcgtgactg cagcagcatc     300
cccagcgtgc ctggctcctg caaggagacc ttcaacctct attactatga ggctgacttt     360
gactcggcca ccaagacctt ccccaactgg atggagaatc catgggtgaa ggtggatacc     420
attgcagccg acgagagctt ctcccaggtg gacctgggtg gccgcgtcat gaaaatcaac     480
accgaggtgc ggagcttcgg acctgtgtcc cgcagcggct tctacctggc cttccaggac     540
tatggcggct gcatgtccct catcgccgtg cgtgtcttct accgcaagtg cccccgcatc     600
atccagaatg cgccatcttc caggaaaacc ctgtcggggg ctgagagcac atcgctggtg     660
gctgcccggg gcagctgcat cgccaatgcg gaagaggtgg atgtacccat caagctctac     720
tgtaacgggg acggcgagtg gctggtgccc atcgggcgct gcatgtgcaa agcaggcttc     780
gaggccgttg agaatggcac cgtctgccga ggttgtccat ctgggacttt caaggccaac     840
caaggggatg aggcctgtac ccactgtccc atcaacagcc ggaccacttc tgaaggggcc     900
accaactgtg tctgccgcaa tggctactac agagcagacc tggaccccct ggacatgccc     960
tgcacaacca tccccctccgc gccccaggct gtgatttcca gtgtcaatga cctcccctc    1020
atgctggagt ggaccccctcc ccgcgactcc ggaggccgag aggacctcgt ctacaacatc    1080
atctgcaaga gctgtggctc gggccggggt gcctgcaccc gctgcgggga caatgtacag    1140
tacgcaccac gccagctagg cctgaccgag ccacgcattt acatcagtga cctgctggcc    1200
cacacccagt acaccttcga gatccaggct gtgaacggcg ttactgacca gagccccttc    1260
tcgcctcagt tcgcctctgt gaacatcacc accaaccagg cagctccatc ggcagtgtcc    1320
atcatgcatc aggtgagccg caccgtggac agcattaccc tgtcgtggtc ccagccagac    1380
cagcccaatg gcgtgatcct ggactatgag ctgcagtact atgagaagga gctcagtgag    1440
tacaacgcca cagccataaa aagccccacc aacacggtca ccgtgcaggg cctcaaagcc    1500
ggcgccatct atgtcttcca ggtgcgggca cgcaccgtgg caggctacgg gcgctacagc    1560
ggcaagatgt acttccagac catgacagaa gccgagtacc agacaagcat ccaggagaag    1620
ttgccactca tcatcggctc ctcggccgct ggcctggtct tcctcattgc tgtggttgtc    1680
atcgccatcg tgtgtaacag acgggggttt gagcgtgctg actcggagta cacggacaag    1740
ctgcaacact acaccagtgg ccacatgacc ccaggcatga gatctacat cgatccttc     1800
acctacgagg accccaacga ggcagtgcgg gagtttgcca aggaaattga catctcctgt    1860
gtcaaaattg agcaggtgat cggagcaggg gagtttggcg aggtctgcag tggccacctg    1920
aagctgccag gcaagagaga gatctttgtg gccatcaaga cgctcaagtc gggctacacg    1980
gagaagcagc gccgggactt cctgagcgaa gcctccatca tgggccagtt cgaccatccc    2040
aacgtcatcc acctggaggg tgtcgtgacc aagagcacac ctgtgatgat catcaccgag    2100
ttcatggaga atggctccct ggactccttt ctccggcaaa acgatgggca gttcacagtc    2160
atccagctgg tgggcatgct tcgggcatc gcagctggca tgaagtacct ggcagacatg    2220
aactatgttc accgtgacct ggctgccgc aacatcctcg tcaacagcaa cctggtctgc    2280
aaggtgtcgg actttgggct ctcacgcttt ctagaggacg atacctcaga ccccacctac    2340
```

| | |
|---|---:|
| accagtgccc tgggcggaaa gatccccatc cgctggacag ccccggaagc catccagtac | 2400 |
| cggaagttca cctcggccag tgatgtgtgg agctacggca ttgtcatgtg ggaggtgatg | 2460 |
| tcctatgggg agcggcccta ctgggacatg accaaccagg atgtaatcaa tgccattgag | 2520 |
| caggactatc ggctgccacc gcccatggac tgcccgagcg ccctgcacca actcatgctg | 2580 |
| gactgttggc agaaggaccg caaccaccgg cccaagttcg gccaaattgt caacacgcta | 2640 |
| gacaagatga tccgcaatcc caacagcctc aaagccatgg cgcccctctc ctctggcatc | 2700 |
| aacctgccgc tgctggaccg cacgatcccc gactacacca gctttaacac ggtggacgag | 2760 |
| tggctggagg ccatcaagat ggggcagtac aaggagagct cgccaatgc cggcttcacc | 2820 |
| tcctttgacg tcgtgtctca gatgatgatg aggacattc tccgggttgg ggtcactttg | 2880 |
| gctggccacc agaaaaaaat cctgaacagt atccaggtga tgcgggcgca gatgaaccag | 2940 |
| attcagtctg tggagggcca gccactcgcc aggaggccac gggccacggg aagaaccaag | 3000 |
| cggtgccagc cacgagacgt caccaagaaa acatgcaact caaacgacgg aaaaaaaaag | 3060 |
| ggaatgggaa aaagaaaac agatcctggg aggggcggg aaatacaagg aatatttttt | 3120 |
| aaagaggatt ctcataagga aagcaatgac tgttcttgcg ggggataa | 3168 |

<210> SEQ ID NO 23
<211> LENGTH: 2997
<212> TYPE: DNA
<213> ORGANISM: Homo sapiens

<400> SEQUENCE: 23

| | |
|---|---:|
| atggccagag cccgcccgcc gccgccgccg tcgccgccgc cggggcttct gccgctgctc | 60 |
| cctccgctgc tgctgctgcc gctgctgctg ctcccgccg ctgccgggc gctggaagag | 120 |
| accctcatgg acacaaaatg ggtaacatct gagttggcgt ggacatctca tccagaaagt | 180 |
| gggtgggaag aggtgagtgg ctacgatgag gccatgaatc ccatccgcac ataccaggtg | 240 |
| tgtaatgtgc gcgagtcaag ccagaacaac tggcttcgca cggggttcat ctggcggcgg | 300 |
| gatgtgcagc gggtctacgt ggagctcaag ttcactgtgc gtgactgcaa cagcatcccc | 360 |
| aacatccccg gctcctgcaa ggagaccttc aacctcttct actacgaggc tgacagcgat | 420 |
| gtggcctcag cctcctcccc cttctggatg gagaacccct acgtgaaagt ggacaccatt | 480 |
| gcacccgatg agagcttctc gcggctggat gccggccgtg tcaacaccaa ggtgcgcagc | 540 |
| tttgggccac tttccaaggc tggcttctac ctggccttcc aggaccaggg cgcctgcatg | 600 |
| tcgctcatct ccgtgcgcgc cttctacaag aagtgtgcat ccaccaccgc aggcttcgca | 660 |
| ctcttccccg agaccctcac tggggcggag cccaccctcgc tggtcattgc tcctggcacc | 720 |
| tgcatcccta cgccgtgga ggtgtcgtg ccactcaagc tctactgcaa cggcgatggg | 780 |
| gagtggatgg tgcctgtggg tgcctgcacc tgtgccaccg ccatgagcc agctgccaag | 840 |
| gagtcccagt gccgccctg tcccctggg agctacaagg cgaagcaggg agaggggccc | 900 |
| tgcctcccat gtcccccaa cagccgtacc acctccccag ccgccagcat ctgcacctgc | 960 |
| cacaataact ctaccgtgc agactcggac tctgcggaca tgcctgtac caccgtgcca | 1020 |
| tctccacccc gaggtgtgat ctccaatgtg aatgaaacct cactgatcct cgagtggagt | 1080 |
| gagccccggg acctggtgt ccgggatgac ctcctgtaca atgtcatctg caagaagtgc | 1140 |
| catgggctg gagggcctc agcctgctca cgctgtgatg acaacgtgga gtttgtgcct | 1200 |
| cggcagctgg gcctgtcgga gcccgggtc cacaccagcc atctgctggc ccacacgcgc | 1260 |
| tacacctttg aggtgcaggc ggtcaacggt gtctcgggca gagccctct gccgcctcgt | 1320 |

```
tatgcggccg tgaatatcac cacaaaccag gctgccccgt ctgaagtgcc cacactacgc   1380
ctgcacagca gctcaggcag cagcctcacc ctatcctggg cacccccaga gcggcccaac   1440
ggagtcatcc tggactacga gatgaagtac tttgagaaga gcgagggcat cgcctccaca   1500
gtgaccagcc agatgaactc cgtgcagctg gacgggcttc ggcctgacgc ccgctatgtg   1560
gtccaggtcc gtgcccgcac agtagctggc tatgggcagt acagccgccc tgccgagttt   1620
gagaccacaa gtgagagagg ctctgggccc agcagctcc aggagcagct tccctcatc    1680 gtgggctccg ctacagctgg gcttgtcttc gtggtggctg tcgtggtcat cgctatcgtc   1740
tgcctcagga gcagcgaca cggctctgat tcggagtaca cggagaagct gcagcagtac    1800
attgctcctg gaatgaaggt ttatattgac ccttttacct acgaggaccc taatgaggct   1860
gttcgggagt ttgccaagga gatcgacgtg tcctgcgtca agatcgagga ggtgatcgga   1920
gctggggaat ttgggaagt gtgccgtggt cgactgaaac agcctggccg ccgagaggtg   1980
tttgtggcca tcaagacgct gaaggtgggc tacaccgaga ggcagcggcg ggacttccta   2040
agcgaggcct ccatcatggg tcagtttgat caccccaata taatccggct cgagggcgtg   2100
gtcaccaaaa gtcggccagt tatgatcctc actgagttca tggaaaactg cgccctggac   2160
tccttcctcc ggctcaacga tgggcagttc acggtcatcc agctggtggg catgttgcgg   2220
ggcattgctg ccggcatgaa gtacctgtcc gagatgaact atgtgcaccg cgacctggct   2280
gctcgcaaca tccttgtcaa cagcaacctg gtctgcaaag tctcagactt ggcctctcc    2340 cgcttcctgg aggatgaccc ctccgatcct acctacacca gttccctggg cgggaagatc   2400
cccatccgct ggactgcccc agaggccata gcctatcgga agttcacttc tgctagtgat   2460
gtctggagct acggaattgt catgtgggag gtcatgagct atggagagcg accctactgg   2520
gacatgagca accaggatgt catcaatgcc gtggagcagg attaccggct gccaccaccc   2580
atggactgtc ccacagcact gcaccagctc atgctggact gctgggtgcg ggaccggaac   2640
ctcaggccca aattctccca gattgtcaat accctggaca agctcatccg caatgctgcc   2700
agcctcaagg tcattgccag cgctcagtct ggcatgtcac agcccctcct ggaccgcacg   2760
gtcccagatt acacaacctt cacgacagtt ggtgattggc tggatgccat caagatgggg   2820
cggtacaagg agagcttcgt cagtgcgggg tttgcatctt ttgacctggt ggcccagatg   2880
acggcagaag acctgctccg tattggggtc accctggccg gccaccagaa gaagatcctg   2940
agcagtatcc aggacatgcg gctgcagatg aaccagacgc tgcctgtgca ggtctga      2997

<210> SEQ ID NO 24
<211> LENGTH: 2964
<212> TYPE: DNA
<213> ORGANISM: Homo sapiens

<400> SEQUENCE: 24
atggagctcc gggtgctgct ctgctgggct tcgttggccg cagctttgga agagaccctg     60
ctgaacacaa aattggaaac tgctgatctg aagtgggtga cattccctca ggtggacggg    120
cagtgggagg aactgagcgg cctggatgag gaacagcaca gcgtgcgcac ctacgaagtg    180
tgtgaagtgc agcgtgcccc gggccaggcc cactggcttc gcacaggttg gtcccacgg    240 cggggcgccg tccacgtgta cgccacgctg cgcttcacca tgctcgagtg cctgtccctg    300
cctcgggctg gcgctcctg caaggagacc ttcaccgtct tctactatga gagcgatgcg    360 gacacacgcca cggccctcac gccagcctgg atggagaacc cctacatcaa ggtggacacg    420
gtggccgcgg agcatctcac ccggaagcgc cctggggccg aggccaccgg gaaggtgaat    480
```

```
gtcaagacgc tgcgtctggg accgctcagc aaggctggct tctacctggc cttccaggac    540
cagggtgcct gcatggccct gctatccctg cacctcttct acaaaaagtg cgcccagctg    600
actgtgaacc tgactcgatt cccggagact gtgcctcggg agctggttgt gcccgtggcc    660
ggtagctgcg tggtggatgc cgtccccgcc cctggcccca gccccagcct ctactgccgt    720
gaggatggcc agtgggccga acagccggtc acgggctgca gctgtgctcc ggggttcgag    780
gcagctgagg ggaacaccaa gtgccgagcc tgtgcccagg gcaccttcaa gcccctgtca    840
ggagaagggt cctgccagcc atgcccagcc aatagccact ctaacaccat tggatctgcc    900
gtctgccagt gccgcgtcgg ggacttccgg gcacgcacag accccggggt gcaccctgc     960 accaccctc cttcggctcc gcggagcgtg gtttcccgcc tgaacggctc ctccctgcac    1020
ctggaatgga gtgcccccct ggagtctggt ggccgagagg acctcaccta cgccctccgc    1080
tgccgggagt gccgacccgg aggctcctgt gcgccctgcg ggggagacct gacttttgac    1140 cccgccccc gggacctggt ggagccctgg gtggtggttc gagggctacg tccggacttc     1200
acctatacct ttgaggtcac tgcattgaac ggggtatcct ccttagccac ggggcccgtc    1260
ccatttgagc ctgtcaatgt caccactgac cgagaggtac ctcctgcagt gtctgacatc    1320
cgggtgacgc ggtcctcacc cagcagcttg agcctggcct gggctgttcc ccgggcaccc    1380
agtggggcgt ggctggacta cgaggtcaaa taccatgaga agggcgccga gggtcccagc    1440
agcgtgcggt tcctgaagac gtcagaaaac cgggcagagc tgcggggct gaagcgggga     1500 gccagctacc tggtgcaggt acgggcgcgc tctgaggccg gctacgggcc cttcggccag    1560
gaacatcaca gccagaccca actggatgag agcgagggct ggcgggagca gctggccctg    1620
attgcgggca cggcagtcgt gggtgtggtc ctggtcctgg tggtcattgt ggtcgcagtt    1680
ctctgcctca ggaagcagag caatgggaga gaagcagaat attcggacaa acacggacag    1740
tatctcatcg acatggtac taaggtctac atcgaccct tcacttatga agaccctaat      1800
gaggctgtga gggaatttgc aaaagagatc gatgtctcct acgtcaagat tgaagaggtg    1860
attggtgcag gtgagtttgg cgaggtgtgc cgggggcggc tcaaggcccc agggaagaag    1920
gagagctgtg tggcaatcaa gaccctgaag ggtggctaca cggagcggca gcggcgtgag    1980
tttctgagcg aggcctccat catgggccag ttcgagcacc ccaatatcat ccgcctggag    2040
ggcgtggtca ccaacagcat gccgtcatg attctcacag agttcatgga gaacggcgcc    2100
ctggactcct tcctgcggct aaacgacgga cagttcacag tcatccagct cgtgggcatg    2160
ctgcggggca tcgcctcggg catgcggtac cttgccgaga tgagctacgt ccaccgagac    2220
ctggctgctc gcaacatcct agtcaacagc aacctcgtct gcaaagtgtc tgactttggc    2280
ctttcccgat tcctggagga gaactcttcc gatcccacct acacgagctc cctgggagga    2340
aagattccca tccgatggac tgccccggag gccattgcct tccggaagtt cacttccgcc    2400
agtgatgcct ggagttacgg gattgtgatg tgggaggtga tgtcatttgg ggagaggccg    2460
tactgggaca tgagcaatca ggacgtgatc aatgccattg aacaggacta ccggctgccc    2520
ccgcccccag actgtcccac ctccctccac cagctcatgc tggactgttg gcagaaagac    2580
cggaatgccc ggccccgctt cccccaggtg gtcagcgccc tggacaagat gatccggaac    2640
cccgccagcc tcaaaatcgt ggcccgggag aatggcgggg cctcacaccc tctcctggac    2700
cagcggcagc ctcactactc agcttttggc tctgtgggcg agtggcttcg ggccatcaaa    2760
atgggaagat acgaagcccg tttcgcagcc gctggctttg ctccttcga gctggtcagc    2820 cagatctctg ctgaggacct gctccgaatc ggagtcactc tggcgggaca ccagaagaaa    2880
```

-continued

| | |
|---|---|
| atcttggcca gtgtccagca catgaagtcc caggccaagc cgggaacccc gggtgggaca | 2940 |
| ggaggaccgg ccccgcagta ctga | 2964 |

<210> SEQ ID NO 25
<211> LENGTH: 1041
<212> TYPE: DNA
<213> ORGANISM: Homo sapiens
<300> PUBLICATION INFORMATION:
<302> TITLE: ephrin-B1
<310> PATENT DOCUMENT NUMBER: NM004429

<400> SEQUENCE: 25

| | |
|---|---|
| atggctcggc ctgggcagcg ttggctcggc aagtggcttg tggcgatggt cgtgtgggcg | 60 |
| ctgtgccggc tcgccacacc gctggccaag aacctggagc ccgtatcctg gagctccctc | 120 |
| aaccccaagt tcctgagtgg gaagggcttg gtgatctatc cgaaaattgg agacaagctg | 180 |
| gacatcatct gccccgagc agaagcaggg cggccctatg agtactacaa gctgtacctg | 240 |
| gtgcggcctg agcaggcagc tgcctgtagc acagttctcg accccaacgt gttggtcacc | 300 |
| tgcaataggc cagagcagga aatacgcttt accatcaagt tccaggagtt cagccccaac | 360 |
| tacatgggcc tggagttcaa gaagcaccat gattactaca ttacctcaac atccaatgga | 420 |
| agcctggagg ggctggaaaa ccgggagggc ggtgtgtgcc gcacacgcac catgaagatc | 480 |
| atcatgaagg ttgggcaaga tcccaatgct gtgacgcctg agcagctgac taccagcagg | 540 |
| cccagcaagg aggcagacaa cactgtcaag atggccacac aggcccctgg tagtcggggc | 600 |
| tccctggggtg actctgatgg caagcatgag actgtgaacc aggaagagaa gagtggccca | 660 |
| ggtgcaagtg ggggcagcag cggggaccct gatggcttct tcaactccaa ggtggcattg | 720 |
| ttcgcggctg tcggtgccgg ttgcgtcatc ttcctgctca tcatcatctt cctgacggtc | 780 |
| ctactactga agctacgcaa gcggcaccgc aagcacacac agcagcgggc ggctgccctc | 840 |
| tcgctcagta ccctggccag tcccaagggg ggcagtggca cagcgggcac cgagcccagc | 900 |
| gacatcatca ttcccttacg gactacagag aacaactact gcccccacta tgagaaggtg | 960 |
| agtggggact acgggcaccc tgtctacatc gtccaagaga tgccgccca gagcccggcg | 1020 |
| aacatctact acaaggtctg a | 1041 |

<210> SEQ ID NO 26
<211> LENGTH: 1002
<212> TYPE: DNA
<213> ORGANISM: Homo sapiens
<300> PUBLICATION INFORMATION:

<400> SEQUENCE: 26

| | |
|---|---|
| atggctgtga aagggactc cgtgtggaag tactgctggg gtgttttgat ggttttatgc | 60 |
| agaactgcga tttccaaatc gatagtttta gagcctatct attggaattc ctcgaactcc | 120 |
| aaatttctac ctggacaagg actggtacta tacccacaga taggagacaa attggatatt | 180 |
| atttgcccca agtggactc taaaactgtt ggccagtatg aatattataa agtttatatg | 240 |
| gttgataaag accaagcaga cagatgcact attaagaagg aaataccccc tctcctcaac | 300 |
| tgtgccaaac cagaccaaga tatcaaattc accatcaagt ttcaagaatt cagccctaac | 360 |
| ctctggggtc tagaatttca gaagaacaaa gattattaca ttatatctac atcaaatggg | 420 |
| tctttggagg gcctggataa ccaggaggga ggggtgtgcc agacaagagc catgaagatc | 480 |
| ctcatgaaag ttggacaaga tgcaagttct gctggatcaa ccaggaataa agatccaaca | 540 |
| agacgtccag aactagaagc tggtacaaat ggaagaagtt cgacaacaag tccctttgta | 600 |

| | |
|---|---|
| aaaccaaatc caggttctag cacagacggc aacagcgccg acattcggg gaacaacatc | 660 |
| ctcggttccg aagtggcctt atttgcaggg attgcttcag gatgcatcat cttcatcgtc | 720 |
| atcatcatca cgctggtggt cctcttgctg aagtaccgga ggagacacag gaagcactcg | 780 |
| ccgcagcaca cgaccacgct gtcgctcagc acactggcca cacccaagcg cagcggcaac | 840 |
| aacaacggct cagagcccag tgacattatc atcccgctaa ggactgcgga cagcgtcttc | 900 |
| tgccctcact acgagaaggt cagcggcgac tacgggcacc cggtgtacat cgtccaggag | 960 |
| atgcccccgc agagcccggc gaacatttac tacaaggtct ga | 1002 |

<210> SEQ ID NO 27
<211> LENGTH: 1023
<212> TYPE: DNA
<213> ORGANISM: Homo sapiens

<400> SEQUENCE: 27

| | |
|---|---|
| atggggcccc cccattctgg gccgggggc gtgcgagtcg gggccctgct gctgctgggg | 60 |
| gttttggggc tggtgtctgg gctcagcctg gagcctgtct actggaactc ggcgaataag | 120 |
| aggttccagg cagagggtgg ttatgtgctg taccctcaga tcgggaccg gctagacctg | 180 |
| ctctgccccc gggcccggcc tcctggccct cactcctctc ctaattatga gttctacaag | 240 |
| ctgtacctgg taggggtgc tcagggccgg cgctgtgagg caccccctgc cccaaacctc | 300 |
| cttctcactt gtgatcgccc agacctggat ctccgcttca ccatcaagtt ccaggagtat | 360 |
| agccctaatc tctggggcca cgagttccgc tcgcaccacg attactacat cattgccaca | 420 |
| tcggatggga cccggagggg cctggagagc ctgcaggag gtgtgtgcct aaccagaggc | 480 |
| atgaaggtgc ttctccgagt gggacaaagt ccccgaggag gggctgtccc ccgaaaacct | 540 |
| gtgtctgaaa tgcccatgga aagagaccga ggggcagccc acagcctgga gcctgggaag | 600 |
| gagaacctgc caggtgaccc caccagcaat gcaacctccc ggggtgctga aggcccctg | 660 |
| cccccctccca gcatgcctgc agtggctggg gcagcagggg ggctggcgct gctcttgctg | 720 |
| ggcgtggcag gggctggggg tgccatgtgt tggcggagac ggcgggccaa gccttcggag | 780 |
| agtcgccacc ctggtcctgg ctccttcggg aggggagggt ctctgggcct ggggggtgga | 840 |
| ggtgggatgg gacctcggga ggctgagcct ggggagctag ggatagctct gcgggggtggc | 900 |
| ggggctgcag atcccccctt ctgccccac tatgagaagg tgagtggtga ctatgggcat | 960 |
| cctgtgtata tcgtgcagga tgggccccc cagagccctc caaacatcta ctacaaggta | 1020 |
| tga | 1023 |

<210> SEQ ID NO 28
<211> LENGTH: 3399
<212> TYPE: DNA
<213> ORGANISM: Homo sapiens
<300> PUBLICATION INFORMATION:
<302> TITLE: telomerase reverse transcriptase
<310> PATENT DOCUMENT NUMBER: AF015950

<400> SEQUENCE: 28

| | |
|---|---|
| atgccgcgcg ctccccgctg ccgagccgtg cgctccctgc tgcgcagcca ctaccgcgag | 60 |
| gtgctgccgc tggccacgtt cgtgcggcgc ctggggccc agggctggcg gctggtgcag | 120 |
| cgcgggaccc ggcggctttc ccgcgcgctg gtgcccagt gctggtgtg cgtgccctgg | 180 |
| gacgcacggc cgcccccgc cgccccctcc ttcgccagg tgtcctgcct gaaggagctg | 240 |
| gtggcccgag tgctgcagag gctgtgcgag cgcggcgcga gaacgtgct ggccttcggc | 300 |
| ttcgcgctgc tggacggggc ccgcgggggc cccccgagg ccttcaccac cagcgtgcgc | 360 |

-continued

```
agctacctgc ccaacacggt gaccgacgca ctgcggggga gcggggcgtg ggggctgctg    420
ctgcgccgcg tgggcgacga cgtgctggtt cacctgctgg cacgctgcgc gctctttgtg    480
ctggtggctc ccagctgcgc ctaccaggtg tgcgggccgc cgctgtacca gctcggcgct    540
gccactcagg cccggccccc gccacacgct agtggacccc gaaggcgtct gggatgcgaa    600
cgggcctgga accatagcgt cagggaggcc ggggtccccc tgggcctgcc agccccgggt    660
gcgaggaggc gcgggggcag tgccagccga agtctgccgt tgcccaagag gcccaggcgt    720
ggcgctgccc ctgagccgga gcggacgccc gttgggcagg ggtcctgggc ccacccgggc    780
aggacgcgtg gaccgagtga ccgtggtttc tgtgtggtgt cacctgccag acccgccgaa    840
gaagccacct cttggaggg tgcgctctct ggcacgcgcc actcccaccc atccgtgggc    900
cgccagcacc acgcgggccc cccatccaca tcgcggccac cacgtccctg ggacacgcct    960
tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactccccg caggttgccc    1140
cgcctgcccc agcgctactg gcaaatgcgg cccctgtttc tggagctgct gggaaccac     1200 gcgcagtgcc cctacggggt gctcctcaag acgcactgcc cgctgcgagc tgcggtcacc    1260
ccagcagccg gtgtctgtgc ccgggagaag ccccagggct ctgtggcggc ccccgaggag    1320
gaggacacag accccgtcg cctggtgcag ctgctccgcc agcacagcag ccctggcag    1380 gtgtacggct tcgtgcgggc ctgcctgcgc ggctggtgc ccccaggcct ctgggctcc     1440 aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca aaccccagaa cacgtactgc    2220
gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460 agggcaagt cctacgtcca gtgccagggg atcccgcagg gctccatcct ctccacgctg    2520
ctctgcagcc tgtgctacgg cgacatggag aacaagctgt ttgcggggat tcggcgggac    2580
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
```

```
cagatgccgg cccacggcct attccctggg tgcggcctgc tgctggatac ccggaccctg    2820
gaggtgcaga gcgactactc cagctatgcc cggacctcca tcagagccag tctcaccttc    2880
aaccgcggct tcaaggctgg gaggaacatg cgtcgcaaac tctttggggt cttgcggctg    2940
aagtgtcaca gcctgtttct ggatttgcag gtgaacagcc tccagacggt gtgcaccaac    3000
atctacaaga tcctcctgct gcaggcgtac aggtttcacg catgtgtgct gcagctccca    3060
tttcatcagc aagtttggaa gaaccccaca tttttcctgc gcgtcatctc tgacacggcc    3120
tccctctgct actccatcct gaaagccaag aacgcaggga tgtcgctggg ggccaagggc    3180
gccgccggcc ctctgccctc cgaggccgtg cagtggctgt gccaccaagc attcctgctc    3240
aagctgactc gacaccgtgt cacctacgtg ccactcctgg ggtcactcag gacagcccag    3300
acgcagctga gtcggaagct cccggggacg acgctgactg ccctggaggc cgcagccaac    3360
ccggcactgc cctcagactt caagaccatc ctggactga                          3399
```

<210> SEQ ID NO 29
<211> LENGTH: 567
<212> TYPE: DNA
<213> ORGANISM: Homo sapiens
<300> PUBLICATION INFORMATION:
<302> TITLE: K-ras
<310> PATENT DOCUMENT NUMBER: M54968

<400> SEQUENCE: 29

```
atgactgaat ataaacttgt ggtagttgga gcttgtggcg taggcaagag tgccttgacg     60
atacagctaa ttcagaatca ttttgtggac gaatatgatc aacaataga ggattcctac    120 aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaagaag    540 tcaaagacaa agtgtgtaat tatgtaa                                       567
```

<210> SEQ ID NO 30
<211> LENGTH: 3840
<212> TYPE: DNA
<213> ORGANISM: Homo sapiens
<300> PUBLICATION INFORMATION:
<302> TITLE: mdr-1
<310> PATENT DOCUMENT NUMBER: AF016535

<400> SEQUENCE: 30

```
atggatcttg aaggggaccg caatggagga gcaaagaaga gaactttttt taaactgaac     60
aataaaagtg aaaagataa gaaggaaaag aaaccaactg tcagtgtatt ttcaatgttt    120
cgctattcaa attggcttga caagttgtat atggtggtgg aactttggc tgccatcatc    180 catgggctg acttcctctc atgatgctg gtgtttggag aaatgacaga tatctttgca    240
aatgcaggaa atttagaaga tctgatgtca aacatcacta tagaagtga tatcaatgat    300 acagggttct tcatgaatct ggaggaagac atgaccaggt atgcctatta ttacagtgga    360
attggtgctg gggtgctggt tgctgcttac attcaggttt cattttggtg cctggcagct    420
ggaagacaaa tacacaaaat tagaaaacag tttttttcatg ctataatgcg acaggagata    480
```

```
ggctggtttg atgtgcacga tgttggggag cttaacaccc gacttacaga tgatgtctcc    540
aagattaatg aaggaattgg tgacaaaatt ggaatgttct ttcagtcaat ggcaacattt    600
ttcactgggt ttatagtagg atttacacgt ggttggaagc taaccttgt gattttggcc     660
atcagtcctg ttcttggact gtcagctgct gtctgggcaa agatactatc ttcatttact    720
gataaagaac tcttagcgta tgcaaaagct ggagcagtag ctgaagaggt cttggcagca    780
attagaactg tgattgcatt tggaggacaa agaaagaac ttgaaaggta caacaaaaat     840
ttagaagaag ctaaaagaat tgggataaag aaagctatta cagccaatat ttctataggt    900
gctgctttcc tgctgatcta tgcatcttat gctctggcct tctggtatgg gaccaccttg    960
gtcctctcag gggaatattc tattggacaa gtactcactg tattttctgt attaattggg   1020
gcttttagtg ttggacaggc atctccaagc attgaagcat ttgcaaatgc aagaggagca   1080
gcttatgaaa tcttcaagat aattgataat aagccaagta ttgacagcta ttcgaagagt   1140
gggcacaaac cagataatat taagggaaat ttggaattca gaaatgttca cttcagttac   1200
ccatctcgaa aagaagttaa gatcttgaag ggtctgaacc tgaaggtgca gagtgggcag   1260
acggtggccc tggttggaaa cagtggctgt gggaagagca caacagtcca gctgatgcag   1320
aggctctatg accccacaga ggggatggtc agtgttgatg gacaggatat taggaccata   1380
aatgtaaggt ttctacggga atcattggt gtggtgagtc aggaacctgt attgtttgcc    1440
accacgatag ctgaaaacat tcgctatggc cgtgaaaatg tcaccatgga tgagattgag   1500
aaagctgtca aggaagccaa tgcctatgac tttatcatga actgcctca taaatttgac    1560
accctggttg gagagagagg ggcccagttg agtggtgggc agaagcagag gatcgccatt   1620
gcacgtgccc tggttcgcaa ccccaagatc ctcctgctgg atgaggccac gtcagccttg   1680
gacacagaaa gcgaagcagt ggttcaggtg gctctggata aggccagaaa aggtcggacc   1740
accattgtga tagctcatcg tttgtctaca gttcgtaatg ctgacgtcat cgctggtttc   1800
gatgatggag tcattgtgga gaaaggaaat catgatgaac tcatgaaaga gaaaggcatt   1860
tacttcaaac ttgtcacaat gcagacagca ggaaatgaag ttgaattaga aaatgcagct   1920
gatgaatcca aaagtgaaat tgatgccttg gaaatgtctt caaatgattc aagatccagt   1980
ctaataagaa aaagatcaac tcgtaggagt gtccgtggat cacaagccca agacagaaag   2040
cttagtacca agagggctct ggatgaaagt atacctccag tttccttttg gaggattatg   2100
aagctaaatt taactgaatg gccttatttt gttgttggtg tattttgtgc cattataaat   2160
ggaggcctgc aaccagcatt tgcaataata ttttcaaaga ttataggggt ttttacaaga   2220
attgatgatc ctgaaacaaa acgacagaat agtaacttgt tttcactatt gtttctagcc   2280
cttggaatta tttctttat tacattttc cttcagggtt tcacatttgg caaagctgga   2340
gagatcctca ccaagcggct ccgatacatg gttttccgat ccatgctcag acaggatgtg   2400
agttggtttg atgaccctaa aaacaccact ggagcattga ctaccaggct cgccaatgat   2460
gctgctcaag ttaaagggc tataggttcc aggcttgctg taattaccca gaatatagca    2520
aatcttggga caggaataat tatatccttc atctatggtt ggcaactaac actgttactc   2580
ttagcaattg tacccatcat tgcaatagca ggagttgttg aaatgaaat gttgtctgga   2640
caagcactga aagataagaa agaactagaa ggtgctggga gatcgctac tgaagcaata   2700
gaaaacttcc gaaccgttgt ttctttgact caggagcaga gtttgaaca tatgtatgct   2760
cagagtttgc aggtaccata cagaaactct ttgaggaaag cacacatctt tggaattaca   2820
ttttccttca cccaggcaat gatgtatttt tcctatgctg gatgtttccg gtttggagcc   2880
```

```
tacttggtgg cacataaact catgagcttt gaggatgttc tgttagtatt ttcagctgtt    2940
gtctttggtg ccatggccgt ggggcaagtc agttcatttg ctcctgacta tgccaaagcc    3000
aaaatatcag cagcccacat catcatgatc attgaaaaaa ccccttttgat tgacagctac   3060 agcacggaag gcctaatgcc aacacattg aaggaaatg tcacatttgg tgaagttgta     3120
ttcaactatc ccacccgacc ggacatccca gtgcttcagg gactgagcct ggaggtgaag    3180
aagggccaga cgctggctct ggtgggcagc agtggctgtg ggaagagcac agtggtccag    3240
ctcctggagc ggttctacga ccccttggca gggaaagtgc tgcttgatgg caaagaaata    3300
aagcgactga atgttcagtg gctccgagca cacctgggca tcgtgtccca ggagcccatc    3360
ctgtttgact gcagcattgc tgagaacatt gcctatggag acaacagccg ggtggtgtca    3420
caggaagaga ttgtgagggc agcaaaggag gccaacatac atgccttcat cgagtcactg    3480
cctaataaat atagcactaa agtaggagac aaaggaactc agctctctgg tggccagaaa    3540
caacgcattg ccatagctcg tgcccttgtt agacagcctc atattttgct tttggatgaa    3600
gccacgtcag ctctggatac agaaagtgaa aaggttgtcc aagaagccct ggacaaagcc    3660
agagaaggcc gcacctgcat tgtgattgct caccgcctgt ccaccatcca gaatgcagac    3720
ttaatagtgg tgtttcagaa tggcagagtc aaggagcatg gcacgcatca gcagctgctg    3780
gcacagaaag gcatctattt ttcaatggtc agtgtccagg ctggaacaaa gcgccagtga    3840

<210> SEQ ID NO 31
<211> LENGTH: 1318
<212> TYPE: DNA
<213> ORGANISM: Homo sapiens
<300> PUBLICATION INFORMATION:
<302> TITLE: UPAR (urokinase-type plasminogen activator receptor)
<310> PATENT DOCUMENT NUMBER: XM009232

<400> SEQUENCE: 31
atgggtcacc cgccgctgct gccgctgctg ctgctgctcc acacctgcgt cccagcctct      60
tggggcctgc ggtgcatgca gtgtaagacc aacgggatt gccgtgtgga agagtgcgcc     120
ctgggacagg acctctgcag gaccacgatc gtgcgcttgt gggaagaagg agaagagctg     180
gagctggtgg agaaaagctg tacccactca gagaagacca acaggaccct gagctatcgg      240
actggcttga gatcaccag ccttaccgag gttgtgtgtg ggttagactt gtgcaaccag     300
ggcaactctg gccgggctgt cacctattcc cgaagccgtt acctcgaatg catttcctgt     360
ggctcatcag acatgagctg tgagaggggc cggcaccaga gcctgcagtg ccgcagccct     420
gaagaacagt gcctggatgt ggtgacccac tggatccagg aaggtgaaga agggcgtcca     480
aaggatgacc gccacctccg tggctgtggc taccttcccg gctgcccggg ctccaatggt     540
ttccacaaca cgacaccttt ccacttcctg aaatgctgca caccaccaa atgcaacgag     600 ggcccaatcc tggagcttga aaatctgccg cagaatggcc gccagtgtta cagctgcaag     660
gggaacagca cccatggatg ctcctctgaa gagactttcc tcattgactg ccgaggcccc     720
atgaatcaat gtctggtagc caccggcact cacgaaccga aaaccaaag ctatatggta      780 agaggctgtg caaccgcctc aatgtgccaa catgcccacc tgggtgacgc cttcagcatg     840
aaccacattg atgtctcctg ctgtactaaa agtggctgta accacccaga cctggatgtc     900
cagtaccgca gtggggctgc tcctcagcct ggccctgccc atctcagcct caccatcacc     960
ctgctaatga ctgccagact gtggggaggc actctcctct ggacctaaac ctgaaatccc    1020
cctctctgcc ctggctggat ccgggggacc cctttgccct tccctcggct cccagcccta    1080
```

```
cagacttgct gtgtgacctc aggccagtgt gccgacctct ctgggcctca gttttcccag    1140
ctatgaaaac agctatctca caaagttgtg tgaagcagaa gagaaaagct ggaggaaggc    1200
cgtgggccaa tgggagagct cttgttatta ttaatattgt tgccgctgtt gtgttgttgt    1260
tattaattaa tattcatatt atttattta tacttacata aagattttgt accagtgg      1318
```

<210> SEQ ID NO 32
<211> LENGTH: 636
<212> TYPE: DNA
<213> ORGANISM: Homo sapiens
<300> PUBLICATION INFORMATION:
<302> TITLE: Bak
<310> PATENT DOCUMENT NUMBER: U16811

<400> SEQUENCE: 32

```
atggcttcgg ggcaaggccc aggtcctccc aggcaggagt gcggagagcc tgccctgccc     60
tctgcttctg aggagcaggt agcccaggac acagaggagg ttttccgcag ctacgttttt    120
taccgccatc agcaggaaca ggaggctgaa ggggtggctg cccctgccga cccagagatg    180
gtcaccttac ctctgcaacc tagcagcacc atggggcagg tgggacggca gctcgccatc    240 atcgggacg acatcaaccg acgctatgac tcagagttcc agaccatgtt gcagcacctg    300
cagcccacgg cagagaatgc ctatgagtac ttcaccaaga ttgccaccag cctgtttgag    360
agtggcatca attggggccg tgtggtggct cttctgggct tcggctaccg tctggcccta    420
cacgtctacc agcatggcct gactggcttc ctaggccagg tgacccgctt cgtggtcgac    480
ttcatgctgc atcactgcat tgcccggtgg attgcacaga ggggtggctg ggtggcagcc    540
ctgaacttgg gcaatggtcc catcctgaac gtgctggtgg ttctgggtgt ggttctgttg    600
ggccagtttg tggtacgaag attcttcaaa tcatga                              636
```

<210> SEQ ID NO 33
<211> LENGTH: 579
<212> TYPE: DNA
<213> ORGANISM: Homo sapiens
<300> PUBLICATION INFORMATION:
<302> TITLE: Bax alpha
<310> PATENT DOCUMENT NUMBER: L22473

<400> SEQUENCE: 33

```
atggacgggt ccggggagca gcccagaggc ggggggccca ccagctctga gcagatcatg     60
aagacagggg ccttttgct tcagggtttc atccaggatc gagcagggcg aatggggggg    120
gaggcacccg agctggccct ggaccccgtg cctcaggatg cgtccaccaa gaagctgagc    180
gagtgtctca gcgcatcgg ggacgaactg gacagtaaca tggagctgca gaggatgatt    240
gccgccgtgg acacagactc cccccgagag gtctttttcc gagtggcagc tgacatgttt    300
tctgacggca acttcaactg gggccgggtt gtcgcccttt tctactttgc cagcaaactg    360
gtgctcaagg ccctgtgcac caaggtgccg gaactgatca gaaccatcat gggctggaca    420
ttggacttcc tccgggagcg gctgttgggc tggatccaag accagggtgg ttgggacggc    480
ctcctctcct actttgggac gcccacgtgg cagaccgtga ccatctttgt ggcgggagtg    540
ctcaccgcct cgctcaccat ctggaagaag atgggctga                           579
```

<210> SEQ ID NO 34
<211> LENGTH: 657
<212> TYPE: DNA
<213> ORGANISM: Homo sapiens
<300> PUBLICATION INFORMATION:
<302> TITLE: Bax beta
<310> PATENT DOCUMENT NUMBER: L22474

-continued

<400> SEQUENCE: 34

| | | | | | |
|---|---|---|---|---|---|
| atggacgggt | ccggggagca | gcccagaggc | ggggggccca | ccagctctga | gcagatcatg | 60 |
| aagacagggg | cccttttgct | tcagggtttc | atccaggatc | gagcagggcg | aatggggggg | 120 |
| gaggcacccg | agctggccct | ggacccggtg | cctcaggatg | cgtccaccaa | gaagctgagc | 180 |
| gagtgtctca | agcgcatcgg | ggacgaactg | gacagtaaca | tggagctgca | gaggatgatt | 240 |
| gccgccgtgg | acacagactc | cccccgagag | gtcttttttcc | gagtggcagc | tgacatgttt | 300 |
| tctgacggca | acttcaactg | ggccgggtt | gtcgcccttt | tctactttgc | cagcaaactg | 360 |
| gtgctcaagg | ccctgtgcac | caaggtgccg | gaactgatca | gaaccatcat | gggctggaca | 420 |
| ttggacttcc | tccgggagcg | gctgttgggc | tggatccaag | accagggtgg | ttgggtgaga | 480 |
| ctcctcaagc | ctcctcaccc | ccaccaccgc | gccctcacca | ccgcccctgc | cccaccgtcc | 540 |
| ctgcccccccg | ccactcctct | gggaccctgg | gccttctgga | gcaggtcaca | gtggtgccct | 600 |
| ctccccatct | tcagatcatc | agatgtggtc | tataatgcgt | tttccttacg | tgtctga | 657 |

<210> SEQ ID NO 35
<211> LENGTH: 432
<212> TYPE: DNA
<213> ORGANISM: Homo sapiens
<300> PUBLICATION INFORMATION:
<302> TITLE: Bax delta
<310> PATENT DOCUMENT NUMBER: U19599

<400> SEQUENCE: 35

| | | | | | |
|---|---|---|---|---|---|
| atggacgggt | ccggggagca | gcccagaggc | ggggggccca | ccagctctga | gcagatcatg | 60 |
| aagacagggg | cccttttgct | tcaggggatg | attgccgccg | tggacacaga | ctccccccga | 120 |
| gaggtctttt | tccgagtggc | agctgacatg | tttttctgacg | gcaacttcaa | ctggggccgg | 180 |
| gttgtcgccc | ttttctactt | tgccagcaaa | ctggtgctca | aggccctgtg | caccaaggtg | 240 |
| ccggaactga | tcagaaccat | catgggctgg | acattggact | tcctccggga | gcggctgttg | 300 |
| ggctggatcc | aagaccaggg | tggttgggac | ggcctcctct | cctactttgg | gacgcccacg | 360 |
| tggcagaccg | tgaccatctt | tgtggcggga | gtgctcaccg | cctcgctcac | catctggaag | 420 |
| aagatgggct | ga | | | | | 432 |

<210> SEQ ID NO 36
<211> LENGTH: 495
<212> TYPE: DNA
<213> ORGANISM: Homo sapiens
<300> PUBLICATION INFORMATION:
<302> TITLE: Bax epsolin
<310> PATENT DOCUMENT NUMBER: AF007826

<400> SEQUENCE: 36

| | | | | | |
|---|---|---|---|---|---|
| atggacgggt | ccggggagca | gcccagaggc | ggggggccca | ccagctctga | gcagatcatg | 60 |
| aagacagggg | cccttttgct | tcagggtttc | atccaggatc | gagcagggcg | aatggggggg | 120 |
| gaggcacccg | agctggccct | ggacccggtg | cctcaggatg | cgtccaccaa | gaagctgagc | 180 |
| gagtgtctca | agcgcatcgg | ggacgaactg | gacagtaaca | tggagctgca | gaggatgatt | 240 |
| gccgccgtgg | acacagactc | cccccgagag | gtcttttttcc | gagtggcagc | tgacatgttt | 300 |
| tctgacggca | acttcaactg | ggccgggtt | gtcgcccttt | tctactttgc | cagcaaactg | 360 |
| gtgctcaagg | ctggcgtgaa | atggcgtgat | ctgggctcac | tgcaacctct | gcctcctggg | 420 |
| ttcaagcgat | tcacctgcct | cagcatccca | aggagctggg | attacaggcc | ctgtgcacca | 480 |
| aggtgccgga | actga | | | | | 495 |

<210> SEQ ID NO 37
<211> LENGTH: 582
<212> TYPE: DNA
<213> ORGANISM: Homo sapiens
<300> PUBLICATION INFORMATION:
<302> TITLE: bcl-w
<310> PATENT DOCUMENT NUMBER: U59747

<400> SEQUENCE: 37

| | | | | | |
|---|---|---|---|---|---|
| atggcgaccc | cagcctcggc | cccagacaca | cgggctctgg | tggcagactt | tgtaggttat | 60 |
| aagctgaggc | agaagggtta | tgtctgtgga | gctggcccg | gggagggccc | agcagctgac | 120 |
| ccgctgcacc | aagccatgcg | ggcagctgga | gatgagttcg | agacccgctt | ccggcgcacc | 180 |
| ttctctgatc | tggcggctca | gctgcatgtg | accccaggct | cagcccagca | acgcttcacc | 240 |
| caggtctccg | acgaactttt | tcaaggggc | cccaactggg | gccgccttgt | agccttcttt | 300 |
| gtctttgggg | ctgcactgtg | tgctgagagt | gtcaacaagg | agatggaacc | actggtggga | 360 |
| caagtgcagg | agtggatggt | ggcctacctg | gagacgcggc | tggctgactg | gatccacagc | 420 |
| agtgggggct | gggcggagtt | cacagctcta | tacggggacg | gggccctgga | ggaggcgcgg | 480 |
| cgtctgcggg | aggggaactg | ggcatcagtg | aggacagtgc | tgacggggc | cgtggcactg | 540 |
| ggggccctgg | taactgtagg | ggcctttttt | gctagcaagt | ga | | 582 |

<210> SEQ ID NO 38
<211> LENGTH: 2481
<212> TYPE: DNA
<213> ORGANISM: Homo sapiens
<300> PUBLICATION INFORMATION:
<302> TITLE: HIF-alpha
<310> PATENT DOCUMENT NUMBER: U22431

<400> SEQUENCE: 38

| | | | | | |
|---|---|---|---|---|---|
| atggagggcg | ccggcggcgc | gaacgacaag | aaaaagataa | gttctgaacg | tcgaaaagaa | 60 |
| aagtctcgag | atgcagccag | atctcggcga | agtaaagaat | ctgaagtttt | ttatgagctt | 120 |
| gctcatcagt | tgccacttcc | acataatgtg | agttcgcatc | ttgataaggc | ctctgtgatg | 180 |
| aggcttacca | tcagctattt | gcgtgtgagg | aaacttctgg | atgctggtga | tttggatatt | 240 |
| gaagatgaca | tgaaagcaca | gatgaattgc | tttatttga | aagccttgga | tggttttgtt | 300 |
| atggttctca | cagatgatgg | tgacatgatt | tacatttctg | ataatgtgaa | caaatacatg | 360 |
| ggattaactc | agtttgaact | aactggacac | agtgtgtttg | attttactca | tccatgtgac | 420 |
| catgaggaaa | tgagagaaat | gcttacacac | agaaatggcc | ttgtgaaaaa | gggtaaagaa | 480 |
| caaaacacac | agcgaagctt | ttttctcaga | atgaagtgta | ccctaactag | ccgaggaaga | 540 |
| actatgaaca | taaagtctgc | aacatggaag | gtattgcact | gcacaggcca | cattcacgta | 600 |
| tatgatacca | acagtaacca | acctcagtgt | gggtataaga | aaccacctat | gacctgcttg | 660 |
| gtgctgattt | gtgaacccat | tcctcaccca | tcaaatattg | aaattccttt | agatagcaag | 720 |
| actttcctca | gtcgacacag | cctggatatg | aaattttctt | attgtgatga | agaattacc | 780 |
| gaattgatgg | gatatgagcc | agaagaactt | ttaggccgct | caatttatga | atattatcat | 840 |
| gctttggact | ctgatcatct | gaccaaaact | catcatgata | tgtttactaa | aggacaagtc | 900 |
| accacaggac | agtacaggat | gcttgccaaa | agaggtggat | atgtctgggt | tgaaactcaa | 960 |
| gcaactgtca | tatataacac | caagaattct | caaccacagt | gcattgtatg | tgtgaattac | 1020 |
| gttgtgagtg | gtattattca | gcacgacttg | attttctccc | ttcaacaaac | agaatgtgtc | 1080 |
| cttaaaccgg | ttgaatcttc | agatatgaaa | atgactcagc | tattcaccaa | agttgaatca | 1140 |

```
gaagatacaa gtagcctctt tgacaaactt aagaaggaac ctgatgcttt aactttgctg    1200
gccccagccg ctggagacac aatcatatct ttagattttg gcagcaacga cacagaaact    1260
gatgaccagc aacttgagga agtaccatta tataatgatg taatgctccc ctcacccaac    1320
gaaaaattac agaatataaa tttggcaatg tctccattac ccaccgctga aacgccaaag    1380
ccacttcgaa gtagtgctga ccctgcactc aatcaagaag ttgcattaaa attagaacca    1440
aatccagagt cactggaact ttcttttacc atgccccaga ttcaggatca gacacctagt    1500
ccttccgatg gaagcactag acaaagttca cctgagccta atagtcccag tgaatattgt    1560
ttttatgtgg atagtgatat ggtcaatgaa ttcaagttgg aattggtaga aaaacttttt    1620
gctgaagaca cagaagcaaa gaacccattt tctactcagg acacagattt agacttggag    1680
atgttagctc cctatatccc aatggatgat gacttccagt tacgttcctt cgatcagttg    1740
tcaccattag aaagcagttc cgcaagccct gaaagcgcaa gtcctcaaag cacagttaca    1800
gtattccagc agactcaaat acaagaacct actgctaatg ccaccactac cactgccacc    1860
actgatgaat taaaaacagt gacaaaagac cgtatggaag acattaaaat attgattgca    1920
tctccatctc ctacccacat acataaagaa actactagtg ccacatcatc accatataga    1980
gatactcaaa gtcggacagc ctcaccaaac agagcaggaa aaggagtcat agaacagaca    2040
gaaaaatctc atccaagaag ccctaacgtg ttatctgtcg ctttgagtca agaactaca    2100 gttcctgagg aagaactaaa tccaaagata ctagctttgc agaatgctca gagaaagcga    2160
aaaatggaac atgatggttc acttttcaa gcagtaggaa ttggaacatt attacagcag    2220
ccagacgatc atgcagctac tacatcactt tcttggaaac gtgtaaaagg atgcaaatct    2280
agtgaacaga atgaatgga gcaaaagaca attattttaa taccctctga tttagcatgt    2340
agactgctgg ggcaatcaat ggatgaaagt ggattaccac agctgaccag ttatgattgt    2400
gaagttaatg ctcctataca aggcagcaga aacctactgc agggtgaaga attactcaga    2460
gctttggatc aagttaactg a                                              2481

<210> SEQ ID NO 39
<211> LENGTH: 481
<212> TYPE: DNA
<213> ORGANISM: Homo sapiens
<300> PUBLICATION INFORMATION:
<302> TITLE: ID1
<310> PATENT DOCUMENT NUMBER: X77956

<400> SEQUENCE: 39
atgaaagtcg ccagtggcag caccgccacc gccgccgcgg gccccagctg cgcgctgaag      60
gccggcaaga cagcgagcgg tgcgggcgag gtggtgcgct gtctgtctga gcagagcgtg     120
gccatctcgc gctgccgggg cgccggggcg cgcctgcctg ccctgctgga cgagcagcag     180
gtaaacgtgt gctctacga catgaacggc tgttactcac gcctcaagga gctggtgccc     240
accctgcccc agaaccgcaa ggtgagcaag gtggagattc tccagcacgt catcgactac     300
atcagggacc ttcagttgga gctgaactcg gaatccgaag ttgggacccc cggggggcga     360
gggctgccgg tccgggctcc gctcagcacc ctcaacggcg agatcagcgc cctgacggcc     420
gaggcggcat gcgttcctgc ggacgatcgc atcttgtgtc gctgaatggt gaaaaaaaaa     480
a                                                                    481

<210> SEQ ID NO 40
<211> LENGTH: 110
<212> TYPE: DNA
```

```
<213> ORGANISM: Homo sapiens
<300> PUBLICATION INFORMATION:
<302> TITLE: ID2B
<310> PATENT DOCUMENT NUMBER: M96843

<400> SEQUENCE: 40
tgaaagcctt cagtcccgtg aggtccatta ggaaaaacag cctgttggac caccgcctgg      60
gcatctccca gagcaaaacc ccggtggatg acctgatgag cctgctgtaa               110

<210> SEQ ID NO 41
<211> LENGTH: 486
<212> TYPE: DNA
<213> ORGANISM: Homo sapiens
<300> PUBLICATION INFORMATION:
<302> TITLE: ID4
<310> PATENT DOCUMENT NUMBER: Y07958

<400> SEQUENCE: 41
atgaaggcgg tgagcccggt gcgcccctcg ggccgcaagg cgccgtcggg ctgcggcggc      60
ggggagctgg cgctgcgctg cctggccgag cacggccaca gctgggtgg ctccgcagcc     120 gcggcggcgg cggcggcggc agcgcgctgt aaggcggccg aggcggcggc cgacgagccg     180
gcgctgtgcc tgcagtgcga tatgaacgac tgctatagcc gcctgcggag gctggtgccc     240
accatcccgc caacaagaa agtcagcaaa gtggagatcc tgcagcacgt tatcgactac     300
atcctggacc tgcagctggc gctggagacg caccccggccc tgctgaggca gccaccaccg     360
cccgcgccgc cacaccaccc ggccgggacc tgtccagccg cgccgccgcg accccgctc     420 actgcgctca acaccgaccc ggccggcgcg gtgaacaagc agggcgacag cattctgtgc     480
cgctga                                                               486

<210> SEQ ID NO 42
<211> LENGTH: 462
<212> TYPE: DNA
<213> ORGANISM: Homo sapiens
<300> PUBLICATION INFORMATION:
<302> TITLE: IGF1
<310> PATENT DOCUMENT NUMBER: NM000618

<400> SEQUENCE: 42
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca cccctcaagc ctgccaagtc agctcgctct     360
gtccgtgccc agcgccacac cgacatgccc aagacccaga aggaagtaca tttgaagaac     420
gcaagtagag ggagtgcagg aaacaagaac tacaggatgt ag                       462

<210> SEQ ID NO 43
<211> LENGTH: 591
<212> TYPE: DNA
<213> ORGANISM: Homo sapiens
<300> PUBLICATION INFORMATION:
<302> TITLE: PDGFA
<310> PATENT DOCUMENT NUMBER: NM002607

<400> SEQUENCE: 43
atgaggacct tggcttgcct gctgctcctc ggctgcggat acctcgccca tgttctggcc      60
```

-continued

```
gaggaagccg agatcccccg cgaggtgatc gagaggctgg cccgcagtca gatccacagc    120
atccgggacc tccagcgact cctggagata gactccgtag ggagtgagga ttctttggac    180
accagcctga gagctcacgg ggtccacgcc actaagcatg tgcccgagaa gcggcccctg    240
cccattcgga ggaagagaag catcgaggaa gctgtcccccg ctgtctgcaa gaccaggacg    300
gtcatttacg agattcctcg gagtcaggtc gaccccacgt ccgccaactt cctgatctgg    360
cccccgtgcg tggaggtgaa acgctgcacc ggctgctgca acacgagcag tgtcaagtgc    420
cagccctccc gcgtccacca ccgcagcgtc aaggtggcca aggtggaata cgtcaggaag    480
aagccaaaat taaagaagt ccaggtgagg ttagaggagc atttggagtg cgcctgcgcg    540
accacaagcc tgaatccgga ttatcgggaa gaggacacgg atgtgaggtg a             591
```

```
<210> SEQ ID NO 44
<211> LENGTH: 528
<212> TYPE: DNA
<213> ORGANISM: Homo sapiens
<300> PUBLICATION INFORMATION:
<302> TITLE: PDGFRA
<310> PATENT DOCUMENT NUMBER: XM003568

<400> SEQUENCE: 44
```

```
atggccaagc ctgaccacgc taccagtgaa gtctacgaga tcatggtgaa atgctggaac     60
agtgagccgg agaagagacc ctccttttac cacctgagtg agattgtgga gaatctgctg    120
cctggacaat ataaaaagag ttatgaaaaa attcacctgg acttcctgaa gagtgaccat    180
cctgctgtgg cacgcatgcg tgtggactca gacaatgcat acattggtgt cacctacaaa    240
aacgaggaag acaagctgaa ggactgggag ggtggtctgg atgagcagag actgagcgct    300
gacagtggct acatcattcc tctgcctgac attgaccctg tccctgagga ggaggacctg    360
ggcaagagga acagacacag ctcgcagacc tctgaagaga gtgccattga cgggttcc     420 agcagttcca ccttcatcaa gagagaggac gagaccattg aagacatcga catgatggat    480
gacatcggca tagactcttc agacctggtg gaagacagct cctgtaa                  528
```

```
<210> SEQ ID NO 45
<211> LENGTH: 1911
<212> TYPE: DNA
<213> ORGANISM: Homo sapiens
<300> PUBLICATION INFORMATION:
<302> TITLE: PDGFRB
<310> PATENT DOCUMENT NUMBER: XM003790

<400> SEQUENCE: 45
```

```
atgcggcttc cgggtgcgat gccagctctg gccctcaaag gcgagctgct gttgctgtct     60
ctcctgttac ttctggaacc acagatctct caggggcctgg tcgtcacacc cccggggcca    120
gagcttgtcc tcaatgtctc cagcaccttc gttctgacct gctcgggttc agctccggtg    180
gtgtgggaac ggatgtccca ggagccccca caggaaatgg ccaaggccca ggatggcacc    240
ttctccagcg tgctcacact gaccaacctc actgggctag acacgggaga atacttttgc    300
acccacaatg actcccgtgg actggagacc gatgagcgga aacggctcta catctttgtg    360
ccagatccca ccgtgggctt cctccctaat gatgccgagg aactattcat ctttctcacg    420
gaaataactg agatcaccat tccatgccga gtaacagacc cacagctggt ggtgacactg    480
cacgagaaga aggggacgt tgcactgcct gtcccctatg atcaccaacg tggcttttct    540
ggtatctttg aggacagaag ctacatctgc aaaaccacca ttgggggacag ggaggtggat    600 tctgatgcct actatgtcta cagactccag gtgtcatcca tcaacgtctc tgtgaacgca    660
```

```
gtgcagactg tggtccgcca gggtgagaac atcaccctca tgtgcattgt gatcgggaat      720
gaggtggtca acttcgagtg gacataccc  cgcaaagaaa gtgggcggct ggtggagccg      780
gtgactgact tcctcttgga tatgccttac cacatccgct ccatcctgca catccccagt      840
gccgagttag aagactcggg gacctacacc tgcaatgtga cggagagtgt gaatgaccat      900
caggatgaaa aggccatcaa catcaccgtg gttgagagcg gctacgtgcg gctcctggga      960
gaggtgggca cactacaatt tgctgagctg catcggagcc ggacactgca ggtagtgttc     1020
gaggcctacc caccgcccac tgtcctgtgg ttcaaagaca accgcaccct gggcgactcc     1080
agcgctggcg aaatcgccct gtccacgcgc aacgtgtcgg agacccggta tgtgtcagag     1140
ctgacactgg ttcgcgtgaa ggtggcagag gctggccact acaccatgcg ggccttccat     1200
gaggatgctg aggtccagct ctccttccag ctacagatca atgtccctgt ccgagtgctg     1260
gagctaagtg agagccaccc tgacagtggg gaacagacag tccgctgtcg tggccggggc     1320
atgccccagc cgaacatcat ctggtctgcc tgcagagacc tcaaaaggtg tccacgtgag     1380
ctgccgccca cgctgctggg gaacagttcc gaagaggaga gccagctgga gactaacgtg     1440
acgtactggg aggaggagca ggagtttgag gtggtgagca cactgcgtct gcagcacgtg     1500
gatcggccac tgtcggtgcg ctgcacgctg cgcaacgctg tgggccagga cacgcaggag     1560
gtcatcgtgg tgccacactc cttgccctt  aaggtggtgg tgatctcagc catcctggcc     1620
ctggtggtgc tcaccatcat ctcccttatc atcctcatca tgctttggca gaagaagcca     1680
cgttacgaga tccgatggaa ggtgattgag tctgtgagct ctgacggcca tgagtacatc     1740
tacgtggacc ccatgcagct gccctatgac tccacgtggg agctgccgcg ggaccagctt     1800
gtgctgggac gcaccctcgg ctctggggcc tttgggcagg tggtggaggc cacggttcat     1860
ggcctgagcc attttcaagc cccaatgaaa gtggccgtca aaaatgctta a              1911
```

<210> SEQ ID NO 46
<211> LENGTH: 1176
<212> TYPE: DNA
<213> ORGANISM: Homo sapiens
<300> PUBLICATION INFORMATION:
<302> TITLE: TGFbeta1
<310> PATENT DOCUMENT NUMBER: NM000660

<400> SEQUENCE: 46

```
atgccgccct ccgggctgcg gctgctgccg ctgctgctac cgctgctgtg gctactggtg       60
ctgacgcctg gccgccggc  cgcgggacta tccacctgca agactatcga catggagctg      120
gtgaagcgga gcgcatcga  ggccatccgc ggccagatcc tgtccaagct gcggctcgcc      180
agccccccga gccaggggga ggtgccgccc ggccgctgc  cgaggccgt  gctcgccctg      240 tacaacagca cccgcgaccg ggtggccggg gagagtgcag aaccggagcc cgagcctgag      300
gccgactact acgccaagga ggtcacccgc gtgctaatgg tggaaaccca caacgaaatc      360
tatgacaagt tcaagcagag tacacacagc atatatatgt tcttcaacac atcagagctc      420
cgagaagcgg tacctgaacc cgtgttgctc tcccggcag  agctgcgtct gctgaggagg      480
ctcaagttaa aagtggagca gcacgtggag ctgtaccaga atacagcaa  caattcctgg      540 cgatacctca gcaaccggct gctggcaccc agcgactcgc cagagtggtt atcttttgat      600
gtcaccggag ttgtgcggca gtggttgagc cgtgagggga aaattgaggg ctttcgcctt      660
agcgcccact gctcctgtga cagcagggat aacacactgc aagtggacat caacgggttc      720
actaccggcc gccgaggtga cctggccacc attcatggca tgaaccggcc tttcctgctt      780
ctcatggcca ccccgctgga gagggccag  catctgcaaa gctcccggca ccgccgagcc      840
```

```
ctggacacca actattgctt cagctccacg gagaagaact gctgcgtgcg gcagctgtac      900
attgacttcc gcaaggacct cggctggaag tggatccacg agcccaaggg ctaccatgcc      960
aacttctgcc tcgggccctg ccctacatt tggagcctgg acacgcagta cagcaaggtc     1020
ctggccctgt acaaccagca taacccgggc gcctcggcgg cgccgtgctg cgtgccgcag     1080
gcgctggagc cgctgcccat cgtgtactac gtgggccgca agcccaaggt ggagcagctg     1140
tccaacatga tcgtgcgctc ctgcaagtgc agctga                              1176
```

<210> SEQ ID NO 47
<211> LENGTH: 1245
<212> TYPE: DNA
<213> ORGANISM: Homo sapiens
<300> PUBLICATION INFORMATION:
<302> TITLE: TGFbeta2
<310> PATENT DOCUMENT NUMBER: NM003238

<400> SEQUENCE: 47

```
atgcactact gtgtgctgag cgcttttctg atcctgcatc tggtcacggt cgcgctcagc       60
ctgtctacct gcagcacact cgatatggac cagttcatgc gcaagaggat cgaggcgatc      120
cgcgggcaga tcctgagcaa gctgaagctc accagtcccc cagaagacta tcctgagccc      180
gaggaagtcc ccccggaggt gatttccatc tacaacagca ccagggactt gctccaggag      240
aaggcgagcc ggaggcggc cgcctgcgag cgcgagagga gcgacgaaga gtactacgcc      300
aaggaggttt acaaaataga catgccgccc ttcttcccct ccgaaaatgc catcccgccc      360
actttctaca gaccctactt cagaattgtt cgatttgacg tctcagcaat ggagaagaat      420
gcttccaatt tggtgaaagc agagttcaga gtctttcgtt tgcagaaccc aaaagccaga      480
gtgcctgaac aacggattga gctatatcag attctcaagt ccaaagattt aacatctcca      540
acccagcgct acatcgacag caaagttgtg aaaacaagag cagaaggcga atggctctcc      600
ttcgatgtaa ctgatgctgt tcatgaatgg cttcaccata agacaggaa cctgggattt      660 aaaataagct acactgtcc ctgctgcact tttgtaccat ctaataatta catcatccca      720
aataaaagtg aagaactaga agcaagattt gcaggtattg atggcaccc cacatatacc      780 agtggtgatc agaaaactat aaagtccact aggaaaaaaa acagtgggaa gacccccacat      840 ctcctgctaa tgttattgcc ctcctacaga cttgagtcac aacagaccaa ccggcggaag      900
aagcgtgctt tggatgcggc ctattgcttt agaaatgtgc aggataattg ctgcctacgt      960
ccactttaca ttgatttcaa gagggatcta gggtggaaat ggatacacga acccaaaggg     1020
tacaatgcca acttctgtgc tggagcatgc ccgtatttat ggagttcaga cactcagcac     1080
agcagggtcc tgagcttata taataccata aatccagaag catctgcttc tccttgctgc     1140
gtgtcccaag atttagaacc tctaaccatt ctctactaca ttggcaaaac acccaagatt     1200
gaacagcttt ctaatatgat tgtaaagtct tgcaaatgca gctaa                    1245
```

<210> SEQ ID NO 48
<211> LENGTH: 1239
<212> TYPE: DNA
<213> ORGANISM: Homo sapiens
<300> PUBLICATION INFORMATION:
<302> TITLE: TGFbeta3
<310> PATENT DOCUMENT NUMBER: XM007417

<400> SEQUENCE: 48

```
atgaagatgc acttgcaaag ggctctggtg gtcctggccc tgctgaactt tgccacggtc       60
agcctctctc tgtccacttg caccaccttg gacttcggcc acatcaagaa gaagagggtg     120
```

```
gaagccatta ggggacagat cttgagcaag ctcaggctca ccagcccccc tgagccaacg      180
gtgatgaccc acgtccccta tcaggtcctg gcccttaca acagcacccg ggagctgctg      240
gaggagatgc atggggagag ggaggaaggc tgcacccagg aaaacaccga gtcggaatac      300
tatgccaaag aaatccataa attcgacatg atccaggggc tggcggagca caacgaactg      360
gctgtctgcc ctaaaggaat tacctccaag gttttccgct tcaatgtgtc ctcagtggag      420
aaaaatagaa ccaacctatt ccgagcagaa ttccgggtct tgcgggtgcc caaccccagc      480
tctaagcgga tgagcagag gatcgagctc ttccagatcc ttcggccaga tgagcacatt      540
gccaaacagc gctatatcgg tggcaagaat ctgcccacac ggggcactgc cgagtggctg      600
tcctttgatg tcactgacac tgtgcgtgag tggctgttga agagagagtc caacttaggt      660
ctagaaatca gcattcactg tccatgtcac acctttcagc ccaatggaga tatcctggaa      720
aacattcacg aggtgatgga aatcaaattc aaaggcgtgg acaatgagga tgaccatggc      780
cgtggagatc tggggcgcct caagaagcag aaggatcacc acaaccctca tctaatcctc      840
atgatgattc ccccacaccg gctcgacaac ccgggccagg ggggtcagag gaagaagcgg      900
gctttggaca ccaattactg cttccgcaac ttggaggaga actgctgtgt gcgccccctc      960
tacattgact ccgacagga tctgggctgg aagtgggtcc atgaacctaa gggctactat     1020
gccaacttct gctcaggccc ttgcccatac ctccgcagtg cagacacaac ccacagcacg     1080
gtgctgggac tgtacaacac tctgaaccct gaagcatctg cctcgccttg ctgcgtgccc     1140
caggacctgg agccctgac catcctgtac tatgttggga ggaccccaa agtggagcag     1200 ctctccaaca tggtggtgaa gtcttgtaaa tgtagctga                           1239

<210> SEQ ID NO 49
<211> LENGTH: 1704
<212> TYPE: DNA
<213> ORGANISM: Homo sapiens
<300> PUBLICATION INFORMATION:
<302> TITLE: TGFbetaR2
<310> PATENT DOCUMENT NUMBER: XM003094

<400> SEQUENCE: 49
atgggtcggg ggctgctcag gggcctgtgg ccgctgcaca tcgtcctgtg gacgcgtatc       60
gccagcacga tccaccgcca cgttcagaag tcggttaata cgacatgat agtcactgac      120 aacaacggtg cagtcaagtt tccacaactg tgtaaatttt gtgatgtgag attttccacc      180
tgtgacaacc agaaatcctg catgagcaac tgcagcatca cctccatctg tgagaagcca      240
caggaagtct gtgtggctgt atggagaaag aatgacgaga acataacact agagacagtt      300
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata acaccagcaa tcctgacttg      480
ttgctagtca tatttcaagt gacaggcatc agcctcctgc caccactggg agttgccata     540
tctgtcatca tcatcttcta ctgctaccgc gttaaccggc agcagaagct gagttcaacc     600
tgggaaaccg gcaagacgcg gaagctcatg gagttcagcg agcactgtgc catcatcctg     660
gaagatgacc gctctgacat cagctccacg tgtgccaaca acatcaacca caacacagag     720
ctgctgccca ttgagctgga caccctggtg gggaaaggtc gctttgctga ggtctataag     780
gccaagctga tgcagaacac ttcagagcag tttgagacag tggcagtcaa gatctttccc     840
tatgaggagt atgccttcttg gaagacagag aaggacatct tctcagacat caatctgaag     900
```

```
catgagaaca tactccagtt cctgacggct gaggagcgga agacggagtt ggggaaacaa      960
tactggctga tcaccgcctt ccacgccaag ggcaacctac aggagtacct gacgcggcat     1020
gtcatcagct gggaggacct gcgcaagctg ggcagctccc tcgcccgggg gattgctcac     1080
ctccacagtg atcacactcc atgtggggag cccaagatgc ccatcgtgca cagggacctc     1140
aagagctcca atatcctcgt gaagaacgac ctaacctgct gcctgtgtga ctttgggctt     1200
tccctgcgtc tggaccctac tctgtctgtg atgacctgg ctaacagtgg gcaggtggga     1260
actgcaagat acatggctcc agaagtccta gaatccagga tgaatttgga gaatgttgag     1320
tccttcaagc agaccgatgt ctactccatg gctctggtgc tctgggaaat gacatctcgc     1380
tgtaatgcag tgggagaagt aaaagattat gagcctccat ttggttccaa ggtgcgggag     1440
caccctgtg tcgaaagcat gaaggacaac gtgttgagag atcgagggcg accagaaatt     1500
cccagcttct ggctcaacca ccagggcatc cagatggtgt gtgagacgtt gactgagtgc     1560
tgggaccacg acccagaggc ccgtctcaca gcccagtgtg tggcagaacg cttcagtgag     1620
ctggagcatc tggacaggct ctcggggagg agctgctcgg aggagaagat tcctgaagac     1680
ggctccctaa acactaccaa atag                                           1704

<210> SEQ ID NO 50
<211> LENGTH: 609
<212> TYPE: DNA
<213> ORGANISM: Homo sapiens
<300> PUBLICATION INFORMATION:
<302> TITLE: TGFbeta3
<310> PATENT DOCUMENT NUMBER: XM001924

<400> SEQUENCE: 50
atgtctcatt acaccattat tgagaatatt tgtcctaaag atgaatctgt gaaattctac       60
agtcccaaga gagtgcactt tcctatcccg caagctgaca tggataagaa gcgattcagc      120
tttgtcttca gcctgtcttc aacacctca ctgctctttc tacagtgtga gctgacgctg      180
tgtacgaaga tggagaagca ccccagaag ttgcctaagt gtgtgcctcc tgacgaagcc      240
tgcacctcgc tggacgcctc gataatctgg gccatgatgc agaataagaa gacgttcact      300
aagccccttg ctgtgatcca ccatgaagca gaatctaaag aaaaaggtcc aagcatgaag      360
gaaccaaatc caattctcc accaattttc catggtctgg acaccctaac cgtgatgggc      420
attgcgtttg cagcctttgt gatcggagca ctcctgacgg ggccttgtg gtacatctat      480
tctcacacag gggagacagc aggaaggcag caagtcccca cctccccgcc agcctcggaa      540
aacagcagtg ctgcccacag catcggcagc acgcagagca cgccttgctc cagcagcagc      600
acggcctag                                                            609

<210> SEQ ID NO 51
<211> LENGTH: 3633
<212> TYPE: DNA
<213> ORGANISM: Homo sapiens
<300> PUBLICATION INFORMATION:
<302> TITLE: EGFR
<310> PATENT DOCUMENT NUMBER: X00588

<400> SEQUENCE: 51
atgcgaccct ccgggacggc cggggcagcg ctcctggcgc tgctggctgc gctctgcccg       60
gcgagtcggg ctctggagga aaagaaagtt tgccaaggca cgagtaacaa gctcacgcag      120
ttgggcactt ttgaagatca ttttctcagc ctccagagga tgttcaataa ctgtgaggtg      180
gtccttggga atttggaaat tacctatgtg cagaggaatt atgatctttc cttcttaaag      240
```

```
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg agctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat ccgagacga agccacgtgc    780
aaggacacct gcccccccact catgctctac aaccccacca cgtaccagat ggatgtgaac    840
cccgagggca atacagcttt tggtgccacc tgcgtgaaga agtgtccccg taattatgtg    900
gtgacagatc acgctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactgata ttctgaaaac cgtaaggaa    1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc agtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca cacccctggt ctggaagtac gcagacgccg ccatgtgtg ccacctgtgc   1860
catccaaaact gcacctacgg atgcactggg ccaggtcttg aaggctgtcc aacgaatggg   1920
cctaagatcc cgtccatcgc cactgggatg gtggggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta aagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
```

```
atggcattgg aatcaatttt acacagaatc tatacccacc agagtgatgt ctggagctac    2700
ggggtgaccg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc    2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 52
<211> LENGTH: 3768
<212> TYPE: DNA
<213> ORGANISM: Homo sapiens
<300> PUBLICATION INFORMATION:
<302> TITLE: ERBB2
<310> PATENT DOCUMENT NUMBER: NM004448

<400> SEQUENCE: 52

```
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac caggcctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acaataccac ccctgtcaca ggggcctccc caggaggcct gcgggagctg     420
cagcttcgaa gcctcacaga gatcttgaaa ggaggggtct tgatccagcg gaaccccag     480 ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
tccatgccca tccccgaggg ccggtataca ttcggcgcca gctgtgtgac tgcctgtccc     900
tacaactacc tttctacgga cgtgggatcc tgcaccctcg tctgccccct gcacaaccaa     960
gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat    1080
```

```
atccaggagt tgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccgggac gaattctgca caatggcgcc    1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac aagctctgc tccacactgc caaccggcca    1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcgtctctgc ggtggttggc   1980
attctgctgg tcgtggtctt gggggtggtc tttgggatcc tcatcaagcg acggcagcag   2040
aagatccgga gtacacgat gcggagactg ctgcaggaaa cggagctggt ggagccgctg    2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca agagtcccaa ccatgtcaaa   2580
attacagact cgggctggc tcggctgctg acattgacg agacagagta ccatgcagat   2640 ggggcaagg tgcccatcaa gtggatggcg ctggagtcca ttctccgccg gcggttcacc   2700
caccagagtg atgtgtggag ttatggtgtg actgtgtggg agctgatgac ttttggggcc   2760
aaaccttacg atgggatccc cagcccggag atccctgacc tgctggaaaa gggggagcgg   2820
ctgccccagc cccccatctg caccattgat gtctacatga tcatggtcaa atgttggatg   2880
attgactctg aatgtcggcc aagattccgg gagttggtgt ctgaattctc ccgcatggcc   2940
agggaccccc agcgctttgt ggtcatccag aatgaggact gggcccagc cagtcccttg   3000 gacagcacct tctaccgctc actgctggag gacgatgaca tgggggacct ggtggatgct   3060
gaggagtatc tggtacccca gcagggcttc ttctgtccag accctgcccc gggcgctggg   3120
ggcatggtcc accacaggca ccgcagctca tctaccagga gtgcggtgg ggacctgaca    3180 ctagggctgg agccctctga agaggaggcc cccaggtctc cactggcacc ctccgaaggg   3240
gctggctccg atgtatttga tggtgacctg ggaatggggg cagccaaggg gctgcaaagc   3300 ctcccccacac atgacccag ccctctacag cggtacagtg aggacccac agtacccctg    3360 ccctctgaga ctgatggcta cgttgccccc ctgacctgca gccccagcc tgaatatgtg   3420 aaccagccag atgttcggcc ccagccccct tcgccccgag agggccctct gcctgctgcc   3480
```

| | |
|---|---:|
| cgacctgctg gtgccactct ggaaagggcc aagactctct ccccaggaa gaatggggtc | 3540 |
| gtcaaagacg tttttgcctt tggggtgcc gtggagaacc ccgagtactt gacacccag | 3600 |
| ggaggagctg cccctcagcc ccaccctcct cctgccttca gcccagcctt cgacaacctc | 3660 |
| tattactggg accaggaccc accagagcgg ggggctccac ccagcacctt caaagggaca | 3720 |
| cctacggcag agaacccaga gtacctgggt ctggacgtgc cagtgtga | 3768 |

<210> SEQ ID NO 53
<211> LENGTH: 1986
<212> TYPE: DNA
<213> ORGANISM: Homo sapiens
<300> PUBLICATION INFORMATION:
<302> TITLE: ERBB3
<310> PATENT DOCUMENT NUMBER: XM006723

<400> SEQUENCE: 53

| | |
|---|---:|
| atgcacaact tcagtgtttt ttccaatttg acaaccattg gaggcagaag cctctacaac | 60 |
| cggggcttct cattgttgat catgaagaac ttgaatgtca catctctggg cttccgatcc | 120 |
| ctgaaggaaa ttagtgctgg gcgtatctat ataagtgcca ataggcagct ctgctaccac | 180 |
| cactctttga actggaccaa ggtgcttcgg gggcctacgg aagagcgact agacatcaag | 240 |
| cataatcggc cgcgcagaga ctgcgtggca gagggcaaag tgtgtgaccc actgtgctcc | 300 |
| tctgggggat gctggggccc aggccctggt cagtgcttgt cctgtcgaaa ttatagccga | 360 |
| ggaggtgtct gtgtgaccca ctgcaacttt ctgaatgggg agcctcgaga atttgcccat | 420 |
| gaggccgaat gcttctcctg ccacccggaa tgccaaccca tggagggcac tgccacatgc | 480 |
| aatggctcgg gctctgatac ttgtgctcaa tgtgcccatt tcgagatgg cccccactgt | 540 |
| gtgagcagct gcccccatgg agtcctaggt gccaaggggc caatctacaa gtacccagat | 600 |
| gttcagaatg aatgtcggcc ctgccatgag aactgcaccc aggggtgtaa aggaccagag | 660 |
| cttcaagact gtttaggaca aacactggtg ctgatcggca aaacccatct gacaatggct | 720 |
| ttgacagtga tagcaggatt ggtagtgatt tcatgatgc tgggcggcac ttttctctac | 780 |
| tggcgtgggc gccggattca gaataaaagg gctatgaggc gatacttgga acggggtgag | 840 |
| agcatagagc ctctggaccc cagtgagaag gctaacaaag tcttggccag aatcttcaaa | 900 |
| gagacagagc taaggaagct taaagtgctt ggctcgggtg tctttggaac tgtgcacaaa | 960 |
| ggagtgtgga tccctgaggg tgaatcaatc aagattccag tctgcattaa agtcattgag | 1020 |
| gacaagagtg gacggcagag ttttcaagct gtgacagatc atatgctggc cattggcagc | 1080 |
| ctggaccatg cccacattgt aaggctgctg ggactatgcc agggtcatc tctgcagctt | 1140 |
| gtcactcaat atttgcctct gggttctctg ctggatcatg tgagacaaca ccgggggca | 1200 |
| ctgggccac agctgctgct caactgggga gtacaaattg ccaagggaat gtactacctt | 1260 |
| gaggaacatg gtatggtgca tagaaacctg gctgcccgaa acgtgctact caagtcaccc | 1320 |
| agtcaggttc aggtggcaga ttttggtgtg gctgacctgc tgcctcctga tgataagcag | 1380 |
| ctgctataca gtgaggccaa gactccaatt aagtggatgg cccttgagag tatccactt | 1440 |
| gggaaataca cacaccagag tgatgtctgg agctatggtg tgacagtttg ggagttgatg | 1500 |
| accttcgggg cagagcccta tgcagggcta cgattggctg aagtaccaga cctgctagag | 1560 |
| aaggggagc ggttggcaca gcccagatc tgcacaattg atgtctacat ggtgatggtc | 1620 |
| aagtgttgga tgattgatga gaacattcgc ccaaccttta aagaactagc caatgagttc | 1680 |
| accaggatgg cccgagaccc accacggtat ctggtcataa agagagagag tgggcctgga | 1740 |

```
atagccctg ggccagagcc ccatggtctg acaaacaaga agctagagga agtagagctg    1800
gagccagaac tagacctaga cctagacttg aagcagagg aggacaacct ggcaaccacc    1860
acactgggct ccgccctcag cctaccagtt ggaacactta atcggccacg tgggagccag    1920
agccttttaa gtccatcatc tggatacatg cccatgaacc agggtaatct tggggttctt    1980
ccttag                                                               1986
```

<210> SEQ ID NO 54
<211> LENGTH: 1437
<212> TYPE: DNA
<213> ORGANISM: Homo sapiens
<300> PUBLICATION INFORMATION:
<302> TITLE: ERBB4
<310> PATENT DOCUMENT NUMBER: XM002260

<400> SEQUENCE: 54

```
atgatgtacc tggaagaaag acgactcgtt catcgggatt tggcagcccg taatgtctta     60
gtgaaatctc caaccatgt gaaaatcaca gattttgggc tagccagact cttggaagga    120
gatgaaaaag agtacaatgc tgatggagga aagatgccaa ttaaatggat ggctctggag    180
tgtatacatt acaggaaatt cacccatcag agtgacgttt ggagctatgg agttactata    240
tgggaactga tgacctttgg aggaaaaccc tatgatggaa ttccaacgcg agaaatccct    300
gatttattag agaaaggaga acgtttgcct cagcctccca tctgcactat tgacgtttac    360
atggtcatgg tcaaatgttg gatgattgat gctgacagta gacctaaatt taggaactg    420 gctgctgagt tttcaaggat ggctcgagac cctcaaagat acctagttat tcagggtgat    480
gatcgtatga agcttcccag tccaaatgac agcaagttct ttcagaatct cttggatgaa    540
gaggatttgg aagatatgat ggatgctgag gagtacttgg tccctcaggc tttcaacatc    600
ccacctccca tctatacttc cagagcaaga attgactcga ataggagtga aattggacac    660
agccctcctc ctgcctacac ccccatgtca ggaaaccagt ttgtataccg agatggaggt    720
tttgctgctg aacaaggagt gtctgtgccc tacagagccc aactagcac aattccagaa    780 gctcctgtgg cacagggtgc tactgctgag atttttgatg actcctgctg taatggcacc    840
ctacgcaagc cagtggcacc ccatgtccaa gaggacagta gcacccagag gtacagtgct    900
gaccccaccg tgtttgcccc agaacggagc ccacgaggag agctggatga ggaaggttac    960
atgactccta tgcgagacaa acccaaacaa gaatacctga atccagtgga ggagaaccct   1020
tttgtttctc ggagaaaaaa tggagacctt caagcattgg ataatcccga atatcacaat   1080
gcatccaatg gtccacccaa ggccgaggat gagtatgtga atgagccact gtacctcaac   1140
acctttgcca acaccttggg aaaagctgag tacctgaaga caacatact gtcaatgcca   1200 gagaaggcca agaaagcgtt tgacaaccct gactactgga ccacagcct gccacctcgg   1260 agcacccttc agcacccaga ctacctgcag gagtacagca caaatatttt ttataaacag   1320
aatgggcgga tccggcctat tgtggcagag aatcctgaat acctctctga gttctccctg   1380
aagccaggca ctgtgctgcc gcctccacct tacagacacc ggaatactgt ggtgtaa      1437
```

<210> SEQ ID NO 55
<211> LENGTH: 627
<212> TYPE: DNA
<213> ORGANISM: Homo sapiens
<300> PUBLICATION INFORMATION:
<302> TITLE: FGF10
<310> PATENT DOCUMENT NUMBER: NM004465

<400> SEQUENCE: 55

```
atgtggaaat ggatactgac acattgtgcc tcagcctttc ccacctgcc cggctgctgc      60 tgctgctgct ttttgttgct gttcttggtg tcttccgtcc ctgtcacctg ccaagcccctt    120 ggtcaggaca tggtgtcacc agaggccacc aactcttctt cctcctcctt ctcctctcct    180
tccagcgcgg gaaggcatgt gcggagctac aatcacttc aaggagatgt ccgctggaga    240
aagctattct ctttcaccaa gtactttctc aagattgaga gaacgggaa ggtcagcggg    300 accaagaagg agaactgccc gtacagcatc ctggagataa catcagtaga atcggagtt    360 gttgccgtca agccattaa cagcaactat tacttagcca tgaacaagaa ggggaaactc    420
tatggctcaa agaatttaa caatgactgt aagctgaagg agaggataga ggaaaatgga    480
tacaatacct atgcatcatt taactggcag cataatggga ggcaaatgta tgtggcattg    540
aatggaaaag gagctccaag gagaggacag aaaacacgaa ggaaaaacac ctctgctcac    600
tttcttccaa tggtggtaca ctcatag                                         627

<210> SEQ ID NO 56
<211> LENGTH: 679
<212> TYPE: DNA
<213> ORGANISM: Homo sapiens
<300> PUBLICATION INFORMATION:
<302> TITLE: FGF11
<310> PATENT DOCUMENT NUMBER: XM008660

<400> SEQUENCE: 56
aatggcggcg ctggccagta gcctgatccg gcagaagcgg gaggtccgcg agcccggggg    60
cagccggccg gtgtcggcgc agcggcgcgt gtgtccccgc ggcaccaagt ccctttgcca    120
gaagcagctc ctcatcctgc tgtccaaggt gcgactgtgc gggggcggc ccgcgcggcc    180 ggaccgcggc ccggagcctc agctcaaagg catcgtcacc aaactgttct gccgccaggg    240
tttctacctc caggcgaatc ccgacggaag catccagggc accccagagg ataccagctc    300
cttcacccac ttcaacctga tccctgtggg cctccgtgtg gtcaccatcc agagcgccaa    360
gctgggtcac tacatggcca tgaatgctga gggactgctc tacagttcgc cgcatttcac    420
agctgagtgt cgctttaagg agtgtgtctt tgagaattac tacgtcctgt acgcctctgc    480
tctctaccgc cagcgtcgtt ctggccgggc ctggtacctc ggcctggaca aggagggcca    540
ggtcatgaag ggaaaccgag ttaagaagac caaggcagct gcccactttc tgcccaagct    600
cctggaggtg gccatgtacc aggagccttc tctccacagt gtccccgagg cctccccttc    660 cagtcccccct gccccctga                                                679

<210> SEQ ID NO 57
<211> LENGTH: 732
<212> TYPE: DNA
<213> ORGANISM: Homo sapiens
<300> PUBLICATION INFORMATION:
<302> TITLE: FGF12
<310> PATENT DOCUMENT NUMBER: NM021032

<400> SEQUENCE: 57
atggctgcgg cgatagccag ctccttgatc cggcagaagc ggcaggcgag ggagtccaac    60
agcgaccgag tgtcggcctc caagcgccgc tccagcccca gcaaagacgg gcgctccctg    120
tgcgagaggc acgtcctcgg ggtgttcagc aaagtgcgct tctgcagcgg ccgcaagagg    180
ccggtgaggc ggagaccaga acccagctc aaagggattg tgacaaggtt attcagccag    240
cagggatact tcctgcagat gcacccagat ggtaccattg atgggaccaa ggacgaaaac    300
agcgactaca ctctcttcaa tctaattccc gtgggcctgc gtgtagtggc catccaagga    360
```

| | |
|---|---|
| gtgaaggcta gcctctatgt ggccatgaat ggtgaaggct atctctacag ttcagatgtt | 420 |
| ttcactccag aatgcaaatt caaggaatct gtgtttgaaa actactatgt gatctattct | 480 |
| tccacactgt accgccagca agaatcaggc cgagcttggt ttctgggact caataaagaa | 540 |
| ggtcaaatta tgaagggaa cagagtgaag aaaaccaagc cctcatcaca ttttgtaccg | 600 |
| aaacctattg aagtgtgtat gtacagagaa ccatcgctac atgaaattgg agaaaaacaa | 660 |
| gggcgttcaa ggaaaagttc tggaacacca accatgaatg gaggcaaagt tgtgaatcaa | 720 |
| gattcaacat ag | 732 |

<210> SEQ ID NO 58
<211> LENGTH: 738
<212> TYPE: DNA
<213> ORGANISM: Homo sapiens
<300> PUBLICATION INFORMATION:
<302> TITLE: FGF13
<310> PATENT DOCUMENT NUMBER: XM010269

<400> SEQUENCE: 58

| | |
|---|---|
| atggcggcgg ctatcgccag ctcgctcatc cgtcagaaga ggcaagcccg cgagcgcgag | 60 |
| aaatccaacg cctgcaagtg tgtcagcagc cccagcaaag caagaccag ctgcgacaaa | 120 |
| aacaagttaa atgtcttttc ccgggtcaaa ctcttcggct ccaagaagag gcgcagaaga | 180 |
| agaccagagc ctcagcttaa gggtatagtt accaagctat acagccgaca aggctaccac | 240 |
| ttgcagctgc aggcggatgg aaccattgat ggcaccaaag atgaggacag cacttacact | 300 |
| ctgtttaacc tcatccctgt gggtctgcga gtggtggcta tccaaggagt tcaaaccaag | 360 |
| ctgtacttgg caatgaacag tgagggatac ttgtacacct cggaactttt cacacctgag | 420 |
| tgcaaattca agaatcagt gtttgaaaat tattatgtga catattcatc aatgatatac | 480 |
| cgtcagcagc agtcaggccg agggtggtat ctgggtctga caaagaagg agagatcatg | 540 |
| aaaggcaacc atgtgaagaa gaacaagcct gcagctcatt ttctgcctaa ccactgaaa | 600 |
| gtggccatgt acaaggagcc atcactgcac gatctcacgg agttctcccg atctggaagc | 660 |
| gggaccccaa ccaagagcag aagtgtctct ggcgtgctga acggaggcaa atccatgagc | 720 |
| cacaatgaat caacgtag | 738 |

<210> SEQ ID NO 59
<211> LENGTH: 624
<212> TYPE: DNA
<213> ORGANISM: Homo sapiens
<300> PUBLICATION INFORMATION:
<302> TITLE: FGF16
<310> PATENT DOCUMENT NUMBER: NM003868

<400> SEQUENCE: 59

| | |
|---|---|
| atggcagagg tggggggcgt cttcgcctcc ttggactggg atctacacgg cttctcctcg | 60 |
| tctctgggga acgtgccctt agctgactcc ccaggtttcc tgaacgagcg cctgggccaa | 120 |
| atcgaggga agctgcagcg tggctcaccc acagacttcg cccacctgaa ggggatcctg | 180 |
| cggcgccgcc agctctactg ccgcaccggc ttccacctgg agatcttccc caacggcacg | 240 |
| gtgcacggga cccgccacga ccacagccgc ttcggaatcc tggagtttat cagcctggct | 300 |
| gtggggctga tcagcatccg gggagtggac tctggcctgt acctaggaat gaatgagcga | 360 |
| ggagaactct atggtcgaa gaaactcaca cgtgaatgtg ttttccggga acagtttgaa | 420 |
| gaaaactggt acaacaccta tgcctcaacc ttgtacaaac attcggactc agagagacag | 480 |
| tattacgtgg ccctgaacaa agatggctca ccccgggagg atacaggac taaacgacac | 540 |

-continued

| cagaaattca ctcactttt acccaggcct gtagatcctt ctaagttgcc ctccatgtcc | 600 |
| agagacctct ttcactatag gtaa | 624 |

<210> SEQ ID NO 60
<211> LENGTH: 651
<212> TYPE: DNA
<213> ORGANISM: Homo sapiens
<300> PUBLICATION INFORMATION:
<302> TITLE: FGF17
<310> PATENT DOCUMENT NUMBER: XM005316

<400> SEQUENCE: 60

| atgggagccg cccgcctgct gcccaacctc actctgtgct tacagctgct gattctctgc | 60 |
| tgtcaaactc aggggagaa tcacccgtct cctaatttta accagtacgt gagggaccag | 120 |
| ggcgccatga ccgaccagct gagcaggcgg cagatccgcg agtaccaact ctacagcagg | 180 |
| accagtggca agcacgtgca ggtcaccggg cgtcgcatct ccgccaccgc cgaggacggc | 240 |
| aacaagtttg ccaagctcat agtggagacg gacacgtttg gcagccgggt tcgcatcaaa | 300 |
| ggggctgaga gtgagaagta catctgtatg aacaagaggg gcaagctcat cgggaagccc | 360 |
| agcgggaaga gcaaagactg cgtgttcacg gagatcgtgc tggagaacaa ctatacggcc | 420 |
| ttccagaacg cccggcacga gggctggttc atggccttca cgcggcaggg gcggccccgc | 480 |
| caggcttccc gcagccgcca gaaccagcgc gaggcccact tcatcaagcg cctctaccaa | 540 |
| ggccagctgc ccttccccaa ccacgccgag aagcagaagc agttcgagtt tgtgggctcc | 600 |
| gcccccaccc gccggaccaa gcgcacacgg cggccccagc ccctcacgta g | 651 |

<210> SEQ ID NO 61
<211> LENGTH: 624
<212> TYPE: DNA
<213> ORGANISM: Homo sapiens
<300> PUBLICATION INFORMATION:
<302> TITLE: FGF18
<310> PATENT DOCUMENT NUMBER: AF075292

<400> SEQUENCE: 61

| atgtattcag cgccctccgc ctgcacttgc ctgtgtttac acttcctgct gctgtgcttc | 60 |
| caggtacagg tgctggttgc cgaggagaac gtggacttcc gcatccacgt ggagaaccag | 120 |
| acgcgggctc gggacgatgt gagccgtaag cagctgcggc tgtaccagct ctacagccgg | 180 |
| accagtggga aacacatcca ggtcctgggc cgcaggatca gtgcccgcgg cgaggatggg | 240 |
| gacaagtatg cccagctcct agtggagaca gacaccttcg gtagtcaagt ccggatcaag | 300 |
| ggcaaggaga cggaattcta cctgtgcatg aaccgcaaag gcaagctcgt ggggaagccc | 360 |
| gatggcacca gcaaggagtg tgtgttcatc gagaaggttc tggagaacaa ctatacggcc | 420 |
| ctgatgtcgg ctaagtactc cggctggtac gtgggcttca ccaagaaggg gcggccgcgg | 480 |
| aagggcccca gacccgggga gaaccagcag gacgtgcatt tcatgaagcg ctaccccaag | 540 |
| gggcagccgg agcttcagaa gcccttcaag tacacgacgg tgaccaagag gtcccgtcgg | 600 |
| atccggccca cacaccctgc ctag | 624 |

<210> SEQ ID NO 62
<211> LENGTH: 651
<212> TYPE: DNA
<213> ORGANISM: Homo sapiens
<300> PUBLICATION INFORMATION:
<302> TITLE: FGF19
<310> PATENT DOCUMENT NUMBER: AF110400

<400> SEQUENCE: 62

```
atgcggagcg ggtgtgtggt ggtccacgta tggatcctgg ccggcctctg gctggccgtg      60
gccgggcgcc ccctcgcctt ctcggacgcg ggccccacg tgcactacgg ctggggcgac     120
cccatccgcc tgcggcacct gtacacctcc ggccccacg gctctccag ctgcttcctg      180
cgcatccgtg ccgacggcgt cgtggactgc gcgcggggcc agagcgcgca cagtttgctg    240
gagatcaagg cagtcgctct gcggaccgtg ccatcaagg gcgtgcacag cgtgcggtac     300
ctctgcatgg gcgccgacgg caagatgcag gggctgcttc agtactcgga ggaagactgt    360
gctttcgagg aggagatccg cccagatggc tacaatgtgt accgatccga agcaccgc      420
ctcccggtct ccctgagcag tgccaaacag cggcagctgt acaagaacag aggctttctt    480
ccactctctc atttcctgcc catgctgccc atggtcccag aggagcctga ggacctcagg    540
ggccacttgg aatctgacat gttctcttcg cccctggaga ccgacagcat ggacccattt    600
gggcttgtca ccggactgga ggccgtgagg agtcccagct ttgagaagta a             651
```

<210> SEQ ID NO 63
<211> LENGTH: 468
<212> TYPE: DNA
<213> ORGANISM: Homo sapiens

<400> SEQUENCE: 63

```
atggctgaag gggaaatcac caccttcaca gccctgaccg agaagtttaa tctgcctcca     60
gggaattaca agaagcccaa actcctctac tgtagcaacg ggggccactt cctgaggatc    120
cttccggatg gcacagtgga tgggacaagg acaggagcg accagcacat tcagctgcag     180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468
```

<210> SEQ ID NO 64
<211> LENGTH: 636
<212> TYPE: DNA
<213> ORGANISM: Homo sapiens
<300> PUBLICATION INFORMATION:
<302> TITLE: FGF20
<310> PATENT DOCUMENT NUMBER: NM019851

<400> SEQUENCE: 64

```
atggctccct tagccgaagt cgggggcttt ctgggcggcc tggagggctt gggccagcag     60
gtgggttcgc atttcctgtt gcctcctgcc ggggagcggc cgccgctgct gggcgagcgc    120
aggagcgcgg cggagcggag cgcccgcggc gggccggggg ctgcgcagct ggcgcacctg    180
cacggcatcc tgcgccgccg gcagctctat tgccgcaccg gcttccacct gcagatcctg    240
cccgacggca gcgtgcaggg cacccggcag gaccacagcc tcttcggtat cttggaattc    300
atcagtgtgg cagtgggact ggtcagtatt gaggtgtgg acagtggtct ctatcttgga    360
atgaatgaca aggagaact ctatggatca gagaaactta cttccgaatg catctttagg     420
gagcagtttg aagagaactg gtataacacc tattcatcta acatatataa acatggagac    480
actggccgca ggtattttgt ggcacttaac aaagacggaa ctccaagaga tggcgccagg    540
tccaagaggc atcagaaatt tacacatttc ttacctagac cagtggatcc agaaagagtt    600
ccagaattgt acaaggacct actgatgtac acttga                              636
```

<210> SEQ ID NO 65
<211> LENGTH: 630
<212> TYPE: DNA
<213> ORGANISM: Homo sapiens
<300> PUBLICATION INFORMATION:
<302> TITLE: FGF21
<310> PATENT DOCUMENT NUMBER: XM009100

<400> SEQUENCE: 65

```
atggactcgg acgagaccgg gttcgagcac tcaggactgt gggtttctgt gctggctggt      60
cttctgctgg agcctgcca ggcacacccc atccctgact ccagtcctct cctgcaattc      120
gggggccaag tccggcagcg gtacctctac acagatgatg cccagcagac agaagcccac      180
ctggagatca gggaggatgg gacggtgggg ggcgctgctg accagagccc cgaaagtctc      240
ctgcagctga aagccttgaa gccgggagtt attcaaatct gggagtcaa gacatccagg      300 ttcctgtgcc agcggccaga tggggccctg tatggatcgc tccactttga ccctgaggcc      360
tgcagcttcc gggagctgct tcttgaggac ggatacaatg tttaccagtc cgaagcccac      420
ggcctcccgc tgcacctgcc agggaacaag tccccacacc gggaccctgc accccgagga      480
ccagctcgct tcctgccact accaggcctg ccccccgcac tcccgagcc acccggaatc      540 ctggcccccc agcccccga tgtgggctcc tcggaccctc tgagcatggt gggaccttcc      600
cagggccgaa gccccagcta cgcttcctga                                       630
```

<210> SEQ ID NO 66
<211> LENGTH: 513
<212> TYPE: DNA
<213> ORGANISM: Homo sapiens
<300> PUBLICATION INFORMATION:
<302> TITLE: FGF22
<310> PATENT DOCUMENT NUMBER: XM009271

<400> SEQUENCE: 66

```
atgcgccgcc gcctgtggct gggcctggcc tggctgctgc tggcgcgggc gccggacgcc      60
gcgggaaccc cgagcgcgtc gcggggaccg cgcagctacc cgcacctgga gggcgacgtg      120
cgctggcggc gcctcttctc ctccactcac ttcttcctgc gcgtggatcc cggcggccgc      180
gtgcagggca cccgctggcg ccacggccag gacagcatcc tggagatccg ctctgtacac      240
gtgggcgtcg tggtcatcaa agcagtgtcc tcaggcttct acgtggccat gaaccgccgg      300
ggccgcctct acgggtcgcg actctacacc gtggactgca ggttccggga gcgcatcgaa      360
gagaacggcc acaacaccta cgcctcacag cgctggcgcc gccgcggcca gcccatgttc      420
ctggcgctgg acaggagggg ggggccccgg ccaggcggcc ggacgcggcg gtaccacctg      480
tccgcccact cctgccccgt cctggtctcc tga                                   513
```

<210> SEQ ID NO 67
<211> LENGTH: 621
<212> TYPE: DNA
<213> ORGANISM: Homo sapiens
<300> PUBLICATION INFORMATION:
<302> TITLE: FGF4
<310> PATENT DOCUMENT NUMBER: NM002007

<400> SEQUENCE: 67

```
atgtcggggc ccgggacggc cgcggtagcg ctgctcccgg cggtcctgct ggccttgctg      60
gcgccctggg cgggccgagg gggcgccgcc gcacccactg cacccaacgg cacgctggag      120
gccgagctgg agccgcgctg ggagagcctg gtggcgctct cgttggcgcg cctgccggtg      180
gcagcgcagc ccaaggaggc ggccgtccag agcggcgccg cgactacct gctgggcatc      240
```

```
aagcggctgc ggcggctcta ctgcaacgtg ggcatcggct tccacctcca ggcgctcccc      300
gacggccgca tcggcggcgc gcacgcggac acccgcgaca gcctgctgga gctctcgccc      360
gtggagcggg gcgtggtgag catcttcggc gtggccagcc ggttcttcgt ggccatgagc      420
agcaagggca agctctatgg ctcgcccttc ttcaccgatg agtgcacgtt caaggagatt      480
ctccttccca caactacaa cgcctacgag tcctacaagt accccggcat gttcatcgcc       540
ctgagcaaga atgggaagac caagaagggg aaccgagtgt cgcccaccat gaaggtcacc      600
cacttcctcc ccaggctgtg a                                                621

<210> SEQ ID NO 68
<211> LENGTH: 597
<212> TYPE: DNA
<213> ORGANISM: Homo sapiens
<300> PUBLICATION INFORMATION:
<302> TITLE: FGF6
<310> PATENT DOCUMENT NUMBER: NM020996

<400> SEQUENCE: 68
atgtcccggg gagcaggacg tctgcagggc acgctgtggg ctctcgtctt cctaggcatc      60
ctagtgggca tggtggtgcc ctcgcctgca ggcacccgtg ccaacaacac gctgctggac     120
tcgaggggct ggggcaccct gctgtccagg tctcgcgcgg ggctagctgg agagattgcc     180
ggggtgaact gggaaagtgg ctatttggtg gggatcaagc ggcagcggag gctctactgc     240
aacgtgggca tcggctttca cctccaggtg ctccccgacg gccggatcag cgggacccac     300
gaggagaacc cctacagcct gctggaaatt tccactgtgg agcgaggcgt ggtgagtctc     360
tttggagtga gaagtgccct cttcgttgcc atgaacagta aaggaagatt gtacgcaacg     420
cccagcttcc aagaagaatg caagttcaga gaaaccctcc tgcccaacaa ttacaatgcc     480
tacgagtcag acttgtacca agggacctac attgccctga gcaaatacgg acgggtaaag     540
cggggcagca aggtgtcccc gatcatgact gtcactcatt tccttcccag gatctaa        597

<210> SEQ ID NO 69
<211> LENGTH: 150
<212> TYPE: DNA
<213> ORGANISM: Homo sapiens
<300> PUBLICATION INFORMATION:
<302> TITLE: FGF7
<310> PATENT DOCUMENT NUMBER: XM007559

<400> SEQUENCE: 69
atgtcttggc aatgcacttc atacacaatg actaatctat actgtgatga tttgactcaa      60
aaggagaaaa gaaattatgt agttttcaat tctgattcct attcaccttt tgtttatgaa     120
tggaaagctt tgtgcaaaat atacatataa                                      150

<210> SEQ ID NO 70
<211> LENGTH: 628
<212> TYPE: DNA
<213> ORGANISM: Homo sapiens
<300> PUBLICATION INFORMATION:
<302> TITLE: FGF9
<310> PATENT DOCUMENT NUMBER: XM007105

<400> SEQUENCE: 70
gatggctccc ttaggtgaag ttgggaacta tttcggtgtg caggatgcgg taccgtttgg      60
gaatgtgccc gtgttgccgg tggacagccc ggttttgtta agtgaccacc tgggtcagtc     120
cgaagcaggg gggctcccca ggggacccgc agtcacggac ttggatcatt taaaggggat     180
```

| | |
|---|---|
| tctcaggcgg aggcagctat actgcaggac tggatttcac ttagaaatct tccccaatgg | 240 |
| tactatccag ggaaccagga aagaccacag ccgatttggc attctggaat ttatcagtat | 300 |
| agcagtgggc ctggtcagca ttcgaggcgt ggacagtgga ctctacctcg ggatgaatga | 360 |
| gaagggggag ctgtatggat cagaaaaact aacccaagag tgtgtattca gagaacagtt | 420 |
| cgaagaaaac tggtataata cgtactcatc aaacctatat aagcacgtgg acactggaag | 480 |
| gcgatactat gttgcattaa ataaagatgg accccgaga aagggacta ggactaaacg | 540 |
| gcaccagaaa ttcacacatt ttttacctag accagtggac cccgacaaag tacctgaact | 600 |
| gtataaggat attctaagcc aaagttga | 628 |

<210> SEQ ID NO 71
<211> LENGTH: 2469
<212> TYPE: DNA
<213> ORGANISM: Homo sapiens
<300> PUBLICATION INFORMATION:
<302> TITLE: FGFR1
<310> PATENT DOCUMENT NUMBER: NM000604

<400> SEQUENCE: 71

| | |
|---|---|
| atgtggagct ggaagtgcct cctcttctgg gctgtgctgg tcacagccac actctgcacc | 60 |
| gctaggccgt ccccgacctt gcctgaacaa gcccagccct ggggagcccc tgtggaagtg | 120 |
| gagtccttcc tggtccaccc cggtgacctg ctgcagcttc gctgtcggct gcgggacgat | 180 |
| gtgcagagca tcaactggct gcgggacggg gtgcagctgg cggaaagcaa ccgcacccgc | 240 |
| atcacagggg aggaggtgga ggtgcaggac tccgtgcccg cagactccgg cctctatgct | 300 |
| tgcgtaacca gcagcccctc gggcagtgac accacctact tctccgtcaa tgtttcagat | 360 |
| gctctcccct cctcggagga tgatgatgat gatgatgact cctcttcaga ggagaaagaa | 420 |
| acagataaca ccaaaccaaa ccgtatgccc gtagctccat attggacatc cccagaaaag | 480 |
| atggaaaaga aattgcatgc agtgccggct gccaagacag tgaagttcaa atgcccttcc | 540 |
| agtgggaccc caaaccccac actgcgctgg ttgaaaaatg gcaaagaatt caaacctgac | 600 |
| cacagaattg gaggctacaa ggtccgttat gccacctgga gcatcataat ggactctgtg | 660 |
| gtgccctctg acaagggcaa ctacacctgc attgtggaga tgagtacgg cagcatcaac | 720 |
| cacacatacc agctggatgt cgtggagcgg tcccctcacc ggcccatcct gcaagcaggg | 780 |
| ttgcccgcca acaaaacagt ggccctgggt agcaacgtgg agttcatgtg taagggtgtac | 840 |
| agtgacccgc agccgcacat ccagtggcta aagcacatcg aggtgaatgg agcaagatt | 900 |
| ggcccagaca acctgcctta tgtccagatc ttgaagactg ctggagttaa taccaccgac | 960 |
| aaagagatgg aggtgcttca cttaagaaat gtctcctttg aggacgcagg ggagtatacg | 1020 |
| tgcttggcgg gtaactctat cggactctcc catcactctg catggttgac cgttctggaa | 1080 |
| gccctggaag agaggccggc agtgatgacc tcgcccctgt acctggagat catcatctat | 1140 |
| tgcacagggg ccttcctcat ctcctgcatg gtggggtcgg tcatcgtcta caagatgaag | 1200 |
| agtggtacca agaagagtga cttccacagc cagatggctg tgcacaagct ggccaagagc | 1260 |
| atccctctgc gcagacaggt aacagtgtct gctgactcca gtgcatccat gaactctggg | 1320 |
| gttcttctgg ttcggccatc acggctctcc tccagtggga ctcccatgct agcaggggtc | 1380 |
| tctgagtatg agcttcccga agaccctcgc tgggagctgc ctcgggacag actggtctta | 1440 |
| ggcaaacccc tggagagggg ctgctttggg caggtggtgt ggcagaggc tatcgggctg | 1500 |
| gacaaggaca aacccaaccg tgtgaccaaa gtggctgtga agatgttgaa gtcggacgca | 1560 |
| acagagaaag acttgtcaga cctgatctca gaaatggaga tgatgaagat gatcgggaag | 1620 |

| | |
|---|---:|
| cataagaata tcatcaacct gctgggggcc tgcacgcagg atggtccctt gtatgtcatc | 1680 |
| gtggagtatg cctccaaggg caacctgcgg gagtacctgc aggcccggag gcccccaggg | 1740 |
| ctggaatact gctacaaccc cagccacaac ccagaggagc agctctcctc caaggacctg | 1800 |
| gtgtcctgcg cctaccaggt ggcccgaggc atggagtatc tggcctccaa gaagtgcata | 1860 |
| caccgagacc tggcagccag gaatgtcctg gtgacagagg acaatgtgat gaagatagca | 1920 |
| gactttggcc tcgcacggga cattcaccac atcgactact ataaaaagac aaccaacggc | 1980 |
| cgactgcctg tgaagtggat ggcacccgag gcattatttg accggatcta cacccaccag | 2040 |
| agtgatgtgt ggtctttcgg ggtgctcctg tgggagatct tcactctggg cggctcccca | 2100 |
| taccccggtg tgcctgtgga ggaacttttc aagctgctga aggagggtca ccgcatggac | 2160 |
| aagcccagta actgcaccaa cgagctgtac atgatgatgc gggactgctg gcatgcagtg | 2220 |
| ccctcacaga gacccacctt caagcagctg gtggaagacc tggaccgcat cgtggccttg | 2280 |
| acctccaacc aggagtacct ggacctgtcc atgcccctgg accagtactc ccccagcttt | 2340 |
| cccgacaccc ggagctctac gtgctcctca ggggaggatt ccgtcttctc tcatgagccg | 2400 |
| ctgcccgagg agccctgcct gccccgacac ccagcccagc ttgccaatgg cggactcaaa | 2460 |
| cgccgctga | 2469 |

<210> SEQ ID NO 72
<211> LENGTH: 2409
<212> TYPE: DNA
<213> ORGANISM: Homo sapiens
<300> PUBLICATION INFORMATION:
<302> TITLE: FGFR4
<310> PATENT DOCUMENT NUMBER: XM003910

<400> SEQUENCE: 72

| | |
|---|---:|
| atgcggctgc tgctggccct gttgggggtc ctgctgagtg tgcctggggcc tccagtcttg | 60 |
| tccctggagg cctctgagga gtggagcttg agccctgcc tggctcccag cctggagcag | 120 |
| caagagcagg agctgacagt agcccttggg cagcctgtgc ggctgtgctg tgggcgggct | 180 |
| gagcgtggtg gccactggta caaggagggc agtcgcctgg cacctgctgg ccgtgtacgg | 240 |
| ggctggaggg gccgcctaga gattgccagc ttcctacctg aggatgctgg ccgctacctc | 300 |
| tgcctggcac gaggctccat gatcgtcctg cagaatctca ccttgattac aggtgactcc | 360 |
| ttgacctcca gcaacgatga tgaggacccc aagtcccata gggacctctc gaataggcac | 420 |
| agttaccccc agcaagcacc ctactggaca cacccccagc gcatggagaa gaaactgcat | 480 |
| gcagtacctg cggggaacac cgtcaagttc cgctgtccag ctgcaggcaa cccccacgccc | 540 |
| accatccgct ggcttaagga tggacaggcc tttcatgggg agaaccgcat tggaggcatt | 600 |
| cggctgcgcc atcagcactg gagtctcgtg atggagagcg tggtgcccts ggaccgcggc | 660 |
| acatacacct gcctggtaga aaacgctgtg ggcagcatcc gttataacta cctgctagat | 720 |
| gtgctggagc ggtccccgca ccggcccatc ctgcaggccg ggctcccggc caacaccaca | 780 |
| gccgtggtgg gcagcgacgt ggagctgctg tgcaaggtgt acagcgatgc ccagccccac | 840 |
| atccagtggc tgaagcacat cgtcatcaac ggcagcagct tcggagccga cggtttcccc | 900 |
| tatgtgcaag tcctaaagac tgcagacatc aatagctcag aggtgaggt cctgtacctg | 960 |
| cggaacgtgt cagccgagga cgcaggcgag tacacctgcc tcgcaggcaa ttccatcggc | 1020 |
| ctctcctacc agtctgcctg gctcacggtg ctgccagagg aggaccccac atggaccgca | 1080 |
| gcagcgcccg aggccaggta tacggacatc atcctgtacg cgtcgggctc cctggccttg | 1140 |

-continued

| | |
|---|---|
| gctgtgctcc tgctgctggc caggctgtat cgagggcagg cgctccacgg ccggcacccc | 1200 |
| cgcccgcccg ccactgtgca gaagctctcc cgcttccctc tggcccgaca gttctccctg | 1260 |
| gagtcaggct cttccggcaa gtcaagctca tccctggtac gaggcgtgcg tctctcctcc | 1320 |
| agcggccccg ccttgctcgc cggcctcgtg agtctagatc tacctctcga cccactatgg | 1380 |
| gagttccccc gggacaggct ggtgcttggg aagcccctag gcgagggctg ctttggccag | 1440 |
| gtagtacgtg cagaggcctt tggcatggac cctgcccggc ctgaccaagc cagcactgtg | 1500 |
| gccgtcaaga tgctcaaaga caacgcctct gacaaggacc tggccgacct ggtctcggag | 1560 |
| atggaggtga tgaagctgat cggccgacac aagaacatca tcaacctgct tggtgtctgc | 1620 |
| acccaggaag ggcccctgta cgtgatcgtg gagtgcgccg ccaagggaaa cctgcgggag | 1680 |
| ttcctgcggg cccggcgccc cccaggcccc gacctcagcc ccgacggtcc tcggagcagt | 1740 |
| gaggggccgc tctccttccc agtcctggtc tcctgcgcct accaggtggc ccgaggcatg | 1800 |
| cagtatctgg agtcccggaa gtgtatccac cgggacctgg ctgcccgcaa tgtgctggtg | 1860 |
| actgaggaca atgtgatgaa gattgctgac tttgggctgg cccgcggcgt ccaccacatt | 1920 |
| gactactata agaaaaccag caacggccgc ctgcctgtga agtggatggc gcccgaggcc | 1980 |
| ttgtttgacc gggtgtacac acaccagagt gacgtgtggt cttttgggat cctgctatgg | 2040 |
| gagatcttca ccctcggggg ctccccgtat cctggcatcc cggtggagga gctgttctcg | 2100 |
| ctgctgcggg agggacatcg gatggaccga cccccacact gcccccaga gctgtacggg | 2160 |
| ctgatgcgtg agtgctggca cgcagcgccc tcccagaggc ctaccttcaa gcagctggtg | 2220 |
| gaggcgctgg acaaggtcct gctggccgtc tctgaggagt acctcgacct ccgcctgacc | 2280 |
| ttcggaccct attccccctc tggtggggac gccagcagca cctgctcctc cagcgattct | 2340 |
| gtcttcagcc acgaccccct gccattggga tccagctcct tccccttcgg gtctggggtg | 2400 |
| cagacatga | 2409 |

<210> SEQ ID NO 73
<211> LENGTH: 1695
<212> TYPE: DNA
<213> ORGANISM: Homo sapiens
<300> PUBLICATION INFORMATION:
<302> TITLE: MT2MMP
<310> PATENT DOCUMENT NUMBER: D86331

<400> SEQUENCE: 73

| | |
|---|---|
| atgaagcggc cccgctgtgg ggtgccagac cagttcgggg tacgagtgaa agccaacctg | 60 |
| cggcggcgtc ggaagcgcta cgccctcacc gggaggaagt ggaacaacca ccatctgacc | 120 |
| tttagcatcc agaactacac ggagaagttg ggctggtacc actcgatgga ggcggtgcgc | 180 |
| agggccttcc gcgtgtggga gcaggccacg cccctggtct tccaggaggt gccctatgag | 240 |
| gacatccggc tgcggcgaca gaaggaggcc gacatcatgg tactctttgc ctctggcttc | 300 |
| cacggcgaca gctcgccgtt tgatggcacc ggtggctttc tggcccacgc ctatttccct | 360 |
| ggccccggcc taggcgggga cacccatttt gacgcagatg agccctggac cttctccagc | 420 |
| actgacctgc atggaaacaa cctcttcctg gtggcagtgc atgagctggg ccacgcgctg | 480 |
| gggctggagc actccagcaa ccccaatgcc atcatggcgc cgttctacca gtggaaggac | 540 |
| gttgacaact tcaagctgcc cgaggacgat ctccgtggca tccagcagct ctacggtacc | 600 |
| ccagacggtc agccacagcc tacccagcct ctccccactg tgacgccacg gcggccaggc | 660 |
| cggcctgacc accggccgcc ccggcctccc agccaccac cccaggtgg gaagccagag | 720 |
| cggcccccaa agccgggccc cccagtccag ccccgagcca cagagcggcc cgaccagtat | 780 |

```
ggccccaaca tctgcgacgg ggactttgac acagtggcca tgcttcgcgg ggagatgttc      840
gtgttcaagg gccgctggtt ctggcgagtc cggcacaacc gcgtcctgga caactatccc      900
atgcccatcg gcacttctg gcgtggtctg cccggtgaca tcagtgctgc ctacgagcgc       960
caagacggtc gttttgtctt tttcaaaggt gaccgctact ggctctttcg agaagcgaac     1020
ctggagcccg gctacccaca gccgctgacc agctatggcc tgggcatccc ctatgaccgc     1080
attgacacgg ccatctggtg ggagcccaca ggccacacct tcttcttcca agaggacagg     1140
tactggcgct tcaacgagga gacacagcgt ggagaccctg ggtacccaa gcccatcagt      1200 gtctggcagg ggatccctgc ctcccctaaa ggggccttcc tgagcaatga cgcagcctac     1260
acctacttct acaagggcac caaatactgg aaattcgaca atgagcgcct gcggatggag     1320
cccggctacc ccaagtccat cctgcgggac ttcatgggct gccaggagca cgtggagcca     1380
ggcccccgat ggcccgacgt ggcccggccg cccttcaacc cccacgggg tgcagagccc      1440 ggggcggaca gcgcagaggg cgacgtgggg gatgggatg gggactttgg ggccggggtc     1500
aacaaggaca ggggcagccg cgtggtggtg cagatggagg aggtggcacg gacggtgaac     1560
gtggtgatgg tgctggtgcc actgctgctg ctgctctgcg tcctgggcct cacctacgcg     1620
ctggtgcaga tgcagcgcaa gggtgcgcca cgtgtcctgc tttactgcaa gcgctcgctg     1680
caggagtggg tctga                                                      1695

<210> SEQ ID NO 74
<211> LENGTH: 1824
<212> TYPE: DNA
<213> ORGANISM: Homo sapiens
<300> PUBLICATION INFORMATION:
<302> TITLE: MT3MMP
<310> PATENT DOCUMENT NUMBER: D85511

<400> SEQUENCE: 74
atgatcttac tcacattcag cactggaaga cggttggatt tcgtgcatca ttcggggtg       60 ttttcttgc aaaccttgct ttggatttta tgtgctacag tctgcggaac ggagcagtat      120
ttcaatgtgg aggtttggtt acaaaagtac ggctaccttc caccgactga ccccagaatg     180
tcagtgctgc gctctgcaga gaccatgcag tctgccctag ctgccatgca gcagttctat     240
ggcattaaca tgacaggaaa agtggacaga aacacaattg actggatgaa gaagccccga     300
tgcggtgtac ctgaccagac aagaggtagc tccaaatttc atattcgtcg aaagcgatat     360
gcattgacag gacagaaatg gcagcacaag cacatcactt acagtataaa gaacgtaact     420
ccaaaagtag agaccctga gactcgtaaa gctattcgcc gtgcctttga tgtgtggcag      480
aatgtaactc ctctgacatt tgaagaagtt ccctacagtg aattagaaaa tggcaaacgt     540
gatgtggata taaccattat ttttgcatct ggtttccatg gggacagctc tcccttgat     600 ggagagggag gattttggc acatgcctac ttccctggac aggaattgg aggagatacc     660 cattttgact cagatgagcc atggacacta ggaaatccta atcatgatgg aaatgactta     720
tttcttgtag cagtccatga actgggacat gctctgggat tggagcattc caatgacccc     780
actgccatca tggctccatt ttaccagtac atggaaacag acaacttcaa actacctaat     840
gatgatttac agggcatcca gaagatatat ggtccacctg caagattcc tccacctaca     900 agacctctac cgacagtgcc cccacaccgc tctattcctc cggctgaccc aaggaaaaat     960
gacaggccaa aacctcctcg gcctccaacc ggcagaccct cctatcccgg agccaaaccc    1020
aacatctgtg atgggaactt taacactcta gctattcttc gtcgtgagat gtttgtttc     1080
```

```
aaggaccagt ggttttggcg agtgagaaac aacagggtga tggatggata cccaatgcaa    1140
attacttact tctggcgggg cttgcctcct agtatcgatg cagtttatga aaatagcgac    1200
gggaattttg tgttctttaa aggtaacaaa tattgggtgt tcaaggatac aactcttcaa    1260
cctggttacc ctcatgactt gataacccct ggaagtggaa ttccccctca tggtattgat    1320
tcagccattt ggtgggagga cgtcgggaaa acctatttct tcaagggaga cagatattgg    1380
agatatagtg aagaaatgaa aacaatggac cctggctatc ccaagccaat cacagtctgg    1440
aaagggatcc ctgaatctcc tcaggagcca tttgtacaca agaaaatgg ctttacgtat     1500 ttctacaaag gaaaggagta ttggaaattc aacaaccaga tactcaaggt agaacctgga    1560
tatccaagat ccatcctcaa ggattttatg gctgtgatg accaacaga cagagttaaa      1620 gaaggacaca gcccaccaga tgatgtagac attgtcatca aactggacaa cacagccagc    1680
actgtgaaag ccatagctat tgtcattccc tgcatcttgg ccttatgcct ccttgtattg    1740
gtttacactg tgttccagtt caagaggaaa ggaacacccc gccacatact gtactgtaaa    1800
cgctctatgc aagagtgggt gtga                                           1824
```

```
<210> SEQ ID NO 75
<211> LENGTH: 1818
<212> TYPE: DNA
<213> ORGANISM: Homo sapiens
<300> PUBLICATION INFORMATION:
<302> TITLE: MT4MMP
<310> PATENT DOCUMENT NUMBER: AB021225

<400> SEQUENCE: 75
```

```
atgcggcgcc gcgcagcccg ggacccggcc ccgccgcccc cagggcccgg actctcgcgg    60
ctgccgctgc tgccgctgcc gctgctgctg ctgctggcgc tggggacccg cggggggctgc   120 gccgcgccgg aacccgcgcg gcgcgccgag gacctcagcc tgggagtgga gtggctaagc    180
aggttcggtt acctgccccc ggctgacccc acaacagggc agctgcagac gcaagaggag    240
ctgtctaagg ccatcacagc catgcagcag tttggtggcc tggaggccac cggcatcctg    300
gacgaggcca ccctggccct gatgaaaacc cacgctgct ccctgccaga cctccctgtc     360
ctgacccagg ctcgcaggag acgccaggct ccagccccca ccaagtggaa caagaggaac    420
ctgtcgtgga gggtccggac gttcccacgg gactcaccac tggggcacga cacggtgcgt    480
gcactcatgt actacgccct caaggtctgg agcgacattg cgccctgaa cttccacgag     540 gtggcgggca gcaccgccga catccagatc gacttctcca aggccgacca taacgacggc    600
taccccttcg acgccggcg gcaccgtgcc cacgccttct tccccggcca ccaccacacc    660
gccgggtaca cccactttaa cgatgacgag gcctggacct tccgctcctc ggatgcccac    720
gggatggacc tgtttgcagt ggctgtccac gagtttggcc acgccattgg gttaagccat    780
gtggccgctg cacactccat catgcggccg tactaccagg gccgggtggg tgacccgctg    840
cgctacgggc tcccctacga ggacaaggtg cgcgtctggc agctgtacgg tgtgcgggag    900
tctgtgtctc ccacgcgcca gcccgaggag cctcccctgc tgccggagcc cccagacaac    960
cggtccagcg ccccgcccag gaaggacgtg ccccacagat gcagcactca ctttgacgcg   1020
gtggcccaga tccggggtga agctttcttc ttcaaaggca gtacttctg gcggctgacg    1080 cgggaccggc acctggtgtc cctgcagccg gcacagatgc accgcttctg gcggggcctg    1140
ccgctgcacc tggacagcgt ggagccgtg tacgagcgca ccagccgacca caagatcgtc    1200 ttctttaaag agacaggta ctgggtgttc aaggacaata acgtagagga aggataccccg    1260 cgccccgtct ccgacttcag cctcccgcct ggcggcatcg acgctgcctt ctcctgggcc   1320
```

```
cacaatgaca ggacttattt ctttaaggac cagctgtact ggcgctacga tgaccacacg      1380
aggcacatgg accccggcta ccccgcccag agcccctgt ggaggggtgt ccccagcacg      1440
ctggacgacg ccatgcgctg gtccgacggt gcctcctact tcttccgtgg ccaggagtac      1500
tggaaagtgc tggatggcga gctggaggtg gcacccgggt acccacagtc cacggcccgg      1560
gactggctgg tgtgtggaga ctcacaggcc gatggatctg tggctgcggg cgtggacgcg      1620
gcagaggggc cccgcgcccc tccaggacaa catgaccaga gccgctcgga ggacggttac      1680
gaggtctgct catgcacctc tggggcatcc tctcccccgg ggccccaggg cccactggtg      1740
gctgccacca tgctgctgct gctgccgcca ctgtcaccag gcgccctgtg gacagcggcc      1800
caggccctga cgctatga                                                   1818

<210> SEQ ID NO 76
<211> LENGTH: 1938
<212> TYPE: DNA
<213> ORGANISM: Homo sapiens
<300> PUBLICATION INFORMATION:
<302> TITLE: MT5MMP
<310> PATENT DOCUMENT NUMBER: AB021227

<400> SEQUENCE: 76
atgccgagga gccggggcgg ccgcgccgcg ccggggccgc cgccgccgcc gccgccgccg        60
ggccaggccc cgcgctggag ccgctggcgg gtccctgggc ggctgctgct gctgctgctg       120
cccgcgctct gctgcctccc gggcgccgcg cgggcggcgg cggcggcggc ggggcaggg        180 aaccgggcag cggtggcggt ggcggtggcg cgggcggacg aggcggaggc gcccttcgcc       240
gggcagaact ggttaaagtc ctatggctat ctgcttccct atgactcacg ggcatctgcg       300
ctgcactcag cgaaggcctt gcagtcggca gtctccacta tgcagcagtt ttacgggatc       360
ccggtcaccg tgtgttgga tcagacaacg atcgagtgga tgaagaaacc ccgatgtggt       420
gtccctgatc acccccactt aagccgtagg cggagaaaca agcgctatgc cctgactgga       480
cagaagtgga ggcaaaaaca catcacctac agcattcaca actataccc aaaagtgggt       540 gagctagaca cgcggaaagc tattcgccag gctttcgatg tgtggcagaa ggtgaccca       600 ctgacctttg aagaggtgcc ataccatgag atcaaaagtg accggaagga ggcagacatc       660
atgatctttt ttgcttctgg tttccatggc gacagctccc catttgatgg agaagggga       720 ttcctggccc atgcctactt ccctggccca gggattggag agacacccca ctttgactcc       780
gatgagccat ggacgctagg aaacgccaac catgacggga cgacctcttt cctggtggct       840
gtgcatgagc tgggccacgc gctgggactg agcactcca gcgaccccag cgccatcatg      900
gcgcccttct accagtacat ggagacgcac aacttcaagc tgcccaggga cgatctccag      960
ggcatccaga agatctatgg accccagcc gagcctctgg agcccacaag gccactccct     1020
acactccccg tccgcaggat ccactcacca tcggagagga acacgagcg ccagcccagg      1080 ccccctcggc cgcccctcgg ggaccggcca tccacaccag gcaccaaacc caacatctgt     1140
gacggcaact tcaacacagt ggccctcttc cggggcgaga tgtttgtctt taaggatcgc      1200
tggttctggc gtctgcgcaa taaccgagtg caggaggct accccatgca gatcgagcag     1260
ttctggaagg gcctgcctgc ccgcatcgac gcagcctatg aaagggccga tgggagattt     1320
gtcttcttca aaggtgacaa gtattgggtg tttaaggagg tgacggtgga gcctgggtac      1380
ccccacagcc tggggagct gggcagctgt ttgcccccgtg aaggcattga cacagctctg      1440
cgctgggaac ctgtgggcaa gacctacttt ttcaaaggcg agcggtactg gcgctacagc      1500
```

| | |
|---|---|
| gaggagcggc gggccacgga ccctggctac cctaagccca tcaccgtgtg aagggcatc | 1560 |
| ccacaggctc cccaaggagc cttcatcagc aaggaaggat attacaccta tttctacaag | 1620 |
| ggccgggact actggaagtt tgacaaccag aaactgagcg tggagccagg ctacccgcgc | 1680 |
| aacatcctgc gtgactggat gggctgcaac cagaaggagg tggagcggcg aaggagcgg | 1740 |
| cggctgcccc aggacgacgt ggacatcatg gtgaccatca cgatgtgcc gggctccgtg | 1800 |
| aacgccgtgg ccgtggtcat cccctgcatc ctgtccctct gcatcctggt gctggtctac | 1860 |
| accatcttcc agttcaagaa caagacaggc cctcagcctg tcacctacta taagcggcca | 1920 |
| gtccaggaat gggtgtga | 1938 |

<210> SEQ ID NO 77
<211> LENGTH: 1689
<212> TYPE: DNA
<213> ORGANISM: Homo sapiens
<300> PUBLICATION INFORMATION:
<302> TITLE: MT6MMP
<310> PATENT DOCUMENT NUMBER: AJ27137

<400> SEQUENCE: 77

| | |
|---|---|
| atgcggctgc ggctccggct tctggcgctg ctgcttctgc tgctggcacc gcccgcgcgc | 60 |
| gccccgaagc cctcggcgca ggacgtgagc ctgggcgtgg actggctgac tcgctatggt | 120 |
| tacctgccgc caccccaccc tgccaggcc agctgcaga gccctgagaa gttgcgcgat | 180 |
| gccatcaaag tcatgcagag gttcgcgggg ctgccggaga ccggccgcat ggacccaggg | 240 |
| acagtggcca ccatgcgtaa gccccgctgc tccctgcctg acgtgctggg ggtggccggg | 300 |
| ctggtcaggc ggcgtcgccg gtacgctctg agcggcagcg tgtggaagaa gcgaaccctg | 360 |
| acatggaggg tacgttcctt cccccagagc tcccagctga ccaggagac cgtgcgggtc | 420 |
| ctcatgagct atgccctgat ggcctggggc atggagtcag gcctcacatt tcatgaggtg | 480 |
| gattccccc agggccagga gcccgacatc ctcatcgact ttgcccgcgc cttccaccag | 540 |
| gacagctacc ccttcgacgg gttgggggc accctagccc atgccttctt ccctggggag | 600 |
| cacccccatct ccggggacac tcactttgac gatgaggaga cctggacttt tgggtcaaaa | 660 |
| gacggcgagg ggaccgacct gtttgccgtg gctgtccatg agtttggcca cgccctgggc | 720 |
| ctgggccact cctcagcccc caactccatt atgaggccct tctaccaggg tccggtgggc | 780 |
| gaccctgaca gtaccgcct gtctcaggat gaccgcgatg gcctgcagca actctatggg | 840 |
| aaggcgcccc aaaccccata tgacaagccc acaaggaaac ccctggctcc tcgccccag | 900 |
| ccccccggcct cgcccacaca gcccatcc ttccccatcc ctgatcgatg tgagggcaat | 960 |
| tttgacgcca tcgccaacat ccgagggga acttctcttct tcaaaggccc tggttctgg | 1020 |
| cgcctccagc cctccggaca gctggtgtcc ccgcgacccg cacggctgca ccgcttctgg | 1080 |
| gaggggctgc ccgcccaggt gagggtggtg caggccgcct atgctcggca ccgagacggc | 1140 |
| cgaatcctcc tctttagcgg ggccccagttc tgggtgttcc aggaccggca gctggagggc | 1200 |
| ggggcgcggc cgctcacgga gctgggctg ccccgggag aggaggtgga cgccgtgttc | 1260 |
| tcgtggccac agaacgggaa gacctacctg gtccgcggcc ggcagtactg cgctacgac | 1320 |
| gaggcggcgg cgcgcccgga ccccggctac cctcgcgacc tgagcctctg gaaggcgcg | 1380 |
| ccccctccc ctgacgatgt caccgtcagc aacgcaggtg acacctactt cttcaagggc | 1440 |
| gcccactact ggcgcttccc caagaacagc atcaagaccg agccggacgc ccccagccc | 1500 |
| atggggccca ctggctgga ctgccccgcc ccgagctctg gtccccgcgc cccaggccc | 1560 |
| cccaaagcga ccccccgtgtc cgaaacctgc gattgtcagt gcgagctcaa ccaggccgca | 1620 |

```
ggacgttggc ctgctcccat cccgctgctc ctcttgcccc tgctggtggg gggtgtagcc      1680
tcccgctga                                                              1689

<210> SEQ ID NO 78
<211> LENGTH: 1749
<212> TYPE: DNA
<213> ORGANISM: Homo sapiens
<300> PUBLICATION INFORMATION:
<302> TITLE: MTMMP
<310> PATENT DOCUMENT NUMBER: X90925

<400> SEQUENCE: 78
atgtctcccg ccccaagacc ctcccgttgt ctcctgctcc ccctgctcac gctcggcacc        60
gcgctcgcct ccctcggctc ggcccaaagc agcagcttca gccccgaagc ctggctacag       120
caatatggct acctgcctcc cggggaccta cgtacccaca cacagcgctc accccagtca       180
ctctcagcgg ccatcgctgc catgcagaag ttttacggct tgcaagtaac aggcaaagct       240
gatgcagaca ccatgaaggc catgaggcgc ccccgatgtg tgttccaga caagtttggg        300 gctgagatca aggccaatgt tcgaaggaag cgctacgcca tccagggtct caaatggcaa       360
cataatgaaa tcactttctg catccagaat tacaccccca aggtgggcga gtatgccaca       420
tacgaggcca ttcgcaaggc gttccgcgtg tgggagagtg ccacaccact gcgcttccgc       480
gaggtgccct atgcctacat ccgtgagggc catgagaagc aggccgacat catgatcttc       540
tttgccgagg gcttccatgg cgacagcacg cccttcgatg gtgagggcgg cttcctggcc       600
catgcctact cccaggcccc caacattgga ggagacaccc actttgactc tgccgagcct       660
tggactgtca ggaatgagga tctgaatgga aatgacatct tcctggtggc tgtgcacgag       720
ctgggccatg ccctggggct cgagcattcc agtgacccct cggccatcat ggcacccttt       780
taccagtgga tggacacgga gaattttgtg ctgcccgatg atgaccgccg gggcatccag       840
caactttatg ggggtgagtc agggttcccc accaagatgc cccctcaacc caggactacc       900
tcccggcctt ctgttcctga taaacccaaa aaccccacct atgggcccaa catctgtgac       960
gggaactttg acaccgtggc catgctccga ggggagatgt ttgtcttcaa ggagcgctgg      1020
ttctggcggg tgaggaataa ccaagtgatg gatggatacc caatgcccat tggccagttc      1080
tggcgggggc tgcctgcgtc catcaacact gcctacgaga ggaaggatgg caaattcgtc      1140
ttcttcaaag gagacaagca ttgggtgttt gatgaggcgt ccctggaacc tggctacccc      1200
aagcacatta ggagctgggc cgagggctgc ctaccgaca agattgatgc tgctctcttc      1260
tggatgccca atggaaagac ctacttcttc cgtggaaaca agtactaccg tttcaacgaa      1320
gagctcaggg cagtggatag cgagtacccc aagaacatca agtctgggga agggatccct      1380
gagtctccca gagggtcatt catgggcagc gatgaagtct tcacttactt ctacaagggg      1440
aacaaatact ggaaattcaa caaccagaag ctgaaggtag aaccgggcta ccccaagcca      1500
gccctgaggg actggatggg ctgcccatcg ggaggccggc cggatgaggg gactgaggag      1560
gagacggagg tgatcatcat tgaggtggac gaggagggcg gcggggcggt gagcgcggct      1620
gccgtggtgc tgcccgtgct gctgctgctc ctggtgctgg cggtgggcct tgcagtcttc      1680
ttcttcagac gccatgggac ccccaggcga ctgctctact gccagcgttc cctgctggac      1740
aaggtctga                                                              1749

<210> SEQ ID NO 79
<211> LENGTH: 744
<212> TYPE: DNA
```

```
<213> ORGANISM: Homo sapiens
<300> PUBLICATION INFORMATION:
<302> TITLE: FGF1
<310> PATENT DOCUMENT NUMBER: XM003647

<400> SEQUENCE: 79
atggccgcgg ccatcgctag cggcttgatc cgccagaagc ggcaggcgcg ggagcagcac      60
tgggaccggc cgtctgccag caggaggcgg agcagcccca gcaagaaccg cgggctctgc     120
aacggcaacc tggtggatat cttctccaaa gtgcgcatct tcggcctcaa gaagcgcagg     180
ttgcggcgcc aagatcccca gctcaagggt atagtgacca ggttatattg caggcaaggc     240
tactacttgc aaatgcaccc cgatggagct ctcgatggaa ccaaggatga cagcactaat     300
tctacactct tcaacctcat accagtggga ctacgtgttg ttgccatcca gggagtgaaa     360
acagggttgt atatagccat gaatgaagaa ggttacctct acccatcaga acttttacc      420 cctgaatgca gtttaaaga atctgttttt gaaaattatt atgtaatcta ctcatccatg     480
ttgtacagac aacaggaatc tggtagagcc tggtttttgg gattaaataa ggaagggcaa     540
gctatgaaag gaacagagt aaagaaaacc aaaccagcag ctcatttct acccaagcca      600 ttggaagttg ccatgtaccg agaaccatct ttgcatgatg ttggggaaac ggtcccgaag     660
cctggggtga cgccaagtaa agcacaagt gcgtctgcaa taatgaatgg aggcaaacca      720
gtcaacaaga gtaagacaac atag                                           744

<210> SEQ ID NO 80
<211> LENGTH: 468
<212> TYPE: DNA
<213> ORGANISM: Homo sapiens
<300> PUBLICATION INFORMATION:
<302> TITLE: FGF2
<310> PATENT DOCUMENT NUMBER: NM002006

<400> SEQUENCE: 80
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacgatgag      300 tgtttctttt ttgaacgatt ggaatctaat aactacaata cttaccggtc aaggaaatac     360
accagttggt atgtggcact gaaacgaact gggcagtata acttggatc caaaacagga      420 cctgggcaga aagctatact tttctcca atgtctgcta agagctga                   468

<210> SEQ ID NO 81
<211> LENGTH: 756
<212> TYPE: DNA
<213> ORGANISM: Homo sapiens
<300> PUBLICATION INFORMATION:
<302> TITLE: FGF23
<310> PATENT DOCUMENT NUMBER: NM020638

<400> SEQUENCE: 81
atgttggggg cccgcctcag gctctgggtc tgtgccttgt gcagcgtctg cagcatgagc      60
gtcctcagag cctatcccaa tgcctcccca ctgctcggct ccagctgggg tggcctgatc     120
cacctgtaca cagccacagc caggaacagc taccacctgc agatccacaa gaatggccat     180
gtggatggcg caccccatca gaccatctac agtgccctga tgatcagatc agaggatgct     240
ggctttgtgg tgattacagg tgtgatgagc agaagatacc tctgcatgga tttcagaggc     300
```

-continued

```
aacattttg gatcacacta tttcgacccg gagaactgca ggttccaaca ccagacgctg       360
gaaaacgggt acgacgtcta ccactctcct cagtatcact tcctggtcag tctgggccgg       420
gcgaagagag ccttcctgcc aggcatgaac ccaccccgt actccagtt cctgtcccgg        480 aggaacgaga tcccctaat tcacttcaac accccatac cacggcggca cacccggagc       540
gccgaggacg actcggagcg ggaccccctg aacgtgctga agcccgggc ccggatgacc       600 ccggccccgg cctcctgttc acaggagctc ccgagcgccg aggacaacag cccgatggcc       660
agtgacccat tagggtggt caggggcggt cgagtgaaca cgcacgctgg gggaacgggc       720
ccggaaggct gccgcccctt cgccaagttc atctag                                756
```

<210> SEQ ID NO 82
<211> LENGTH: 720
<212> TYPE: DNA
<213> ORGANISM: Homo sapiens
<300> PUBLICATION INFORMATION:
<302> TITLE: FGF3
<310> PATENT DOCUMENT NUMBER: NM005247

<400> SEQUENCE: 82

```
atgggcctaa tctggctgct actgctcagc ctgctggagc ccggctggcc cgcagcgggc        60
cctggggcgc ggttgcggcg cgatgcgggc ggccgtggcg gcgtctacga gcaccttggc       120
ggggcgcccc ggcgccgcaa gctctactgc gccacgaagt accacctcca gctgcacccg       180
agcggccgcg tcaacggcag cctggagaac agcgcctaca gtattttgga gataacggca       240
gtggaggtgg gcattgtggc catcagggt ctcttctccg gcggtacct ggccatgaac         300 aagaggggac gactctatgc ttcggagcac tacagcgccg agtgcgagtt tgtggagcgg       360
atccacgagc tgggctataa tacgtatgcc tcccggctgt accggacggt gtctagtacg       420
cctggggccc gccggcagcc cagcgccgag agactgtggt acgtgtctgt gaacggcaag       480
ggccggcccc gcaggggctt caagacccgc cgcacacaga gtcctccct gttcctgccc        540 cgcgtgctgg accacaggga ccacgagatg gtgcggcagc tacagagtgg gctgcccaga       600 cccctggta aggggtcca gccccgacgg cggcggcaga agcagagccc ggataacctg         660
gagccctctc acgttcaggc ttcgagactg ggctcccagc tggaggccag tgcgcactag       720
```

<210> SEQ ID NO 83
<211> LENGTH: 807
<212> TYPE: DNA
<213> ORGANISM: Homo sapiens
<300> PUBLICATION INFORMATION:
<302> TITLE: FGF5
<310> PATENT DOCUMENT NUMBER: NM004464

<400> SEQUENCE: 83

```
atgagcttgt ccttcctcct cctcctcttc ttcagccacc tgatcctcag cgcctgggct        60
cacggggaga agcgtctcgc ccccaaaggg caacccggac ccgctgccac tgataggaac       120
cctataggct ccagcagcag acagagcagc agtagcgcta tgtcttcctc ttctgcctcc       180
tcctcccccg cagcttctct gggcagccaa ggaagtggc tggagcagag cagtttccag       240
tggagcccct cggggcgccg gaccggcagc ctctactgca gagtgggcat cggtttccat       300
ctgcagatct accccggatgg caaagtcaat ggatcccacg aagccaatat gttaagtgtt       360
ttggaaatat ttgctgtgtc tcaggggatt gtaggaatac gaggagtttt cagcaacaaa       420 ttttttagcga tgtcaaaaaa aggaaaactc catgcaagtg ccaagttcac agatgactgc       480
aagttcaggg agcgttttca agaaaatagc tataataccct atgcctcagc aatacataga       540
```

-continued

| | | |
|---|---|---|
| actgaaaaaa cagggcggga gtggtatgtt gccctgaata aaagaggaaa agccaaacga | 600 | |
| gggtgcagcc cccgggttaa accccagcat atctctaccc attttcttcc aagattcaag | 660 | |
| cagtcggagc agccagaact ttctttcacg gttactgttc ctgaaaagaa aaatccacct | 720 | |
| agccctatca agtcaaagat tcccctttct gcacctcgga aaaataccaa ctcagtgaaa | 780 | |
| tacagactca agtttcgctt tggataa | 807 | |

```
<210> SEQ ID NO 84
<211> LENGTH: 649
<212> TYPE: DNA
<213> ORGANISM: Homo sapiens
<300> PUBLICATION INFORMATION:
<302> TITLE: FGF8
<310> PATENT DOCUMENT NUMBER: NM006119

<400> SEQUENCE: 84
```

| | | |
|---|---|---|
| atgggcagcc cccgctccgc gctgagctgc ctgctgttgc acttgctggt cctctgcctc | 60 | |
| caagcccagg taactgttca gtcctcacct aattttacac agcatgtgag ggagcagagc | 120 | |
| ctggtgacgg atcagctcag ccgccgcctc atccggacct accaactcta cagccgcacc | 180 | |
| agcgggaagc acgtgcaggt cctggccaac aagcgcatca cgccatggc agaggacggc | 240 | |
| gaccccttcg caaagctcat cgtggagacg gacacctttg gaagcagagt tcgagtccga | 300 | |
| ggagccgaga cgggcctcta catctgcatg aacaagaagg ggaagctgat cgccaagagc | 360 | |
| aacggcaaag gcaaggactg cgtcttcacg gagattgtgc tggagaacaa ctacacagcg | 420 | |
| ctgcagaatg ccaagtacga gggctggtac atggccttca cccgcaaggg ccggccccgc | 480 | |
| aagggctcca agacgcggca gcaccagcgt gaggtccact tcatgaagcg gctgccccgg | 540 | |
| ggccaccaca ccaccgagca gagcctgcgc ttcgagttcc tcaactaccc gcccttcacg | 600 | |
| cgcagcctgc gcggcagcca gaggacttgg gccccggaac ccgatagg | 649 | |

```
<210> SEQ ID NO 85
<211> LENGTH: 2466
<212> TYPE: DNA
<213> ORGANISM: Homo sapiens
<300> PUBLICATION INFORMATION:
<302> TITLE: FGFR2
<310> PATENT DOCUMENT NUMBER: NM000141

<400> SEQUENCE: 85
```

| | | |
|---|---|---|
| atggtcagct ggggtcgttt catctgcctg gtcgtggtca ccatggcaac cttgtccctg | 60 | |
| gcccggcccc ccttcagttt agttgaggat accacattag agccagaaga gccaccaacc | 120 | |
| aaataccaaa tctctcaacc agaagtgtac gtggctgcgc agggggagtc gctagaggtg | 180 | |
| cgctgcctgt tgaaagatgc cgccgtgatc agttggacta aggatgggt gcacttgggg | 240 | |
| cccaacaata ggacagtgct tattggggag tacttgcaga taaagggcgc cacgccctaga | 300 | |
| gactccggcc tctatgcttg tactgccagt aggactgtag acagtgaaac ttggtacttc | 360 | |
| atggtgaatg tcacagatgc catctcatcc ggagatgatg aggatgacac cgatggtgcg | 420 | |
| gaagattttg tcagtgagaa cagtaacaac aagagagcac catactggac caacacagaa | 480 | |
| aagatggaaa agcggctcca tgctgtgcct gcggccaaca ctgtcaagtt cgctgcccca | 540 | |
| gccgggggga acccaatgcc aaccatgcgg tggctgaaaa acgggaagga gtttaagcag | 600 | |
| gagcatcgca ttggaggcta caaggtacga aaccagcact ggagcctcat tatggaaagt | 660 | |
| gtggtcccat ctgacaaggg aaattatacc tgtgtggtgg agaatgaata cgggtccatc | 720 | |
| aatcacacgt accacctgga tgttgtggag cgatcgcctc accggcccat cctccaagcc | 780 | |

```
ggactgccgg caaatgcctc cacagtggtc ggaggagacg tagagtttgt ctgcaaggtt      840
tacagtgatg cccagcccca catccagtgg atcaagcacg tggaaaagaa cggcagtaaa      900
tacgggcccg acgggctgcc ctacctcaag gttctcaagg ccgccggtgt taacaccacg      960
gacaaagaga ttgaggttct ctatattcgg aatgtaactt ttgaggacgc tggggaatat     1020
acgtgcttgg cgggtaattc tattgggata tcctttcact ctgcatggtt gacagttctg     1080
ccagcgcctg aagagaaaa ggagattaca gcttccccag actacctgga gatagccatt     1140
tactgcatag gggtcttctt aatcgcctgt atggtggtaa cagtcatcct gtgccgaatg     1200
aagaacacga ccaagaagcc agacttcagc agccagccgg ctgtgcacaa gctgaccaaa     1260
cgtatccccc tgcggagaca ggtaacagtt tcggctgagt ccagctcctc catgaactcc     1320 aacacccccgc tggtgaggat aacaaacgcg ctctcttcaa cggcagacac ccccatgctg     1380 gcagggggtct ccgagtatga acttccagag acccaaaat gggagtttcc aagagataag     1440
ctgacactgg gcaagcccct gggagaaggt tgctttgggc aagtggtcat ggcggaagca     1500
gtgggaattg acaaagacaa gcccaaggag gcggtcaccg tggccgtgaa gatgttgaaa     1560
gatgatgcca cagagaaaga cctttctgat ctggtgtcag agatggagat gatgaagatg     1620
attgggaaac acaagaatat cataaatctt cttggagcct gcacacagga tgggcctctc     1680
tatgtcatag ttgagtatgc ctctaaaggc aacctccgag aatacctccg agcccggagg     1740
ccacccggga tggagtactc ctatgacatt aaccgtgttc ctgaggagca gatgaccttc     1800
aaggacttgg tgtcatgcac ctaccagctg gccagaggca tggagtactt ggcttcccaa     1860
aaatgtattc atcgagattt agcagccaga aatgttttgg taacagaaaa caatgtgatg     1920
aaaatagcag actttggact cgccagagat atcaacaata tagactatta caaaaagacc     1980
accaatgggc ggcttccagt caagtggatg gctccagaag ccctgtttga tagagtatac     2040
actcatcaga gtgatgtctg gtccttcggg gtgttaatgt gggagatctt cactttaggg     2100
ggctcgccct acccagggat tcccgtggag gaacttttta gctgctgaa ggaaggacac     2160 agaatggata gccagccaa ctgcaccaac gaactgtaca tgatgatgag ggactgttgg     2220
catgcagtgc cctcccagag accaacgttc aagcagttgg tagaagactt ggatcgaatt     2280
ctcactctca caaccaatga ggaatacttg gacctcagcc aacctctcga acagtattca     2340
cctagttacc ctgacacaag aagttcttgt tcttcaggag atgattctgt tttttctcca     2400
gaccccatgc cttacgaacc atgccttcct cagtatccac acataaacgg cagtgttaaa     2460
acatga                                                                2466

<210> SEQ ID NO 86
<211> LENGTH: 2421
<212> TYPE: DNA
<213> ORGANISM: Homo sapiens
<300> PUBLICATION INFORMATION:
<302> TITLE: FGFR3
<310> PATENT DOCUMENT NUMBER: NM000142

<400> SEQUENCE: 86
atgggcgccc ctgcctgcgc cctcgcgctc tgcgtggccg tggccatcgt ggccggcgcc       60
tcctcggagt ccttggggac ggagcagcgc gtcgtgggc gagcggcaga agtcccgggc      120
ccagagcccg ccagcagga gcagttggtc ttcggcagcg gggatgctgt ggagctgagc      180 tgtccccgc ccggggtgg tcccatgggg cccactgtct gggtcaagga tggcacaggg      240
ctggtgccct cggagcgtgt cctggtgggg ccccagcggc tgcaggtgct gaatgcctcc      300
```

| | | |
|---|---|---|
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga gcgctccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga acggcagcaa ggtgggcccg | 900 |
| gacggcacac cctacgttac cgtgctcaag acggcgggcg ctaacaccac cgacaaggag | 960 |
| ctagaggttc tctccttgca caacgtcacc tttgaggacg ccggggagta cacctgcctg | 1020 |
| gcgggcaatt ctattgggtt ttctcatcac tctgcgtggc tggtggtgct gccagccgag | 1080 |
| gaggagctgg tggaggctga cgaggcgggc agtgtgtatg caggcatcct cagctacggg | 1140 |
| gtgggcttct tcctgttcat cctggtggtg gcggctgtga cgctctgccg cctgcgcagc | 1200 |
| ccccccaaga aaggcctggg ctcccccacc gtgcacaaga tctcccgctt ccgctcaag | 1260 |
| cgacaggtgt ccctggagtc caacgcgtcc atgagctcca acacaccact ggtgcgcatc | 1320 |
| gcaaggctgt cctcagggga gggccccacg ctggccaatg tctccgagct cgagctgcct | 1380 |
| gccgacccca atgggagct gtctcgggcc cggctgaccc tgggcaagcc ccttggggag | 1440 |
| ggctgcttcg gccaggtggt catggcggag gccatcggca ttgacaagga ccgggccgcc | 1500 |
| aagcctgtca ccgtagccgt gaagatgctg aaagacgatg ccactgacaa ggacctgtcg | 1560 |
| gacctggtgt ctgagatgga gatgatgaag atgatcggga acacaaaaa catcatcaac | 1620 |
| ctgctgggcg cctgcacgca gggcgggccc ctgtacgtgc tggtggagta cgcggccaag | 1680 |
| ggtaacctgc gggagtttct gcgggcgcgg cggccccgg gcctggacta ctccttcgac | 1740 |
| acctgcaagc cgcccgagga gcagctcacc ttcaaggacc tggtgtcctg tgcctaccag | 1800 |
| gtggcccggg gcatggagta cttggcctcc agaagtgca tccacaggga cctggctgcc | 1860 |
| cgcaatgtgc tggtgaccga ggacaacgtg atgaagatcg cagacttcgg gctggcccgg | 1920 |
| gacgtgcaca acctcgacta ctacaagaag acaaccaacg gccggctgcc cgtgaagtgg | 1980 |
| atggcgcctg aggccttgtt tgaccgagtc tacactcacc agagtgacgt ctggtccttt | 2040 |
| ggggtcctgc tctgggagat cttcacgctg ggggctccc cgtaccccgg catccctgtg | 2100 |
| gaggagctct tcaagctgct gaaggagggc caccgcatgg acaagcccgc caactgcaca | 2160 |
| cacgacctgt acatgatcat gcgggagtgc tggcatgccg cgccctccca gaggcccacc | 2220 |
| ttcaagcagc tggtggagga cctggaccgt gtccttaccg tgacgtccac cgacgagtac | 2280 |
| ctggacctgt cggcgccttt cgagcagtac tccccgggtg gccaggacac ccccagctcc | 2340 |
| agctcctcag gggacgactc cgtgtttgcc cacgacctgc tgcccccggc cccacccagc | 2400 |
| agtgggggct cgcggacgtg a | 2421 |

<210> SEQ ID NO 87
<211> LENGTH: 2102
<212> TYPE: DNA
<213> ORGANISM: Homo sapiens
<300> PUBLICATION INFORMATION:
<302> TITLE: HGF
<310> PATENT DOCUMENT NUMBER: E08541

<400> SEQUENCE: 87

```
atgcagaggg acaaggaaaa agaagaaata caattcatga attcaaaaaa tcagcaaaga      60
ctaccctaat caaaatagat ccagcactga agataaaaac caaaaaagtg aatactgcag     120
accaatgtgc taatagatgt actaggaata aaggacttcc attcacttgc aaggcttttg     180
tttttgataa agcaagaaaa caatgcctct ggttcccctt caatagcatg tcaagtggag     240
tgaaaaaga atttggccat gaatttgacc tctatgaaaa caaagactac attagaaact      300
gcatcattgg taaaggacgc agctacaagg aacagtatc tatcactaag agtggcatca      360
aatgtcagcc ctggagttcc atgataccac acgaacacag cttttttgcct tcgagctatc    420
ggggtaaaga cctacaggaa aactactgtc gaaatcctcg aggggaagaa ggggaccct      480
ggtgtttcac aagcaatcca gaggtacgct acgaagtctg tgacattcct cagtgttcag     540
aagttgaatg catgacctgc aatggggaga gttatcgagg tctcatggat catacagaat    600
caggcaagat ttgtcagcgc tgggatcatc agacaccaca ccggcacaaa ttcttgcctg     660
aaagatatcc cgacaagggc tttgatgata attattgccg caatcccgat ggccagccga     720
ggccatggtg ctatactctt gaccctcaca cccgctggga gtactgtgca attaaaacat     780
gcgctgacaa tactatgaat gacactgatg ttcctttgga aacaactgaa tgcatccaag     840
gtcaaggaga aggctacagg ggcactgtca ataccatttg gaatggaatt ccatgtcagc     900
gttgggattc tcagtatcct cacgagcatg acatgactcc tgaaaatttc aagtgcaagg     960
acctacgaga aaattactgc cgaaatccag atgggtctga atcaccctgg tgttttacca   1020
ctgatccaaa catccgagtt ggctactgct cccaaattcc aaactgtgat atgtcacatg   1080
gacaagattg ttatcgtggg aatggcaaaa attatatggg caacttatcc caaacaagat   1140
ctggactaac atgttcaatg tgggacaaga acatggaaga cttacatcgt catatcttct   1200
gggaaccaga tgcaagtaag ctgaatgaga attactgccg aaatccagat gatgatgctc   1260
atggaccctg gtgctacacg ggaaatccac tcattccttg ggattattgc cctatttctc   1320
gttgtgaagg tgataccaca cctacaatag tcaatttaga ccatcccgta atatcttgtg   1380
ccaaaaggaa acaattgcga gttgtaaatg ggattccaac acgaacaaac ataggatgga   1440
tggttagttt gagatacaga aataaacata tctgcggagg atcattgata aaggagagtt   1500
gggttcttac tgcacgacag tgtttccctt ctcgagactt gaaagattat gaagcttggc   1560
ttggaattca tgatgtccac ggaagaggag atgagaaatg caaacaggtt ctcaatgttt   1620
cccagctggt atatggccct gaaggatcag atctggtttt aatgaagctt gccaggcctg   1680
ctgtcctgga tgattttgtt agtacgattg atttacctaa ttatggatgc acaattcctg   1740
aaaagaccag ttgcagtgtt tatggctggg gctacactgg attgatcaac tatgatggcc   1800
tattacgagt ggcacatctc tatataatgg gaaatgagaa atgcagccag catcatcgag   1860
ggaaggtgac tctgaatgag tctgaaatat gtgctggggc tgaaagatt ggatcaggac     1920
catgtgaggg ggattatggt ggcccacttg tttgtgagca acataaaatg agaatggttc   1980
ttggtgtcat tgttcctggt cgtggatgtg ccattccaaa tcgtcctggt atttttgtcc   2040
gagtagcata ttatgcaaaa tggatacaca aaattatttt aacatataag gtaccacagt   2100
ca                                                                   2102
```

<210> SEQ ID NO 88
<211> LENGTH: 360
<212> TYPE: DNA
<213> ORGANISM: Homo sapiens

```
<300> PUBLICATION INFORMATION:
<302> TITLE: ID3
<310> PATENT DOCUMENT NUMBER: XM001539

<400> SEQUENCE: 88
atgaaggcgc tgagcccggt gcgcggctgc tacgaggcgg tgtgctgcct gtcggaacgc    60
agtctggcca tcgcccgggg ccgagggaag ggcccggcag ctgaggagcc gctgagcttg   120
ctggacgaca tgaaccactg ctactcccgc ctgcgggaac tggtacccgg agtcccgaga   180
ggcactcagc ttagccaggt ggaaatccta cagcgcgtca tcgactacat tctcgacctg   240
caggtagtcc tggccgagcc agcccctgga ccccctgatg cccccacct tcccatccag    300 acagccgagc tcactccgga acttgtcatc tccaacgaca aaaggagctt tgccactga    360

<210> SEQ ID NO 89
<211> LENGTH: 743
<212> TYPE: DNA
<213> ORGANISM: Homo sapiens
<300> PUBLICATION INFORMATION:
<302> TITLE: IGF2
<310> PATENT DOCUMENT NUMBER: NM000612

<400> SEQUENCE: 89
atgggaatcc caatggggaa gtcgatgctg gtgcttctca ccttcttggc cttcgcctcg    60
tgctgcattg ctgcttaccg ccccagtgag accctgtgcg gcggggagct ggtggacacc   120
ctccagttcg tctgtgggga ccgcggcttc tacttcagca ggcccgcaag ccgtgtgagc   180
cgtcgcagcc gtggcatcgt tgaggagtgc tgtttccgca gctgtgacct ggccctcctg   240
gagacgtact gtgctacccc cgccaagtcc gagagggacg tgtcgacccc tccgaccgtg   300
cttccggaca acttccccag ataccccgtg ggcaagttct ccaatatga cacctggaag   360 cagtccaccc agcgcctgcg caggggcctg cctgccctcc tgcgtgcccg ccggggtcac   420
gtgctcgcca aggagctcga ggcgttcagg gaggccaaac gtcaccgtcc cctgattgct   480
ctacccaccc aagaccccgc ccacggggc gccccccag agatggccag caatcggaag   540
tgagcaaaac tgccgcaagt ctgcagcccg gcgccaccat cctgcagcct cctcctgacc   600
acggacgttt ccatcaggtt ccatcccgaa aatctctcgg ttccacgtcc cctggggct    660 tctcctgacc cagtccccgt gccccgcctc cccgaaacag gctactctcc tcggcccct    720 ccatcgggct gaggaagcac agc                                           743

<210> SEQ ID NO 90
<211> LENGTH: 7476
<212> TYPE: DNA
<213> ORGANISM: Homo sapiens
<300> PUBLICATION INFORMATION:
<302> TITLE: IGF2R
<310> PATENT DOCUMENT NUMBER: NM000876

<400> SEQUENCE: 90
atgggggccg ccgccggccg gagcccccac ctggggcccg cgcccgcccg ccgcccgcag    60
cgctctctgc tcctgctgca gctgctgctg ctcgtcgctg cccgggtc cacgcaggcc   120 caggccgccc cgttccccga gctgtgcagt tatacatggg aagctgttga taccaaaaat   180
aatgtacttt ataaaatcaa catctgtgga agtgtgata ttgtccagtg cgggccatca   240
agtgctgttt gtatgcacga cttgaagaca cgcacttatc attcagtggg tgactctgtt   300
ttgagaagtg caaccagatc tctcctggaa ttcaacacaa cagtgagctg tgaccagcaa   360
ggcacaaatc acagagtcca gagcagcatt gccttcctgt gtgggaaaac cctgggaact   420
```

```
cctgaatttg taactgcaac agaatgtgtg cactactttg agtggaggac cactgcagcc    480
tgcaagaaag acatatttaa agcaaataag gaggtgccat gctatgtgtt tgatgaagag    540
ttgaggaagc atgatctcaa tcctctgatc aagcttagtg gtgcctactt ggtggatgac    600
tccgatccgg acacttctct attcatcaat gtttgtagag acatagacac actacgagac    660
ccaggttcac agctgcgggc ctgtcccccc ggcactgccg cctgcctggt aagaggacac    720
caggcgtttg atgttggcca gccccgggac ggactgaagc tggtgcgcaa ggacaggctt    780
gtcctgagtt acgtgaggga agaggcagga aagctagact tttgtgatgg tcacagccct    840
gcggtgacta ttacatttgt ttgcccgtcg gagcggagag agggcaccat tcccaaactc    900
acagctaaat ccaactgccg ctatgaaatt gagtggatta ctgagtatgc ctgccacaga    960
gattacctgg aaagtaaaac ttgttctctg agcggcgagc agcaggatgt ctccatagac   1020
ctcacaccac ttgcccagag cggaggttca tcctatattt cagatggaaa agaatatttg   1080
ttttatttga atgtctgtgg agaaactgaa atacagttct gtaataaaaa acaagctgca   1140
gtttgccaag tgaaaaagag cgatacctct caagtcaaag cagcaggaag ataccacaat   1200
cagaccctcc gatattcgga tggagacctc accttgatat attttggagg tgatgaatgc   1260
agctcagggt ttcagcggat gagcgtcata aactttgagt gcaataaaac cgcaggtaac   1320
gatgggaaag gaactcctgt attcacaggg gaggttgact gcacctactt cttcacatgg   1380
gacacggaat acgcctgtgt taaggagaag gaagacctcc tctgcggtgc caccgacggg   1440
aagaagcgct atgacctgtc cgcgctggtc cgccatgcag aaccagagca gaattgggaa   1500
gctgtggatg gcagtcagac ggaaacagag aagaagcatt ttttcattaa tatttgtcac   1560
agagtgctgc aggaaggcaa ggcacgaggg tgtcccgagg acgcggcagt gtgtgcagtg   1620
gataaaaatg gaagtaaaaa tctgggaaaa tttatttcct ctcccatgaa agagaaagga   1680
aacattcaac tctcttattc agatggtgat gattgtggtc atggcaagaa aattaaaact   1740
aatatcacac ttgtatgcaa gccaggtgat ctggaaagtg caccagtgtt gagaacttct   1800
ggggaaggcg gttgctttta tgagtttgag tggcgcacag ctgcggcctg tgtgctgtct   1860
aagacagaag gggagaactg cacggtcttt gactcccagg cagggttttc ttttgactta   1920
tcacctctca caaagaaaaa tggtgcctat aaagttgaga caaagaagta tgactttttat   1980
ataaatgtgt gtgccccggt gtctgtgagc ccctgtcagc cagactcagg agcctgccag   2040
gtggcaaaaa gtgatgagaa gacttggaac ttgggtctga gtaatgcgaa gctttcatat   2100
tatgatggga tgatccaact gaactacaga ggcggcacac cctataacaa tgaaagacac   2160
acaccgagag ctacgctcat cacctttctc tgtgatcgag acgcgggagt gggcttccct   2220
gaatatcagg aagaggataa ctccacctac aacttccggt ggtacaccag ctatgcctgc   2280
ccggaggagc ccctggaatg cgtagtgacc gacccctcca cgctggagca gtacgacctc   2340
tccagtctgg caaatctga aggtggcctt ggaggaaact ggtatgccat ggacaactca   2400
ggggaacatg tcacgtggag gaaatactac attaacgtgt gtcggcctct gaatccagtg   2460
ccgggctgca accgatatgc atcggcttgc cagatgaagt atgaaaaaga tcagggctcc   2520
ttcactgaag tggtttccat cagtaacttg ggaatggcaa agaccggccc ggtggttgag   2580
gacagcggca gcctccttct ggaatacgtg aatgggtcgg cctgcaccac cagcgatggc   2640
agacagacca catataccac gaggatccat ctcgtctgct ccaggggcag gctgaacagc   2700
caccccatct tttctctcaa ctgggagtgt gtggtcagtt tcctgtggaa cacagaggct   2760
gcctgtccca ttcagacaac gacggataca gaccaggctt gctctataag ggatcccaac   2820
```

```
agtggatttg tgtttaatct taatccgcta aacagttcgc aaggatataa cgtctctggc    2880
attgggaaga ttttttatgtt taatgtctgc ggcacaatgc ctgtctgtgg gaccatcctg   2940
ggaaaacctg cttctggctg tgaggcagaa acccaaactg aagagctcaa gaattggaag    3000
ccagcaaggc cagtcggaat tgagaaaagc ctccagctgt ccacagaggg cttcatcact    3060
ctgacctaca aagggcctct ctctgccaaa ggtaccgctg atgcttttat cgtccgcttt    3120
gtttgcaatg atgatgttta ctcagggccc ctcaaattcc tgcatcaaga tatcgactct    3180
gggcaaggga tccgaaacac ttactttgag tttgaaaccg cgttggcctg tgttccttct    3240
ccagtggact gccaagtcac cgacctggct ggaaatgagt acgacctgac tggcctaagc    3300
acagtcagga aaccttggac ggctgttgac acctctgtcg atgggagaaa gaggactttc    3360
tatttgagcg tttgcaatcc tctcccttac attcctggat gccagggcag cgcagtgggg    3420
tcttgcttag tgtcagaagg caatagctgg aatctgggtg tggtgcagat gagtccccaa    3480
gccgcggcga atggatcttt gagcatcatg tatgtcaacg gtgacaagtg tgggaaccag    3540
cgcttctcca ccaggatcac gtttgagtgt gctcagatat cgggctcacc agcatttcag    3600
cttcaggatg gttgtgagta cgtgtttatc tggagaactg tggaagcctg tcccgttgtc    3660
agagtggaag gggacaactg tgaggtgaaa gacccaaggc atggcaactt gtatgacctg    3720
aagcccctgg gcctcaacga caccatcgtg agcgctggcg aatacactta ttacttccgg    3780
gtctgtggga gctttcctc agacgtctgc cccacaagtg acaagtccaa ggtggtctcc    3840
tcatgtcagg aaaagcggga accgcaggga tttcacaaag tggcaggtct cctgactcag    3900
aagctaactt atgaaaatgg cttgttaaaa atgaacttca cggggggga cacttgccat    3960
aaggtttatc agcgctccac agccatcttc ttctactgtg accgcggcac ccagcggcca    4020
gtatttctaa aggagacttc agattgttcc tacttgtttg agtggcgaac gcagtatgcc    4080
tgcccacctt tcgatctgac tgaatgttca ttcaaagatg gggctggcaa ctccttcgac    4140
ctctcgtccc tgtcaaggta cagtgacaac tgggaagcca tcactgggac gggggacccg    4200
gagcactacc tcatcaatgt ctgcaagtct ctggccccgc aggctggcac tgagccgtgc    4260
cctccagaag cagccgcgtg tctgctgggt ggctccaagc ccgtgaacct cggcagggta    4320
agggacggac ctcagtggag agatggcata attgtcctga atacgttga tggcgactta    4380
tgtccagatg ggattcggaa aaagtcaacc accatccgat tcacctgcag cgagagccaa    4440
gtgaactcca ggcccatgtt catcagcgcc gtggaggact gtgagtacac ctttgcctgg    4500
cccacagcca cagcctgtcc catgaagagc aacgagcatg atgactgcca ggtcaccaac    4560
ccaagcacag acacctgttt tgatctgagc tccttaagtg cagggcggg attcacagct    4620
gcttacagcg agaagggggtt ggtttacatg agcatctgtg gggagaatga aaactgccct    4680
cctggcgtgg gggcctgctt tggacagacc aggattagcg tgggcaaggc caacaagagg    4740
ctgagatacg tggaccaggt cctgcagctg gtgtacaagg atgggtcccc ttgtccctcc    4800
aaatccggcc tgagctataa gagtgtgatc agtttcgtgt gcaggcctga ggccgggcca    4860
accaataggc ccatgctcat ctccctggac aagcagacat gcactctctt cttctcctgg    4920
cacacgccgc tggcctgcga gcaagcgacc gaatgttccg tgaggaatgg aagctctatt    4980
gttgacttgt ctccccttat tcatcgcact ggtggttatg aggcttatga tgagagtgag    5040
gatgatgcct ccgataccaa ccctgatttc tacatcaata tttgtcagcc actaaatccc    5100
atgcacgcag tgcctgtcc tgccggagcc gctgtgtgca agttcctat tgatggtccc    5160
cccatagata tcggccgggt agcaggacca ccaatactca atccaatagc aaatgagatt    5220
```

| | |
|---|---|
| tacttgaatt ttgaaagcag tactccttgc ttagcggaca agcatttcaa ctacacctcg | 5280 |
| ctcatcgcgt ttcactgtaa gagaggtgtg agcatgggaa cgcctaagct gttaaggacc | 5340 |
| agcgagtgcg actttgtgtt cgaatgggag actcctgtcg tctgtcctga tgaagtgagg | 5400 |
| atggatggct gtaccctgac agatgagcag ctcctctaca gcttcaactt gtccagcctt | 5460 |
| tccacgagca cctttaaggt gactcgcgac tcgcgcacct acagcgttgg ggtgtgcacc | 5520 |
| tttgcagtcg ggccagaaca aggaggctgt aaggacggag gagtctgtct gctctcaggc | 5580 |
| accaagggg catcctttgg acggctgcaa tcaatgaaac tggattacag caccaggat | 5640 |
| gaagcggtcg ttttaagtta cgtgaatggt gatcgttgcc ctccagaaac cgatgacggc | 5700 |
| gtcccctgtg tcttccccett catattcaat gggaagagct acgaggagtg catcatagag | 5760 |
| agcagggcga agctgtggtg tagcacaact gcggactacg acagagacca cgagtggggc | 5820 |
| ttctgcagac actcaaacag ctaccggaca tccagcatca tatttaagtg tgatgaagat | 5880 |
| gaggacattg ggaggccaca agtcttcagt gaagtgcgtg ggtgtgatgt gacatttgag | 5940 |
| tggaaaacaa aagttgtctg ccctccaaag aagttggagt gcaaattcgt ccagaaacac | 6000 |
| aaaacctacg acctgcggct gctctcctct ctcaccgggt cctggtccct ggtccacaac | 6060 |
| ggagtctcgt actatataaa tctgtgccag aaaatatata aagggcccct gggctgctct | 6120 |
| gaaagggcca gcatttgcag aaggaccaca actggtgacg tccaggtcct gggactcgtt | 6180 |
| cacacgcaga agctgggtgt cataggtgac aaagttgttg tcacgtactc caaaggttat | 6240 |
| ccgtgtggtg gaaataagac cgcatcctcc gtgatagaat tgacctgtac aaagacggtg | 6300 |
| ggcagacctg cattcaagag gtttgatatc gacagctgca cttactactt cagctgggac | 6360 |
| tcccgggctg cctgcgccgt gaagcctcag gaggtgcaga tggtgaatgg gaccatcacc | 6420 |
| aaccctataa atggcaagag cttcagcctc ggagatattt attttaagct gttcagagcc | 6480 |
| tctggggaca tgaggaccaa tggggacaac tacctgtatg agatccaact ttcctccatc | 6540 |
| acaagctcca gaaacccggc gtgctctgga gccaacatat gccaggtgaa gcccaacgat | 6600 |
| cagcacttca gtcggaaagt tggaacctct gacaagacca gtactacct tcaagacggc | 6660 |
| gatctcgatg tcgtgtttgc ctcttcctct aagtgcggaa aggataagac caagtctgtt | 6720 |
| tcttccacca tcttcttcca ctgtgaccct ctggtggagg acgggatccc cgagttcagt | 6780 |
| cacgagactg ccgactgcca gtacctcttc tcttggtaca cctcagccgt gtgtcctctg | 6840 |
| ggggtgggct ttgacagcga gaatcccggg gacgacgggc agatgcacaa ggggctgtca | 6900 |
| gaacggagcc aggcagtcgg cgcggtgctc agcctgctgc tggtggcgct cacctgctgc | 6960 |
| ctgctggccc tgttgctcta caagaaggag aggagggaaa cagtgataag taagctgacc | 7020 |
| acttgctgta ggagaagttc caacgtgtcc tacaaatact caaaggtgaa taaggaagaa | 7080 |
| gagacagatg agaatgaaac agagtggctg atggaagaga tccagctgcc tcctccacgg | 7140 |
| cagggaaagg aagggcagga gaacggccat attaccacca agtcagtgaa agccctcagc | 7200 |
| tccctgcatg gggatgacca ggacagtgag gatgaggttc tgaccatccc agaggtgaaa | 7260 |
| gttcactcgg gcaggggagc tggggcagag agctccacc cagtgagaaa cgcacagagc | 7320 |
| aatgcccttc aggagcgtga ggacgatagg gtggggctgg tcagggggtga aaggcgagg | 7380 |
| aaagggaagt ccagctctgc acagcagaag acagtgagct ccaccaagct ggtgtccttc | 7440 |
| catgacgaca gcgacgagga cctcttacac atctga | 7476 |

<210> SEQ ID NO 91
<211> LENGTH: 4104
<212> TYPE: DNA

<213> ORGANISM: Homo sapiens
<300> PUBLICATION INFORMATION:
<302> TITLE: IGF1R
<310> PATENT DOCUMENT NUMBER: NM000875

<400> SEQUENCE: 91

| | | | | | |
|---|---|---|---|---|---|
| atgaagtctg | gctccggagg | agggtccccg | acctcgctgt | gggggctcct | gtttctctcc | 60 |
| gccgcgctct | cgctctggcc | gacgagtgga | gaaatctgcg | gccaggcat | cgacatccgc | 120 |
| aacgactatc | agcagctgaa | gcgcctggag | aactgcacgg | tgatcgaggg | ctacctccac | 180 |
| atcctgctca | tctccaaggc | cgaggactac | cgcagctacc | gcttccccaa | gctcacggtc | 240 |
| attaccgagt | acttgctgct | gttccgagtg | gctggcctcg | agagcctcgg | agacctcttc | 300 |
| cccaacctca | cggtcatccg | cggctggaaa | ctcttctaca | actacgccct | ggtcatcttc | 360 |
| gagatgacca | atctcaagga | tattgggctt | tacaacctga | ggaacattac | tcgggggggcc | 420 |
| atcaggattg | agaaaaatgc | tgacctctgt | tacctctcca | ctgtggactg | gtccctgatc | 480 |
| ctggatgcgg | tgtccaataa | ctacattgtg | gggaataagc | ccccaaagga | atgtgggac | 540 |
| ctgtgtccag | ggaccatgga | ggagaagccg | atgtgtgaga | agaccaccat | caacaatgag | 600 |
| tacaactacc | gctgctggac | cacaaaccgc | tgccagaaaa | tgtgcccaag | cacgtgtggg | 660 |
| aagcgggcgt | gcaccgagaa | caatgagtgc | tgccacccccg | agtgcctggg | cagctgcagc | 720 |
| gcgcctgaca | acgacacggc | ctgtgtagct | tgccgccact | actactatgc | cggtgtctgt | 780 |
| gtgcctgcct | gcccgcccaa | cacctacagg | tttgagggct | ggcgctgtgt | ggaccgtgac | 840 |
| ttctgcgcca | catcctcag | cgccgagagc | agcgactccg | aggggtttgt | gatccacgac | 900 |
| ggcgagtgca | tgcaggagtg | ccccctcggc | ttcatccgca | acggcagcca | gagcatgtac | 960 |
| tgcatccctt | gtgaaggtcc | ttgcccgaag | gtctgtgagg | aagaaaagaa | aacaaagacc | 1020 |
| attgattctg | ttacttctgc | tcagatgctc | caaggatgca | ccatcttcaa | gggcaatttg | 1080 |
| ctcattaaca | tccgacgggg | gaataacatt | gcttcagagc | tggagaactt | catgggcctc | 1140 |
| atcgaggtgg | tgacgggcta | cgtgaagatc | cgccattctc | atgccttggt | ctccttgtcc | 1200 |
| ttcctaaaaa | accttcgcct | catcctagga | gaggagcagc | tagaagggaa | ttactccttc | 1260 |
| tacgtcctcg | acaaccagaa | cttgcagcaa | ctgtgggact | gggaccaccg | caacctgacc | 1320 |
| atcaaagcag | ggaaaatgta | ctttgctttc | aatcccaaat | tatgtgtttc | gaaatttac | 1380 |
| cgcatggagg | aagtgacggg | gactaaaggg | cgccaaagca | aaggggacat | aaacaccagg | 1440 |
| aacaacgggg | agagagcctc | ctgtgaaagt | gacgtcctgc | atttcacctc | caccaccacg | 1500 |
| tcgaagaatc | gcatcatcat | aacctggcac | cggtaccggc | ccctgactg | cagggatctc | 1560 |
| atcagcttca | ccgtttacta | caaggaagca | ccctttaaga | atgtcacaga | gtatgatggg | 1620 |
| caggatgcct | gcggctccaa | cagctggaac | atggtggacg | tggacctccc | gcccaacaag | 1680 |
| gacgtggagc | ccggcatctt | actacatggg | ctgaagcct | ggactcagta | cgccgtttac | 1740 |
| gtcaaggctg | tgaccctcac | catggtggag | aacgaccata | tccgtgggc | caagagtgag | 1800 |
| atcttgtaca | ttcgcaccaa | tgcttcagtt | ccttccattc | ccttggacgt | tctttcagca | 1860 |
| tcgaactcct | cttctcagtt | aatcgtgaag | tggaacccctc | cctctctgcc | caacggcaac | 1920 |
| ctgagttact | acattgtgcg | ctggcagcgg | cagcctcagg | acggctacct | ttaccggcac | 1980 |
| aattactgct | ccaaagacaa | aatccccatc | aggaagtatg | ccgacggcac | catcgacatt | 2040 |
| gaggaggtca | cagagaaccc | caagactgag | gtgtgtggt | gggagaaagg | gccttgctgc | 2100 |
| gcctgcccca | aaactgaagc | cgagaagcag | gccgagaagg | aggaggctga | ataccgcaaa | 2160 |
| gtctttgaga | atttcctgca | caactccatc | ttcgtgccca | gacctgaaag | gaagcggaga | 2220 |

-continued

```
gatgtcatgc aagtggccaa caccaccatg tccagccgaa gcaggaacac cacggccgca    2280
gacacctaca acatcaccga cccggaagag ctggagacag agtaccctct ctttgagagc    2340
agagtggata acaaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatgagggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga gaagatcacc    3000
atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaga ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga aatggagaat    3300
aatccagtcc tagcacctcc aagcctgagc aagatgattc agatggccgg agagattgca    3360
gacggcatgg catacctcaa cgccaataag ttcgtccaca gagaccttgc tgcccggaat    3420
tgcatggtag ccgaagattt cacagtcaaa atcggagatt ttggtatgac gcgagatatc    3480
tatgagacag actattaccg gaaaggaggc aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
ctgtttgaac tgatgcgcat gtgctggcag tataaccccca agatgaggcc ttccttcctg    3780
gagatcatca gcagcatcaa agaggagatg gagcctggct tccgggaggt ctccttctac    3840
tacagcgagg agaacaagct gccccgagccg gaggagctgg acctggagcc agaaaacatg    3900
gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac gggggccgca gaacgagcg ggccttgccg    4080 ctgccccagt cttcgacctg ctga                                          4104
```

<210> SEQ ID NO 92
<211> LENGTH: 726
<212> TYPE: DNA
<213> ORGANISM: Homo sapiens
<300> PUBLICATION INFORMATION:
<302> TITLE: PDGFB
<310> PATENT DOCUMENT NUMBER: NM002608

<400> SEQUENCE: 92

```
atgaatcgct gctgggcgct cttcctgtct ctctgctgct acctgcgtct ggtcagcgcc      60
gagggggacc ccattcccga ggagctttat gagatgctga gtgaccactc gatccgctcc     120
```

-continued

```
tttgatgatc tccaacgcct gctgcacgga gaccccggag aggaagatgg ggccgagttg    180
gacctgaaca tgacccgctc ccactctgga ggcgagctgg agagcttggc tcgtggaaga    240
aggagcctgg gttccctgac cattgctgag ccggccatga tcgccgagtg caagacgcgc    300
accgaggtgt tcgagatctc ccggcgcctc atagaccgca ccaacgccaa cttcctggtg    360
tggccgccct gtgtggaggt gcagcgctgc tccggctgct gcaacaaccg caacgtgcag    420
tgccgcccca cccaggtgca gctgcgacct gtccaggtga aaagatcga gattgtgcgg     480
aagaagccaa tctttaagaa ggccacggtg acgctggaag accacctggc atgcaagtgt    540
gagacagtgg cagctgcacg gcctgtgacc cgaagcccgg ggggttccca ggagcagcga    600
gccaaaacgc ccaaactcg ggtgaccatt cggacggtgc gagtccgccg gccccccaag    660
ggcaagcacc ggaaattcaa gcacacgcat gacaagacgg cactgaagga gacccttgga    720
gcctag                                                              726
```

<210> SEQ ID NO 93
<211> LENGTH: 1512
<212> TYPE: DNA
<213> ORGANISM: Homo sapiens
<300> PUBLICATION INFORMATION:
<302> TITLE: TGFbetaR1
<310> PATENT DOCUMENT NUMBER: NM004612

<400> SEQUENCE: 93

```
atggaggcgg cggtcgctgc tccgcgtccc cggctgctcc tcctcgtgct ggcggcggcg     60
gcggcggcgg cggcggcgct gctcccgggg gcgacggcgt tacagtgttt ctgccacctc    120
tgtacaaaag acaattttac ttgtgtgaca gatgggctct gctttgtctc tgtcacagag    180
accacagaca aagttataca caacagcatg tgtatagctg aaattgactt aattcctcga    240
gataggccgt ttgtatgtgc accctcttca aaaactgggt ctgtgactac aacatattgc    300
tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat ctgccacaac cgcactgtca ttcaccatcg agtgccaaat    480
gaagaggacc cttcattaga tcgcccttt atttcagagg gtactacgtt gaaagactta    540
atttatgata tgacaacgtc aggttctggc tcaggtttac cattgcttgt tcagagaaca    600
attgcgagaa ctattgtgtt acaagaaagc attggcaaag gtcgatttgg agaagtttgg    660
agaggaaagt ggcgggagaga agaagttgct gttaagatat ctcctctag agaagaacgt    720
tcgtggttcc gtgaggcaga gatttatcaa actgtaatgt tacgtcatga aacatcctg    780
ggatttatag cagcagacaa taaagacaat ggtacttgga ctcagctctg gttggtgtca    840
gattatcatg agcatggatc cctttttgat tacttaaaca gatacacagt tactgtggaa    900
ggaatgataa aacttgctct gtccacggcg agcggtctgg cccatcttca catggagatt    960
gttggtaccc aaggaaagcc agccattgct catagagatt tgaaatcaaa gaatatcttg   1020
gtaaagaaga atggaacttg ctgtattgca gacttaggac tggcagtaag acatgattca   1080
gccacagata ccattgatat tgctccaaac cacagagtgg gaacaaaaag gtacatggcc   1140
cctgaagttc tcgatgattc cataaatatg aaacattttg aatccttcaa acgtgctgac   1200
atctatgcaa tgggcttagt attctgggaa attgctcgac atgttccat ggtggaatt   1260
catgaagatt accaactgcc ttattatgat cttgtacctt ctgacccatc agttgaagaa   1320
atgagaaaag ttgtttgtga acagaagtta aggccaaata tcccaaacag atggcagagc   1380
tgtgaagcct tgagagtaat ggctaaaatt atgagagaat gttggtatgc caatggagca   1440
```

```
gctaggctta cagcattgcg gattaagaaa acattatcgc aactcagtca acaggaaggc    1500
atcaaaatgt aa                                                        1512

<210> SEQ ID NO 94
<211> LENGTH: 4044
<212> TYPE: DNA
<213> ORGANISM: Homo sapiens
<300> PUBLICATION INFORMATION:
<302> TITLE: Flk1
<310> PATENT DOCUMENT NUMBER: AF035121

<400> SEQUENCE: 94
atgcagagca aggtgctgct ggccgtcgcc ctgtggctct gcgtggagac ccgggccgcc      60
tctgtgggtt tgcctagtgt ttctcttgat ctgcccaggc tcagcataca aaaagacata    120
cttacaatta aggctaatac aactcttcaa attacttgca ggggacagag ggacttggac    180
tggctttggc ccaataatca gagtggcagt gagcaaaggg tggaggtgac tgagtgcagc    240
gatggcctct tctgtaagac actcacaatt ccaaaagtga tcggaaatga cactggagcc    300
tacaagtgct ctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480 cttttgtgcaa gatacccaga aaagagattt gttcctgatg gtaacagaat tcctgggac      540 agcaagaagg gcttttactat tcccagctac atgatcagct atgctggcat ggtcttctgt      600
gaagcaaaaa ttaatgatga agttaccag tctattatgt acatagttgt cgttgtaggg      660
tataggattt atgatgtggt tctgagtccg tctcatggaa ttgaactatc tgttggagaa      720
aagcttgtct taaattgtac agcaagaact gaactaaatg tggggattga cttcaactgg      780
gaataccctt cttcgaagca tcagcataag aaacttgtaa accgagacct aaaaacccag      840
tctgggagtg agatgaagaa attttttgagc accttaacta tagatggtgt aacccggagt      900
gaccaaggat tgtacacctg tgcagcatcc agtgggctga tgaccaagaa aacagcaca      960 tttgtcaggg tccatgaaaa acctttttgtt gcttttggaa gtggcatgga atctctggtg    1020
gaagccacgg tggggagcg tgtcagaatc cctgcgaagt accttggtta cccacccca    1080 gaaataaaat ggtataaaaa tggaatacc cttgagtcca atcacaatt aaagcgggg    1140 catgtactga cgattatgga agtgagtgaa agagacacag gaaattacac tgtcatcctt    1200
accaatccca ttcaaaagga aagcagagc atgtggtct ctctggttgt gtatgtccca    1260
ccccagattg gtgagaaatc tctaatctct cctgtggatt cctaccagta cggcaccact    1320
caaacgctga catgtacggt ctatgccatt cctcccccgc atcacatcca ctggtattgg    1380
cagttggagg aagagtgcgc caacgagccc agccaagctg tctcagtgac aaacccatac    1440
ccttgtgaag aatggagaag tgtggaggac ttccagggag aaataaaat tgaagttaat    1500 aaaaatcaat ttgctctaat tgaaggaaaa acaaaactg taagtaccct tgttatccaa    1560
gcggcaaatg tgtcagcttt gtacaaatgt gaagcggtca caaagtcgg agaggagag    1620 agggtgatct ccttccacgt gaccagggt cctgaaatta ctttgcaacc tgacatgcag    1680
cccactgagc aggagagcgt gtcttttgtgg tgcactgcag acagatctac gtttgagaac    1740
ctcacatggt acaagcttgg cccacagcct ctgccaatcc atgtgggaga gttgcccaca    1800
cctgtttgca agaacttgga tactctttgg aaattgaatg ccaccatgtt ctctaatagc    1860
acaaatgaca tttttgatcat ggagcttaag aatgcatcct gcaggaccca aggagactat    1920
```

```
gtctgccttg ctcaagacag gaagaccaag aaaagacatt gcgtggtcag gcagctcaca    1980
gtcctagagc gtgtggcacc cacgatcaca ggaaacctgg agaatcagac gacaagtatt    2040
ggggaaagca tcgaagtctc atgcacggca tctgggaatc cccctccaca gatcatgtgg    2100
tttaaagata atgagaccct tgtagaagac tcaggcattg tattgaagga tgggaaccgg    2160
aacctcacta tccgcagagt gaggaaggag gacgaaggcc tctacacctg ccaggcatgc    2220
agtgttcttg gctgtgcaaa agtggaggca ttttcataa tagaaggtgc ccaggaaaag    2280
acgaacttgg aaatcattat tctagtaggc acggcggtga ttgccatgtt cttctggcta    2340
cttcttgtca tcatcctacg gaccgttaag cgggccaatg gagggaact gaagacaggc    2400 tacttgtcca tcgtcatgga tccagatgaa ctcccattgg atgaacattg tgaacgactg    2460
ccttatgatg ccagcaaatg gaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820
aaaggggcac gattccgtca agggaaagac tacgttggag caatcccgt ggatctgaaa    2880 cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggaccctgcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct gcaagctaa tgctcagcag gatggcaaag actacattgt tcttccgata    3540
tcagagactt tgagcatgga agaggattct ggactctctc tgcctacctc acctgttttcc    3600 tgtatggagg aggaggaagt atgtgacccc aaattccatt atgacaacac agcaggaatc    3660
agtcagtatc tgcagaacag taagcgaaag agccggcctg tgagtgtaaa acatttgaa    3720 gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg aatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaacttt aaagctgata gagattggag tgcaaaccgg tagcacagcc    4020
cagattctcc agcctgactc gggg                                          4044
```

<210> SEQ ID NO 95
<211> LENGTH: 4017
<212> TYPE: DNA
<213> ORGANISM: Homo sapiens
<300> PUBLICATION INFORMATION:
<302> TITLE: Flt1
<310> PATENT DOCUMENT NUMBER: AF063657

```
<400> SEQUENCE: 95
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggaagc agcccataaa      180
tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac cttttcgtaga gatgtacagt    420
gaaatccccg aaattataca catgactgaa ggaagggagc tcgtcattcc ctgccgggtt     480
acgtcaccta acatcactgt tactttaaaa aagtttccac ttgacacttt gatccctgat     540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata agagagcttc cgtaaggcga     840
cgaattgacc aaagcaattc ccatgccaac atattctaca gtgttcttac tattgacaaa     900
atgcagaaca agacaaagg actttatact tgtcgtgtaa ggagtggacc atcattcaaa     960
tctgttaaca cctcagtgca tatatatgat aaagcattca tcactgtgaa acatcgaaaa    1020
cagcaggtgc ttgaaaccgt agctggcaag cggtcttacc ggctctctat gaaagtgaag    1080
gcatttccct cgccggaagt tgtatggtta aagatgggt tacctgcgac tgagaaatct     1140
gctcgctatt tgactcgtgg ctactcgtta attatcaagg acgtaactga agaggatgca    1200
gggaattata caatcttgct gagcataaaa cagtcaaatg tgttaaaaa cctcactgcc     1260
actctaattg tcaatgtgaa accccagatt tacgaaaagg ccgtgtcatc gtttccagac    1320
ccggctctct acccactggg cagcagacaa atcctgactt gtaccgcata tggtatccct    1380
caacctacaa tcaagtggtt ctggcacccc tgtaaccata atcattccga agcaaggtgt    1440
gactttgtt ccaataatga agagtccttt atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga actgtcttg cacagttaac    1740
aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagaga tcaggaagca    1980
ccatacctcc tgcgaaacct cagtgatcac acagtggcca tcagcagttc caccactttta    2040
gactgtcatg ctaatggtgt cccccgagcct cagatcactt ggtttaaaaa caaccacaaa    2100
atacaacaag agcctggaat tatttttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
```

-continued

| | |
|---|---|
| cgaaaaatga aaaggtcttc ttctgaaata aagactgact acctatcaat tataatggac | 2400 |
| ccagatgaag ttcctttgga tgagcagtgt gagcggctcc cttatgatgc cagcaagtgg | 2460 |
| gagtttgccc gggagagact aaactgggc aaatcacttg aagaggggc ttttggaaaa | 2520 |
| gtggttcaag catcagcatt tggcattaag aaatcaccta cgtgccggac tgtggctgtg | 2580 |
| aaaatgctga agaggggc cacggccagc gagtacaaag ctctgatgac tgagctaaaa | 2640 |
| atcttgaccc acattggcca ccatctgaac gtggttaacc tgctgggagc ctgcaccaag | 2700 |
| caaggagggc ctctgatggt gattgttgaa tactgcaaat atggaaatct ctccaactac | 2760 |
| ctcaagagca aacgtgactt attttttctc aacaaggatg cagcactaca catggagcct | 2820 |
| aagaaagaaa aaatggagcc aggcctgaa caaggcaaga accaagact agatagcgtc | 2880 |
| accagcagcg aaagctttgc gagctccggc tttcaggaag ataaaagtct gagtgatgtt | 2940 |
| gaggaagagg aggattctga cggttttctac aaggagccca tcactatgga agatctgatt | 3000 |
| tcttacagtt ttcaagtggc cagaggcatg gagttcctgt cttccagaaa gtgcattcat | 3060 |
| cgggacctgg cagcgagaaa cattctttta tctgagaaca cgtggtgaa gatttgtgat | 3120 |
| tttggccttg cccgggatat ttataagaac cccgattatg tgagaaaagg agatactcga | 3180 |
| cttcctctga atggatggc tcctgaatct atctttgaca aaatctacag caccaagagc | 3240 |
| gacgtgtggt cttacggagt attgctgtgg gaaatcttct ccttaggtgg gtctccatac | 3300 |
| ccaggagtac aaatggatga ggacttttgc agtcgcctga ggaaggcat gaggatgaga | 3360 |
| gctcctgagt actctactcc tgaaatctat cagatcatgc tggactgctg gcacagagac | 3420 |
| ccaaaagaaa ggccaagatt tgcagaactt gtggaaaaac taggtgattt gcttcaagca | 3480 |
| aatgtacaac aggatggtaa agactacatc ccaatcaatg ccatactgac aggaaatagt | 3540 |
| gggtttacat actcaactcc tgccttctct gaggacttct tcaaggaaag tatttcagct | 3600 |
| ccgaagttta attcaggaag ctctgatgat gtcagatatg taaatgcttt caagttcatg | 3660 |
| agcctggaaa gaatcaaaac cttgaagaa cttttaccga atgccacctc catgtttgat | 3720 |
| gactaccagg gcgacagcag cactctgttg gcctctccca tgctgaagcg cttcacctgg | 3780 |
| actgacagca aacccaaggc ctcgctcaag attgacttga gagtaaccag taaaagtaag | 3840 |
| gagtcgggc tgtctgatgt cagcaggccc agtttctgcc attccagctg tgggcacgtc | 3900 |
| agcgaaggca agcgcaggtt cacctacgac cacgctgagc tggaaaggaa aatcgcgtgc | 3960 |
| tgctccccgc cccagacta caactcggtg gtcctgtact ccacccccc catctag | 4017 |

<210> SEQ ID NO 96  
<211> LENGTH: 3897  
<212> TYPE: DNA  
<213> ORGANISM: Homo sapiens  
<300> PUBLICATION INFORMATION:  
<302> TITLE: Flt4  
<310> PATENT DOCUMENT NUMBER: XM003852

<400> SEQUENCE: 96

| | |
|---|---|
| atgcagcggg gcgccgcgct gtgcctgcga ctgtggctct gcctgggact cctggacggc | 60 |
| ctggtgagtg gctactccat gacccccccg accttgaaca tcacggagga gtcacacgtc | 120 |
| atcgacaccg gtgacagcct gtccatctcc tgcaggggac agcacccct cgagtgggct | 180 |
| tggccaggag ctcaggaggc ccagccacc ggagacaagg acagcgagga cacggggtg | 240 |
| gtgcgagact gcgagggcac agacgccagg ccctactgca aggtgttgct gctgcacgag | 300 |
| gtacatgcca acgacacagg cagctacgtc tgctactaca gtacatcaa ggcacgcatc | 360 |

```
gagggcacca cggccgccag ctcctacgtg ttcgtgagag actttgagca gccattcatc    420
aacaagcctg acacgctctt ggtcaacagg aaggacgcca tgtgggtgcc ctgtctggtg    480
tccatccccg gcctcaatgt cacgctgcgc tcgcaaagct cggtgctgtg ccagacggg    540 caggaggtgg tgtgggatga ccggcggggc atgctcgtgt ccacgccact gctgcacgat    600
gccctgtacc tgcagtgcga gaccacctgg ggagaccagg acttcctttc caaccccttc    660
ctggtgcaca tcacaggcaa cgagctctat gacatccagc tgttgcccag gaagtcgctg    720
gagctgctgg tagggagaa gctggtcctg aactgcaccg tgtgggctga gtttaactca    780
ggtgtcacct ttgactggga ctacccaggg aagcaggcag agcggggtaa gtgggtgccc    840
gagcgacgct cccagcagac ccacacagaa ctctccagca tcctgaccat ccacaacgtc    900
agccagcacg acctgggctc gtatgtgtgc aaggccaaca acggcatcca gcgatttcgg    960
gagagcaccg aggtcattgt gcatgaaaat cccttcatca gcgtcgagtg gctcaaagga   1020
cccatcctgg aggccacggc aggagacgag ctggtgaagc tgcccgtgaa gctggcagcg   1080 tacccccgc ccgagttcca gtggtacaag gatggaaagg cactgtccgg gcgccacagt   1140
ccacatgccc tggtgctcaa ggaggtgaca gaggccagca caggcaccta cccctcgcc   1200 ctgtggaact ccgctgctgg cctgaggcgc aacatcagcc tggagctggt ggtgaatgtg   1260 ccccccaga tacatgagaa ggaggcctcc tcccccagca tctactcgcg tcacagccgc   1320
caggccctca cctgcacggc ctacggggtg cccctgcctc tcagcatcca gtggcactgg   1380
cggccctgga cccctgcaa gatgtttgcc cagcgtagtc tccggcggcg gcagcagcaa   1440
gacctcatgc cacagtgccg tgactggagg gcggtgaccg cgcaggatgc cgtgaacccc   1500
atcgagagcc tggacacctg gaccgagttt gtggagggaa agaataagac tgtgagcaag   1560
ctggtgatcc agaatgccaa cgtgtctgcc atgtacaagt gtgtggtctc caacaaggtg   1620
ggccaggatg agcggctcat ctacttctat gtgaccacca tccccgacgg cttcaccatc   1680
gaatccaagc catccgagga gctactagag ggccagccgg tgctcctgag ctgccaagcc   1740
gacagctaca gtacgagca tctgcgctgg taccgcctca acctgtccac gctgcacgat   1800
gcgcacggga acccgcttct gctcgactgc aagaacgtgc atctgttcgc cacccctctg   1860
gccgccagcc tggaggaggt ggcacctggg gcgcgccacg ccacgctcag cctgagtatc   1920
ccccgcgtcg cgcccgagca cgagggccac tatgtgtgcg aagtgcaaga ccggcgcagc   1980
catgacaagc actgccacaa gaagtacctg tcggtgcagg ccctggaagc ccctcggctc   2040
acgcagaact tgaccgacct cctggtgaac gtgagcgact cgctggagat gcagtgcttg   2100
gtggccggag cgcacgcgcc cagcatcgtg tggtacaaag acgagaggct gctggaggaa   2160
aagtctggag tcgacttggc ggactccaac cagaagctga gcatccagcg cgtgcgcgag   2220
gaggatgcgg gacgctatct gtgcagcgtg tgcaacgcca agggctgcgt caactcctcc   2280
gccagcgtgg ccgtggaagg ctccgaggat aagggcagca tggagatcgt gatccttgtc   2340
ggtaccggcg tcatcgctgt cttcttctgg gtcctcctcc tcctcatctt ctgtaacatg   2400
aggaggccgg cccacgcaga catcaagacg ggctacctgt ccatcatcat ggaccccggg   2460
gaggtgcctc tggaggagca atgcgaatac ctgtcctacg atgccagcca gtgggaattc   2520
ccccgagagc ggctgcacct ggggagagtg ctcggctacg cgccttcgg gaaggtggtg   2580 gaagcctccg ctttcggcat ccacaagggc agcagctgtg acaccgtggc cgtgaaaatg   2640
ctgaaagagg cgccacggc cagcgagcag cgcgcgctga tgtcggagct caagatcctc   2700
attcacatcg gcaaccacct caacgtggtc aacctcctcg gggcgtgcac caagccgcag   2760
```

-continued

| | |
|---|---|
| ggcccsctca tggtgatcgt ggagttctgc aagtacggca acctctccaa cttcctgcgc | 2820 |
| gccaagcggg acgccttcag cccctgcgcg gagaagtctc ccgagcagcg cggacgcttc | 2880 |
| cgcgccatgg tggagctcgc caggctggat cggaggcggc cggggagcag cgacagggtc | 2940 |
| ctcttcgcgc ggttctcgaa gaccgagggc ggagcgaggc gggcttctcc agaccaagaa | 3000 |
| gctgaggacc tgtggctgag cccgctgacc atggaagatc ttgtctgcta cagcttccag | 3060 |
| gtggccagag ggatggagtt cctggcttcc gaaagtgca tccacagaga cctggctgct | 3120 |
| cggaacattc tgctgtcgga aagcgacgtg gtgaagatct gtgactttgg ccttgcccgg | 3180 |
| gacatctaca agacccccga ctacgtccgc aagggcagtg cccggctgcc cctgaagtgg | 3240 |
| atggcccctg aaagcatctt cgacaaggtg tacaccacgc agagtgacgt gtggtccttt | 3300 |
| ggggtgcttc tctgggagat cttctctctg ggggcctccc cgtaccctgg ggtgcagatc | 3360 |
| aatgaggagt tctgccagcg gctgagagac ggcacaagga tgagggcccc ggagctggcc | 3420 |
| actcccgcca tacgccgcat catgctgaac tgctggtccg gagaccccaa ggcgagacct | 3480 |
| gcattctcgg agctggtgga gatcctgggg gacctgctcc agggcagggg cctgcaagag | 3540 |
| gaagaggagg tctgcatggc cccgcgcagc tctcagagct cagaagaggg cagcttctcg | 3600 |
| caggtgtcca ccatggccct acacatcgcc caggctgacg ctgaggacag cccgccaagc | 3660 |
| ctgcagcgcc acagcctggc cgccaggtat tacaactggg tgtcctttcc cgggtgcctg | 3720 |
| gccagagggg ctgagacccg tggttcctcc aggatgaaga catttgagga attccccatg | 3780 |
| accccaacga cctacaaagg ctctgtggac aaccagacag acagtgggat ggtgctggcc | 3840 |
| tcggaggagt ttgagcagat agagagcagg catagacaag aaagcggctt caggtag | 3897 |

<210> SEQ ID NO 97
<211> LENGTH: 4071
<212> TYPE: DNA
<213> ORGANISM: Homo sapiens
<300> PUBLICATION INFORMATION:
<302> TITLE: KDR
<310> PATENT DOCUMENT NUMBER: AF063658

<400> SEQUENCE: 97

| | |
|---|---|
| atggagagca aggtgctgct ggccgtcgcc ctgtggctct gcgtggagac ccggggccgcc | 60 |
| tctgtgggtt tgcctagtgt ttctcttgat ctgcccaggc tcagcataca aaagacata | 120 |
| cttacaatta aggctaatac aactcttcaa attacttgca ggggacagag ggacttggac | 180 |
| tggctttggc ccaataatca gagtggcagt gagcaagggg tggaggtgac tgagtgcagc | 240 |
| gatggcctct tctgtaagac actcacaatt ccaaaagtga tcggaaatga cactggagcc | 300 |
| tacaagtgct tctaccggga aactgacttg gcctcggtca tttatgtcta tgttcaagat | 360 |
| tacagatctc catttattgc ttctgttagt gaccaacatg gagtcgtgta cattactgag | 420 |
| aacaaaaaca aaactgtggt gattccatgt ctcgggtcca tttcaaatct caacgtgtca | 480 |
| ctttgtgcaa gataccccag aaaagagattt gttcctgatg taacagaatt cctgggac | 540 |
| agcaagaagg gctttactat tcccagctac atgatcagct atgctggcat ggtcttctgt | 600 |
| gaagcaaaaa ttaatgatga agttaccag tctattatgt acatagttgt cgttgtaggg | 660 |
| tataggattt atgatgtggt tctgagtccg tctcatggaa ttgaactatc tgttggagaa | 720 |
| aagcttgtct taaattgtac agcaagaact gaactaaatg tggggattga cttcaactgg | 780 |
| gaatacccct tcgaagcatc agcataag aaacttgtaa accgagacct aaaaacccag | 840 |
| tctgggagtg agatgaagaa atttttgagc acccttaacta tagatggtgt aacccggagt | 900 |
| gaccaaggat tgtacacctg tgcagcatcc agtgggctga tgaccaagaa gaacagcaca | 960 |

```
tttgtcaggg tccatgaaaa acctttgtt gcttttggaa gtggcatgga atctctggtg    1020
gaagccacgg tgggggagcg tgtcagaatc cctgcgaagt accttggtta cccaccccca    1080
gaaataaaat ggtataaaaa tggaataccc cttgagtcca atcacacaat aaagcgggg     1140 catgtactga cgattatgga agtgagtgaa agagacacag gaaattacac tgtcatcctt    1200
accaatccca tttcaaagga gaagcagagc catgtggtct ctctggttgt gtatgtccca    1260
ccccagattg gtgagaaatc tctaatctct cctgtggatt cctaccagta cggcaccact    1320
caaacgctga catgtacggt ctatgccatt cctcccccgc atcacatcca ctggtattgg    1380
cagttggagg aagagtgcgc caacgagccc agccaagctg tctcagtgac aaacccatac    1440
ccttgtgaag aatggagaag tgtggaggac ttccagggag gaaataaaat tgaagttaat    1500
aaaaatcaat ttgctctaat tgaaggaaaa aacaaaactg taagtaccct tgttatccaa    1560
gcggcaaatg tgtcagcttt gtacaaatgt gaagcggtca acaaagtcgg agaggagag     1620 agggtgatct ccttccacgt gaccagggggt cctgaaatta ctttgcaacc tgacatgcag   1680
cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800
cctgtttgca agaacttgga tactctttgg aaattgaatg ccaccatgtt ctctaatagc   1860
acaaatgaca ttttgatcat ggagcttaag aatgcatcct gcaggacca aggagactat    1920 gtctgccttg ctcaagacag gaagaccaag aaaagacatt gcgtggtcag gcagctcaca    1980
gtcctagagc gtgtggcacc cacgatcaca ggaaacctgg agaatcagac gacaagtatt    2040
ggggaaagca tcgaagtctc atgcacggca tctgggaatc cccctccaca gatcatgtgg    2100
tttaaagata tgagaccct gtagaagac tcaggcattg tattgaagga tgggaaccgg     2160
aacctcacta tccgcagagt gaggaaggag gacgaaggcc tctacacctg ccaggcatgc    2220
agtgttcttg gctgtgcaaa agtggaggca tttttcataa tagaaggtgc ccaggaaaag    2280
acgaacttgg aaatcattat tctagtaggc acggcggtga ttgccatgtt cttctggcta    2340
cttcttgtca tcatcctacg gaccgttaag cgggccaatg gaggggaact gaagacaggc    2400
tacttgtcca tcgtcatgga tccagatgaa ctcccattgg atgaacattg tgaacgactg    2460
ccttatgatg ccagcaaatg ggaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820 aaagggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agcatgga gttcttggca     3060 tcgcgaaagt gtatccacag ggaccctggcg gcacgaaata tcctcttatc ggagaagaac    3120
gtggttaaaa tctgtgactt tggccttggcc cgggatattt ataagatcc agattatgtc    3180 agaaaaggag atgctcgcct cccctttgaaa tggatggccc cagaaacaat ttttgacaga    3240
gtgtacacaa tccagagtga cgtctggtct tttggtgttt tgctgtgga aatattttcc    3300 ttaggtgctt ctccatatcc tggggtaaag attgatgaag aattttgtag gcgattgaaa    3360
```

```
gaaggaacta gaatgagggc ccctgattat actacaccag aaatgtacca gaccatgctg   3420
gactgctggc acggggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgtttcc   3600
tgtatggagg aggaggaagt atgtgacccc aaattccatt atgacaacac agcaggaatc   3660
agtcagtatc tgcagaacag taagcgaaag agccggcctg tgagtgtaaa acatttgaa   3720 gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg aatggtgcc cagcaaaagc agggagtctg tggcatctga aggctcaaac   3900
cagacaagcg gctaccagtc cggatatcac tccgatgaca cagacaccac cgtgtactcc   3960
agtgaggaag cagaactttt aaagctgata gagattggag tgcaaaccgg tagcacagcc   4020
cagattctcc agcctgactc ggggaccaca ctgagctctc tcctgtttta a   4071

<210> SEQ ID NO 98
<211> LENGTH: 1410
<212> TYPE: DNA
<213> ORGANISM: Homo sapiens
<300> PUBLICATION INFORMATION:
<302> TITLE: MMP1
<310> PATENT DOCUMENT NUMBER: M13509

<400> SEQUENCE: 98
atgcacagct ttcctccact gctgctgctg ctgttctggg gtgtggtgtc tcacagcttc     60
ccagcgactc tagaaacaca agagcaagat gtggacttag tccagaaata cctggaaaaa    120
tactacaacc tgaagaatga tgggaggcaa gttgaaaagc ggagaaatag tggcccagtg    180
gttgaaaaat tgaagcaaat gcaggaattc tttgggctga agtgactgg gaaaccagat    240 gctgaaaccc tgaaggtgat gaagcagccc agatgtggag tgcctgatgt ggctcagttt    300
gtcctcactg agggaaaccc tcgctgggag caaacacatc tgaggtacag gattgaaaat    360
tacacgccag atttgccaag agcagatgtg gaccatgcca ttgagaaagc cttccaactc    420
tggagtaatg tcacacctct gacattcacc aaggtctctg agggtcaagc agacatcatg    480
atatcttttg tcaggggaga tcatcgggac aactctcctt tgatggacc tggaggaaat    540 cttgctcatg cttttcaacc aggcccaggt attggagggg atgctcattt tgatgaagat    600
gaaaggtgga ccaacaattt cagagagtac aacttacatc gtgttgcggc tcatgaactc    660
ggccattctc ttggactctc ccattctact gatatcgggg ctttgatgta ccctagctac    720
accttcagtg gtgatgttca gctagctcag gatgacattg atggcatcca agccatatat    780
ggacgttccc aaaatcctgt ccagcccatc ggcccacaaa ccccaaaagc gtgtgacagt    840
aagctaacct tgatgctat aactacgatt cggggagaag tgatgttctt taaagacaga    900
ttctacatgc gcacaaatcc cttctacccg gaagttgagc tcaatttcat ttctgttttc    960
tggccacaac tgccaaatgg gcttgaagct gcttacgaat ttgccgacag agatgaagtc   1020
cggtttttca aagggaataa gtactgggct gttcagggac agaatgtgct acacggatac   1080
cccaaggaca tctacagctc ctttggcttc cctagaactg tgaagcatat cgatgctgct   1140
ctttctgagg aaaacactgg aaaaacctac ttctttgttg ctaacaaata ctggaggtat   1200
gatgaatata aacgatctat ggatccaagt tatcccaaaa tgatagcaca tgactttcct   1260
ggaattggcc acaaagttga tgcagttttc atgaaagatg gatttttcta tttctttcat   1320
```

| | |
|---|---|
| ggaacaagac aatacaaatt tgatcctaaa acgaagagaa ttttgactct ccagaaagct | 1380 |
| aatagctggt tcaactgcag gaaaaattga | 1410 |

<210> SEQ ID NO 99
<211> LENGTH: 1743
<212> TYPE: DNA
<213> ORGANISM: Homo sapiens
<300> PUBLICATION INFORMATION:
<302> TITLE: MMP10
<310> PATENT DOCUMENT NUMBER: XM006269

<400> SEQUENCE: 99

| | |
|---|---|
| aaagaaggta agggcagtga gaatgatgca tcttgcattc cttgtgctgt tgtgtctgcc | 60 |
| agtctgctct gcctatcctc tgagtggggc agcaaaagag gaggactcca acaaggatct | 120 |
| tgcccagcaa tacctagaaa agtactacaa cctcgaaaag gatgtgaaac agtttagaag | 180 |
| aaaggacagt aatctcattg ttaaaaaaat ccaaggaatg cagaagttcc ttgggttgga | 240 |
| ggtgacaggg aagctagaca ctgacactct ggaggtgatg cgcaagccca ggtgtggagt | 300 |
| tcctgacgtt ggtcacttca gctcctttcc tggcatgccg aagtggagga aaacccacct | 360 |
| tacatacagg attgtgaatt atacaccaga tttgccaaga gatgctgttg attctgccat | 420 |
| tgagaaagct ctgaaagtct gggaagaggt gactccactc acattctcca ggctgtatga | 480 |
| aggagaggct gatataatga tctcttttgc agttaaagaa catggagact tttactcttt | 540 |
| tgatggccca ggacacagtt tggctcatgc ctacccacct ggacctgggc tttatggaga | 600 |
| tattcacttt gatgatgatg aaaaatggac agaagatgca tcaggcacca atttattcct | 660 |
| cgttgctgct catgaacttg gccactccct ggggctcttt cactcagcca acactgaagc | 720 |
| tttgatgtac ccactctaca actcattcac agagctcgcc cagttccgcc tttcgcaaga | 780 |
| tgatgtgaat ggcattcagt ctctctacgg acctcccct gcctctactg aggaacccct | 840 |
| ggtgcccaca aaatctgttc cttcgggatc tgagatgcca gccaagtgtg atcctgcttt | 900 |
| gtccttcgat gccatcagca ctctgagggg agaatatctg ttctttaaag acagatattt | 960 |
| ttggcgaaga tcccactgga accctgaacc tgaatttcat ttgatttctg cattttggcc | 1020 |
| ctctcttcca tcatatttgg atgctgcata tgaagttaac agcagggaca ccgttttttat | 1080 |
| ttttaaagga aatgagttct gggccatcag aggaaatgag gtacaagcag gttatccaag | 1140 |
| aggcatccat accctgggtt ttcctccaac cataaggaaa attgatgcag ctgtttctga | 1200 |
| caaggaaaag aagaaaacat acttctttgc agcggacaaa tactgagat ttgatgaaaa | 1260 |
| tagccagtcc atggagcaag gcttccctag actaatagct gatgactttc caggagttga | 1320 |
| gcctaaggtt gatgctgtat tacaggcatt tggattttc tacttcttca gtggatcatc | 1380 |
| acagtttgag tttgaccca atgccaggat ggtgacacac atattaaaga gtaacagctg | 1440 |
| gttacattgc taggcgagat agggggaaga cagatatggg tgttttttaat aaatctaata | 1500 |
| attattcatc taatgtatta tgagccaaaa tggttaattt ttcctgcatg ttctgtgact | 1560 |
| gaagaagatg agccttgcag atatctgcat gtgtcatgaa gaatgtttct ggaattcttc | 1620 |
| acttgctttt gaattgcact gaacagaatt aagaaatact catgtgcaat aggtgagaga | 1680 |
| atgtattttc atagatgtgt tattacttcc tcaataaaaa gttttatttt gggcctgttc | 1740 |
| ctt | 1743 |

<210> SEQ ID NO 100
<211> LENGTH: 1467
<212> TYPE: DNA
<213> ORGANISM: Homo sapiens

```
<300> PUBLICATION INFORMATION:
<302> TITLE: MMP11
<310> PATENT DOCUMENT NUMBER: XM009873

<400> SEQUENCE: 100
atggctccgg ccgcctggct ccgcagcgcg gccgcgcgcg ccctcctgcc cccgatgctg      60
ctgctgctgc tccagccgcc gccgctgctg gccgggctc tgccgccgga cgcccaccac     120
ctccatgccg agaggagggg gccacagccc tggcatgcag ccctgcccag tagcccggca     180
cctgcccctg ccacgcagga agcccccggg cctgccagca gcctcaggcc tccccgctgt     240
ggcgtgcccg acccatctga tgggctgagt gcccgcaacc gacagaagag gttcgtgctt     300
tctggcgggc gctgggagaa acggacctc acctacagga tccttcggtt cccatggcag     360
ttggtgcagg agcaggtgcg gcagacgatg gcagaggccc taaaggtatg gagcgatgtg     420
acgccactca cctttactga ggtgcacgag ggccgtgctg acatcatgat cgacttcgcc     480
aggtactggc atgggacga cctgccgttt gatgggcctg ggggcatcct ggcccatgcc     540
ttcttcccca agactcaccg agaaggggat gtccacttcg actatgatga acctggact      600 atcggggatg accagggcac agacctgctg caggtggcag cccatgaatt tggccacgtg     660
ctggggctgc agcacacaac agcagccaag gccctgatgt ccgccttcta cacctttcgc     720
tacccactga gtctcagccc agatgactgc agggcgttc aacacctata tggccagccc     780
tggcccactg tcacctccag accccagcc ctgggcccc aggctgggat agacaccaat     840
gagattgcac cgctggagcc agacgcccg ccagatgcct gtgaggcctc ctttgacgcg     900
gtctccacca tccgaggcga gctctttttc ttcaaagcgg gctttgtgtg gcgcctccgt     960
gggggccagc tgcagcccgg ctacccagca ttggcctctc gccactggca gggactgccc    1020
agccctgtgg acgctgcctt cgaggatgcc cagggccaca tttggttctt ccaaggtgct    1080
cagtactggg tgtacgacgg tgaaaagcca gtcctgggcc ccgcaccct caccgagctg    1140 ggcctggtga ggttcccggt ccatgctgcc ttggtctggg gtcccgagaa gaacaagatc    1200
tacttcttcc gaggcaggga ctactggcgt ttccaccca gcacccggcg tgtagacagt    1260
cccgtgcccc gcagggccac tgactggaga ggggtgccct ctgagatcga cgctgccttc    1320
caggatgctg atggctatgc ctacttcctg cgcggccgcc tctactggaa gtttgaccct    1380
gtgaaggtga aggctctgga aggcttcccc cgtctcgtgg tcctgacttt ctttggctgt    1440
gccgagcctg ccaacacttt cctctga                                        1467

<210> SEQ ID NO 101
<211> LENGTH: 1653
<212> TYPE: DNA
<213> ORGANISM: Homo sapiens
<220> FEATURE:
<221> NAME/KEY: misc_feature
<222> LOCATION: (626)..(925)
<223> OTHER INFORMATION: n=A, T, G, C or gap
<300> PUBLICATION INFORMATION:
<302> TITLE: MMP12
<310> PATENT DOCUMENT NUMBER: XM006272

<400> SEQUENCE: 101
atgaagtttc ttctaatact gctcctgcag gccactgctt ctggagctct tccctgaac      60 agctctacaa gcctggaaaa aaataatgtg ctatttggtg agagatactt agaaaaattt     120
tatggccttg agataaacaa acttccagtg acaaaatga aatatagtgg aaacttaatg     180
aaggaaaaaa tccaagaaat gcagcacttc ttgggtctga agtgaccgg gcaactggac     240 acatctaccc tggagatgat gcacgcacct cgatgtggag tccccgatgt ccatcattc      300
```

```
agggaaatgc aggggggcc cgtatggagg aaacattata tcacctacag aatcaataat    360
tacacacctg acatgaaccg tgaggatgtt gactacgcaa tccggaaagc tttccaagta    420
tggagtaatg ttaccccctt gaaattcagc aagattaaca caggcatggc tgacattttg    480
gtggttttg cccgtggagc tcatggagac ttccatgctt ttgatggcaa aggtggaatc    540
ctagcccatg cttttggacc tggatctggc attggagggg atgcacattt cgatgaggac    600
gaattctgga ctacacattc aggagnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnngagag gatccaaagg ccgtaatgtt ccccacctac    960
aaatatgttg acatcaacac atttcgcctc tctgctgatg acatacgtgg cattcagtcc   1020
ctgtatggag acccaaaaga gaaccaacgc ttgccaaatc ctgacaattc agraccagct   1080
ctctgtgacc ccaatttgag ttttgatgct gtcactaccg tgggaaataa gatctttttc   1140
ttcaaagaca ggttcttctg gctgaaggtt tctgagagac caaagaccag tgttaattta   1200
atttcttcct tatggccaac cttgccatct ggcattgaag ctgcttatga aattgaagcc   1260
agaaatcaag ttttttcttt taaagatgac aaatactggt taattagcaa tttaagacca   1320
gagccaaatt atcccaagag catacattct tttggttttc ctaactttgt gaaaaaaatt   1380
gatgcagctg ttttttaaccc acgtttttat aggacctact tctttgtaga taaccagtat   1440
tggaggtatg atgaaaggag acagatgatg gaccctggtt atcccaaact gattaccaag   1500
aacttccaag gaatcgggcc taaaattgat gcagtcttct actctaaaaa caaatactac   1560
tatttcttcc aaggatctaa ccaatttgaa tatgacttcc tactccaacg tatcaccaaa   1620
acactgaaaa gcaatagctg gtttggttgt tag                                1653

<210> SEQ ID NO 102
<211> LENGTH: 1416
<212> TYPE: DNA
<213> ORGANISM: Homo sapiens

<400> SEQUENCE: 102
atgcatccag gggtcctggc tgccttcctc ttcttgagct ggactcattg tcgggccctg     60
ccccttccca gtggtggtga tgaagatgat ttgtctgagg aagacctcca gtttgcagag    120
cgctacctga gatcatacta ccatcctaca aatctcgcgg gaatcctgaa ggagaatgca    180
gcaagctcca tgactgagag gctccgagaa atgcagtctt tcttcggctt agaggtgact    240
ggcaaacttg acgataacac cttagatgtc atgaaaaagc caagatgcgg ggttcctgat    300
gtgggtgaat acaatgtttt ccctcgaact cttaaatggt ccaaaatgaa tttaacctac    360
agaattgtga attacacccc tgatatgact cattctgaag tcgaaaaggc attcaaaaaa    420
gccttcaaag tttggtccga tgtaactcct ctgaatttta ccagacttca cgatggcatt    480
gctgacatca tgatctcttt tggaattaag gagcatggcg acttctaccc atttgatggg    540
cctctggct tgctggctca tgctttttcct cctgggccaa attatggagg agatgcccat    600
tttgatgatg atgaaacctg gacaagtagt tccaaaggct acaacttgtt tcttgttgct    660
gcgcatgagt tcggccactc cttaggtctt gaccactcca aggaccctgg agcactcatg    720
tttcctatct acacctacac cggcaaaagc cactttatgc ttcctgatga cgatgtacaa    780
```

```
gggatccagt ctctctatgg tccaggagat gaagacccca accctaaaca tccaaaaacg      840
ccagacaaat gtgacccttc cttatccctt gatgccatta ccagtctccg aggagaaaca      900
atgatcttta aagacagatt cttctggcgc ctgcatcctc agcaggttga tgcggagctg      960 ttttaacga aatcattttg ccagaactt cccaaccgta ttgatgctgc atatgagcac       1020
ccttctcatg acctcatctt catcttcaga ggtagaaaat tttgggctct taatggttat      1080
gacattctgg aaggttatcc caaaaaata tctgaactgg gtcttccaaa agaagttaag      1140
aagataagtg cagctgttca ctttgaggat acaggcaaga ctctcctgtt ctcaggaaac      1200
caggtctgga gatatgatga tactaaccat attatggata aagactatcc gagactaata      1260
gaagaagact tcccaggaat tggtgataaa gtagatgctg tctatgagaa aaatggttat      1320
atctattttt tcaacggacc catacagttt gaatacagca tctggagtaa ccgtattgtt      1380
cgcgtcatgc cagcaaattc cattttgtgg tgttaa                                1416

<210> SEQ ID NO 103
<211> LENGTH: 1749
<212> TYPE: DNA
<213> ORGANISM: Homo sapiens
<300> PUBLICATION INFORMATION:
<302> TITLE: MMP14
<310> PATENT DOCUMENT NUMBER: NM004995

<400> SEQUENCE: 103
atgtctcccg ccccaagacc cccccgttgt ctcctgctcc cctgctcac gctcggcacc        60 gcgctcgcct ccctcggctc ggcccaaagc agcagcttca gccccgaagc ctggctacag       120
caatatggct acctgcctcc cggggaccta cgtacccaca cacagcgctc accccagtca       180
ctctcagcgg ccatcgctgc catgcagaag ttttacggct gcaagtaac aggcaaagct       240 gatgcagaca ccatgaaggc catgaggcgc ccccgatgtg gtgttccaga caagtttggg       300
gctgagatca aggccaatgt tcgaaggaag cgctacgcca tccagggtct caaatggcaa       360
cataatgaaa tcacttttctg catccagaat tacacccccca aggtgggcga gtatgccaca       420
tacgaggcca ttcgcaaggc gttccgcgtg tgggagagtg ccacaccact gcgcttccgc       480
gaggtgccct atgcctacat ccgtgagggc catgagaagc aggccgacat catgatcttc       540
tttgccgagg gcttccatgg cgacagcacg cccttcgatg gtgagggcgg cttcctggcc       600
catgcctact ccccaggccc caacattgga ggagacaccc actttgactc tgccgagcct       660
tggactgtca ggaatgagga tctgaatgga aatgacatct tcctggtggc tgtgcacgag       720
ctgggccatg ccctggggct cgagcattcc agtgacccct cggccatcat ggcccctttt       780
taccagtgga tggacacgga gaattttgtg ctgcccgatg atgaccgccg gggcatccag       840
caactttatg ggggtgagtc agggttcccc accaagatgc ccctcaaccc caggactacc       900
tcccggcctt ctgttcctga taaacccaaa aaccccacct atgggcccaa catctgtgac       960
gggaactttg acaccgtggc catgctccga ggggagatgt tgtcttcaa ggagcgctgg      1020 ttctggcggg tgaggaataa ccaagtgatg gatggtaccc caatgccat ggccagttc      1080 tggcggggcc tgcctgcgtc catcaacact gcctacgaga ggaaggatgg caaattcgtc      1140
ttcttcaaag agacaagca ttgggtgttt gatgaggcgt ccctggaacc tggctacccc      1200
aagcacatta ggagctgggg ccgagggctg cctaccgaca gattgatgc tgctctcttc      1260 tggatgccca atgaaagac ctacttcttc cgtggaaaca gtactaccg tttcaacgaa      1320 gagctcaggg cagtggatag cgagtacccc aagaacatca agtctgggga agggatccct      1380
```

-continued

| | |
|---|---|
| gagtctccca gagggtcatt catgggcagc gatgaagtct tcacttactt ctacaagggg | 1440 |
| aacaaatact ggaaattcaa caaccagaag ctgaaggtag aaccgggcta ccccaagtca | 1500 |
| gccctgaggg actggatggg ctgcccatcg ggaggccggc cggatgaggg gactgaggag | 1560 |
| gagacggagg tgatcatcat tgaggtggac gaggaggggcg gcggggcggt gagcgcggct | 1620 |
| gccgtggtgc tgcccgtgct gctgctgctc ctggtgctgg cggtgggcct tgcagtcttc | 1680 |
| ttcttcagac gccatgggac ccccaggcga ctgctctact ccagcgttc cctgctggac | 1740 |
| aaggtctga | 1749 |

<210> SEQ ID NO 104
<211> LENGTH: 2010
<212> TYPE: DNA
<213> ORGANISM: Homo sapiens
<300> PUBLICATION INFORMATION:
<302> TITLE: MMP15
<310> PATENT DOCUMENT NUMBER: NM002428

<400> SEQUENCE: 104

| | |
|---|---|
| atgggcagcg acccgagcgc gcccggacgg ccgggctgga cgggcagcct cctcggcgac | 60 |
| cgggaggagg cggcgcggcc gcgactgctg ccgctgctcc tggtgcttct gggctgcctg | 120 |
| ggccttggcg tagcggccga agacgcggag gtccatgccg agaactggct gcggctttat | 180 |
| ggctacctgc ctcagcccag ccgccatatg tccaccatgc gttccgccca gatcttggcc | 240 |
| tcggcccttg cagagatgca gcgcttctac gggatcccag tcaccggtgt gctcgacgaa | 300 |
| gagaccaagg agtggatgaa gcggcccgc tgtggggtgc agaccagtt cggggtacga | 360 |
| gtgaaagcca acctgcggcg gcgtcggaag cgctacgccc tcaccgggag gaagtggaac | 420 |
| aaccaccatc tgacctttag catccagaac tacacggaga agttgggctg gtaccactcg | 480 |
| atggaggcgg tgcgcagggc cttccgcgtg tgggagcagg ccacgcccct ggtcttccag | 540 |
| gaggtgccct atgaggacat ccggctgcgg cgacagaagg aggccgacat catggtactc | 600 |
| tttgcctctg gcttccacgg cgacagctcg ccgtttgatg gcaccggtgg ctttctggcc | 660 |
| cacgccattt ccctggcccc cggcctaggc ggggacaccc attttgacgc agatgagccc | 720 |
| tggaccttct ccagcactga cctgcatgga acaacctct tcctggtggc agtgcatgag | 780 |
| ctgggccacg cgctggggct ggagcactcc agcaacccca tgccatcat ggcgccgttc | 840 |
| taccagtgga aggacgttga caacttcaag ctgcccgagg acgatctccg tggcatccag | 900 |
| cagctctacg gtaccccaga cggtcagcca cagcctaccc agcctctccc cactgtgacg | 960 |
| ccacggcggc caggccggcc tgaccaccgg ccgccccggc ctccccagcc accaccccca | 1020 |
| ggtgggaagc cagagcggcc cccaaagccg ggccccccag tccagcccg agccacagag | 1080 |
| cggcccgacc agtatggccc caacatctgc gacggggact tgacacagt ggccatgctt | 1140 |
| cgcgggggaga tgttcgtgtt caagggccgc tggttctggc gagtccggca caaccgcgtc | 1200 |
| ctggacaact atcccatgcc catcgggcac ttctggcgtg tctgcccgg tgacatcagt | 1260 |
| gctgcctacg agcgccaaga cggtcgtttt gtcttttttca aggtgaccg ctactggctc | 1320 |
| tttcgagaag cgaacctgga gcccggctac ccacagccgc tgaccagcta ggcctgggc | 1380 |
| atcccctatg accgcattga cacggccatc tggtgggagc ccacaggcca caccttcttc | 1440 |
| ttccaagagg acaggtactg gcgcttcaac gaggagacac agcgtggaga ccctgggtac | 1500 |
| cccaagccca tcagtgtctg cagggggatc cctgcctccc ctaaaggggc cttcctgagc | 1560 |
| aatgacgcag cctacaccta cttctacaag ggcaccaaat actggaaatt cgacaatgag | 1620 |
| cgcctgcgga tggagcccgg ctaccccaag tccatcctgc gggacttcat gggctgccag | 1680 |

```
gagcacgtgg agccaggccc ccgatggccc gacgtggccc ggccgccctt caacccccac    1740
gggggtgcag agcccggggc ggacagcgca gagggcgacg tggggatgg ggatggggac    1800 tttggggccg gggtcaacaa ggacggggc agccgcgtgg tggtgcagat ggaggaggtg    1860
gcacggacgg tgaacgtggt gatggtgctg gtgccactgc tgctgctgct ctgcgtcctg    1920
ggcctcacct acgcgctggt gcagatgcag cgcaagggtg cgccacgtgt cctgctttac    1980
tgcaagcgct cgctgcagga gtgggtctga                                     2010
```

<210> SEQ ID NO 105
<211> LENGTH: 1824
<212> TYPE: DNA
<213> ORGANISM: Homo sapiens
<300> PUBLICATION INFORMATION:
<302> TITLE: MMP16
<310> PATENT DOCUMENT NUMBER: NM005941

<400> SEQUENCE: 105

```
atgatcttac tcacattcag cactggaaga cggttggatt tcgtgcatca ttcggggtg      60 tttttcttgc aaaccttgct ttggatttta tgtgctacag tctgcggaac ggagcagtat    120
ttcaatgtgg aggtttggtt acaaaagtac ggctaccttc caccgactga ccccagaatg    180
tcagtgctgc gctctgcaga gaccatgcag tctgccctag ctgccatgca gcagttctat    240
ggcattaaca tgacaggaaa agtggacaga acacaattg actggatgaa gagcccga      300 tgcggtgtac ctgaccagac aagaggtagc tccaaatttc atattcgtcg aaagcgatat    360
gcattgacag gacagaaatg gcagcacaag cacatcactt acagtataaa gaacgtaact    420
ccaaaagtag agaccctga gactcgtaaa gctattcgcc gtgcctttga tgtgtggcag    480
aatgtaactc ctctgacatt tgaagaagtt ccctacagtg aattagaaaa tggcaaacgt    540
gatgtggata taaccattat ttttgcatct ggtttccatg gggacagctc tccctttgat    600
ggagagggag gattttttggc acatgcctac ttccctggac caggaattgg aggagatacc    660 catttttgact cagatgagcc atggacacta ggaaatccta atcatgatgg aaatgactta    720
tttcttgtag cagtccatga actgggacat gctctggat tggagcattc caatgacccc    780
actgccatca tggctccatt ttaccagtac atggaaacag acaacttcaa actacctaat    840
gatgatttac agggcatcca gaaaatatat ggtccacctg caagattcc tccacctaca    900 agacctctac cgacagtgcc cccacaccgc tctattcctc cggctgaccc caggaaaaat    960
gacaggccaa aacctcctcg gcctccaacc ggcagaccct cctatcccgg agccaaaccc    1020
aacatctgtg atgggaactt taacactcta gctattcttc gtcgtgagat gtttgttttc    1080
aaggaccagt ggtttttggcg agtgagaaac aacagggtga tggatggata cccaatgcaa    1140
attacttact ctggcgggg cttgcctcct agtatcgatg cagtttatga aaatagcgac    1200
gggaattttg tgttctttaa aggtaacaaa tattgggtgt tcaaggatac aactcttcaa    1260
cctggttacc ctcatgactt gataaccctt ggaagtggaa ttcccctca tggtattgat    1320 tcagccattt ggtgggagga cgtcgggaaa acctatttct tcaagggaga cagatattgg    1380
agatatagtg aagaaatgaa aacaatggac cctggctatc ccaagccaat cacagtctgg    1440
aaagggatcc ctgaatctcc tcagggagca tttgtacaca agaaaatgg ctttacgtat    1500 ttctacaaag gaaaggagta ttggaaattc aacaaccaga tactcaaggt agaacctgga    1560
catccaagat ccatcctcaa ggattttatg ggctgtgatg gaccaacaga cagagttaaa    1620
gaaggacaca gcccaccaga tgatgtagac attgtcatca aactggacaa cacagccagc    1680
```

-continued

| actgtgaaag ccatagctat tgtcattccc tgcatcttgg ccttatgcct ccttgtattg | 1740 |
| gtttacactg tgttccagtt caagaggaaa ggaacacccc gccacatact gtactgtaaa | 1800 |
| cgctctatgc aagagtgggt gtga | 1824 |

<210> SEQ ID NO 106
<211> LENGTH: 1560
<212> TYPE: DNA
<213> ORGANISM: Homo sapiens
<300> PUBLICATION INFORMATION:
<302> TITLE: MMP17
<310> PATENT DOCUMENT NUMBER: NM004141

<400> SEQUENCE: 106

| atgcagcagt ttggtggcct ggaggccacc ggcatcctgg acgaggccac cctggccctg | 60 |
| atgaaaaccc cacgctgctc cctgccagac ctccctgtcc tgacccaggc tcgcaggaga | 120 |
| cgccaggctc cagccccac caagtggaac aagaggaacc tgtcgtggag ggtccggacg | 180 |
| ttcccacggg actcaccact ggggcacgac acggtgcgtg cactcatgta ctacgccctc | 240 |
| aaggtctgga gcgacattgc gccctgaac ttccacgagg tggcgggcag caccgccgac | 300 |
| atccagatcg acttctccaa ggccgaccat aacgacggct accccttcga cggccccggc | 360 |
| ggcaccgtgg cccacgcctt cttccccggc caccaccaca ccgccgggga cacccactt | 420 |
| gacgatgacg aggcctggac cttccgctcc tcggatgccc acgggatgga cctgtttgca | 480 |
| gtggctgtcc acgagtttgg ccacgccatt gggttaagcc atgtggccgc tgcacactcc | 540 |
| atcatgcggc cgtactacca gggccgtg ggtgacccgc tgcgctacgg gctcccctac | 600 |
| gaggacaagg tgcgcgtctg gcagctgtac ggtgtgcggg agtctgtgtc tcccacggcg | 660 |
| cagcccgagg agcctcccct gctgccgag cccccagaca accggtccag cgccccgccc | 720 |
| aggaaggacg tgccccacag atgcagcact cactttgacg cggtggccca gatccggggt | 780 |
| gaagctttct tcttcaaagg caagtacttc tggcggctga cgcggaccg gcacctggtg | 840 |
| tccctgcagc cggcacagat gcaccgcttc tggcggggcc tgccgctgca cctggacagc | 900 |
| gtggacgccg tgtacgagcg caccagcgac cacaagatcg tcttctttaa aggagacagg | 960 |
| tactgggtgt tcaaggacaa taacgtagag gaaggatacc cgcgccccgt ctccgacttc | 1020 |
| agcctcccgc ctggcggcat cgacgctgcc ttctcctggg cccacaatga caggacttat | 1080 |
| ttctttaagg accagctgta ctggcgctac gatgaccaca cgaggcacat ggaccccggc | 1140 |
| taccccgccc agagccccct gtggagggt gtccccagca cgctggacga cgccatgcgc | 1200 |
| tggtccgacg gtgcctccta cttcttccgt ggccaggagt actggaaagt gctggatggc | 1260 |
| gagctggagg tggcacccgg gtacccacag tccacggccc gggactggct ggtgtgtgga | 1320 |
| gactcacagg ccgatggatc tgtggctgcg ggcgtggacg cggcagaggg gccccgcgcc | 1380 |
| cctccaggac aacatgacca gagccgctcg gaggacggtt acgaggtctg ctcatgcacc | 1440 |
| tctggggcat cctctccccc gggggcccca ggcccactgg tggctgccac catgctgctg | 1500 |
| ctgctgccgc cactgtcacc aggcgccctg tggacagcgg cccaggccct gacgctatga | 1560 |

<210> SEQ ID NO 107
<211> LENGTH: 1983
<212> TYPE: DNA
<213> ORGANISM: Homo sapiens
<300> PUBLICATION INFORMATION:
<302> TITLE: MMP2
<310> PATENT DOCUMENT NUMBER: NM004530

<400> SEQUENCE: 107

```
atggaggcgc taatggcccg gggcgcgctc acgggtcccc tgagggcgct ctgtctcctg      60
ggctgcctgc tgagccacgc cgccgccgcg ccgtcgccca tcatcaagtt ccccggcgat     120
gtcgccccca aaacggacaa agagttggca gtgcaatacc tgaacacctt ctatggctgc     180
cccaaggaga gctgcaacct gtttgtgctg aaggacacac taagaagat gcagaagttc     240
tttggactgc cccagacagg tgatcttgac cagaatacca tcgagaccat gcggaagcca     300
cgctgcggca acccagatgt ggccaactac aacttcttcc ctcgcaagcc caagtgggac     360
aagaaccaga tcacatacag gatcattggc tacacacctg atctggaccc agagacagtg     420
gatgatgcct ttgctcgtgc cttccaagtc tggagcgatg tgaccccact gcggttttct     480
cgaatccatg atggagaggc agacatcatg atcaactttg ccgctgggcga gcatggcgat     540
ggataccccc ttgacggtaa ggacggactc ctggctcatg ccttcgcccc aggcactggt     600
gttgggggag actcccattt tgatgacgat gagctatgga ccttgggaga aggccaagtg     660
gtccgtgtga agtatggcaa cgccgatggg gagtactgca gttccccctt cttgttcaat     720
ggcaaggagt acaacagctg cactgatact ggccgcagcg atggcttcct ctggtgctcc     780
accacctaca actttgagaa ggatggcaag tacggcttct gtcccccatga agccctgttc     840
accatgggcg gcaacgctga aggacagccc tgcaagtttc cattccgctt ccagggcaca     900
tcctatgaca gctgcaccac tgaggggcgc acggatggct accgctggtg cggcaccact     960
gaggactacg accgcgacaa gaagtatggc ttctgccctg agaccgccat gtccactgtt    1020
ggtgggaact cagaaggtgc ccctgtgtc ttccccttca ctttcctggg caacaaatat    1080
gagagctgca ccagcgccgg ccgcagtgac ggaaagatgt ggtgtgcgac cacagccaac    1140
tacgatgacg accgcaagtg gggcttctgc cctgaccaag ggtacagcct gttcctcgtg    1200
gcagcccacg agtttggcca cgccatgggg ctggagcact ccaagaccc tggggccctg    1260
atggcaccca tttacaccta caccaagaac ttccgtctgt cccaggatga catcaagggc    1320
attcaggagc tctatggggc ctctcctgac attgaccttg gcaccggccc cacccccaca    1380
ctgggccctg tcactcctga gatctgcaaa caggacattg tatttgatgg catcgctcag    1440
atccgtggtg agatcttctt cttcaaggac cggttcattt ggcggactgt gacgccacgt    1500
gacaagccca tggggccccct gctggtggcc acattctggc ctgagctccc ggaaaagatt    1560
gatgcggtat acgaggcccc acaggaggag aaggctgtgt ctctttgcagg gaatgaatac    1620
tggatctact cagccagcac cctggagcga gggtaccccca agccactgac cagcctggga    1680
ctgccccctg atgtccagcg agtggatgcc gcctttaact ggagcaaaaa caagaagaca    1740
tacatctttg ctggagacaa attctggaga tacaatgagg tgaagaagaa aatggatcct    1800
ggctttccca gctcatcgc agatgcctgg aatgccatcc ccgataacct ggatgccgtc    1860
gtggacctgc agggcggcgg tcacagctac ttcttcaagg gtgcctatta cctgaagctg    1920
gagaaccaaa gtctgaagag cgtgaagttt ggaagcatca aatccgactg gctaggctgc    1980
tga                                                                  1983

<210> SEQ ID NO 108
<211> LENGTH: 1434
<212> TYPE: DNA
<213> ORGANISM: Homo sapiens
<300> PUBLICATION INFORMATION:
<302> TITLE: MMP2
<310> PATENT DOCUMENT NUMBER: XM006271
<300> PUBLICATION INFORMATION:
<302> TITLE: MMP3
<310> PATENT DOCUMENT NUMBER: XM006271
```

-continued

<400> SEQUENCE: 108

```
atgaagagtc ttccaatcct actgttgctg tgcgtggcag tttgctcagc ctatccattg      60
gatggagctg caaggggtga ggacaccagc atgaaccttg ttcagaaata tctagaaaac     120
tactacgacc tcgaaaaaga tgtgaaacag tttgttagga gaaaggacag tggtcctgtt     180
gttaaaaaaa tccgagaaat gcagaagttc cttggattgg aggtgacggg gaagctggac     240
tccgacactc tggaggtgat gcgcaagccc aggtgtggag ttcctgacgt tggtcacttc     300
agaaccttc ctggcatccc gaagtggagg aaaacccacc ttacatacag gattgtgaat      360
tatacaccag atttgccaaa agatgctgtt gattctgctg ttgagaaagc tctgaaagtc     420
tgggaagagg tgactccact cacattctcc aggctgtatg aaggagaggc tgatataatg     480
atctctttg cagttagaga acatggagac ttttaccctt ttgatggacc tggaaatgtt      540
ttggcccatg cctatgcccc tgggccaggg attaatggag atgcccactt tgatgatgat     600
gaacaatgga caaggatac aacagggacc aatttatttc tcgttgctgc tcatgaaatt     660
ggccactccc tgggtctctt tcactcagcc aacactgaag ctttgatgta cccactctat     720
cactcactca cagacctgac tcggttccgc ctgtctcaag atgatataaa tggcattcag     780
tccctctatg gacctccccc tgactcccct gagaccccc tggtacccac ggaacctgtc     840
cctcagaac ctgggacgcc agccaactgt gatcctgctt tgtcctttga tgctgtcagc      900
actctgaggg gagaaatcct gatctttaaa gacaggcact tttggcgcaa atccctcagg     960
aagcttgaac tgaattgca tttgatctct tcattttggc catctcttcc ttcaggcgtg     1020
gatgccgcat atgaagttac tagcaaggac ctcgttttca tttttaaagg aaatcaattc     1080
tgggccatca gaggaaatga ggtacgagct ggatacccaa gaggcatcca caccctaggt     1140
ttccctccaa ccgtgaggaa aatcgatgca gccatttctg ataaggaaaa gaacaaaaca     1200
tatttctttg tagaggacaa atactggaga tttgatgaga agagaaattc catggagcca     1260
ggctttccca agcaaatagc tgaagacttt ccagggattg actcaaagat tgatgctgtt     1320
tttgaagaat ttgggttctt ttatttcttt actggatctt cacagttgga gtttgaccca     1380
aatgcaaaga aagtgacaca cactttgaag agtaacagct ggcttaattg ttga          1434
```

<210> SEQ ID NO 109
<211> LENGTH: 1404
<212> TYPE: DNA
<213> ORGANISM: Homo sapiens
<300> PUBLICATION INFORMATION:
<302> TITLE: MMP8
<310> PATENT DOCUMENT NUMBER: NM002424

<400> SEQUENCE: 109

```
atgttctccc tgaagacgct tccatttctg ctcttactcc atgtgcagat ttccaaggcc      60
tttcctgtat cttctaaaga gaaaaataca aaaactgttc aggactacct ggaaaagttc     120
taccaattac caagcaacca gtatcagtct acaaggaaga atggcactaa tgtgatcgtt     180
gaaaagctta agaaatgca gcgatttttt gggttgaatg tgacggggaa gccaaatgag     240
gaaactctgg acatgatgaa aaagcctcgc tgtggagtgc ctgacagtgg tggttttatg     300
ttaaccccag gaaccccaa gtgggaacgc actaacttga cctacaggat tcgaaactat     360
accccacagc tgtcagaggc tgaggtagaa agagctatca aggatgcctt gaactctgg      420
agtgttgcat cacctctcat cttcaccagg atctcacagg gagaggcaga tatcaacatt     480
gcttttacc aaaagagatca cggtgacaat tctccatttg atggaccaa tggaatcctg     540
gctcatgcct ttcagccagg ccaaggtatt ggaggagatg ctcattttga tgccgaagaa     600
```

```
acatggacca acacctccgc aaattacaac ttgtttcttg ttgctgctca tgaatttggc    660
cattctttgg ggctcgctca ctcctctgac cctggtgcct tgatgtatcc caactatgct    720
ttcagggaaa ccagcaacta ctcactccct caagatgaca tcgatggcat tcaggccatc    780
tatggacttt caagcaaccc tatccaacct actggaccaa gcacacccaa accctgtgac    840
cccagtttga catttgatgc tatcaccaca ctccgtggag aaatactttt ctttaaagac    900
aggtacttct ggagaaggca tcctcagcta caaagagtcg aaatgaattt tatttctcta    960
ttctggccat cccttccaac tggtatacag gctgcttatg aagatttga cagagacctc   1020 attttcctat ttaaaggcaa ccaatactgg gctctgagtg gctatgatat tctgcaaggt   1080
tatcccaagg atatcaaa ctatggcttc cccagcagcg tccaagcaat tgacgcagct   1140
gttttctaca gaagtaaaac atacttcttt gtaaatgacc aattctggag atatgataac   1200
caaagacaat tcatggagcc aggttatccc aaaagcatat caggtgcctt tccaggaata   1260
gagagtaaag ttgatgcagt ttttccagcaa gaacatttct tccatgtctt cagtggacca   1320
agatattacg catttgatct tattgctcag agagttacca gagttgcaag aggcaataaa   1380
tggcttaact gtagatatgg ctga                                          1404

<210> SEQ ID NO 110
<211> LENGTH: 2124
<212> TYPE: DNA
<213> ORGANISM: Homo sapiens
<300> PUBLICATION INFORMATION:
<302> TITLE: MMP9
<310> PATENT DOCUMENT NUMBER: XM009491

<400> SEQUENCE: 110
atgagcctct ggcagcccct ggtcctggtg ctcctggtgc tgggctgctg ctttgctgcc     60
cccagacagc gccagtccac ccttgtgctc ttccctggag acctgagaac caatctcacc    120
gacaggcagc tggcagagga atacctgtac cgctatggtt acactcgggt ggcagagatg    180
cgtggagagt cgaaatctct ggggcctgcg ctgctgcttc tccagaagca actgtccctg    240
cccgagaccg gtgagctgga tagcgccacg ctgaaggcca tgcgaacccc acggtgcggg    300
gtcccagacc tgggcagatt ccaaaccttt gagggcgacc tcaagtggca ccaccacaac    360
atcacctatt ggatccaaaa ctactcggaa gacttgccgc gggcggtgat tgacgacgcc    420
tttgcccgcg ccttcgcact gtggagcgcg gtgacgccgc tcaccttcac tcgcgtgtac    480
agccgggacg cagacatcgt catccagttt ggtgtcgcgg agcacggaga cgggtatccc    540
ttcgacggga aggacgggct cctggcacac gccttcctc ctggccccgg cattcaggga    600
gacgcccatt tcgacgatga cgagttgtgg tccctgggca agggcgtcgt ggttccaact    660
cggtttggaa acgcagatgg cgcggcctgc cacttcccct tcatcttcga gggccgctcc    720
tactctgcct gcaccaccga cggtcgctcc gacggcttgc cctggtgcag taccacggcc    780
aactacgaca ccgacgaccg gtttggcttc tgccccagcg agagactcta cacccaggac    840
ggcaatgctg atgggaaacc ctgccagttt ccattcatct tccaaggcca atcctactcc    900
gcctgcacca cggacggtcg ctccgacggc taccgctggt gcgccaccac cgccaactac    960
gaccgggaca gctcttcgg cttctgcccg acccgagctg actcgacggt gatgggggc   1020 aactcggcgg gggagctgtg cgtcttcccc ttcactttcc tgggtaagga gtactcgacc   1080
tgtaccagcg agggccgcgg agatgggcgc tctggtgcg ctaccacctc gaactttgac   1140
agcgacaaga agtggggctt ctgcccggac caaggataca gttgtcct cgtggcggcg   1200
```

-continued

| | |
|---|---|
| catgagttcg gccacgcgct gggcttagat cattcctcag tgccggaggc gctcatgtac | 1260 |
| cctatgtacc gcttcactga gggggcccccc ttgcataagg acgacgtgaa tggcatccgg | 1320 |
| cacctctatg gtcctcgccc tgaacctgag ccacggcctc aaccaccac cacaccgcag | 1380 |
| cccacggctc ccccgacggt ctgccccacc ggaccccca ctgtccaccc ctcagagcgc | 1440 |
| cccacagctg gccccacagg tccccctca gctggcccca caggtccccc cactgctggc | 1500 |
| ccttctacgg ccactactgt gccttttgagt ccggtggacg atgcctgcaa cgtgaacatc | 1560 |
| ttcgacgcca tcgcggagat tgggaaccag ctgtatttgt tcaaggatgg gaagtactgg | 1620 |
| cgattctctg agggcagggg gagccggccg cagggcccct tccttatcgc cgacaagtgg | 1680 |
| cccgcgctgc cccgcaagct ggactcggtc tttgaggagc ggctctccaa gaagcttttc | 1740 |
| ttcttctctg ggcgccaggt gtgggtgtac acaggcgcgt cggtgctggg cccgaggcgt | 1800 |
| ctggacaagc tgggcctggg agccgacgtg gcccaggtga ccggggccct ccggagtggc | 1860 |
| aggggggaaga tgctgctgtt cagcgggcgg cgcctctgga ggttcgacgt gaaggcgcag | 1920 |
| atggtggatc cccggagcgc cagcgaggtg gaccggatgt tccccggggt gcctttggac | 1980 |
| acgcacgacg tcttccagta ccgagagaaa gcctatttct gccaggaccg cttctactgg | 2040 |
| cgcgtgagtt cccggagtga gttgaaccag gtggaccaag tgggctacgt gacctatgac | 2100 |
| atcctgcagt gccctgagga ctag | 2124 |

<210> SEQ ID NO 111
<211> LENGTH: 2019
<212> TYPE: DNA
<213> ORGANISM: Homo sapiens
<300> PUBLICATION INFORMATION:
<302> TITLE: PKC alpha
<310> PATENT DOCUMENT NUMBER: NM002737

<400> SEQUENCE: 111

| | |
|---|---|
| atggctgacg ttttcccggg caacgactcc acggcgtctc aggacgtggc caaccgcttc | 60 |
| gcccgcaaag gggcgctgag gcagaagaac gtgcacgagg tgaaggacca caaattcatc | 120 |
| gcgcgcttct tcaagcagcc caccttctgc agccactgca ccgacttcat ctgggggttt | 180 |
| gggaaacaag gcttccagtg ccaagtttgc tgttttgtgg tccacaagag gtgccatgaa | 240 |
| tttgttactt tttcttgtcc gggtgcggat aagggacccg acactgatga ccccaggagc | 300 |
| aagcacaagt tcaaaatcca cacttacgga agccccacct tctgcgatca ctgtgggtca | 360 |
| ctgctctatg gacttatcca tcaagggatg aaatgtgaca cctgcgatat gaacgttcac | 420 |
| aagcaatgcg tcatcaatgt ccccagcctc tgcggaatgg atcacactga agagggggg | 480 |
| cggatttacc taaaggctga ggttgctgat gaaaagctcc atgtcacagt acgagatgca | 540 |
| aaaaatctaa tccctatgga tccaaacggg ctttcagatc cttatgtgaa gctgaaactt | 600 |
| attcctgatc caagaatgaa aagcaagcaa aaaccaaaa ccatccgctc cacactaaat | 660 |
| ccgcagtgga atgagtcctt tacattcaaa ttgaaacctt cagacaaaga ccgacgactg | 720 |
| tctgtagaaa tctgggactg ggatcgaaca acaaggaatg acttcatggg atccctttcc | 780 |
| tttggagttt cggagctgat gaagatgccg gccagtggat ggtacaagtt gcttaaccaa | 840 |
| gaagaaggtg agtactacaa cgtacccatt ccggaagggg acgaggaagg aaacatggaa | 900 |
| ctcaggcaga aattcgagaa agccaaactt ggccctgctg caacaaagt catcagtccc | 960 |
| tctgaagaca ggaaacaacc ttccaacaac cttgaccgag tgaaactcac ggacttcaat | 1020 |
| ttcctcatgg tgttgggaaa gggggagtttt ggaaggtga tgcttgccga caggaagggc | 1080 |
| acagaagaac tgtatgcaat caaaatcctg aagaaggatg tggtgattca ggatgatgac | 1140 |

```
gtggagtgca ccatggtaga aaagcgagtc ttggccctgc ttgacaaacc cccgttcttg    1200
acgcagctgc actcctgctt ccagacagtg gatcggctgt acttcgtcat ggaatatgtc    1260
aacggtgggg acctcatgta ccacattcag caagtaggaa aatttaagga accacaagca    1320
gtattctatg cggcagagat ttccatcgga ttgttctttc ttcataaaag aggaatcatt    1380
tatagggatc tgaagttaga taacgtcatg ttggattcag aaggacatat caaaattgct    1440
gactttggga tgtgcaagga acacatgatg gatgagtca cgaccaggac cttctgtggg    1500
actccagatt atatcgcccc agagataatc gcttatcagc cgtatggaaa atctgtggac    1560
tggtgggcct atggcgtcct gttgtatgaa atgcttgccg ggcagcctcc atttgatggt    1620
gaagatgaag acgagctatt tcagtctatc atggagcaca acgtttccta tccaaaatcc    1680
ttgtccaagg aggctgtttc tatctgcaaa ggactgatga ccaaacaccc agccaagcgg    1740
ctgggctgtg ggcctgaggg ggagagggac gtgagagagc atgccttctt ccggaggatc    1800
gactgggaaa actggagaa cagggagatc cagccaccat tcaagcccaa agtgtgtggc    1860
aaaggagcag agaactttga caagttcttc acacgaggac agcccgtctt aacaccacct    1920
gatcagctgg ttattgctaa catagaccag tctgattttg aagggttctc gtatgtcaac    1980
ccccagtttg tgcaccccat cttacagagt gcagtatga                          2019

<210> SEQ ID NO 112
<211> LENGTH: 2022
<212> TYPE: DNA
<213> ORGANISM: Homo sapiens
<300> PUBLICATION INFORMATION:
<302> TITLE: PKC beta
<310> PATENT DOCUMENT NUMBER: X07109

<400> SEQUENCE: 112
atggctgacc cggctgcggg gccgccgccg agcgagggcg aggagagcac cgtgcgcttc     60
gcccgcaaag gcgccctccg gcagaagaac gtgcatgagg tcaagaacca caaattcacc    120
gcccgcttct tcaagcagcc caccttctgc agccactgca ccgacttcat ctgggcttc     180 gggaagcagg gattccagtg ccaagtttgc tgctttgtgg tgcacaagcg gtgccatgaa    240
tttgtcacat tctcctgccc tggcgctgac aagggtccag cctccgatga ccccgcagc    300 aaacacaagt ttaagatcca cacgtactcc agccccacgt tttgtgacca ctgtgggtca    360
ctgctgtatg gactcatcca ccaggggatg aaatgtgaca cctgcatgat gaatgtgcac    420
aagcgctgcg tgatgaatgt cccagcctg tgtggcacgg accacacgga gcgccgcggc    480
cgcatctaca tccaggccca catcgacagg gacgtcctca ttgtcctcgt aagagatgct    540
aaaaaccttg tacctatgga ccccaatggc ctgtcagatc cctacgtaaa actgaaactg    600
attcccgatc ccaaaagtga gagcaaacag aagaccaaaa ccatcaaatg ctcctcaac    660 cctgagtgga atgagacatt tagatttcag ctgaaagaat cggacaaaga cagaagactg    720
tcagtagaga tttgggattg ggattgacc agcaggaatg acttcatggg atctttgtcc    780
tttgggattt ctgaacttca gaaggccagt gttgatggct ggtttaagtt actgagccag    840
gaggaaggcg agtacttcaa tgtgcctgtg ccaccagaag gaagtgaggc caatgaagaa    900
ctgcggcaga aatttgagag ggccaagatc agtcagggaa ccaaggtccc ggaagaaaag    960
acgaccaaca ctgtctccaa atttgacaac aatggcaaca gagaccggat gaaactgacc   1020
gattttaact tcctaatggt gctgggggaa ggcagctttg gcaaggtcat gcttttcagaa  1080 cgaaaaggca cagatgagct ctatgctgtg aagatcctga agaaggacgt tgtgatccaa   1140
```

| | |
|---|---|
| gatgatgacg tggagtgcac tatggtggag aagcgggtgt tggccctgcc tgggaagccg | 1200 |
| cccttcctga cccagctcca ctcctgcttc cagaccatgg accgcctgta ctttgtgatg | 1260 |
| gagtacgtga atggggcga cctcatgtat cacatccagc aagtcggccg gttcaaggag | 1320 |
| ccccatgctg tattttacgc tgcagaaatt gccatcggtc tgttcttctt acagagtaag | 1380 |
| ggcatcattt accgtgacct aaaacttgac aacgtgatgc tcgattctga gggacacatc | 1440 |
| aagattgccg attttggcat gtgtaaggaa acatctggg atggggtgac aaccaagaca | 1500 |
| ttctgtggca ctccagacta catcgccccc gagataattg cttatcagcc ctatgggaag | 1560 |
| tccgtggatt ggtgggcatt tggagtcctg ctgtatgaaa tgttggctgg gcaggcaccc | 1620 |
| tttgaagggg aggatgaaga tgaactcttc caatccatca tggaacacaa cgtagcctat | 1680 |
| cccaagtcta tgtccaagga agctgtggcc atctgcaaag gctgatgac aaacaccca | 1740 |
| ggcaaacgtc tgggttgtgg acctgaaggc gaacgtgata tcaaagagca tgcatttttc | 1800 |
| cggtatattg attgggagaa acttgaacgc aaagagatcc agcccccctta taagccaaaa | 1860 |
| gcttgtgggc gaaatgctga aaacttcgac cgattttca cccgccatcc accagtccta | 1920 |
| acacctcccg accaggaagt catcaggaat attgaccaat cagaattcga aggatttcc | 1980 |
| tttgttaact ctgaattttt aaaacccgaa gtcaagagct aa | 2022 |

<210> SEQ ID NO 113
<211> LENGTH: 2031
<212> TYPE: DNA
<213> ORGANISM: Homo sapiens
<300> PUBLICATION INFORMATION:
<302> TITLE: PKC delta
<310> PATENT DOCUMENT NUMBER: NM006254

<400> SEQUENCE: 113

| | |
|---|---|
| atggcgccgt tcctgcgcat cgccttcaac tcctatgagc tgggctccct gcaggccgag | 60 |
| gacgaggcga accagccctt ctgtgccgtg aagatgaagg aggcgctcag cacagagcgt | 120 |
| gggaaaacac tggtgcagaa aagccgacc atgtatcctg agtggaagtc gacgttcgat | 180 |
| gcccacatct atgaggggcg cgtcatccag attgtgctaa tgcgggcagc agaggagcca | 240 |
| gtgtctgagg tgaccgtggg tgtgtcggtg ctggccgagc gctgcaagaa gaacaatggc | 300 |
| aaggctgagt tctggctgga cctgcagcct caggccaagg tgttgatgtc tgttcagtat | 360 |
| ttcctggagg acgtggattg caaacaatct atgcgcagtg aggacgaggc caagttccca | 420 |
| acgatgaacc gccgcggagc catcaaacag gccaaaatcc actacatcaa gaaccatgag | 480 |
| tttatcgcca ccttctttgg gcaacccacc ttctgttctg tgtgcaaaga ctttgtctgg | 540 |
| ggcctcaaca gcaaggcta caatgcagg caatgtaacg ctgccatcca aagaaatgc | 600 |
| atcgacaaga tcatcggcag atgcactggc accgcggcca cagccgggga cactatattc | 660 |
| cagaaagaac gcttcaacat cgacatgccg caccgcttca aggttcacaa ctacatgagc | 720 |
| cccaccttct gtgaccactg cggcagcctg ctctggggac tggtgaagca gggattaaag | 780 |
| tgtgaagact gcggcatgaa tgtgcaccat aaatgccggg agaaggtggc caacctctgc | 840 |
| ggcatcaacc agaagctttt ggctgaggcc ttgaaccaag tcacccagag agcctcccgg | 900 |
| agatcagact cagcctcctc agagcctgtt gggatatatc agggtttcga agaagacc | 960 |
| ggagttgctg gggaggacat gcaagacaac agtgggacct acggcaagat ctgggagggc | 1020 |
| agcagccaagt gcaacatcaa caacttcatc ttccacaagg tcctgggcaa aggcagcttc | 1080 |
| gggaaggtgt gcttggagag ctgaaggggc agaggagagt actctgccat caaggccctc | 1140 |
| aagaaggatg tggtcctgat cgacgacgac gtggagtgca ccatggttga aagcgggtg | 1200 |

```
ctgacacttg ccgcagagaa tccctttctc acccacctca tctgcacctt ccagaccaag    1260
gaccacctgt tctttgtgat ggagttcctc aacgggggg acctgatgta ccacatccag     1320
gacaaaggcc gctttgaact ctaccgtgcc acgttttatg ccgctgagat aatgtgtgga    1380
ctgcagtttc tacacagcaa gggcatcatt tacagggacc tcaaactgga caatgtgctg    1440
ttggaccggg atggccacat caagattgcc gactttggga tgtgcaaaga gaacatattc    1500
ggggagagcc gggccagcac cttctgcggc acccctgact atatcgcccc tgagatccta    1560
cagggcctga agtacacatt ctctgtggac tggtggtctt tcgggtcct tctgtacgag     1620 atgctcattg ccagtcccc cttccatggt gatgatgagg atgaactctt cgagtccatc     1680
cgtgtggaca cgccacatta tccccgctgg atcaccaagg agtccaagga catcctggag    1740
aagctctttg aagggaacc aaccaagagg ctgggaatga cggaaacat caaaatccac      1800 cccttcttca agaccataaa ctggactctg ctggaaaagc ggaggttgga gccacccttc    1860
aggcccaaag tgaagtcacc cagagactac agtaactttg accaggagtt cctgaacgag    1920
aaggcgcgcc tctcctacag cgacaagaac ctcatcgact ccatggacca gtctgcattc    1980
gctggcttct cctttgtgaa ccccaaattc gagcacctcc tggaagattg a            2031
```

<210> SEQ ID NO 114
<211> LENGTH: 2049
<212> TYPE: DNA
<213> ORGANISM: Homo sapiens
<300> PUBLICATION INFORMATION:
<302> TITLE: PKC eta
<310> PATENT DOCUMENT NUMBER: NM006255

<400> SEQUENCE: 114

```
atgtcgtctg gcaccatgaa gttcaatggc tatttgaggg tccgcatcgg tgaggcagtg     60
gggctgcagc ccacccgctg gtccctgcgc cactcgctct tcaagaaggg ccaccagctg    120
ctggacccct atctgacggt gagcgtggac caggtgcgcg tgggccagac cagcaccaag    180
cagaagacca acaaacccac gtacaacgag gagttttgcg ctaacgtcac cgacggcggc    240
cacctcgagt tggccgtctt ccacgagacc ccctgggct acgacttcgt ggccaactgc     300
accctgcagt tccaggagct cgtcggcacg accggcgcct cggacacctt cgagggttgg    360
gtggatctcg agccagaggg gaaagtattt gtggtaataa cccttaccgg gagtttcact    420
gaagctactc tccagagaga ccggatcttc aaacatttta ccaggaagcg ccaaagggct    480
atgcgaaggc gagtccacca gatcaatgga cacaagttca tggccacgta tctgaggcag    540
cccacctact gctctcactg cagggagttt atctggggag tgtttgggaa cagggttat    600 cagtgccaag tgtgcacctg tgtcgtccat aaacgctgcc atcatctaat gttacagcc    660 tgtacttgcc aaaacaatat taacaaagtg gattcaaaga ttgcagaaca gaggttcggg    720
atcaacatcc cacacaagtt cagcatccac aactacaaag tgccaacatt ctgcgatcac    780
tgtggctcac tgctctgggg aataatgcga caaggacttc agtgtaaaat atgtaaaatg    840
aatgtgcata ttcgatgtca agcgaacgtg gcccctaact gtggggtaaa tgcggtggaa    900
cttgccaaga ccctggcagg gatgggtctc caacccggaa atatttctcc aacctcgaaa    960 ctcgttttcca gatcgaccct aagacgacag ggaaaggaga gcagcaaaga aggaaatggg   1020
attggggtta attcttccaa ccgacttggt atcgacaact ttgagttcat ccgagtgttg   1080
gggaagggga gttttgggaa ggtgatgctt gcaagagtaa agaaacagg agacctctat   1140 gctgtgaagg tgctgaagaa ggacgtgatt ctgctggatg atgatgtgga atgcaccatg    1200
```

-continued

```
accgagaaaa ggatcctgtc tctggcccgc aatcacccct tcctcactca gttgttctgc    1260
tgctttcaga cccccgatcg tctgtttttt gtgatggagt ttgtgaatgg gggtgacttg    1320
atgttccaca ttcagaagtc tcgtcgtttt gatgaagcac gagctcgctt ctatgctgca    1380
gaaatcattt cggctctcat gttcctccat gataaaggaa tcatctatag agatctgaaa    1440
ctggacaatg tcctgttgga ccacgagggt cactgtaaac tggcagactt cggaatgtgc    1500
aaggagggga tttgcaatgg tgtcaccacg gccacattct gtggcacgcc agactatatc    1560
gctccagaga tcctccagga aatgctgtac gggcctgcag tagactggtg ggcaatgggc    1620
gtgttgctct atgagatgct ctgtggtcac gcgcctttg aggcagagaa tgaagatgac    1680
ctctttgagg ccatactgaa tgatgaggtg gtctacccta cctggctcca tgaagatgcc    1740
acagggatcc taaaatcttt catgaccaag aaccccacca tgcgcttggg cagcctgact    1800
cagggaggcg agcacgccat cttgagacat cctttttta aggaaatcga ctgggcccag    1860
ctgaaccatc gccaaataga accgcctttc agacccagaa tcaaatcccg agaagatgtc    1920
agtaattttg accctgactt cataaaggaa gagccagttt taactccaat tgatgaggga    1980
catcttccaa tgattaacca ggatgagttt agaaactttt cctatgtgtc tccagaattg    2040
caaccatag                                                            2049
```

<210> SEQ ID NO 115
<211> LENGTH: 948
<212> TYPE: DNA
<213> ORGANISM: Homo sapiens
<300> PUBLICATION INFORMATION:
<302> TITLE: PKC epsilon
<310> PATENT DOCUMENT NUMBER: XM002370

<400> SEQUENCE: 115

```
atgttggcag aactcaaggg caaagatgaa gtatatgctg tgaaggtctt aaagaaggac     60
gtcatccttc aggatgatga cgtggactgc acaatgacag agaagaggat tttggctctg    120
gcacggaaac acccgtacct tacccaactc tactgctgct ccagaccaa ggaccgcctc    180 tttttcgtca tggaatatgt aaatggtgga gacctcatgt ttcagattca gcgctcccga    240
aaattcgacg agcctcgttc acggttctat gctgcagagg tcacatcggc cctcatgttc    300
ctccaccagc atggagtcat ctacagggat ttgaaactgg acaacatcct tctggatgca    360
gaaggtcact gcaagctggc tgacttcggg atgtgcaagg aagggattct gaatggtgtg    420
acgaccacca cgttctgtgg gactcctgac tacatagctc ctgagatcct gcaggagttg    480
gagtatggcc cctccgtgga ctggtgggcc ctggggtgc tgatgtacga gatgatggct    540
ggacagcctc cctttgaggc cgacaatgag gacgacctat ttgagtccat cctccatgac    600
gacgtgctgt acccagtctg gctcagcaag gaggctgtca gcatcttgaa agctttcatg    660
acgaagaatc cccacaagcg cctgggctgt gtggcatcgc agaatggcga ggacgccatc    720
aagcagcacc cattcttcaa agagattgac tgggtgctcc tggagcagaa agagatcaag    780
ccacccttca aaccacgcat taaaccaaaa gagacgtca ataattttga ccaagacttt    840
acccgggaag agccggtact cacccttgtg gacgaagcaa ttgtaaagca gatcaaccag    900
gaggaattca aggtttctc ctactttggt gaagacctga tgccctga                 948
```

<210> SEQ ID NO 116
<211> LENGTH: 1764
<212> TYPE: DNA
<213> ORGANISM: Homo sapiens
<300> PUBLICATION INFORMATION:
<302> TITLE: PKC iota -continued

<310> PATENT DOCUMENT NUMBER: NM002740

<400> SEQUENCE: 116

| | |
|---|---|
| atgtcccaca cggtcgcagg cggcggcagc ggggaccatt cccaccaggt ccgggtgaaa | 60 |
| gcctactacc gcggggatat catgataaca cattttgaac cttccatctc ctttgagggc | 120 |
| ctttgcaatg aggttcgaga catgtgttct tttgacaacg aacagctctt caccatgaaa | 180 |
| tggatagatg aggaaggaga cccgtgtaca gtatcatctc agttggagtt agaagaagcc | 240 |
| tttagacttt atgagctaaa caaggattct gaactcttga ttcatgtgtt cccttgtgta | 300 |
| ccagaacgtc ctgggatgcc ttgtccagga gaagataaat ccatctaccg tagaggtgca | 360 |
| cgccgctgga gaaagcttta ttgtgccaat ggccacactt tccaagccaa gcgtttcaac | 420 |
| aggcgtgctc actgtgccat ctgcacagac cgaatatggg gacttggacg ccaaggatat | 480 |
| aagtgcatca actgcaaact cttggttcat aagaagtgcc ataaactcgt cacaattgaa | 540 |
| tgtgggcggc attcttttgcc acaggaacca gtgatgccca tggatcagtc atccatgcat | 600 |
| tctgaccatg cacagacagt aattccatat aatccttcaa gtcatgagag tttggatcaa | 660 |
| gttggtgaag aaaagaggc aatgaacacc agggaaagtg gcaaagcttc atccagtcta | 720 |
| ggtcttcagg attttgattt gctccgggta ataggaagag gaagttatgc caaagtactg | 780 |
| ttggttcgat taaaaaaaac agatcgtatt tatgcaatga agttgtgaa aaaagagctt | 840 |
| gttaatgatg atgaggatat tgattgggta cagacagaga agcatgtgtt tgagcaggca | 900 |
| tccaatcatc cttccttgt tgggctgcat tcttgctttc agacagaaag cagattgttc | 960 |
| tttgttatag agtatgtaaa tggaggagac ctaatgtttc atatgcagcg acaaagaaaa | 1020 |
| cttcctgaag aacatgccag attttactct gcagaaatca gtctagcatt aaattatctt | 1080 |
| catgagcgag ggataattta tagagatttg aaactggaca atgtattact ggactctgaa | 1140 |
| ggccacatta aactcactga ctacggcatg tgtaaggaag gattacgcc aggagataca | 1200 |
| accagcactt tctgtggtac tcctaattac attgctcctg aaattttaag aggagaagat | 1260 |
| tatggtttca gtgttgactg gtgggctctt ggagtgctca tgtttgagat gatggcagga | 1320 |
| aggtctccat tgatattgt tgggagctcc gataaccctg accagaacac agaggattat | 1380 |
| ctcttccaag ttatttgga aaaacaaatt cgcataccac gttctctgtc tgtaaaagct | 1440 |
| gcaagtgttc tgaagagttt tcttaataag gaccctaagg aacgattggg ttgtcatcct | 1500 |
| caaacaggat ttgctgatat tcagggacac ccgttcttcc gaaatgttga ttgggatatg | 1560 |
| atggagcaaa acaggtggt acctcccttt aaaccaaata tttctgggga atttggtttg | 1620 |
| gacaactttg attctcagtt tactaatgaa cctgtccagc tcactccaga tgacgatgac | 1680 |
| attgtgagga agattgatca gtctgaattt gaaggttttg agtatatcaa tcctcttttg | 1740 |
| atgtctgcag aagaatgtgt ctga | 1764 |

<210> SEQ ID NO 117
<211> LENGTH: 2451
<212> TYPE: DNA
<213> ORGANISM: Homo sapiens
<300> PUBLICATION INFORMATION:
<302> TITLE: PKC mu
<310> PATENT DOCUMENT NUMBER: XM007234

<400> SEQUENCE: 117

| | |
|---|---|
| atgtatgata agatcctgct ttttcgccat gaccctacct ctgaaaacat ccttcagctg | 60 |
| gtgaaagcgg ccagtgatat ccaggaaggc gatcttatta agtggtctt gtcagcttcc | 120 |
| gccacctttg aagactttca gattcgtccc cacgctctct ttgttcattc atacagagct | 180 |

```
ccagctttct gtgatcactg tggagaaatg ctgtggggc tggtacgtca aggtcttaaa    240
tgtgaagggt gtggtctgaa ttaccataag agatgtgcat ttaaaatacc caacaattgc   300
agcggtgtga ggcggagaag gctctcaaac gtttccctca ctggggtcag caccatccgc   360
acatcatctg ctgaactctc tacaagtgcc cctgatgagc cccttctgca aaaatcacca   420
tcagagtcgt ttattggtcg agagaagagg tcaaattctc aatcatacat tggacgacca   480
attcaccttg acaagatttt gatgtctaaa gttaaagtgc cgcacacatt tgtcatccac   540
tcctacaccc ggcccacagt gtgccagtac tgcaagaagc ttctgaaggg cttttcagg    600 cagggcttgc agtgcaaaga ttgcagattc aactgccata acgttgtgc accgaaagta    660 ccaaacaact gccttggcga agtgaccatt aatggagatt tgcttagccc tggggcagag    720
tctgatgtgg tcatggaaga aggagtgat gacaatgata gtgaaaggaa cagtgggctc     780
atggatgata tggaagaagc aatggtccaa gatgcagaga tggcaatggc agagtgccag    840
aacgacagtg gcgagatgca agatccagac ccagaccacg aggacgccaa cagaaccatc    900
agtccatcaa caagcaacaa tatcccactc atgagggtag tgcagtctgt caaacacacg    960
aagaggaaaa gcagcacagt catgaaagaa ggatggatgg tccactacac cagcaaggac   1020
acgctgcgga acggcacta ttggagattg atagcaaat gtattaccct ctttcagaat     1080
gacacaggaa gcaggtacta caaggaaatt cctttatctg aaattttgtc tctggaacca   1140
gtaaaaactt cagctttaat tcctaatggg gccaatcctc attgtttcga aatcactacg   1200
gcaaatgtag tgtattatgt gggagaaaat gtggtcaatc cttccagccc atcaccaaat   1260
aacagtgttc tcaccagtgg cgttggtgca gatgtggcca ggatgtggga gatagccatc   1320
cagcatgccc ttatgcccgt cattcccaag ggctcctccg tgggtacagg aaccaacttg   1380
cacagagata tctctgtgag tatttcagta tcaaattgcc agattcaaga aaatgtggac   1440
atcagcacag tatatcagat ttttcctgat gaagtactgg gttctggaca gtttggaatt   1500
gtttatggag aaaacatcg taaaacagga agagatgtag ctattaaaat cattgacaaa   1560
ttacgatttc caacaaaaca agaaagccag cttcgtaatg aggttgcaat tctacagaac   1620
cttcatcacc ctggtgttgt aaatttggag tgtatgtttg agacgcctga aagagtgttt   1680
gttgttatgg aaaaactcca tggagacatg ctggaaatga tcttgtcaag tgaaaagggc   1740
aggttgccag agcacataac gaagttttta attactcaga tactcgtggc tttgcggcac   1800
cttcatttta aaaatatcgt tcactgtgac ctcaaaccag aaaatgtgtt gctagcctca   1860
gctgatcctt ttcctcaggt gaaactttgt gattttggtt ttgcccggat cattggagag   1920
aagtctttcc ggaggtcagt ggtgggtacc cccgcttacc tggctcctga ggtcctaagg   1980
aacaagggct acaatcgctc tctagacatg tggtctgttg gggtcatcat ctatgtaagc   2040
ctaagcggca cattcccatt taatgaagat gaagacatac acgaccaaat tcagaatgca   2100
gctttcatgt atccaccaaa tccctggaag gaaatatctc atgaagccat tgatcttatc   2160
aacaatttgc tgcaagtaaa aatgagaaag cgctacagtg tggataagac cttgagccac   2220
ccttggctac aggactatca gacctggtta gatttgcgag agctggaatg caaaatcggg   2280
gagcgctaca tcacccatga aagtgatgac ctgaggtggg agaagtatgc aggcgagcag   2340
gggctgcagt accccacaca cctgatcaat ccaagtgcta gccacagtga cactcctgag   2400
actgaagaaa cagaaatgaa agccctcggt gagcgtgtca gcatcctatg a            2451
```

<210> SEQ ID NO 118
<211> LENGTH: 2673

```
<212> TYPE: DNA
<213> ORGANISM: Homo sapiens
<300> PUBLICATION INFORMATION:
<302> TITLE: PKC nu
<310> PATENT DOCUMENT NUMBER: NM005813

<400> SEQUENCE: 118
```

| | | | | | |
|---|---|---|---|---|---|
| atgtctgcaa | ataattcccc | tccatcagcc | cagaagtctg | tattacccac | agctattcct | 60 |
| gctgtgcttc | cagctgcttc | tccgtgttca | agtcctaaga | cgggactctc | tgcccgactc | 120 |
| tctaatggaa | gcttcagtgc | accatcactc | accaactcca | gaggctcagt | gcatacagtt | 180 |
| tcatttctac | tgcaaattgg | cctcacacg | gagagtgtta | ccattgaagc | ccaggaactg | 240 |
| tctttatctg | ctgtcaagga | tcttgtgtgc | tccatagttt | atcaaaagtt | tccagagtgt | 300 |
| ggattctttg | gcatgtatga | caaaattctt | ctctttcgcc | atgacatgaa | ctcagaaaac | 360 |
| attttgcagc | tgattacctc | agcagatgaa | atacatgaag | gagacctagt | ggaagtggtt | 420 |
| ctttcagctt | tagccacagt | agaagacttc | cagattcgtc | cacatactct | ctatgtacat | 480 |
| tcttacaaag | ctcctacttt | ctgtgattac | tgtggtgaga | tgctgtgggg | attggtacgt | 540 |
| caaggactga | aatgtgaagg | ctgtggatta | aattaccata | acgatgtgc | cttcaagatt | 600 |
| ccaaataact | gtagtggagt | aagaaagaga | cgtctgtcaa | atgtatcttt | accaggaccc | 660 |
| ggcctctcag | ttccaagacc | cctacagcct | gaatatgtag | cccttcccag | tgaagagtca | 720 |
| catgtccacc | aggaaccaag | taagagaatt | ccttcttgga | gtggtcgccc | aatctggatg | 780 |
| gaaaagatgg | taatgtgcag | agtgaaagtt | ccacacacat | ttgctgttca | ctcttacacc | 840 |
| cgtcccacga | tatgtcagta | ctgcaagcgg | ttactgaaag | gcctcttcg | ccaaggaatg | 900 |
| cagtgtaaag | attgcaaatt | caactgccat | aaacgctgtg | catcaaaagt | accaagagac | 960 |
| tgccttggag | aggttacttt | caatggagaa | ccttccagtc | tgggaacaga | tacagatata | 1020 |
| ccaatggata | ttgacaataa | tgacataaat | agtgatagta | gtcggggttt | ggatgacaca | 1080 |
| gaagagccat | caccccaga | agataagatg | ttcttcttgg | atccatctga | tctcgatgtg | 1140 |
| gaaagagatg | aagaagccgt | taaaacaatc | agtccatcaa | caagcaataa | tattccgcta | 1200 |
| atgaggggttg | tacaatccat | caagcacaca | aagaggaaga | gcagcacaat | ggtgaaggaa | 1260 |
| gggtggatgg | tccattacac | cagcagggat | aacctgagaa | agaggcatta | ttggagactt | 1320 |
| gacagcaaat | gtctaacatt | atttcagaat | gaatctggat | caaagtatta | taggaaaatt | 1380 |
| ccactttcag | aaattctccg | catatcttca | ccacgagatt | tcacaaacat | ttcacaaggc | 1440 |
| agcaatccac | actgttttga | aatcattact | gatactatgg | tatacttcgt | tggtgagaac | 1500 |
| aatggggaca | gctctcataa | tcctgttctt | gctgccactg | gagttggact | tgatgtagca | 1560 |
| cagagctggg | aaaaagcaat | tcgccaagcc | ctcatgcctg | ttactcctca | agcaagtgtt | 1620 |
| tgcacttctc | cagggcaagg | gaaagatcac | aaagatttgt | ctacaagtat | ctctgtatct | 1680 |
| aattgtcaga | ttcaggagaa | tgtggatatc | agtactgttt | accagatctt | tgcagatgag | 1740 |
| gtgcttggtt | caggccagtt | tggcatcgtt | tatggaggaa | acatagaaa | gactgggagg | 1800 |
| gatgtggcta | ttaaagtaat | tgataagatg | agattcccca | caaaacaaga | aagtcaactc | 1860 |
| cgtaatgaag | tggctatttt | acagaatttg | caccatcctg | ggattgtaaa | cctggaatgt | 1920 |
| atgtttgaaa | ccccagaacg | agtctttgta | gtaatggaaa | agctgcatgg | agatatgttg | 1980 |
| gaaatgattc | tatccagtga | aaaagtcgg | cttccagaac | gaattactaa | attcatggtc | 2040 |
| acacagatac | ttgttgcttt | gaggaatctg | cattttaaga | atattgtgca | ctgtgattta | 2100 |
| aagccagaaa | atgtgctgct | tgcatcagca | gagccatttc | ctcaggtgaa | gctgtgtgac | 2160 |

-continued

| | |
|---|---|
| tttggatttg cacgcatcat tggtgaaaag tcattcagga gatctgtggt aggaactcca | 2220 |
| gcatacttag cccctgaagt tctccggagc aaaggttaca accgttccct agatatgtgg | 2280 |
| tcagtgggag ttatcatcta tgtgagcctc agtggcacat ttccttttaa tgaggatgaa | 2340 |
| gatataaatg accaaatcca aaatgctgca tttatgtacc caccaaatcc atggagagaa | 2400 |
| atttctggtg aagcaattga tctgataaac aatctgcttc aagtgaagat gagaaaacgt | 2460 |
| tacagtgttg acaaatctct tagtcatccc tggctacagg actatcagac ttggcttgac | 2520 |
| cttagagaat ttgaaactcg cattggagaa cgttacatta cacatgaaag tgatgatgct | 2580 |
| cgctgggaaa tacatgcata cacacataac cttgtatacc caaagcactt cattatggct | 2640 |
| cctaatccag atgatatgga agaagatcct taa | 2673 |

<210> SEQ ID NO 119
<211> LENGTH: 2121
<212> TYPE: DNA
<213> ORGANISM: Homo sapiens
<300> PUBLICATION INFORMATION:
<302> TITLE: PKC tau
<310> PATENT DOCUMENT NUMBER: NM006257

<400> SEQUENCE: 119

| | |
|---|---|
| atgtcgccat tcttcggat tggcttgtcc aactttgact gcgggtcctg ccagtcttgt | 60 |
| cagggcgagg ctgttaaccc ttactgtgct gtgctcgtca agagtatgt cgaatcagag | 120 |
| aacgggcaga tgtatatcca gaaaaagcct accatgtacc caccctggga cagcactttt | 180 |
| gatgcccata tcaacaaggg aagagtcatg cagatcattg tgaaaggcaa aaacgtggac | 240 |
| ctcatctctg aaaccaccgt ggagctctac tcgctggctg agaggtgcag gaagaacaac | 300 |
| gggaagacag aaatatggtt agagctgaaa cctcaaggcc gaatgctaat gaatgcaaga | 360 |
| tactttctgg aaatgagtga cacaaaggac atgaatgaat ttgagacgga aggcttcttt | 420 |
| gctttgcatc agcgccgggg tgccatcaag caggcaaagg tccaccacgt caagtgccac | 480 |
| gagttcactg ccaccttctt cccacagccc acattttgct ctgtctgcca cgagtttgtc | 540 |
| tggggcctga caaacagggg ctaccagtgc cgacaatgca atgcagcaat tcacaagaag | 600 |
| tgtattgata agttatagc aaagtgcaca ggatcagcta tcaatagccg agaaaccatg | 660 |
| ttccacaagg agagattcaa aattgacatg ccacacagat ttaaagtcta caattacaag | 720 |
| agcccgacct tctgtgaaca ctgtgggacc ctgctgtggg gactggcacg gcaaggactc | 780 |
| aagtgtgatg catgtggcat gaatgtgcat catagatgcc agacaaaggt ggccaacctt | 840 |
| tgtggcataa accagaagct aatggctgaa gcgctggcca tgattgagag cactcaacag | 900 |
| gctcgctgct taagagatac tgaacagatc ttcagagaag tccggttga aattggtctc | 960 |
| ccatgctcca tcaaaaatga agcaaggccg ccatgtttac cgacaccggg aaaaagagag | 1020 |
| cctcagggca tttcctggga gtctccgttg gatgaggtgg ataaaatgtg ccatcttcca | 1080 |
| gaacctgaac tgaacaaaga aagaccatct ctgcagatta aactaaaaat tgaggatttt | 1140 |
| atcttgcaca aaatgttggg gaaggaagt tttggcaagg tcttcctggc agaattcaag | 1200 |
| aaaaccaatc aattttttcgc aataaaggcc ttaagaaag atgtggtctt gatggacgat | 1260 |
| gatgttgagt gcacgatggt agagaagaga gttcttttcct tggcctggga gcatccgttt | 1320 |
| ctgacgcaca tgttttgtac attccagacc aaggaaaacc tctttttttgt gatggagtac | 1380 |
| ctcaacggag gggacttaat gtaccacatc aaagctgcc acaagttcga cctttccaga | 1440 |
| gcgacgtttt atgctgctga aatcattctt ggtctgcagt tccttcattc caaaggaata | 1500 |
| gtctacaggg acctgaagct agataacatc ctgttagaca agatggaca tatcaagatc | 1560 |

```
gcggattttg gaatgtgcaa ggagaacatg ttaggagatg ccaagacgaa taccttctgt    1620
gggacacctg actacatcgc cccagagatc ttgctgggtc agaaatacaa ccactctgtg    1680
gactggtggt ccttcggggt tctcctttat gaaatgctga ttggtcagtc gcctttccac    1740
gggcaggatg aggaggagct cttccactcc atccgcatgg acaatccctt ttacccacgg    1800
tggctgagaa aggaagcaaa ggaccttctg gtgaagctct tcgtgcgaga acctgagaag    1860
aggctgggcg tgagggagaa catccgccag caccctttgt ttcgggagat caactgggag    1920
gaacttgaac ggaaggagat tgacccaccg ttccggccga agtgaaatc accatttgac     1980 tgcagcaatt tcgacaaaga attcttaaac gagaagcccc ggctgtcatt tgccgacaga    2040
gcactgatca acagcatgga ccagaatatg ttcaggaact tttccttcat gaaccccggg    2100
atggagcggc tgatatcctg a                                              2121
```

<210> SEQ ID NO 120
<211> LENGTH: 1779
<212> TYPE: DNA
<213> ORGANISM: Homo sapiens
<300> PUBLICATION INFORMATION:
<302> TITLE: PKC zeta
<310> PATENT DOCUMENT NUMBER: NM2744

<400> SEQUENCE: 120

```
atgcccagca ggaccgaccc caagatggaa gggagcggcg gccgcgtccg cctcaaggcg      60
cattacgggg gggacatctt catcaccagc gtggacgccg ccgcgaccct tcgaggagctc    120 tgtgaggaag tgagagacat gtgtcgtctg caccagcagc acccgctcac cctcaagtgg    180
gtggacagcg aaggtgaccc ttgcacggtg tcctcccaga tggagctgga agaggctttc    240
cgcctggccc gtcagtgcag ggatgaaggc ctcatcattc atgttttccc gagcaccccct   300 gagcagcctg gctgccatg tccgggagaa gacaaatcta tctaccgccg ggagccaga     360 agatggagga agctgtaccg tgccaacggc cacctcttcc aagccaagcg ctttaacagg    420
agagcgtact gcggtcagtg cagcgagagg atatggggcc tcgcgaggca aggctacagg    480
tgcatcaact gcaaactgct ggtccataag cgctgccacg gcctcgtccc gctgacctgc    540
aggaagcata tggattctgt catgccttcc aagagcctc cagtagacga caagaacgag    600
gacgccgacc ttccttccga ggagacagat ggaattgctt acatttcctc atcccggaag    660
catgacagca ttaagacgaa ctcggaggac cttaagccag ttatcgatgg gatggatgga    720
atcaaaatct ctcaggggct ggggctgcag gactttgacc taatcagagt catcgggcgc    780
gggagctacg ccaaggttct cctggtgcgg ttgaagaaga tgaccaaaat ttacgccatg    840
aaagtggtga gaaagagct ggtgcatgat gacgaggata ttgactgggt acagacagag    900
aagcacgtgt ttgagcaggc atccagcaac cccttcctgg tcggattaca ctcctgcttc    960
cagacgacaa gtcggttgtt cctggtcatt gagtacgtca acggcgggga cctgatgttc   1020
cacatgcaga ggcagaggaa gctccctgag gagcacgcca ggttctacgc ggccgagatc   1080
tgcatcgccc tcaacttcct gcacgagagg gggatcatct acaggacct gaagctggac   1140 aacgtcctcc tggatgcgga cgggcacatc aagctcacag actacggcat gtgcaaggaa   1200
ggcctgggcc ctggtgacac aacgagcact ttctgcggaa ccccgaatta catcgcccc     1260 gaaatcctgc ggggagagga gtacgggttc agcgtggact ggtgggcgct gggagtcctc   1320
atgtttgaga tgatggccgg gcgctccccg ttcgacatca tcaccgacaa cccggacatg   1380
aacacagagg actaccttt ccaagtgatc ctggagaagc ccatccggat cccccggttc   1440
```

-continued

| | |
|---|---|
| ctgtccgtca aagcctccca tgttttaaaa ggattttaa ataaggaccc caaagagagg | 1500 |
| ctcggctgcc ggccacagac tggattttct gacatcaagt cccacgcgtt cttccgcagc | 1560 |
| atagactggg acttgctgga gaagaagcag gcgctccctc cattccagcc acagatcaca | 1620 |
| gacgactacg tctggacaa ctttgacaca cagttcacca gcgagcccgt gcagctgacc | 1680 |
| ccagacgatg aggatgccat aaagaggatc gaccagtcag agttcgaagg ctttgagtat | 1740 |
| atcaacccat tattgctgtc caccgaggag tcggtgtga | 1779 |

<210> SEQ ID NO 121
<211> LENGTH: 576
<212> TYPE: DNA
<213> ORGANISM: Homo sapiens
<300> PUBLICATION INFORMATION:
<302> TITLE: VEGF
<310> PATENT DOCUMENT NUMBER: NM003376

<400> SEQUENCE: 121

| | |
|---|---|
| atgaactttc tgctgtcttg ggtgcattgg agccttgcct tgctgctcta cctccaccat | 60 |
| gccaagtggt cccaggctgc acccatggca gaaggaggag ggcagaatca tcacgaagtg | 120 |
| gtgaagttca tggatgtcta tcagcgcagc tactgccatc caatcgagac cctggtggac | 180 |
| atcttccagg agtaccctga tgagatcgag tacatcttca agccatcctg tgtgcccctg | 240 |
| atgcgatgcg ggggctgctg caatgacgag ggcctggagt gtgtgcccac tgaggagtcc | 300 |
| aacatcacca tgcagattat gcggatcaaa cctcaccaag gccagcacat aggagagatg | 360 |
| agcttcctac agcacaacaa atgtgaatgc agaccaaaga agatagagc aagacaagaa | 420 |
| aatccctgtg ggccttgctc agagcggaga aagcatttgt ttgtacaaga tccgcagacg | 480 |
| tgtaaatgtt cctgcaaaaa cacagactcg cgttgcaagg cgaggcagct tgagttaaac | 540 |
| gaacgtactt gcagatgtga caagccgagg cggtga | 576 |

<210> SEQ ID NO 122
<211> LENGTH: 624
<212> TYPE: DNA
<213> ORGANISM: Homo sapiens
<300> PUBLICATION INFORMATION:
<302> TITLE: VEGF B
<310> PATENT DOCUMENT NUMBER: NM003377

<400> SEQUENCE: 122

| | |
|---|---|
| atgagccctc tgctccgccg cctgctgctc gccgcactcc tgcagctggc ccccgcccag | 60 |
| gcccctgtct cccagcctga tgccctggc caccagagga agtggtgtc atggatagat | 120 |
| gtgtatactc gcgctacctg ccagccccgg gaggtggtgg tgcccttgac tgtggagctc | 180 |
| atgggcaccg tggccaaaca gctggtgccc agctgcgtga ctgtgcagcg ctgtggtggc | 240 |
| tgctgccctg acgatggcct ggagtgtgtg cccactgggc agcaccaagt ccggatgcag | 300 |
| atcctcatga tccggtaccc gagcagtcag ctggggagat gtccctgga agaacacagc | 360 |
| cagtgtgaat gcagacctaa aaaaaggac agtgctgtga agccagacag ggctgccact | 420 |
| ccccaccacc gtccccagcc ccgttctgtt ccgggctggg actctgcccc cggagcaccc | 480 |
| tccccagctg acatcacccca tcccactcca gccccaggcc cctctgccca cgctgcaccc | 540 |
| agcaccacca gcgccctgac ccccggacct gccgccgccg ctgccgacgc cgcagcttcc | 600 |
| tccgttgcca agggcggggc ttag | 624 |

<210> SEQ ID NO 123
<211> LENGTH: 1260
<212> TYPE: DNA

```
<213> ORGANISM: Homo sapiens
<300> PUBLICATION INFORMATION:
<302> TITLE: VEGF C
<310> PATENT DOCUMENT NUMBER: NM005429

<400> SEQUENCE: 123
atgcacttgc tgggcttctt ctctgtggcg tgttctctgc tcgccgctgc gctgctcccg      60
ggtcctcgcg aggcgcccgc cgccgccgcc gccttcgagt ccggactcga cctctcggac     120
gcggagcccg acgcgggcga ggccacggct tatgcaagca agatctgga ggagcagtta     180 cggtctgtgt ccagtgtaga tgaactcatg actgtactct acccagaata ttggaaaatg    240
tacaagtgtc agctaaggaa aggaggctgg caacataaca gagaacaggc caacctcaac   300
tcaaggacag aagagactat aaaatttgct gcagcacatt ataatacaga gatcttgaaa    360
agtattgata atgagtggag aaagactcaa tgcatgccac gggaggtgtg tatagatgtg    420
gggaaggagt ttggagtcgc gacaaacacc ttctttaaac ctccatgtgt gtccgtctac     480
agatgtgggg gttgctgcaa tagtgagggg ctgcagtgca tgaacaccag cacgagctac    540
ctcagcaaga cgttatttga aattacagtg cctctctctc aaggccccaa accagtaaca    600
atcagttttg ccaatcacac ttcctgccga tgcatgtcta aactggatgt ttacagacaa    660
gttcattcca ttattagacg ttccctgcca gcaacactac cacagtgtca ggcagcgaac    720
aagacctgcc ccaccaatta catgtggaat aatcacatct gcagatgcct ggctcaggaa   780
gattttatgt tttcctcgga tgctggagat gactcaacag atggattcca tgacatctgt    840
ggaccaaaca aggagctgga tgaagagacc tgtcagtgtg tctgcagagc ggggcttcgg    900
cctgccagct gtggacccca caagaactac acagaaact catgccagtg tgtctgtaaa    960
aacaaactct cccccagcca atgtgggcc aaccgagaat tgatgaaaaa cacatgccag   1020
tgtgtatgta aagaacctg ccccagaaat caaccctaa atcctggaaa atgtgcctgt   1080
gaatgtacag aaagtccaca gaatgcttg ttaaaaggaa agaagttcca ccaccaaaca   1140
tgcagctgtt acagacggcc atgtacgaac cgccagaagg cttgtgagcc aggatttca   1200 tatagtgaag aagtgtgtcg ttgtgtccct tcatattgga aaagaccaca aatgagctaa   1260

<210> SEQ ID NO 124
<211> LENGTH: 1074
<212> TYPE: DNA
<213> ORGANISM: Homo sapiens
<300> PUBLICATION INFORMATION:
<302> TITLE: VEGF D
<310> PATENT DOCUMENT NUMBER: AJ000185

<400> SEQUENCE: 124
atattcaaaa tgtacagaga gtgggtagtg gtgaatgttt tcatgatgtt gtacgtccag      60
ctggtgcagg gctccagtaa tgaacatgga ccagtgaagc gatcatctca gtccacattg    120
gaacgatctg aacagcagat cagggctgct tctagtttgg aggaactact tcgaattact    180
cactctgagg actggaagct gtggagatgc aggctgaggc tcaaaagttt taccagtatg    240
gactctcgct cagcatccca tcggtccact aggtttgcgg caactttcta tgacattgaa    300
acactaaaag ttatagatga agaatggcaa agaactcagt gcagccctag agaaacgtgc    360
gtggaggtgg ccagtgagct ggggaagagt accaacacat tcttcaagcc ccttgtgtg    420 aacgtgttcc gatgtggtgg ctgttgcaat gaagagagcc ttatctgtat gaacaccagc    480
acctcgtaca tttccaaaca gctctttgag atatcagtgc ctttgacatc agtacctgaa    540
ttagtgcctg ttaaagttgc caatcataca ggttgtaagt gcttgccaac agccccccgc   600
```

```
catccatact caattatcag aagatccatc cagatccctg aagaagatcg ctgttcccat      660
tccaagaaac tctgtcctat tgacatgcta tgggatagca acaaatgtaa atgtgttttg      720
caggaggaaa atccacttgc tggaacagaa gaccactctc atctccagga accagctctc      780
tgtgggccac acatgatgtt tgacgaagat cgttgcgagt gtgtctgtaa aacaccatgt      840
cccaaagatc taatccagca ccccaaaaac tgcagttgct ttgagtgcaa agaaagtctg      900
gagacctgct gccagaagca caagctattt caccccagaca cctgcagctg tgaggacaga      960 tgccccttc ataccagacc atgtgcaagt ggcaaaacag catgtgcaaa gcattgccgc      1020
tttccaaagg agaaaagggc tgcccagggg ccccacagcc gaaagaatcc ttga           1074
```

<210> SEQ ID NO 125
<211> LENGTH: 1314
<212> TYPE: DNA
<213> ORGANISM: Homo sapiens
<300> PUBLICATION INFORMATION:
<302> TITLE: E2F
<310> PATENT DOCUMENT NUMBER: M96577

<400> SEQUENCE: 125

```
atggccttgg ccggggcccc tgcgggcggc ccatgcgcgc cggcgctgga ggccctgctc       60
ggggccggcg cgctgcggct gctcgactcc tcgcagatcg tcatcatctc cgccgcgcag      120
gacgccagcg ccccgccggc tcccaccggc cccgcgcgc cgccgccgg ccctgcgac       180 cctgacctgc tgctcttcgc cacaccgcag gcgccccggc ccacacccag tgcgccgcgg      240
cccgcgctcg gccgcccgcc ggtgaagcgg aggctggacc tggaaactga ccatcagtac      300
ctggccgaga gcagtgggcc agctcggggc agaggccgcc atccaggaaa aggtgtgaaa      360 tccccgggg agaagtcacg ctatgagacc tcactgaatc tgaccaccaa gcgcttcctg      420
gagctgctga gccactcggc tgacggtgtc gtcgacctga actgggctgc cgaggtgctg      480
aaggtgcaga gcggcgcat ctatgacatc accaacgtcc ttgagggcat ccagctcatt      540
gccaagaagt ccaagaacca catccagtgg ctgggcagcc acaccacagt gggcgtcggc      600
ggacggcttg agggggttgac ccaggacctc cgacagctgc aggagagcga gcagcagctg      660
gaccacctga tgaatatctg tactacgcag ctgcgcctgc tctccgagga cactgacagc      720
cagcgcctgg cctacgtgac gtgtcaggac cttcgtagca ttgcagaccc tgcagagcag      780
atggttatgg tgatcaaagc ccctcctgag acccagctcc aagccgtgga ctcttcggag      840
aactttcaga tctccctta gagcaaacaa ggcccgatcg atgttttcct gtgccctgag      900
gagaccgtag gtgggatcag ccctgggaag accccatccc aggaggtcac ttctgaggag      960
gagaacaggg ccactgactc tgccaccata gtgtcaccac caccatcatc tccccctca      1020 tccctcacca cagatcccag ccagtctcta ctcagcctgg agcaagaacc gctgttgtcc      1080
cggatgggca gcctgcgggc tcccgtggac gaggaccgcc tgtccccgct ggtggcggcc      1140
gactcgctcc tggagcatgt gcgggaggac ttctccggcc tcctcctga ggagttcatc      1200 agcctttccc cacccacga ggccctcgac taccacttcg gcctcgagga gggcgagggc      1260
atcagagacc tcttcgactg tgactttggg gacctcaccc cctggatttt ctga           1314
```

<210> SEQ ID NO 126
<211> LENGTH: 166
<212> TYPE: DNA
<213> ORGANISM: Human papillomavirus
<300> PUBLICATION INFORMATION:
<302> TITLE: EBER-1
<310> PATENT DOCUMENT NUMBER: Jo2078

-continued

<400> SEQUENCE: 126

```
ggacctacgc tgccctagag gttttgctag ggaggagacg tgtgtggctg tagccacccg      60
tcccgggtac aagtcccggg tggtgaggac ggtgtctgtg gttgtcttcc cagactctgc     120
tttctgccgt cttcggtcaa gtaccagctg gtggtccgca tgtttt                    166
```

<210> SEQ ID NO 127
<211> LENGTH: 172
<212> TYPE: DNA
<213> ORGANISM: Hepatitis C virus
<300> PUBLICATION INFORMATION:
<302> TITLE: EBER-2
<310> PATENT DOCUMENT NUMBER: J02078

<400> SEQUENCE: 127

```
ggacagccgt tgccctagtg gtttcggaca caccgccaac gctcagtgcg gtgctaccga      60
cccgaggtca gtcccggggg gaggagaaga gaggcttccc gcctagagca tttgcaagtc     120
aggattctct aatccctctg ggagaagggt attcggcttg ccgctatttt tt            172
```

<210> SEQ ID NO 128
<211> LENGTH: 651
<212> TYPE: DNA
<213> ORGANISM: Hepatitis C virus
<300> PUBLICATION INFORMATION:
<302> TITLE: NS2
<310> PATENT DOCUMENT NUMBER: AJ238799

<400> SEQUENCE: 128

```
atggaccggg agatggcagc atcgtgcgga ggcgcggttt tcgtaggtct gatactcttg      60
accttgtcac cgcactataa gctgttcctc gctaggctca tatggtggtt acaatatttt     120
atcaccaggg ccgaggcaca cttgcaagtg tggatccccc ccctcaacgt tcgggggggc     180
cgcgatgccg tcatcctcct cacgtgcgcg atccacccag agctaatctt taccatcacc     240
aaaatcttgc tcgccatact cggtccactc atggtgctcc aggctggtat aaccaaagtg     300
ccgtacttcg tgcgcgcaca cgggctcatt cgtgcatgca tgctggtgcg gaaggttgct     360
gggggtcatt atgtccaaat ggctctcatg aagttggccg cactgacagg tacgtacgtt     420
tatgaccatc tcaccccact gcgggactgg gcccacgcgg gcctacgaga ccttgcggtg     480
gcagttgagc ccgtcgtctt ctctgatatg gagaccaagg ttatcacctg ggggcagac      540
accgcggcgt gtgggacat catcttgggc ctgcccgtct ccgcccgcag ggggagggag     600
atacatctgg gaccggcaga cagccttgaa gggcaggggt ggcgactcct c              651
```

<210> SEQ ID NO 129
<211> LENGTH: 161
<212> TYPE: DNA
<213> ORGANISM: Hepatitis C virus
<300> PUBLICATION INFORMATION:
<302> TITLE: NS4A
<310> PATENT DOCUMENT NUMBER: AJ238799

<400> SEQUENCE: 129

```
gcacctgggt gctggtaggc ggagtcctag cagctctggc cgcgtattgc ctgacaacag      60
gcagcgtggt cattgtgggc aggatcatct tgtccggaaa gccggccatc attcccgaca     120
gggaagtcct ttaccgggag ttcgatgaga tggaagagtg c                         161
```

<210> SEQ ID NO 130
<211> LENGTH: 783
<212> TYPE: DNA
<213> ORGANISM: Hepatitis C virus

```
<300> PUBLICATION INFORMATION:
<302> TITLE: NS4B
<310> PATENT DOCUMENT NUMBER: AJ238799

<400> SEQUENCE: 130
gcctcacacc tcccttacat cgaacaggga atgcagctcg ccgaacaatt caaacagaag      60
gcaatcgggt tgctgcaaac agccaccaag caagcggagg ctgctgctcc cgtggtggaa     120
tccaagtggc ggaccctcga agccttctgg gcgaagcata tgtggaattt catcagcggg     180
atacaatatt tagcaggctt gtccactctg cctggcaacc ccgcgatagc atcactgatg     240
gcattcacag cctctatcac cagcccgctc accacccaac ataccctcct gtttaacatc     300
ctggggggat gggtggccgc ccaacttgct cctcccagcg ctgcttctgc tttcgtaggc     360
gccggcatcg ctggagcggc tgttggcagc ataggccttg ggaaggtgct tgtggatatt     420
ttggcaggtt atggagcagg ggtggcaggc cgcgctcgtg gcctttaaggt catgagcggc     480
gagatgccct ccaccgagga cctggttaac ctactccctg ctatcctctc ccctggcgcc     540
ctagtcgtcg gggtcgtgtg cgcagcgata ctgcgtcggc acgtgggccc aggggagggg     600
gctgtgcagt ggatgaaccg gctgatagcg ttcgcttcgc ggggtaacca cgtctccccc     660
acgcactatg tgcctgagag cgacgctgca gcacgtgtca ctcagatcct ctctagtctt     720
accatcactc agctgctgaa gaggcttcac cagtggatca cgaggactg ctccacgcca     780
tgc                                                                 783

<210> SEQ ID NO 131
<211> LENGTH: 1341
<212> TYPE: DNA
<213> ORGANISM: Hepatitis C virus
<300> PUBLICATION INFORMATION:
<302> TITLE: NS5A
<310> PATENT DOCUMENT NUMBER: AJ238799

<400> SEQUENCE: 131
tccggctcgt ggctaagaga tgtttgggat tggatatgca cggtgttgac tgatttcaag      60
acctggctcc agtccaagct cctgccgcga ttgccgggag tccccttctt ctcatgtcaa     120
cgtgggtaca agggagtctg gcggggcgac ggcatcatgc aaaccacctg cccatgtgga     180
gcacagatca ccggacatgt gaaaaacggt tccatgagga tcgtggggcc taggacctgt     240
agtaacacgt ggcatggaac attccccatt aacgcgtaca ccacgggccc ctgcacgccc     300
tccccggcgc caaattattc tagggcgctg tggcgggtgg ctgctgagga gtacgtggag     360
gttacgcggg tgggggattt ccactacgtg acggcgcatga ccactgacaa cgtaaagtgc     420
ccgtgtcagg ttccggcccc cgaattcttc acagaagtgg atggggtgcg gttgcacagg     480
tacgctccag cgtgcaaacc cctcctacgg gaggaggtca cattcctggt cgggctcaat     540
caatacctgg ttgggtcaca gctcccatgc gagcccgaac cggacgtagc agtgctcact     600
tccatgctca ccgaccccctc ccacattacg gcggagacgg ctaagcgtag gctggccagg     660
ggatctcccc cctccttggc cagctcatca gctagccagc tgtctgcgcc ttccttgaag     720
gcaacatgca ctacccgtca tgactccccg acgctgacc tcatcgaggc caacctcctg     780
tggcggcagg agatgggcgg gaacatcacc cgcgtggagt cagaaaataa ggtagtaatt     840
ttggactctt cgagccgcct ccaagcggag gaggatgaga ggaagtatc cgttccggcg     900
gagatcctgc ggaggtccag gaaattccct cgagcgatgc ccatatgggc acgcccggat     960
tacaacccctc cactgttaga gtcctggaag gacccggact acgtccctcc agtggtacac    1020
gggtgtccat tgccgcctgc caaggcccct ccgataccac ctccacggag gaagaggacg    1080
```

```
gttgtcctgt cagaatctac cgtgtcttct gccttggcgg agctcgccac aaagaccttc    1140
ggcagctccg aatcgtcggc cgtcgacagc ggcacggcaa cggcctctcc tgaccagccc    1200
tccgacgacg gcgacgcggg atccgacgtt gagtcgtact cctccatgcc ccccttgag    1260 ggggagccgg gggatcccga tctcagcgac gggtcttggt ctaccgtaag cgaggaggct    1320
agtgaggacg tcgtctgctg c                                              1341
```

<210> SEQ ID NO 132  
<211> LENGTH: 1772  
<212> TYPE: DNA  
<213> ORGANISM: Hepatitis C virus  
<300> PUBLICATION INFORMATION:  
<302> TITLE: NS5B  
<310> PATENT DOCUMENT NUMBER: AJ238799

<400> SEQUENCE: 132
tcgatgtcct acacatggac aggcgccctg atcacgccat gcgctgcgga ggaaaccaag 60
ctgcccatca atgcactgag caactctttg ctccgtcacc acaacttggt ctatgctaca 120
acatctcgca gcgcaagcct gcggcagaag aaggtcacct ttgacagact gcaggtcctg 180
gacgaccact accgggacgt gctcaaggag atgaaggcga aggcgtccac agttaaggct 240
aaacttctat ccgtggagga agcctgtaag ctgacgcccc cacattcggc cagatctaaa 300
tttggctatg gggcaaagga cgtccggaac ctatccagca aggccgttaa ccacatccgc 360
tccgtgtgga aggacttgct ggaagacact gagacaccaa ttgacaccac catcatggca 420
aaaaatgagg ttttctgcgt ccaaccagag aagggggggc gcaagccagc tcgccttatc 480
gtattcccag atttgggggt tcgtgtgtgc gagaaaatgg ccctttacga tgtggtctcc 540
accctccctc aggccgtgat gggctcttca tacggattcc aatactctcc tggacagcgg 600
gtcgagttcc tggtgaatgc ctggaaagcg aagaaatgcc ctatgggctt cgcatatgac 660
acccgctgtt ttgactcaac ggtcactgag aatgacatcc gtgttgagga gtcaatctac 720
caatgttgtg acttggcccc cgaagccaga caggccataa ggtcgctcac agagcggctt 780
tacatcgggg gccccctgac taattctaaa gggcagaact gcggctatcg ccggtgccgc 840
gcgagcggtg tactgacgac cagctgcggt aataccctca catgttactt gaaggccgct 900
gcggcctgtc gagctgcgaa gctccaggac tgcacgatgc tcgtatgcgg agacgacctt 960
gtcgttatct gtgaaagcgc ggggacccaa gaggacgagg cgagcctacg ggccttcacg 1020
gaggctatga ctagatactc tgcccccct ggggacccgc ccaaaccaga atacgacttg 1080
gagttgataa catcatgctc ctccaatgtg tcagtcgcgc acgatgcatc tggcaaaagg 1140
gtgtactatc tcacccgtga ccccaccacc ccccttgcgc gggctgcgtg ggagacagct 1200
agacacactc cagtcaattc ctggctaggc aacatcatca tgtatgcgcc caccttgtgg 1260
gcaaggatga tcctgatgac tcatttcttc tccatccttc tagctcagga acaacttgaa 1320
aaagccctag attgtcagat ctacggggcc tgttactcca ttgagccact tgacctacct 1380
cagatcattc aacgactcca tggccttagc gcattttcac tccatagtta ctctccaggt 1440
gagatcaata gggtggcttc atgcctcagg aaacttgggg taccgccctt gcgagtctgg 1500
agacatcggg ccagaagtgt ccgcgctagg ctactgtccc aggggggag ggctgccact 1560 tgtggcaagt acctcttcaa ctgggcagta aggaccaagc tcaaactcac tccaatcccg 1620
gctgcgtccc agttggattt atccagctgg ttcgttgctg gttacagcgg gggagacata 1680
tatcacagcc tgtctcgtgc ccgaccccgc tggttcatgt ggtgcctact cctactttct 1740

```
gtaggggtag gcatctatct actccccaac cg                                   1772
```

<210> SEQ ID NO 133
<211> LENGTH: 1892
<212> TYPE: DNA
<213> ORGANISM: Hepatitis C virus
<300> PUBLICATION INFORMATION:
<302> TITLE: NS3
<310> PATENT DOCUMENT NUMBER: AJ238799

<400> SEQUENCE: 133

```
cgcctattac ggcctactcc aacagacgc gaggcctact tggctgcatc atcactagcc        60
tcacaggccg ggacaggaac caggtcgagg gggaggtcca agtggtctcc accgcaacac       120
aatctttcct ggcgacctgc gtcaatggcg tgtgttggac tgtctatcat ggtgccggct       180
caaagaccct tgccggccca aagggcccaa tcacccaaat gtacaccaat gtggaccagg       240
acctcgtcgg ctggcaagcg ccccccgggg cgcgttcctt gacaccatgc acctgcggca       300
gctcggacct ttacttggtc acgaggcatg ccgatgtcat tccggtgcgc ggcggggcg        360
acagcagggg gagcctactc tcccccaggc ccgtctccta cttgaagggc tcttcgggcg       420
gtccactgct ctgcccctcg gggcacgctg tgggcatctt tcgggctgcc gtgtgcaccc       480
gaggggttgc gaaggcggtg gactttgtac ccgtcgagtc tatggaaacc actatgcggt       540
ccccggtctt cacggacaac tcgtcccctc ggccgtacc gcagacattc caggtggccc        600
atctacacgc ccctactggt agcggcaaga gcactaaggt gccggctgcg tatgcagccc       660
aagggtataa ggtgcttgtc ctgaacccgt ccgtcgccgc caccctaggt ttcggggcgt       720
atatgtctaa ggcacatggt atcgaccctaa acatcagaac cggggtaagg accatcacca       780
cgggtgcccc catcacgtac tccacctatg caagtttct tgccgacggt ggttgctctg       840
ggggcgccta tgacatcata atatgtgatg agtgccactc aactgactcg accactatcc       900
tgggcatcgg cacagtcctg gaccaagcgg agacggctgg agcgcgactc gtcgtgctcg       960
ccaccgctac gcctccggga tcggtcaccg tgccacatcc aaacatcgag gaggtggctc      1020
tgtccagcac tggagaaatc ccctttatg gcaaagccat ccccatcgag accatcaagg       1080
gggggaggca cctcattttc tgccattcca agaagaaatg tgatgagctc gccgcgaagc      1140
tgtccggcct cggactcaat gctgtagcat attaccgggg ccttgatgta tccgtctac        1200
caactagcgg agacgtcatt gtcgtagcaa cggacgctct aatgacgggc tttaccggcg      1260
atttcgactc agtgatcgac tgcaatacat gtgtcaccca gacagtcgac ttcagcctgg      1320
acccgacctt caccattgag acgacgaccg tgccacaaga cgcggtgtca cgctcgcagc      1380
ggcgaggcag gactggtagg ggcaggatgg gcatttacag gtttgtgact ccaggagaac      1440
ggccctcggg catgttcgat tcctcggttc tgtgcgagtg ctatgacgcg ggctgtgctt      1500
ggtacgagct cacgcccgcc gagacctcag ttaggttgcg ggcttaccta aacacaccag      1560
ggttgccggt ctgccaggac catctggagt tctgggagag cgtctttaca ggcctcaccc      1620
acatagacgc ccatttcttg tcccagacta agcaggcagg agacaacttc ccctacctgg      1680
tagcatacca ggctacggtg tgcgccaggg ctcaggctcc acctccatcg tgggaccaaa      1740
tgtggaagtg tctcatacgg ctaaagccta cgctgcacgg gccaacgccc ctgctgtata      1800
ggctgggagc cgttcaaaac gaggttacta ccacacaccc cataaccaaa tacatcatgg      1860
catgcatgtc ggctgacctg gaggtcgtca cg                                   1892
```

<210> SEQ ID NO 134
<211> LENGTH: 822

```
-continued

<212> TYPE: DNA
<213> ORGANISM: Homo sapiens
<300> PUBLICATION INFORMATION:
<302> TITLE: stmn cell factor
<310> PATENT DOCUMENT NUMBER: M59964

<400> SEQUENCE: 134
atgaagaaga cacaaacttg gattctcact tgcatttatc ttcagctgct cctatttaat      60
cctctcgtca aaactgaagg gatctgcagg aatcgtgtga ctaataatgt aaaagacgtc     120
actaaattgg tggcaaatct tccaaaagac tacatgataa ccctcaaata tgtccccggg     180
atggatgttt tgccaagtca ttgttggata agcgagatgg tagtacaatt gtcagacagc     240
ttgactgatc ttctggacaa gttttcaaat atttctgaag gcttgagtaa ttattccatc     300
atagacaaac ttgtgaatat agtcgatgac cttgtggagt gcgtcaaaga aaactcatct     360
aaggatctaa aaaatcatt caagagccca gaacccaggc tctttactcc tgaagaattc     420
tttagaattt ttaatagatc cattgatgcc ttcaaggact ttgtagtggc atctgaaact     480
agtgattgtg tggtttcttc aacattaagt cctgagaaag attccagagt cagtgtcaca     540
aaaccattta tgttaccccc tgttgcagcc agctcccta ggaatgacag cagtagcagt     600
aataggaagg ccaaaaatcc ccctggagac tccagcctac actgggcagc catggcattg     660
ccagcattgt tttctcttat aattggcttt gcttttggag ccttatactg aagaagaga     720
cagccaagtc ttacaagggc agttgaaaat atacaaatta tgaagagga taatgagata     780
agtatgttgc aagagaaaga gagagagttt caagaagtgt aa                       822

<210> SEQ ID NO 135
<211> LENGTH: 483
<212> TYPE: DNA
<213> ORGANISM: Homo sapiens
<300> PUBLICATION INFORMATION:
<302> TITLE: TGFalpha
<310> PATENT DOCUMENT NUMBER: AF123238

<400> SEQUENCE: 135
atggtcccct cggctggaca gctcgccctg ttcgctctgg gtattgtgtt ggctgcgtgc      60
caggccttgg agaacagcac gtccccgctg agtgcagacc cgcccgtggc tgcagcagtg     120
gtgtcccatt ttaatgactg cccagattcc cacactcagt tctgcttcca tggaacctgc     180
aggttttgg tgcaggagga caagccagca tgtgtctgcc attctgggta cgttggtgca     240
cgctgtgagc atgcggacct cctggccgtg gtggctgcca gccagaagaa gcaggccatc     300
accgccttgg tggtggtctc catcgtggcc ctggctgtcc ttatcatcac atgtgtgctg     360
atacactgct gccaggtccg aaaacactgt gagtggtgcc gggccctcat ctgccggcac     420
gagaagccca cgcgcctcct gaagggaaga accgcttgct gccactcaga acagtggtc     480
tga                                                                   483

<210> SEQ ID NO 136
<211> LENGTH: 1071
<212> TYPE: DNA
<213> ORGANISM: Homo sapiens
<300> PUBLICATION INFORMATION:
<302> TITLE: GD3 synthase
<310> PATENT DOCUMENT NUMBER: NM003034

<400> SEQUENCE: 136
atgagcccct gcgggcgggc ccggcgacaa acgtccagag gggccatggc tgtactggcg      60
tggaagttcc cgcggacccg gctgcccatg ggagccagtg ccctctgtgt cgtggtcctc     120
```

```
tgttggctct acatcttccc cgtctaccgg ctgcccaacg agaaagagat cgtgcagggg    180
gtgctgcaac agggcacggc gtggaggagg aaccagaccg cggccagagc gttcaggaaa    240
caaatggaag actgctgcga ccctgcccat ctctttgcta tgactaaaat gaattcccct    300
atggggaaga gcatgtggta tgacgggag ttttttatact cattcaccat tgacaattca    360
acttactctc tcttcccaca ggcaaccccca ttccagctgc cattgaagaa atgcgcggtg    420
gtgggaaatg gtgggattct gaagaagagt ggctgtggcc gtcaaataga tgaagcaaat    480
tttgtcatgc gatgcaatct ccctcctttg tcaagtgaat acactaagga tgttggatcc    540
aaaagtcagt tagtgacagc taatcccagc ataattcggc aaaggtttca gaaccttctg    600
tggtccagaa agacatttgt ggacaacatg aaaatctata accacagtta catctacatg    660 cctgccttt ctatgaagac aggaacagag ccatctttga gggtttatta tacactgtca    720
gatgttggtg ccaatcaaac agtgctgttt gccaacccca actttctgcg tagcattgga    780
aagttctgga aaagtagagg aatccatgcc aagcgcctgt ccacaggact ttttctggtg    840
agcgcagctc tgggtctctg tgaagaggtg gccatctatg gcttctggcc cttctctgtg    900
aatatgcatg agcagcccat cagccaccac tactatgaca acgtcttacc cttttctggc    960
ttccatgcca tgcccgagga atttctccaa ctctggtatc ttcataaaat cggtgcactg   1020
agaatgcagc tggacccatg tgaagatacc tcactccagc ccacttccta g            1071

<210> SEQ ID NO 137
<211> LENGTH: 744
<212> TYPE: DNA
<213> ORGANISM: Homo sapiens
<300> PUBLICATION INFORMATION:
<302> TITLE: FGF14
<310> PATENT DOCUMENT NUMBER: NM004115

<400> SEQUENCE: 137
atggccgcgg ccatcgctag cggcttgatc cgccagaagc ggcaggcgcg ggagcagcac     60
tgggaccggc cgtctgccag caggaggcgg agcagcccca gcaagaaccg cgggctctgc    120
aacggcaacc tggtggatat cttctccaaa gtgcgcatct tcggcctcaa gaagcgcagg    180
ttgcggcgcc aagatcccca gctcaagggt atagtgacca ggttatattg caggcaaggc    240
tactacttgc aaatgcaccc cgatggagct ctcgatggaa ccaaggatga cagcactaat    300
tctacactct tcaacctcat accagtggga ctacgtgttg ttgccatcca gggagtgaaa    360
acagggttgt atatagccat gaatggagaa ggttacctct acccatcaga acttttttacc    420 cctgaatgca agtttaaaga atctgttttt gaaaattatt atgtaatcta ctcatccatg    480
ttgtacagac aacaggaatc tggtagagcc tggttttttgg gattaaataa ggaagggcaa    540
gctatgaaag ggaacagagt aaagaaaacc aaaccagcag ctcattttct acccaagcca    600
ttggaagttg ccatgtaccg agaaccatct ttgcatgatg ttggggaaac ggtcccgaag    660
cctggggtga cgccaagtaa aagcacaagt gcgtctgcaa taatgaatgg aggcaaacca    720
gtcaacaaga gtaagacaac atag                                           744

<210> SEQ ID NO 138
<211> LENGTH: 1503
<212> TYPE: DNA
<213> ORGANISM: Human immunodeficiency virus
<300> PUBLICATION INFORMATION:
<302> TITLE: gag (HIV)
<310> PATENT DOCUMENT NUMBER: NC001802

<400> SEQUENCE: 138
```

| | |
|---|---|
| atgggtgcga gagcgtcagt attaagcggg ggagaattag atcgatggga aaaaattcgg | 60 |
| ttaaggccag ggggaaagaa aaatataaaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acaaataatc cacctatccc agtaggagaa | 780 |
| atttataaaa gatggataat cctgggatta aataaaatag taagaatgta tagccctacc | 840 |
| agcattctgg acataagaca aggaccaaag gaaccctta gagactatgt agaccggttc | 900 |
| tataaaactc taagagccga gcaagcttca caggaggtaa aaaattggat gacagaaacc | 960 |
| ttgttggtcc aaaatgcgaa cccagattgt aagactattt taaaagcatt gggaccagcg | 1020 |
| gctacactag aagaaatgat gacagcatgt caggggagtag gaggacccgg ccataaggca | 1080 |
| agagttttgg ctgaagcaat gagccaagta acaaattcag ctaccataat gatgcagaga | 1140 |
| ggcaatttta ggaaccaaag aaagattgtt aagtgtttca attgtggcaa agaagggcac | 1200 |
| acagccagaa attgcagggc ccctaggaaa aagggctgtt ggaaatgtgg aaggaagga | 1260 |
| caccaaatga aagattgtac tgagagacag gctaattttt tagggaagat ctggccttcc | 1320 |
| tacaagggaa ggccagggaa ttttcttcag agcagaccag agccaacagc cccaccagaa | 1380 |
| gagagcttca ggtctggggt agagacaaca actccccctc agaagcagga gccgatagac | 1440 |
| aaggaactgt atcctttaac ttcccctcagg tcactctttg gcaacgaccc ctcgtcacaa | 1500 |
| taa | 1503 |

<210> SEQ ID NO 139
<211> LENGTH: 1101
<212> TYPE: DNA
<213> ORGANISM: Human immunodeficiency virus
<300> PUBLICATION INFORMATION:
<302> TITLE: TARBP2
<310> PATENT DOCUMENT NUMBER: NM004178

<400> SEQUENCE: 139

| | |
|---|---|
| atgagtgaag aggagcaagg ctccggcact accacgggct gcgggctgcc tagtatagag | 60 |
| caaatgctgg ccgccaaccc aggcaagacc ccgatcagcc ttctgcagga gtatgggacc | 120 |
| agaatagggga agacgcctgt gtacgaccttt ctcaaagccg agggccaagc ccaccagcct | 180 |
| aatttcacct tccgggtcac cgttggcgac accagctgca ctggtcaggg ccccagcaag | 240 |
| aaggcagcca agcacaaggc agctgaggtg gccctcaaac acctcaaagg ggggagcatg | 300 |
| ctggagccgg ccctggagga cagcagttct ttttctcccc tagactcttc actgcctgag | 360 |
| gacattccgg ttttactgc tgcagcagct gctaccccag ttccatctgt agtcctaacc | 420 |
| aggagccccc ccatgaact gcagcccct gtctccctc agcagtctga gtgcaacccc | 480 |
| gttggtgctc tgcaggagct ggtggtgcag aaaggctggc ggttgccgga gtacacagtg | 540 |

```
acccaggagt ctgggccagc ccaccgcaaa gaattcacca tgacctgtcg agtggagcgt      600
ttcattgaga ttgggagtgg cacttccaaa aaattggcaa agcggaatgc ggcggccaaa      660
atgctgcttc gagtgcacac ggtgcctctg gatgcccggg atggcaatga ggtggagcct      720
gatgatgacc acttctccat tggtgtgggc ttccgcctgg atggtcttcg aaaccggggc      780
ccaggttgca cctgggattc tctacgaaat tcagtaggag agaagatcct gtccctccgc      840
agttgctccc tgggctccct gggtgccctg ggccctgcct gctgccgtgt cctcagtgag      900
ctctctgagg agcaggcctt tcacgtcagc tacctggata ttgaggagct gagcctgagt      960
ggactctgcc agtgcctggt ggaactgtcc acccagccgg ccactgtgtg tcatggctct     1020
gcaaccacca gggaggcagc ccgtggtgag gctgcccgcc gtgccctgca gtacctcaag     1080
atcatggcag gcagcaagtg a                                              1101

<210> SEQ ID NO 140
<211> LENGTH: 219
<212> TYPE: DNA
<213> ORGANISM: Human immunodeficiency virus
<300> PUBLICATION INFORMATION:
<302> TITLE: TAT (HIV)
<310> PATENT DOCUMENT NUMBER: U44023

<400> SEQUENCE: 140
atggagccag tagatcctag cctagagccc tggaagcatc caggaagtca gcctaagact       60
gcttgtacca cttgctattg taaagagtgt tgctttcatt gccaagtttg tttcataaca      120
aaaggcttag gcatctccta tggcaggaag aagcggagac agcgacgaag aactcctcaa      180
ggtcatcaga ctaatcaagt ttctctatca aagcagtaa                             219

<210> SEQ ID NO 141
<211> LENGTH: 22
<212> TYPE: RNA
<213> ORGANISM: Synthetic sequence
<220> FEATURE:
<223> OTHER INFORMATION: Description of the synthetic sequence: sense
      strand (R1A) of a dsRNA that is homologous to an MDR1 sequence

<400> SEQUENCE: 141
ccaucucgaa aagaaguuaa ga                                                22

<210> SEQ ID NO 142
<211> LENGTH: 24
<212> TYPE: RNA
<213> ORGANISM: Synthetic sequence
<220> FEATURE:
<223> OTHER INFORMATION: Description of the synthetic sequence:
      antisense strand (R1B) of a dsRNA, that it
      complementary to an MDR1 sequence

<400> SEQUENCE: 142
ucuuaacuuc uuuucgagau gggu                                              24

<210> SEQ ID NO 143
<211> LENGTH: 22
<212> TYPE: RNA
<213> ORGANISM: Synthetic sequence
<220> FEATURE:
<223> OTHER INFORMATION: Description of the synthetic sequence: sense
      strand (R2A) of a dsRNA that is homologous to an MDR1 sequence

<400> SEQUENCE: 143
uauagguucc aggcuugcug ua                                                22
```

```
<210> SEQ ID NO 144
<211> LENGTH: 22
<212> TYPE: RNA
<213> ORGANISM: Synthetic sequence
<220> FEATURE:
<223> OTHER INFORMATION: Description of the synthetic sequence: sense
      strand (R3A) of a dsRNA that is homologous to an MDR1 sequence

<400> SEQUENCE: 144
ccagagaagg ccgcaccugc au                                                  22

<210> SEQ ID NO 145
<211> LENGTH: 24
<212> TYPE: RNA
<213> ORGANISM: Synthetic sequence
<220> FEATURE:
<223> OTHER INFORMATION: Description of the synthetic sequence:
      antisense strand (R3B) of a dsRNA, that it
      complementary to an MDR1 sequence

<400> SEQUENCE: 145
augcaggugc ggccuucucu ggcu                                                24

<210> SEQ ID NO 146
<211> LENGTH: 21
<212> TYPE: RNA
<213> ORGANISM: Synthetic sequence
<220> FEATURE:
<223> OTHER INFORMATION: Description of the synthetic sequence: sense
      strand (R4A) of a dsRNA that is homologous to an MDR1 sequence

<400> SEQUENCE: 146
ccaucucgaa aagaaguuaa g                                                   21

<210> SEQ ID NO 147
<211> LENGTH: 21
<212> TYPE: RNA
<213> ORGANISM: Synthetic sequence
<220> FEATURE:
<223> OTHER INFORMATION: Description of the synthetic sequence:
      antisense strand (R4B) of a dsRNA, that it
      complementary to an MDR1 sequence

<400> SEQUENCE: 147
uaacuucuuu ucgagauggg u                                                   21

<210> SEQ ID NO 148
<211> LENGTH: 22
<212> TYPE: RNA
<213> ORGANISM: Synthetic sequence
<220> FEATURE:
<223> OTHER INFORMATION: Description of the synthetic sequence: sense
      strand (S1A) of a dsRNA, that is homologous to the YFP- and
      GFP sequence, respectively

<400> SEQUENCE: 148
ccacaugaag cagcacgacu uc                                                  22

<210> SEQ ID NO 149
<211> LENGTH: 22
<212> TYPE: RNA
<213> ORGANISM: Synthetic sequence
<220> FEATURE:
<223> OTHER INFORMATION: Description of the synthetic sequence:
      antisense strand(S1B) of a dsRNA that is
      complementary to the YFP- and GFP sequence, respectively

<400> SEQUENCE: 149
```

-continued gaagucgugc ugcuucaugu gg                                      22

<210> SEQ ID NO 150
<211> LENGTH: 21
<212> TYPE: RNA
<213> ORGANISM: Synthetic sequence
<220> FEATURE:
<223> OTHER INFORMATION: Description of the synthetic sequence:
      antisense strand(S7A) of a dsRNA that is homologous
      to the YFP- and GFP sequence, respectively

<400> SEQUENCE: 150
ccacaugaag cagcacgacu u                                       21

<210> SEQ ID NO 151
<211> LENGTH: 21
<212> TYPE: RNA
<213> ORGANISM: Synthetic sequence
<220> FEATURE:
<223> OTHER INFORMATION: Description of the synthetic sequence:
      antisense strand(S7B) of a dsRNA, that is
      complementary to the YFP- and GFP sequence, respectively

<400> SEQUENCE: 151
gucgugcugc uucauguggu c                                       21

<210> SEQ ID NO 152
<211> LENGTH: 24
<212> TYPE: RNA
<213> ORGANISM: Synthetic sequence
<220> FEATURE:
<223> OTHER INFORMATION: Description of the synthetic sequence:
      antisense strand(R2B) of a dsRNA that is
      complementary to the MDR-1 sequence

<400> SEQUENCE: 152
uacagcaagc cuggaaccua uagc                                    24

<210> SEQ ID NO 153
<211> LENGTH: 22
<212> TYPE: RNA
<213> ORGANISM: Synthetic sequence
<220> FEATURE:
<223> OTHER INFORMATION: Description of the synthetic sequence: sense
      strand (K1A) of a dsRNA that is homologous to the 5'-UTR of
      the neomycin sequence

<400> SEQUENCE: 153
acaggaugag gaucguuucg ca                                      22

<210> SEQ ID NO 154
<211> LENGTH: 22
<212> TYPE: RNA
<213> ORGANISM: Synthetic sequence
<220> FEATURE:
<223> OTHER INFORMATION: Description of the synthetic sequence:
      antisense strand(K1B) of a dsRNA that is
      complementary to the 5'-UTR of the neomycin sequence

<400> SEQUENCE: 154
ugcgaaacga uccucauccu gu                                      22

<210> SEQ ID NO 155
<211> LENGTH: 21
<212> TYPE: RNA
<213> ORGANISM: Synthetic sequence
<220> FEATURE:
<223> OTHER INFORMATION: Description of the synthetic sequence: sense
      strand (K3A) of a dsRNA that is homologous to the 5'-UTR of the

```
                          neomycin sequence

<400> SEQUENCE: 155
gaugaggauc guuucgcaug a                                              21

<210> SEQ ID NO 156
<211> LENGTH: 21
<212> TYPE: RNA
<213> ORGANISM: Synthetic sequence
<220> FEATURE:
<223> OTHER INFORMATION: Description of the synthetic sequence:
      antisense strand(K3B) of a dsRNA that
      complementary to the 5'-UTR of the neomycin sequence

<400> SEQUENCE: 156
augcgaaacg auccucaucc u                                              21

<210> SEQ ID NO 157
<211> LENGTH: 24
<212> TYPE: RNA
<213> ORGANISM: Synthetic sequence
<220> FEATURE:
<223> OTHER INFORMATION: Description of the synthetic sequence: sense
      strand (K2A) of a dsRNA that is homologous to the 5'-UTR of the
      neomycin sequence

<400> SEQUENCE: 157
acaggaugag gaucguuucg caug                                           24

<210> SEQ ID NO 158
<211> LENGTH: 24
<212> TYPE: RNA
<213> ORGANISM: Synthetic sequence
<220> FEATURE:
<223> OTHER INFORMATION: Description of the synthetic sequence:
      antisense strand(K2B) of a dsRNA that is
      complementary to the 5'-UTR of the neomycin sequence

<400> SEQUENCE: 158
ugcgaaacga uccucauccu gucu                                           24

<210> SEQ ID NO 159
<211> LENGTH: 24
<212> TYPE: RNA
<213> ORGANISM: Synthetic sequence
<220> FEATURE:
<223> OTHER INFORMATION: Description of the synthetic sequence:
      antisense strand(S4B) of a dsRNA that is
      complementary to the YFP- and GFP sequence, respectively

<400> SEQUENCE: 159
gaagucgugc ugcuucaugu gguc                                           24

<210> SEQ ID NO 160
<211> LENGTH: 24
<212> TYPE: RNA
<213> ORGANISM: Synthetic sequence
<220> FEATURE:
<223> OTHER INFORMATION: Description of the synthetic sequence: sense
      strand (PKC1 A) of a dsRNA that is homologous to the
      proteinkinase C sequence

<400> SEQUENCE: 160
cuucuccgcc ucacaccgcu gcaa                                           24

<210> SEQ ID NO 161
<211> LENGTH: 22
<212> TYPE: RNA
```

```
<213> ORGANISM: Synthetic sequence
<220> FEATURE:
<223> OTHER INFORMATION: Description of the synthetic sequence:
      antisense strand(PKC2 B) of a dsRNA that is
      complementary to the proteinkinase C sequence

<400> SEQUENCE: 161
gcagcggugu gaggcggaga ag                                            22

<210> SEQ ID NO 162
<211> LENGTH: 21
<212> TYPE: RNA
<213> ORGANISM: Synthetic sequence
<220> FEATURE:
<223> OTHER INFORMATION: Description of the synthetic sequence:
      antisense strand(S12B) of a dsRNA that is
      complementary to the YFP- and GFP sequence, respectively

<400> SEQUENCE: 162
aagucgugcu gcuucaugug g                                             21

<210> SEQ ID NO 163
<211> LENGTH: 23
<212> TYPE: RNA
<213> ORGANISM: Synthetic sequence
<220> FEATURE:
<223> OTHER INFORMATION: Description of the synthetic sequence:
      antisense strand(S11B) of a dsRNA that is
      complementary to the YFP- and GFP sequence, respectively

<400> SEQUENCE: 163
aagucgugcu gcuucaugug guc                                           23

<210> SEQ ID NO 164
<211> LENGTH: 20
<212> TYPE: RNA
<213> ORGANISM: Synthetic sequence
<220> FEATURE:
<223> OTHER INFORMATION: Description of the synthetic sequence: sense
      strand (S13A) of a dsRNA that is homologous to the YFP- and
      GFP sequence, respectively

<400> SEQUENCE: 164
ccacaugaag cagcacgacu                                               20

<210> SEQ ID NO 165
<211> LENGTH: 22
<212> TYPE: RNA
<213> ORGANISM: Synthetic sequence
<220> FEATURE:
<223> OTHER INFORMATION: Description of the synthetic sequence:
      antisense strand(S13B) of a dsRNA that is
      complementary to the YFP- and GFP sequence, respectively

<400> SEQUENCE: 165
agucgugcug cuucaugugg uc                                            22

<210> SEQ ID NO 166
<211> LENGTH: 20
<212> TYPE: RNA
<213> ORGANISM: Synthetic sequence
<220> FEATURE:
<223> OTHER INFORMATION: Description of the synthetic sequence:
      antisense strand(S14B) of a dsRNA that is
      complementary to the YFP- and GFP sequence, respectively

<400> SEQUENCE: 166
agucgugcug cuucaugugg                                               20
```

```
<210> SEQ ID NO 167
<211> LENGTH: 24
<212> TYPE: RNA
<213> ORGANISM: Synthetic sequence
<220> FEATURE:
<223> OTHER INFORMATION: Description of the synthetic sequence: sense
      strand (S4A) of a dsRNA that is homologous to the YFP- and
      GFP sequence, respectively

<400> SEQUENCE: 167
ccacaugaag cagcacgacu ucuu                                          24

<210> SEQ ID NO 168
<211> LENGTH: 21
<212> TYPE: RNA
<213> ORGANISM: Synthetic sequence
<220> FEATURE:
<223> OTHER INFORMATION: Description of the synthetic sequence: sense
      strand (ES-7A) of a dsRNA that is homologous to the human
      EGFR sequence

<400> SEQUENCE: 168
aacaccgcag caugucaaga u                                             21

<210> SEQ ID NO 169
<211> LENGTH: 21
<212> TYPE: RNA
<213> ORGANISM: Synthetic sequence
<220> FEATURE:
<223> OTHER INFORMATION: Description of the synthetic sequence:
      antisense strand(ES-7B) of a dsRNA that is
      complementary to the human EGFR sequence

<400> SEQUENCE: 169
cuugacaugc ugcgguguuu u                                             21

<210> SEQ ID NO 170
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-8A) of a dsRNA that is homologous to the human
      EGFR sequence

<400> SEQUENCE: 170
aaguuaaaau ucccgucgcu au                                            22

<210> SEQ ID NO 171
<211> LENGTH: 22
<212> TYPE: RNA
<213> ORGANISM: Synthetic sequence
<220> FEATURE:
<223> OTHER INFORMATION: Description of the synthetic sequence:
      antisense strand(ES-8B) of a dsRNA that is
      complementary to the human EGFR sequence

<400> SEQUENCE: 171
ugauagcgac gggaauuuua ac                                            22

<210> SEQ ID NO 172
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-2A) of a dsRNA that is homologous to the human
      EGFR sequence
```

```
<400> SEQUENCE: 172
agugugaucc aagcuguccc aa                                              22

<210> SEQ ID NO 173
<211> LENGTH: 24
<212> TYPE: RNA
<213> ORGANISM: Synthetic sequence
<220> FEATURE:
<223> OTHER INFORMATION: Description of the synthetic sequence:
      antisense strand(ES-5B) of a dsRNA that is
      complementary to the human EGFR sequence

<400> SEQUENCE: 173
uugggacagc uuggaucaca cuuu                                            24
```

We claim:

1. A double-stranded ribonucleic acid (dsRNA) for inhibiting the expression of a target gene in a cell, comprising a complementary RNA strand and a sense RNA strand, wherein the sense RNA strand comprises a nucleotide sequence which is substantially identical to the corresponding part of the target gene, wherein the complementary RNA strand comprises a complementary nucleotide sequence which is complementary to an mRNA transcript formed during expression of the target gene, wherein the complementary strand specifically hybridizes with the mRNA transcript, wherein the complementary RNA strand comprises a 3'-end and a 5'-end, wherein the 3'-end has a nucleotide overhang of 1 to 4 nucleotides and wherein the dsRNA at the 5'-end of the complementary RNA strand is blunt, and wherein the dsRNA is 20 to less than 25 base pairs in length and wherein the two RNA strands of the dsRNA are separate and non-linked.

2. The dsRNA of claim 1, wherein the nucleotide overhang is 1 or 2 nucleotides in length.

3. The dsRNA of claim 1, wherein the nucleotides of the nucleotide overhang are replaced with nucleoside thiophosphates.

4. The dsRNA of claim 1, wherein at least one of the complementary RNA strand and the sense RNA strand is 22 nucleotides in length.

5. The dsRNA of claim 1, wherein at least one of the complementary RNA strand and the sense RNA strand is 24 nucleotides in length.

6. The dsRNA of claim 1, wherein at least one of the complementary RNA strand and the sense RNA strand is 21 nucleotides in length.

7. The dsRNA of claim 1, wherein the target gene comprises EGFR.

8. The dsRNA of claim 1, wherein the target gene comprises MDR1.

9. The dsRNA of claim 1, wherein the target gene comprises MDR1 or EGFR.

10. A method of inhibiting the expression of the target gene in the cell, the method comprising:
(a) introducing into the cell the double-stranded ribonucleic acid (dsRNA) of claim 1 for inhibiting the expression of the target gene in the cell; and
(b) maintaining the cell produced in step (a) for a time sufficient to obtain degradation of the mRNA transcript of the target gene, thereby inhibiting expression of the target gene in the cell.

11. The method of claim 10, wherein the nucleotide overhang is 1 or 2 nucleotides in length.

12. The method of claim 10, wherein the nucleotides of the nucleotide overhang are replaced with nucleoside thiophosphates.

13. The method of claim 10, wherein at least one of the complementary RNA strand and the sense RNA strand is 22 nucleotides in length.

14. The method of claim 10, wherein at least one of the complementary RNA strand and the sense RNA strand is 24 nucleotides in length.

15. The method of claim 10, wherein at least one of the complementary RNA strand and the sense RNA strand is 21 nucleotides in length.

16. The method of claim 10, wherein the target gene comprises EGFR.

17. The method of claim 10, wherein the target gene comprises MDR1.

18. The method of claim 10, wherein the target gene comprises MDR1 or EGFR.

* * * * *